US008921499B2

(12) United States Patent
Shin et al.

(10) Patent No.: US 8,921,499 B2
(45) Date of Patent: Dec. 30, 2014

(54) METHOD OF PREPARING ETHYLENE-α-OLEFIN-DIENE COPOLYMER

(75) Inventors: Dong Cheol Shin, Daejeon (KR); Ho Seong Lee, Seoul (KR); Seong Kyun Kim, Daejeon (KR); Sang Ick Lee, Daejeon (KR); Sun Young Kim, Daejeon (KR); Jong Sok Hahn, Daejeon (KR); Chan Woong Jeon, Daejeon (KR); Jeong Hwan Kim, Daejeon (KR)

(73) Assignees: SK Innovation Co., Ltd., Seoul (KR); SK Global Chemical Co., Ltd., Seoul (KR)

( * ) Notice: Subject to any disclaimer, the term of this patent is extended or adjusted under 35 U.S.C. 154(b) by 0 days.

(21) Appl. No.: 13/640,988

(22) PCT Filed: Jun. 8, 2012

(86) PCT No.: PCT/KR2012/004512

§ 371 (c)(1), (2), (4) Date: Oct. 12, 2012

(87) PCT Pub. No.: WO2012/169812

PCT Pub. Date: Dec. 13, 2012

(65) Prior Publication Data

US 2014/0179885 A1 Jun. 26, 2014

(30) Foreign Application Priority Data

Jun. 9, 2011 (KR) ........................ 10-2011-0055719
Jun. 1, 2012 (KR) ........................ 10-2012-0059443

(51) Int. Cl.

| | |
|---|---|
| ***C08F 4/6592*** | (2006.01) |
| ***C08F 4/642*** | (2006.01) |
| ***C08F 4/643*** | (2006.01) |
| ***C08F 210/16*** | (2006.01) |
| ***C08F 210/18*** | (2006.01) |
| ***C08F 210/06*** | (2006.01) |
| ***C08F 4/76*** | (2006.01) |
| ***C07F 17/00*** | (2006.01) |
| *C08F 4/659* | (2006.01) |

(52) U.S. Cl.

CPC ................. *C08F 210/06* (2013.01); *C08F 4/76* (2013.01); *C07F 17/00* (2013.01); *C08F 210/18* (2013.01); *C08F 4/65908* (2013.01); *C08F 4/65912* (2013.01); *Y10S 526/943* (2013.01)

USPC ........... 526/160; 526/133; 526/161; 526/165; 526/339; 526/943; 502/103; 502/152; 502/167

(58) Field of Classification Search

CPC ............... C08F 4/6592; C08F 4/65908; C08F 4/65912; C08F 210/02; C08F 210/16; C08F 210/18; C08F 2420/02

USPC ................. 526/133, 160, 161, 165, 339, 943; 502/103, 152, 167

See application file for complete search history.

(56) References Cited

U.S. PATENT DOCUMENTS

| | | | |
|---|---|---|---|
| 4,752,597 | A | 6/1988 | Turner |
| 5,055,438 | A | 10/1991 | Canich |
| 5,103,030 | A | 4/1992 | Rohrmann et al. |
| 5,198,401 | A | 3/1993 | Turner et al. |
| 5,703,187 | A | 12/1997 | Timmers |
| 6,329,478 | B1 | 12/2001 | Katayama et al. |

FOREIGN PATENT DOCUMENTS

| | | | |
|---|---|---|---|
| EP | 0320762 | A2 | 6/1989 |
| EP | 0372632 | A1 | 6/1990 |
| EP | 0416815 | A2 | 3/1991 |
| EP | 0420436 | A1 | 4/1991 |
| EP | 0842939 | A1 | 5/1998 |
| EP | 1866322 | B1 | 2/2010 |
| JP | 6392621 | A | 4/1988 |
| JP | 284405 | A | 3/1990 |
| JP | 32347 | A | 1/1991 |
| KR | 1020050112135 | A | 11/2005 |

OTHER PUBLICATIONS

Dietrich, "Control of Stereoerror Formation with High-Activity 'Dual-Side' Zirconocene Catalysts: A Novel Strategy to Design the Properties of Thermoplastic Elastic Polypropenes", J. Am. Chem. Soc., 1999, p. 4348-4355, vol. 121.

Rigby, "Ferrocenes derived from cyclopenta[l]phenanthrene: dibenzindene—metal complexes that resist haptotripic shifts", Journal of Organometallic Chemistry, 2001, p. 372-381, vol. 637-639.

*Primary Examiner* — Caixia Lu

(74) *Attorney, Agent, or Firm* — The Webb Law Firm

(57) ABSTRACT

The present invention relates to a method of preparing an ethylene-α-olefin-diene copolymer and an ethylene-α-olefin-diene copolymer prepared thereby, by using a transition metal compound based on a cyclopenta[b]fluorenyl group as a catalyst.

12 Claims, No Drawings

METHOD OF PREPARING ETHYLENE-α-OLEFIN-DIENE COPOLYMER

TECHNICAL FIELD

The present invention relates to a method of preparing an ethylene-α-olefin-diene copolymer and an ethylene-α-olefin-diene copolymer prepared thereby, and more particularly to a method of preparing an ethylene-α-olefin-diene copolymer and an ethylene-α-olefin-diene copolymer prepared thereby, by using a transition metal compound based on a cyclopenta[b]fluorenyl group as a catalyst.

BACKGROUND ART

In the prior art, so-called Ziegler-Natta catalyst consisting of a titanium or vanadium compound as a primary catalyst component and an alkylaluminum compound as cocatalyst component have been generally used for preparing ethylene homopolymers or copolymers of ethylene and α-olefin. Although a Ziegler-Natta catalytic system exhibits high activity on ethylene polymerization, the catalytic system has disadvantages in that molecular weight distribution of the produced polymer is broad due to non-uniform catalyst activation point, and especially, composition distribution thereof is not uniform in the copolymers of ethylene and α-olefin.

Recently, so-called metallocene catalytic systems consisting of a metallocene compound of Group 4 transition metal in the Periodic Table of Elements, such as titanium, zirconium and hafnium, and methylaluminoxane as a cocatalyst have been developed. The metallocene catalytic system is a homogeneous catalyst having a mono-modal catalyst activation point, and thus, can provide prepare polyethylene having narrower molecular weight distribution and more homogenous composition distribution as compared with the existing Ziegler-Natta catalyst system. For example, European Patent Laid-Open Publication Nos. 320,762 and 372,632; Japanese Patent Laid-Open Publication Nos. Sho 63-092621, Hei 02-84405 and Hei 03-2347 reported that ethylene may be polymerized with high activity by activating metallocene compounds such as $Cp_2TiCl_2$, $Cp_2ZrCl_2$, $Cp_2ZrMeCl$, $Cp_2ZrMe_2$, ethylene$(IndH_4)_2ZrCl_2$ by using methylaluminoxane as a cocatalyst, to prepare polyethylene having a molecular weight distribution (Mw/Mn) in the range from 1.5 to 2.0. However, it is difficult to obtain high-molecular weight polymers by using the above catalytic system, and further, when solution polymerization executed at a high temperature of 100° C. or higher is employed, polymerizing activity abruptly decreases and β-dehydrogenation is predominant. Therefore, the system has been known to be not suitable for preparing high-molecular weight polymers having a weight average molecular weight (Mw) of 100,000 or more.

Meanwhile, there was reported so-called geo-restrictive non-metallocene based catalysts (also referred to as single activation point catalysts) where the transition metals are linked in a ring type, as catalysts for preparing high-molecular weight polymers with high catalytic activity in ethylene homopolymerization or copolymerization of ethylene and α-olefin in the solution polymerization conditions. European Patent Nos. 0416815 and 0420436 suggest an example where amide group is linked to one cyclopentadiene ligand in a ring type, and European Patent No. 0842939 shows an example of the catalyst where phenol-based ligand as an electron donor compound is linked to cyclopentadiene ligand in a ring type. This geo-restrictive catalyst may remarkably improve reactivity with higher α-olefins due to lowered sterical hinderance effect of the catalyst itself, but has many difficulties in the commercial use thereof. Therefore, it has been important to secure more competitive catalytic systems in requiring commercialized catalysts based on economical feasibility, that is, excellent high-temperature activity, excellent reactivity with higher α-olefins, and capability to prepare high-molecular weight polymers.

DISCLOSURE OF INVENTION

Technical Problem

In order to overcome the problems of the prior art, the present inventors conducted extensive studies, and found that a transition metal compound having a structure where a Group 4 transition metal in the Periodic Table of Elements as a core metal is linked with a cyclopenta[b]fluorenyl group that has a rigid plane structure even though it is not in a hetero ring; has abundant electrons widely non-localized; and allows a substituent contributing to improvement in solubility and performance to be easily inducible at position 9 thereof, via an amido group substituted with a silyl group was advantageous in obtaining high-efficiency and high-molecular weight polymers in polymerization of an ethylene-α-olefin-diene copolymer, and thus, completed the present invention.

An object of the present invention is to provide a method of preparing an ethylene-1-olefin-diene copolymer by using a transition metal compound based on a cyclopenta[b]fluorenyl group as a catalyst.

Another object of the present invention is to provide an ethylene-α-olefin-diene copolymer prepared by the method.

Solution to Problem

An aspect of the present invention for achieving the above objects provides a method of preparing an ethylene-α-olefin-diene copolymer by using a transition metal compound based on a cyclopenta[b]fluorenyl group represented by Chemical Formula 1 below. More specifically, a transition metal compound having a structure where a Group 4 transition metal in the Periodic Table of Elements as a core metal is linked with a cyclopenta[b]fluorenyl group that has a rigid plane structure even though it is not in a hetero ring; has abundant electrons widely non-localized; and allows a substituent contributing to improvement in solubility and performance to be easily inducible at position 9 thereof, via an amido group substituted with a silyl group, to thereby have an advantageous structure in obtaining high-efficiency and high-molecular weight ethylene-α-olefin-diene copolymers, is used as a primary catalyst.

[Chemical Formula 1]

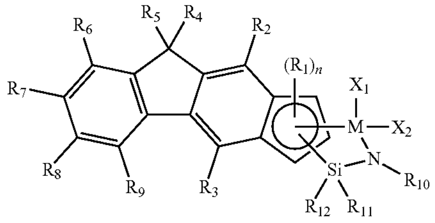

In Chemical Formula 1, M is a Group 4 transition metal in the Periodic Table of Elements;

n is an integer of 1 or 2, each $R_1$ may be the same or different when n is 2;

$R_1$ is hydrogen, (C1-C50)alkyl, halo(C1-C50)alkyl, (C3-C50)cycloalkyl, (C6-C30)aryl, (C6-C30)aryl(C1-C50)alkyl, ((C1-C50)alkyl(C6-C30)aryl)(C1-C50)alkyl, $—NR^aR^b$, $—SiR^cR^dR^e$, or 5- through 7-membered N-heterocycloalkyl containing at least one nitrogen atom;

$R_2$ and $R_3$ each are independently hydrogen, (C1-C50) alkyl, (C1-C50)alkoxy, halo(C1-C50)alkyl, (C3-C50)cycloalkyl, (C6-C30) aryl, (C6-C30)aryloxy, (C1-C50)alkyl (C6-C30)aryloxy, (C6-C30)aryl(C1-C50)alkyl, ((C1-C50) alkyl(C6-C30)aryl)(C1-C50)alkyl, $—NR^aR^b$ or $—SiR^cR^dR^e$;

$R_4$, $R_5$, $R_{10}$, $R_{11}$ and $R_{12}$ each are independently (C1-C50) alkyl, halo(C1-C50)alkyl, (C3-C50)cycloalkyl, (C6-C30) aryl, (C6-C30)aryl(C1-C50)alkyl, ((C1-C50)alkyl(C6-C30) aryl)(C1-C50)alkyl, $—NR^aR^b$, or $—SiR^cR^dR^e$, and $R_{11}$ and $R_{12}$ may be linked via (C4-C7)alkylene to form a ring;

$R_6$, $R_7$, $R_8$ and $R_9$ each are independently hydrogen, (C1-C50)alkyl, halo(C1-C50)alkyl, (C3-C50)cycloalkyl, (C1-C50)alkoxy, (C6-C30)aryl, (C6-C30)aryl(C1-C50)alkyl, ((C1-C50)alkyl(C6-C30)aryl)(C1-C50)alkyl, (C6-C30)aryloxy, (C1-C50)alkyl(C6-C30)aryloxy, N-carbazolyl, $—NR^aR^b$, or $—SiR^cR^dR^e$, or may be linked to an adjacent substituent via (C1-C5)alkylene to form a ring, and at least one $—CH_2—$ of the alkylene may be substituted by a hetero atom selected from —O—, —S—, and —NR'—, and the alkylene may be further substituted with (C1-C50)alkyl;

aryl of $R_1$ to $R_{12}$ may be further substituted with at least one substituent selected from the group consisting of (C1-C50) alkyl, halo(C1-C50)alkyl, (C1-C50)alkoxy, (C6-C30)aryloxy, (C6-C30)aryl, (C1-C50)alkyl(C6-C30)aryl, and (C6-C30)aryl(C1-C50)alkyl;

R' and $R^a$ to $R^e$ each are independently (C1-C50)alkyl or (C6-C30)aryl; and $X_1$ and $X_2$ each are independently halogen, (C1-C50)alkyl, (C2-C50)alkenyl, (C3-C50)cycloalkyl, (C6-C30)aryl, (C6-C30)aryl(C1-C50)alkyl, ((C1-C50)alkyl(C6-C30)aryl)(C1-C50)alkyl, (C1-C50)alkoxy, (C6-C30)aryloxy, (C1-C50) alkyl(C6-C30)aryloxy, (C1-C50)alkoxy(C6-C30)aryloxy, (C1-C50)alkylidene, or an anion or dianion ligand consisting of 60 or less atoms containing N, P, O, S, Si, and halogen, except hydrogen, provided that one of $X_1$ and $X_2$ is a dianion ligand, the other is ignored.

An example of the transition metal compound based on the cyclopenta[b]fluorenyl group represented by Chemical Formula 1 above may include a transition metal compound represented by Chemical Formula 2 or 3 below:

[Chemical Formula 2]

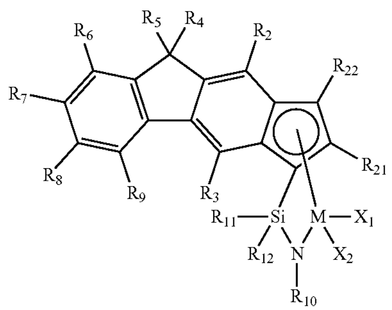

-continued

[Chemical Formula 3]

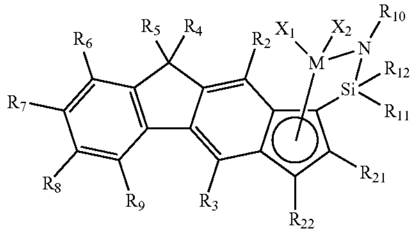

In Chemical Formulas 2 and 3, M, $R_2$ to $R_{12}$, $X_1$ and $X_2$ has the same definition in Chemical Formula 1; $R_{21}$ and $R_{22}$ each are independently hydrogen, (C1-C50)alkyl, halo(C1-C50) alkyl, (C3-C50)cycloalkyl, (C6-C30)aryl, (C6-C30)aryl(C1-C50)alkyl, ((C1-C50)alkyl(C6-C30)aryl)(C1-C50)alkyl, $—NR^aR^b$, $—SiR^cR^dR^e$, or 5- through 7-membered N-heterocycloalkyl containing at least one nitrogen atom; aryl of $R_1$ may be further substituted with at least one substituent selected from the group consisting of halogen, (C1-C50) alkyl, halo(C1-C50)alkyl, (C1-C50)alkoxy, (C6-C30)aryloxy, (C6-C30)aryl, (C1-C50)alkyl(C6-C30)aryl, and (C6-C30)aryl(C1-C50)alkyl; and $R^a$ to $R^e$ each are independently (C1-C50)alkyl or (C6-C30)aryl.

Another aspect of the present invention for achieving the above objects provides an ethylene-α-olefin-diene copolymer prepared by the method of preparing an ethylene-α-olefin-diene copolymer, by using a transition metal catalyst composition containing the transition metal compound.

Hereinafter, the present invention will be described in more detail.

The Group 4 transition metal in the Periodic Table of Elements, M, is preferably titanium (Ti), zirconium (Zr), or hafnium (Hf).

The term "alkyl" described herein includes a straight chain type or a branched chain type.

The term "aryl" described herein is an organic radical derived from aromatic hydrocarbon by the removal of one hydrogen atom, and may include a single ring or a fused ring containing, properly 4 to 7 ring atoms, and preferably 5 or 6 ring atoms. Specific examples thereof include phenyl, naphthyl, biphenyl, anthryl, fluorenyl, phenanthryl, triphenyl, pyrenyl, perylenyl, chrysenyl, naphthacenyl, fluoranthenyl, or the like, but are not limited thereto.

For example, (C1-C50)alkyl may be methyl, ethyl, n-propyl, isopropyl, n-butyl, isobutyl, sec-butyl, tert-butyl, n-pentyl, neopentyl, amyl, n-hexyl, n-octyl, n-decyl, n-dodecyl, n-tetradecyl, n-hexadecyl, n-pentadecyl, n-octadecyl, n-icosyl, or n-docosyl; (C3-C50)cycloalkyl may be, for example, cyclopropyl, cyclobutyl, cyclopentyl, cyclohexyl, cycloheptyl, cyclooctyl, cyclodecyl, or cyclododecyl; (C6-C30)aryl or (C1-C50)alkyl(C6-C30)aryl may be, for example, phenyl, 2-tolyl, 3-tolyl, 4-tolyl, 2,3-xylyl, 2,4-xylyl, 2,5-xylyl, 2,6-xylyl, 3,4-xylyl, 3,5-xylyl, 2,3,4-trimethylphenyl, 2,3,5-trimethylphenyl, 2,3,6-trimethylphenyl, 2,4,6-trimethylphenyl, 3,4,5-trimethylphenyl, 2,3,4,5-tetramethylphenyl, 2,3,4,6-tetramethylphenyl, 2,3,5,6-tetramethylphenyl, pentamethylphenyl, ethylphenyl, n-propylphenyl, isopropylphenyl, n-butylphenyl, sec-butylphenyl, tert-butylphenyl, n-pentylphenyl, neopentylphenyl, n-hexylphenyl, n-octylphenyl, n-decylphenyl, n-dodecylphenyl, n-tetradecylphenyl, biphenyl, fluorenyl, triphenyl, naphthyl, or anthracenyl; (C6-C30) aryl(C1-C50) alkyl or ((C1-C50)alkyl(C6-C30)aryl)(C1-C50)alkyl may be, for example, benzyl, (2-methylphenyl) methyl, (3-methylphenyl)methyl, (4-methylphenyl)methyl, (2,3-dimethylphenyl)methyl, (2,4-dimethylphenyl)methyl, (2,5-dimethylphenyl)methyl, (2,6-dimethylphenyl)methyl, (3,4-dimethylphenyl)methyl, (4,6-dimethylphenyl)methyl, (2,3,4-trimethylphenyl)methyl, (2,3,5-trimethylphenyl)methyl, (2,3,6-trimethyl-phenyl)methyl, (3,4,5-trimethylphenyl)methyl, (2,4,6-trimethylphenyl)methyl, (2,3,4,5-tetramethylphenyl)methyl, (2,3,4,6-tetramethylphenyl)methyl, (2,3,5,6-tetramethylphenyl)methyl, (pentamethylphenyl) methyl, (ethylphenyl)methyl, (n-propylphenyl)methyl, (isopropylphenyl)methyl, (n-butylphenyl)methyl, (sec-butylphenyl)methyl, (tert-butylphenyl)methyl, (n-pentylphenyl) methyl, (neopentylphenyl)methyl, (n-hexylphenyl)methyl, (n-octylphenyl)methyl, (n-decylphenyl)methyl, (n-dodecylphenyl)methyl, (n-tetradecylphenyl)methyl, naphthylmethyl, or anthracenylmethyl; and (C1-C50)alkoxy may be, for example, methoxy, ethoxy, n-propoxy, isopropoxy, n-butoxy, sec-butoxy, tert-butoxy, n-pentyloxy, neopentyloxy, n-hexyloxy, n-octyloxy, n-dodecyloxy, n-pentadecyloxy, or n-eicosyloxy.

Preferably, each $R_1$ is independently hydrogen, methyl, ethyl, n-propyl, isopropyl, n-butyl, phenyl, naphthyl, biphenyl, 2-isopropylphenyl, 3,5-xylyl, 2,4,6-trimethylphenyl, benzyl, dimethylamino, or pyrrolidino;

preferably, $R_2$ and $R_3$ are independently hydrogen, methyl, ethyl, n-propyl, isopropyl, n-butyl, phenyl, naphthyl, biphenyl, 2-isopropylphenyl, 3,5-xylyl, 2,4,6-trimethylphenyl, benzyl, methoxy, ethoxy, isopropoxy, phenoxy, 4-tert-butylphenoxy, or naphthoxy;

preferably, $R_4$ and $R_5$ each are independently methyl, ethyl, n-propyl, isopropyl, n-butyl, isobutyl, 2-methylbutyl, sec-butyl, tert-butyl, n-pentyl, neopentyl, amyl, n-hexyl, n-octyl, n-decyl, n-dodecyl, n-tetradecyl, n-hexadecyl, n-pentadecyl, n-octadecyl, n-icosyl, n-docosyl, phenyl, 2-tolyl, 3-tolyl, 4-tolyl, 2,3-xylyl, 2,4-xylyl, 2,5-xylyl, 2,6-xylyl, 3,4-xylyl, 3,5-xylyl, 2,3,4-trimethylphenyl, 2,3,5-trimethylphenyl, 2,3,6-trimethylphenyl, 2,4,6-trimethylphenyl, 3,4,5-trimethylphenyl, 2,3,4,5-tetramethylphenyl, 2,3,4,6-tetramethylphenyl, 2,3,5,6-tetramethylphenyl, pentamethylphenyl, ethylphenyl, n-propylphenyl, isopropylphenyl, n-butylphenyl, sec-butylphenyl, tert-butylphenyl, n-pentylphenyl, neopentylphenyl, n-hexylphenyl, n-octylphenyl, n-decylphenyl, n-dodecylphenyl, n-tetradecylphenyl, biphenyl, fluorenyl, triphenyl, naphthyl, anthracenyl, benzyl, (2-methylphenyl) methyl, (3-methylphenyl)methyl, (4-methylphenyl)methyl, (2,3-dimethylphenyl)methyl, (2,4-dimethylphenyl)methyl, (2,5-dimethylphenyl)methyl, (2,6-dimethylphenyl)methyl, (3,4-dimethylphenyl)methyl, (4,6-dimethylphenyl)methyl, (2,3,4-trimethylphenyl)methyl, (2,3,5-trimethylphenyl)methyl, (2,3,6-trimethylphenyl)methyl, (3,4,5-trimethylphenyl) methyl, (2,4,6-trimethylphenyl)methyl, (2,3,4,5-tetramethylphenyl)methyl, (2,3,4,6-tetramethylphenyl)methyl, (2,3,5,6-tetramethylphenyl)methyl, (pentamethylphenyl)methyl, (ethylphenyl)methyl, (n-propylphenyl)methyl, (isopropylphenyl)methyl, (n-butylphenyl)methyl, (sec-butylphenyl) methyl, (tert-butylphenyl)methyl, (n-pentylphenyl)methyl, (neopentylphenyl)methyl, (n-hexylphenyl)methyl, (n-octylphenyl)methyl, (n-decylphenyl)methyl, (n-dodecylphenyl)methyl, (n-tetradecylphenyl)methyl, naphthylmethyl, anthracenylmethyl, 4-methoxyphenyl, 3,4-dimethoxyphenyl, or 4-(hexyloxy)-3,5-dimethylphenyl;

preferably, $R_6$ to $R_9$ each are independently hydrogen, methyl, ethyl, n-propyl, isopropyl, n-butyl, isobutyl, 2-methylbutyl, sec-butyl, tert-butyl, n-pentyl, neopentyl, amyl, n-hexyl, n-octyl, n-decyl, n-dodecyl, n-pentadecyl, phenyl, 2-tolyl, 3-tolyl, 4-tolyl, 2,3-xylyl, 2,4-xylyl, 2,5-xylyl, 3,4-xylyl, 3,5-xylyl, 2,3,4-trimethylphenyl, trimethylphenyl, 2,3,6-trimethylphenyl, 2,4,6-trimethylphenyl, 3,4,5-trimethylphenyl, 2,3,4,5-tetramethylphenyl, 2,3,4,6-tetramethylphenyl, 2,3,5,6-tetramethylphenyl, pentamethylphenyl, ethylphenyl, n-propylphenyl, isopropylphenyl, n-butylphenyl, sec-butylphenyl, tert-butylphenyl, n-pentylphenyl, neopentylphenyl, n-hexylphenyl, n-octylphenyl, n-decylphenyl, n-dodecylphenyl, n-tetradecylphenyl, biphenyl, fluorenyl, 2,7-di-tert-butyl-9-p-tolyl-9H-fluoren-9-yl, triphenyl, naphthyl, anthracenyl, benzyl, (2-methylphenyl)methyl, (3-methylphenyl)methyl, (4-methylphenyl)methyl, (2,3-dimethylphenyl)methyl, (2,4-dimethylphenyl)methyl, (2,5-dimethylphenyl)methyl, (2,6-dimethylphenyl)methyl, (3,4-dimethylphenyl)methyl, (4,6-dimethylphenyl)methyl, (2,3,4-trimethylphenyl)methyl, (2,3,5-trimethylphenyl)methyl, (2,3,6-trimethyl-phenyl)methyl, (3,4,5-trimethylphenyl)methyl, (2,4,6-trimethylphenyl) methyl, (2,3,4,5-tetramethylphenyl)methyl, (2,3,4,6-tetramethylphenyl)methyl, (2,3,5,6-tetramethylphenyl)methyl, (pentamethylphenyl)methyl, (ethylphenyl)methyl, (n-propylphenyl)methyl, (isopropylphenyl)methyl, (n-butylphenyl) methyl, (sec-butylphenyl)methyl, (tert-butylphenyl)methyl, (n-pentylphenyl)methyl, (neopentylphenyl)methyl, (n-hexylphenyl)methyl, (n-octylphenyl)methyl, (n-decylphenyl)methyl, (n-dodecylphenyl)methyl, (n-tetradecylphenyl)methyl, naphthylmethyl, anthracenylmethyl, 4-methoxyphenyl, 3,4-dimethoxyphenyl, methoxy, ethoxy, isopropoxy, n-butoxy, n-hexyloxy, 2-methylbutyl, phenoxy, 4-tert-butylphenoxy, naphthoxy, trimethylsilyl, triphenylsilyl, dimethylamino, diphenylamino, or 9H-carbazol-9-yl, or may be linked to an adjacent substituent via

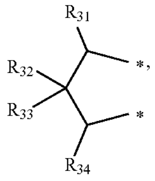
,
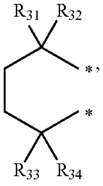
, or
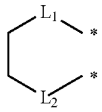

to form a ring, $L_1$ and $L_2$ each are independently —O—, —S—, or —NR'— [each R' is independently (C1-C50)alkyl or (C6-C30)aryl], $R_{31}$ to $R_{34}$ each, independently, have the same definition as $R_4$ and $R_5$, and more preferably, hydrogen, methyl, or n-tetradecyl;

preferably, $R_{11}$ and $R_{12}$ each are independently methyl, ethyl, n-propyl, isopropyl, n-butyl, isobutyl, 2-methylbutyl, sec-butyl, tert-butyl, n-pentyl, neopentyl, amyl, n-hexyl, n-octyl, n-decyl, n-dodecyl, n-pentadecyl, phenyl, 2-tolyl, 3-tolyl, 4-tolyl, 2,3-xylyl, 2,4-xylyl, 2,5-xylyl, 2,6-xylyl, 3,4-xylyl, 3,5-xylyl, 2,3,4-trimethylphenyl, 2,3,5-trimethylphenyl, 2,3,6-trimethylphenyl, 2,4,6-trimethylphenyl, 3,4,5-trimethylphenyl, 2,3,4,5-tetramethylphenyl, 2,3,4,6-tetramethylphenyl, 2,3,5,6-tetramethylphenyl, pentamethylphenyl, ethylphenyl, n-propylphenyl, isopropylphenyl, n-butylphenyl, sec-butylphenyl, tert-butylphenyl, n-pentylphenyl, neopentylphenyl, n-hexylphenyl, n-octylphenyl, n-decylphenyl, n-dodecylphenyl, n-tetradecylphenyl, biphenyl, fluorenyl, triphenyl, naphthyl, anthracenyl, benzyl, (2-methylphenyl)methyl, (3-methylphenyl)methyl, (4-methylphenyl)methyl, (2,3-dimethylphenyl)methyl, (2,4-dimethylphenyl)methyl, (2,5-dimethylphenyl)methyl, (2,6-dimethylphenyl)methyl, (3,4-dimethylphenyl)methyl, (4,6-dimethylphenyl)methyl, (2,3,4-trimethylphenyl)methyl, (2,3,5-trimethylphenyl)methyl, (2,3,6-trimethyl-phenyl)methyl, (3,4,5-trimethylphenyl)methyl, (2,4,6-trimethylphenyl) methyl, (2,3,4,5-tetramethylphenyl)methyl, (2,3,4,6-tetramethylphenyl)methyl, (2,3,5,6-tetramethylphenyl)methyl, (pentamethylphenyl)methyl, (ethylphenyl)methyl, (n-propylphenyl)methyl, (isopropylphenyl)methyl, (n-butylphenyl) methyl, (sec-butylphenyl)methyl, (tert-butylphenyl)methyl, (n-pentylphenyl)methyl, (neopentylphenyl)methyl, (n-hexylphenyl)methyl, (n-octylphenyl)methyl, (n-decylphenyl)methyl, (n-tetradecylphenyl)methyl, naphthylmethyl, anthracenylmethyl, 4-methoxyphenyl, or 3,4-dimethoxyphenyl, or $R_{11}$ and $R_{12}$ may be linked to each other via butylene or pentylene to form a ring;

$R_{10}$ is methyl, ethyl, n-propyl, isopropyl, n-butyl, isobutyl, 2-methylbutyl, sec-butyl, tert-butyl, n-pentyl, neopentyl, amyl, n-hexyl, n-octyl, n-decyl, n-dodecyl, n-pentadecyl, cyclohexyl, phenyl, 2-tolyl, 3-tolyl, 4-tolyl, 2,3-xylyl, 2,4-xylyl, 2,5-xylyl, 2,6-xylyl, 3,4-xylyl, 3,5-xylyl, 2,3,4-trimethylphenyl, 2,3,5-trimethylphenyl, 2,3,6-trimethylphenyl, 2,4,6-trimethylphenyl, 3,4,5-trimethylphenyl, 2,3,4,5-tetramethylphenyl, 2,3,4,6-tetramethylphenyl, 2,3,5,6-tetramethylphenyl, pentamethylphenyl, ethylphenyl, n-propylphenyl, isopropylphenyl, n-butylphenyl, sec-butylphenyl, tert-butylphenyl, n-pentylphenyl, neopentylphenyl, n-hexylphenyl, n-octylphenyl, n-decylphenyl, n-dodecylphenyl, n-tetradecylphenyl, biphenyl, fluorenyl, triphenyl, naphthyl, anthracenyl, benzyl, (2-methylphenyl)methyl, (3-methylphenyl)methyl, (4-methylphenyl)methyl, (2,3-dimethylphenyl)methyl, (2,4-dimethylphenyl)methyl, (2,5-dimethylphenyl)methyl, (2,6-dimethylphenyl)methyl, (3,4-dimethylphenyl)methyl, (4,6-dimethylphenyl)methyl, (2,3,4-trimethylphenyl)methyl, (2,3,5-trimethylphenyl)methyl, (2,3,6-trimethylphenyl)methyl, (3,4,5-trimethylphenyl)methyl, (2,4,6-trimethylphenyl)methyl, (2,3,4,5-tetramethylphenyl)methyl, (2,3,4,6-tetramethylphenyl)methyl, (2,3,5,6-tetramethylphenyl)methyl, (pentamethylphenyl)methyl, (ethylphenyl)methyl, (n-propylphenyl)methyl, (isopropylphenyl)methyl, (n-butylphenyl)methyl, (sec-butylphenyl)methyl, (tert-butylphenyl)methyl, (n-pentylphenyl)methyl, (neopentylphenyl)methyl, (n-hexylphenyl)methyl, (n-octylphenyl)methyl, (n-decylphenyl)methyl, (n dodecylphenyl)methyl, (n-tetradecylphenyl)methyl, naphthylmethyl, anthracenylmethyl, 2-methoxyphenyl, or 3,4-dimethoxyphenyl.

In the definitions of substituents $X_1$ and $X_2$, examples of halogen atom may include fluorine, chlorine, bromine, and iodine atom; examples of (C1-C50)alkyl may include methyl, ethyl, n-propyl, isopropyl, n-butyl, sec-butyl, tert-butyl, n-pentyl, neopentyl, amyl, n-hexyl, n-octyl, n-decyl, n-dodecyl, n-pentadecyl, and n-eicosyl; examples of (C3-C50)cycloalkyl may include cyclopropyl, cyclobutyl, cyclopentyl, cyclohexyl, cycloheptyl, and adamantyl; examples of (C6-C30)aryl may include phenyl and naphthyl; examples of (C6-C30)aryl(C1-C50)alkyl or ((C1-C50)alkyl(C6-C30)aryl)(C1-C50)alkyl may include benzyl, (2-methylphenyl)methyl, (3-methylphenyl)methyl, (4-methylphenyl)methyl, (2,3-dimethylphenyl)methyl, (2,4-dimethylphenyl)methyl, (2,5-dimethylphenyl)methyl, (2,6-dimethylphenyl)methyl, (3,4-dimethylphenyl)methyl, (4,6-dimethylphenyl)methyl, (2,3,4-trimethylphenyl)methyl, (2,3,5-trimethylphenyl)methyl, (2,3,6-trimethyl-phenyl)methyl, (3,4,5-trimethylphenyl)methyl, (2,4,6-trimethylphenyl)methyl, (2,3,4,5-tetramethylphenyl)methyl, (2,3,4,6-tetramethylphenyl)methyl, (2,3,5,6-tetramethylphenyl)methyl, (pentamethylphenyl)methyl, (ethylphenyl)methyl, (n-propylphenyl)methyl, (isopropylphenyl)methyl, (n-butylphenyl)methyl, (sec-butylphenyl)methyl, (tert-butylphenyl)methyl, (n-pentylphenyl)methyl, (neopentylphenyl)methyl, (n-hexylphenyl)methyl, (n-octylphenyl)methyl, (n-decylphenyl)methyl, (n-dodecylphenyl)methyl, (n-tetradecylphenyl)methyl, naphthylmethyl, and anthracenylmethyl; examples of (C1-C50)alkoxy may include methoxy, ethoxy, n-propoxy, isopropoxy, n-butoxy, sec-butoxy, tert-butoxy, n-pentyloxy, neopentyloxy, n-hexyloxy, n-octyloxy, n-dodecyloxy, n-pentadecyloxy, and n-eicosyloxy; examples of (C6-C30)aryloxy may include phenoxy, 4-tert-butylphenoxy, or 4-methoxyphenoxy, the anion or dianion ligand consisting of 60 or less atoms containing N, P, O, S, Si, and halogen, except for hydrogen may be —$OSiR^fR^gR^h$, —$SR^i$ [$R^f$ to $R^i$ each are independently (C1-C50)alkyl, (C6-C30)aryl, (C3-C50)cycloalkyl], —$NR^jR^k$, or —$PR^lR^m$ [$R^j$ to $R^m$ each are independently (C1-C50)alkyl, (C6-C30)aryl, (C6-C30)aryl(C1-C50)alkyl, (C3-C20)cycloalkyl, tri(C1-C50)alkylsilyl, or tri(C6-C30)arylsilyl]. Examples of –$OSiR^fR^gR^h$ may include trimethylsiloxy, triethylsiloxy, tri-n-propylsiloxy, triisopropylsiloxy, tri-n-butylsiloxy, tri-sec-butylsiloxy, tri-tert-butylsiloxy, tri-isobutylsiloxy, tert-butyldimethylsiloxy, tri-n-pentylsiloxy, tri-n-hexylsiloxy, or tricyclohexylsiloxy; examples of —$NR^jR^k$ may include dimethylamino, diethylamino, di-n-propylamino, diisopropylamino, di-n-butylamino, di-sec-butylamino, di-tert-butylamino, diisobutylamino, tert-butylisopropylamino, di-n-hexylamino, di-n-octylamino, di-n-decylamino, diphenylamino, dibenzylamino, methylethylamino, methylphenylamino, benzylhexylamino, bis(trimethylsilyl)amino, or bis(tert-butyldimethylsilyl)amino; examples of —$PR^lR^m$ may include dimethylphosphine, diethylphosphine, di-n-propylphosphine, diisopropylphosphine, di-n-butylphosphine, di-sec-butylphosphine, di-tert-butylphosphine, diisobutylphosphine, tert-butylisopropylphosphine, di-n-hexylphosphine, di-n-octylphosphine, di-n-decylphosphine, diphenylphosphine, dibenzylphosphine, methylethylphosphine, methylphenylphosphine, benzylhexylphosphine, bis(trimethylsilyl)phosphine, and bis(tert-butyldimethylsilyl)phosphine; examples of —$SR^i$ may include methylthio, ethylthio, propylthio, isopropylthio, butylthio, or isopentylthio.

$X_1$ and $X_2$ each are independently fluorine, chlorine, bromine, methyl, ethyl, isopropyl, amyl, benzyl, methoxy, ethoxy, isopropoxy, tert-butoxy, phenoxy, 4-tert-butylphenoxy, trimethylsiloxy, tert-butyldimethylsiloxy, dimethylamino, diphenylamino, dimethylphosphino, diethylphosphino, diphenylphosphino, ethylthio, or isopropylthio.

The above transition metal compound may be selected from compounds of the structures below, but is not limited thereto:

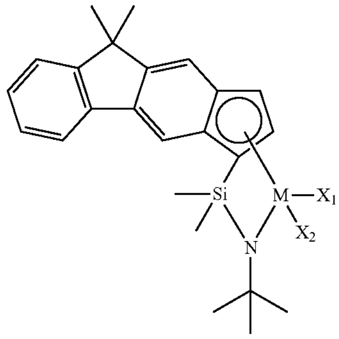

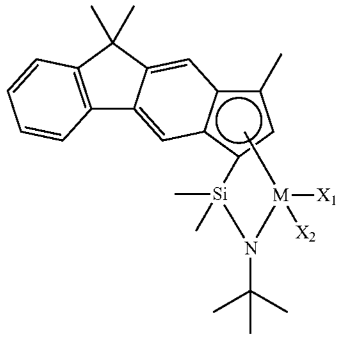

-continued
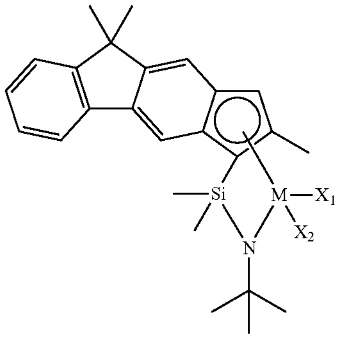
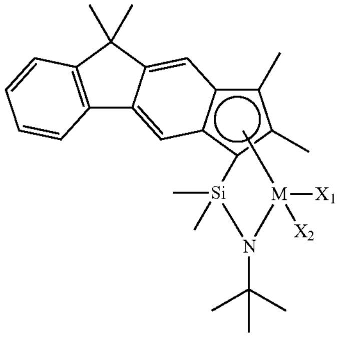
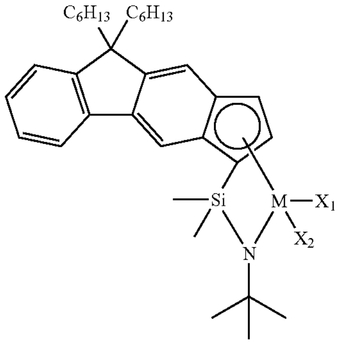
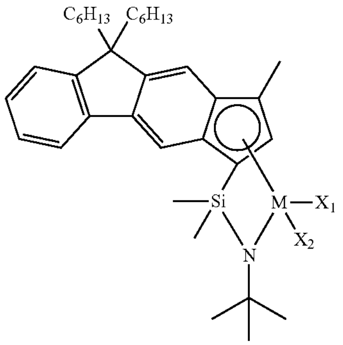
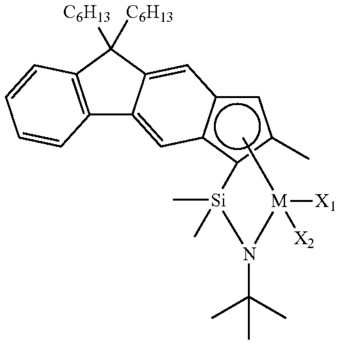
-continued
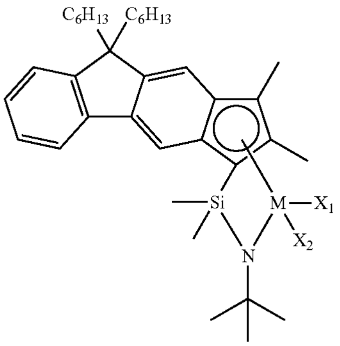
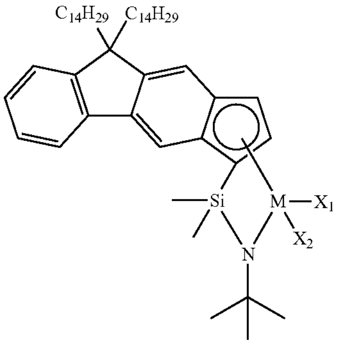
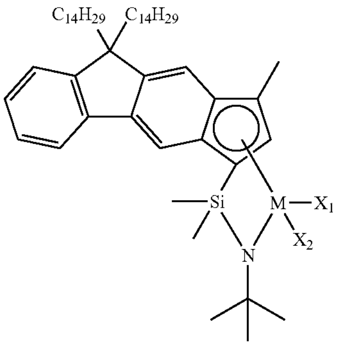
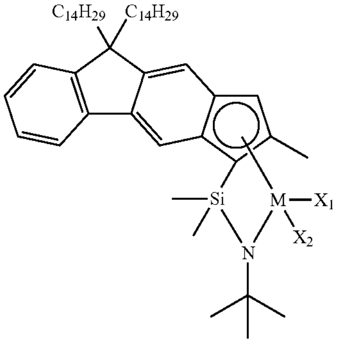
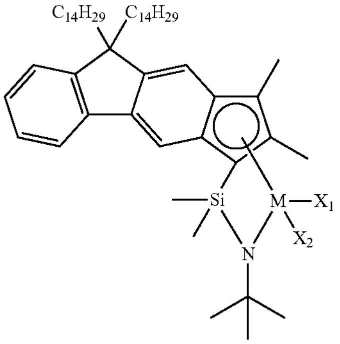

-continued
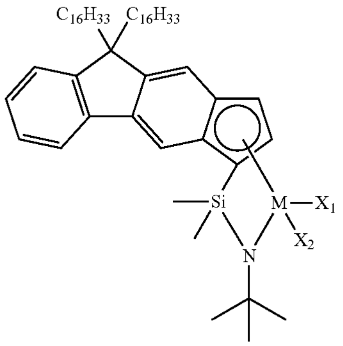
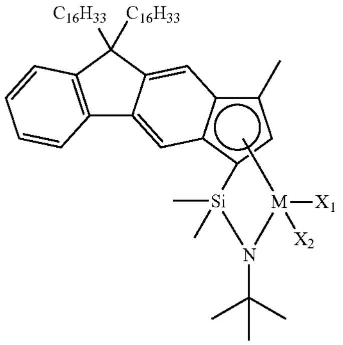
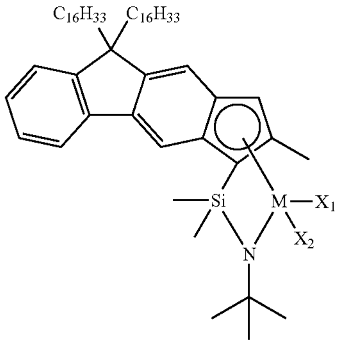
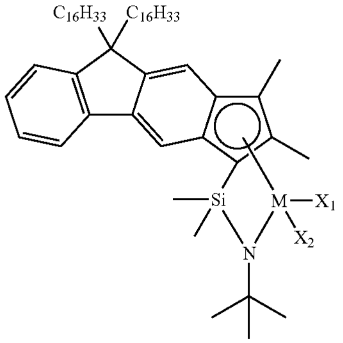
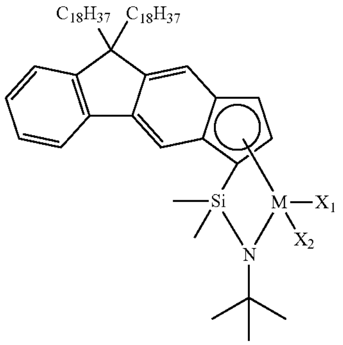
-continued
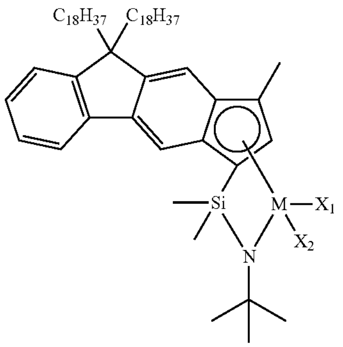
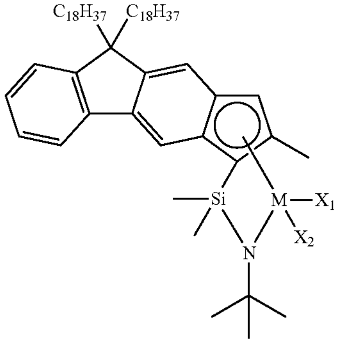
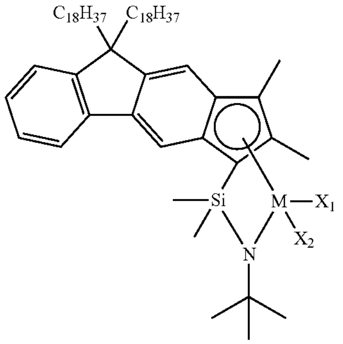
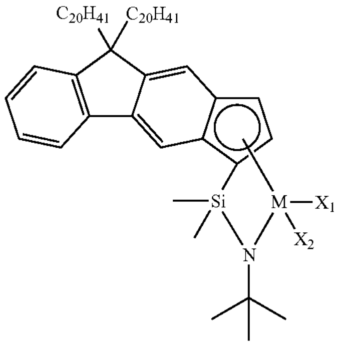
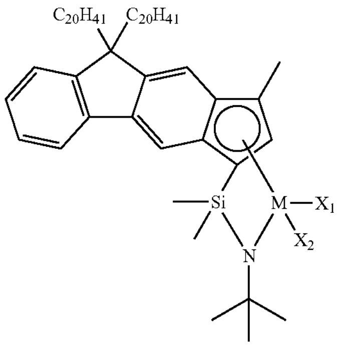

-continued
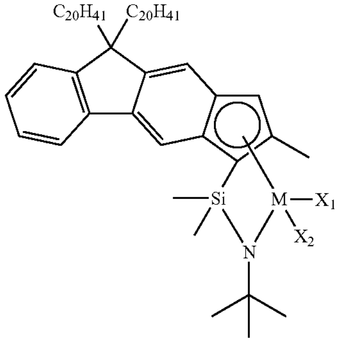
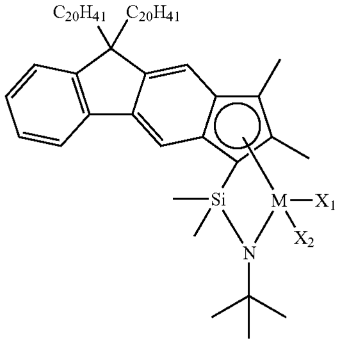
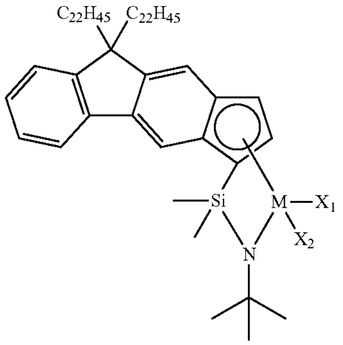
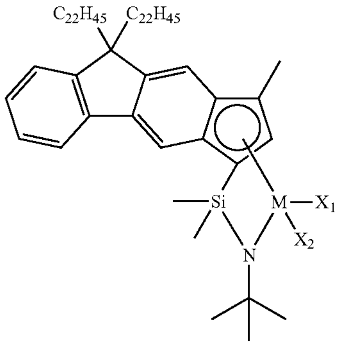
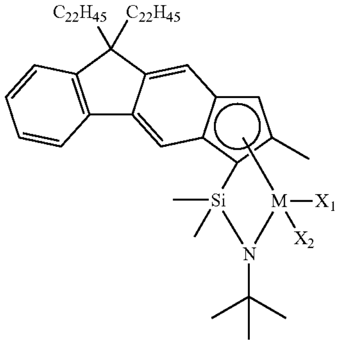
-continued
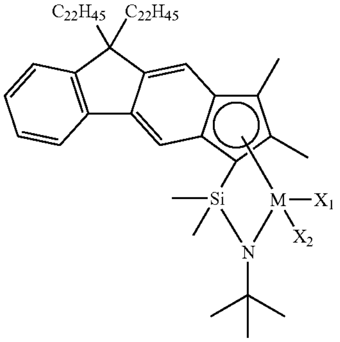
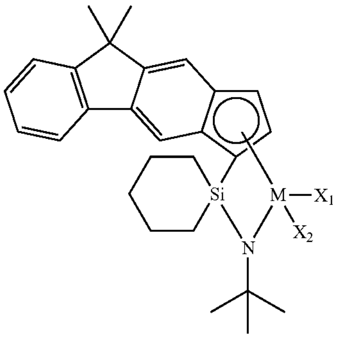
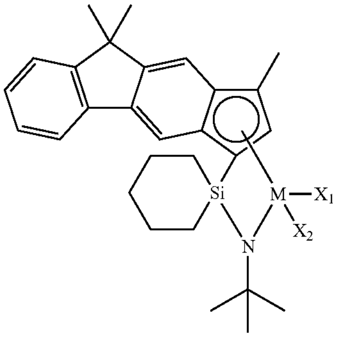
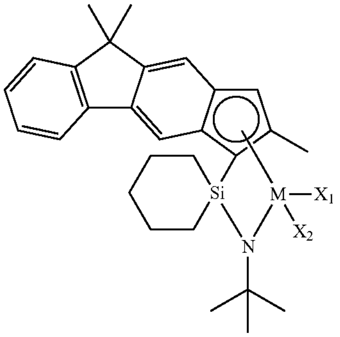
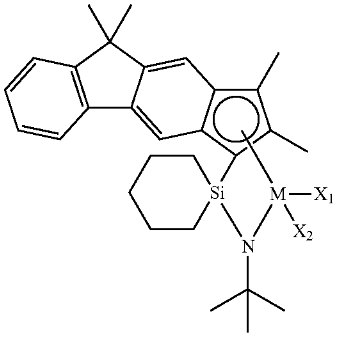

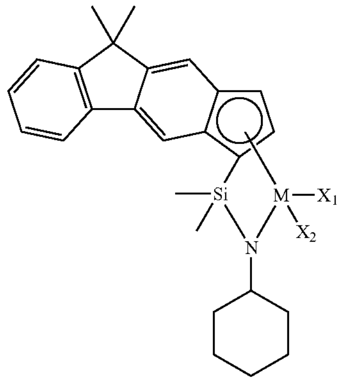
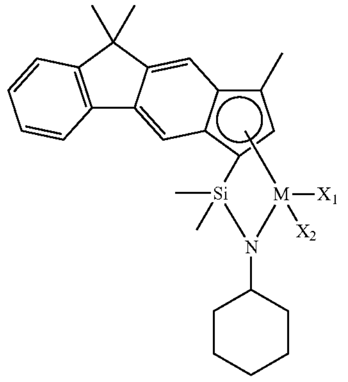
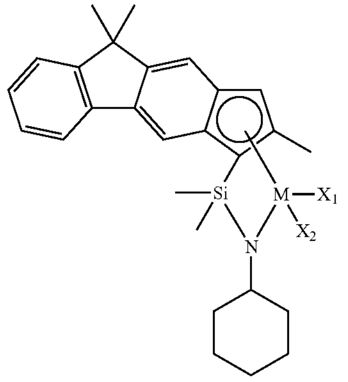
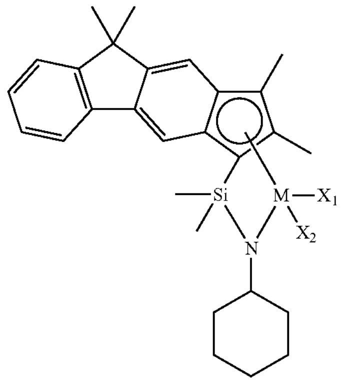
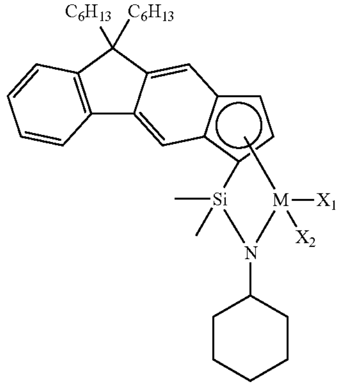
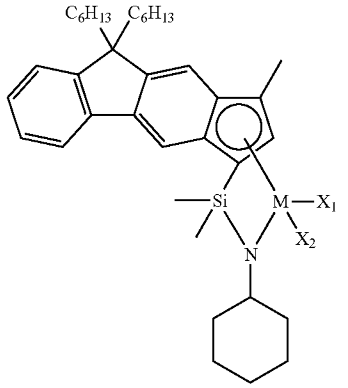
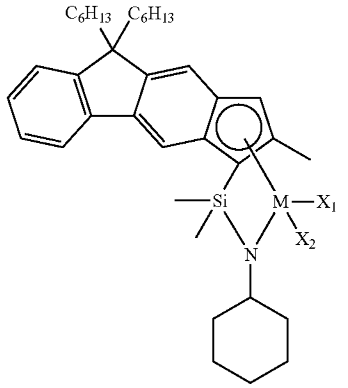
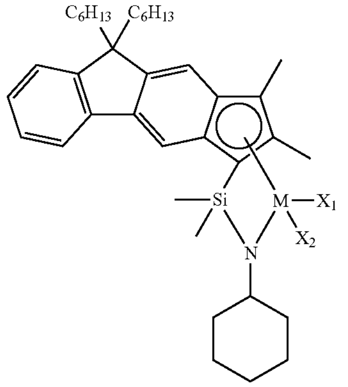

-continued
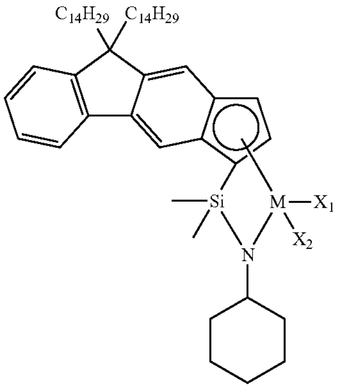
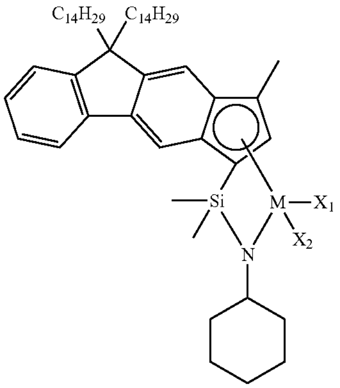
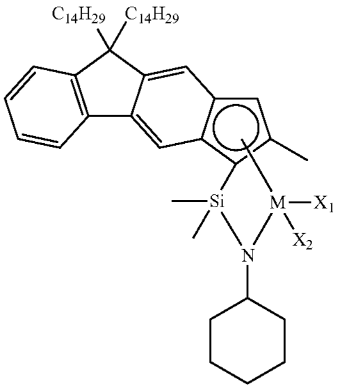
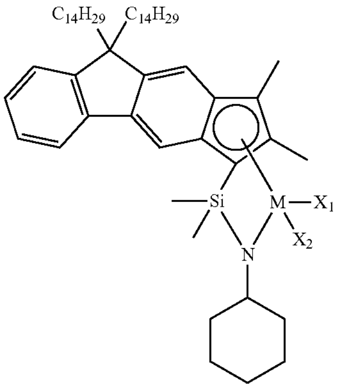
-continued
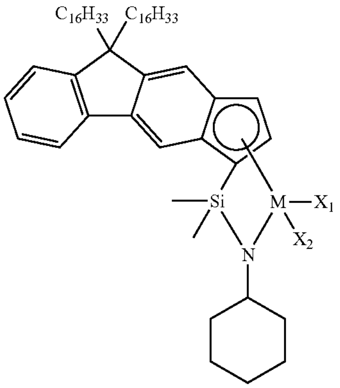
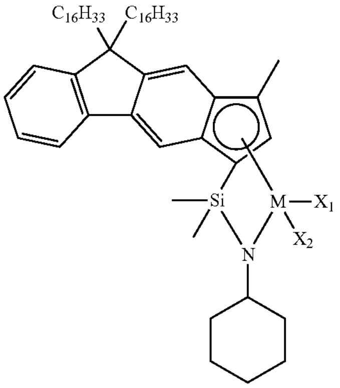
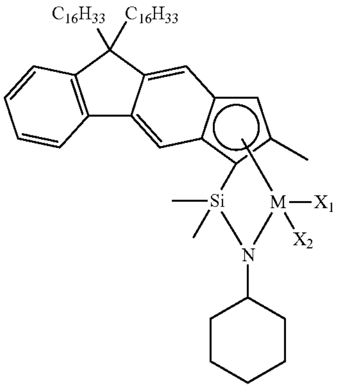
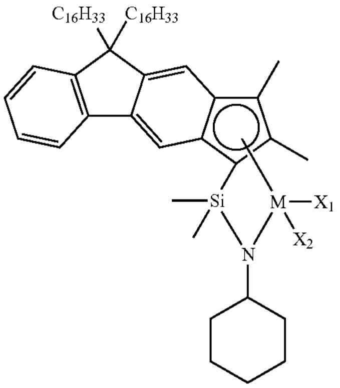

-continued
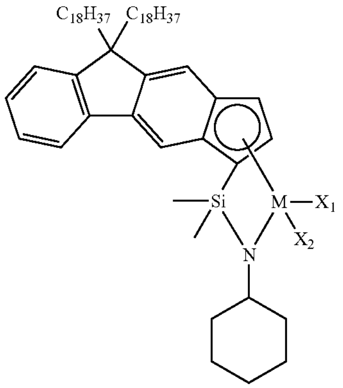
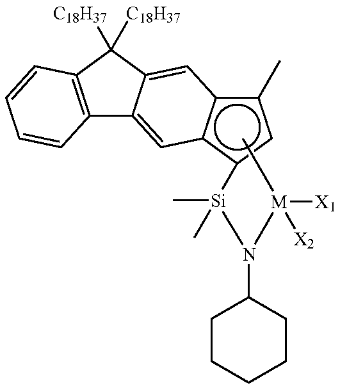
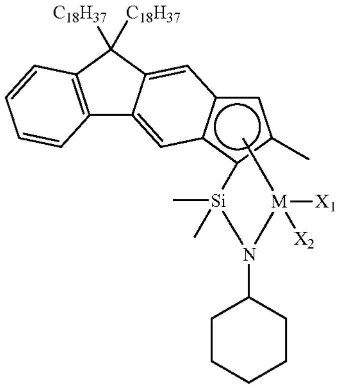
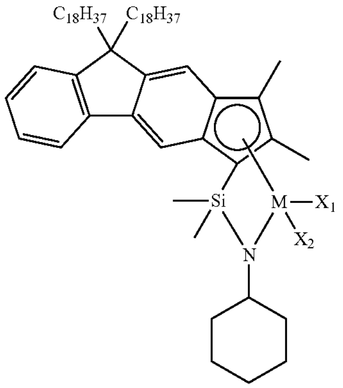
-continued
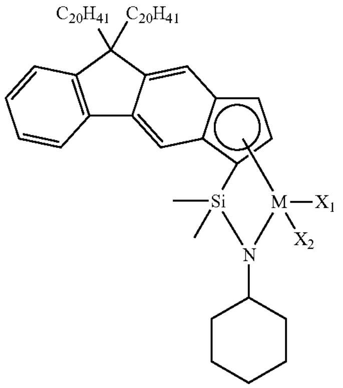
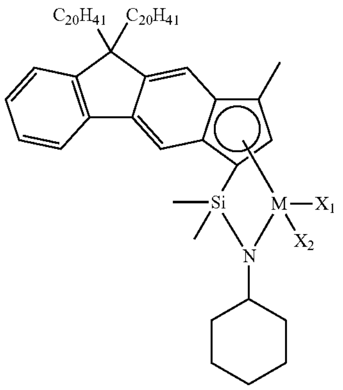
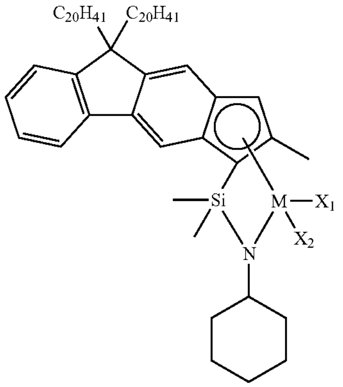
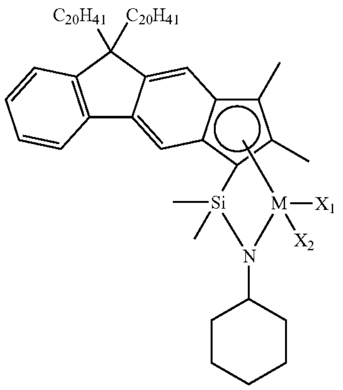

-continued
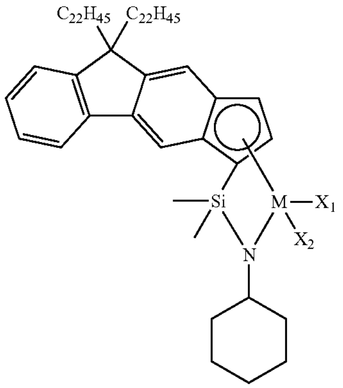
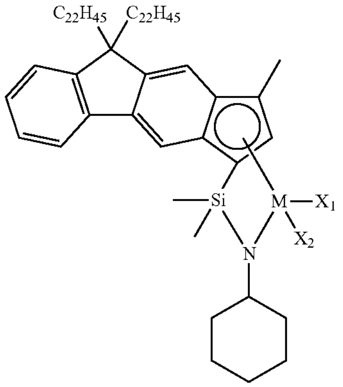
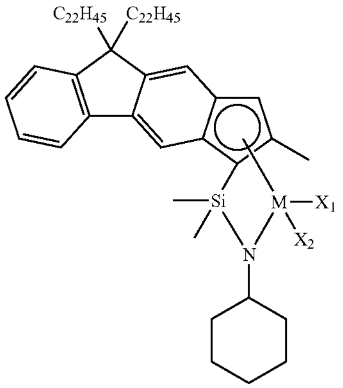
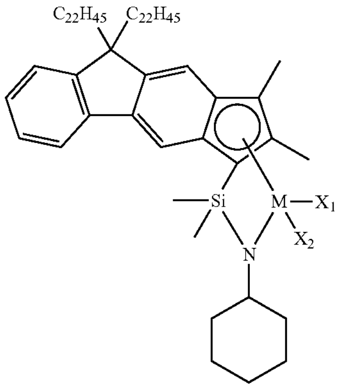
-continued
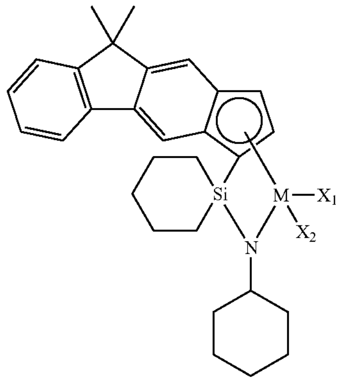
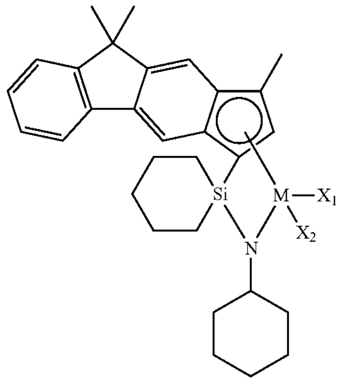
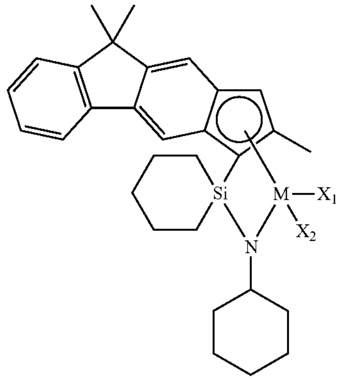
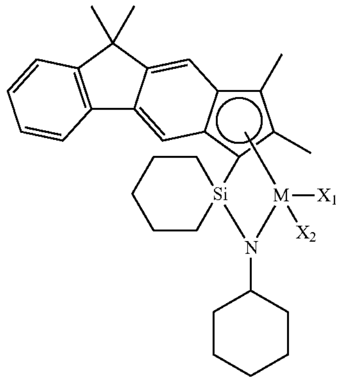

-continued
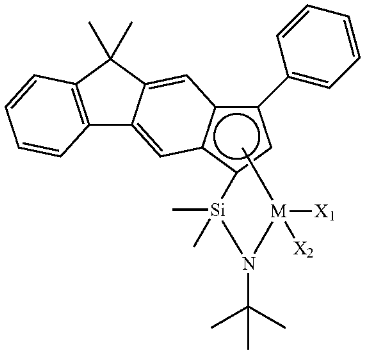
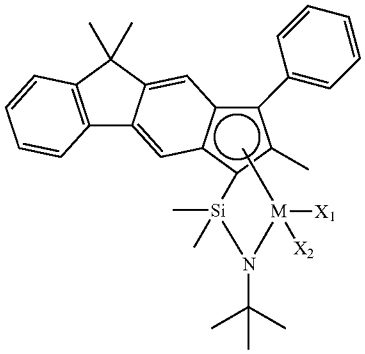
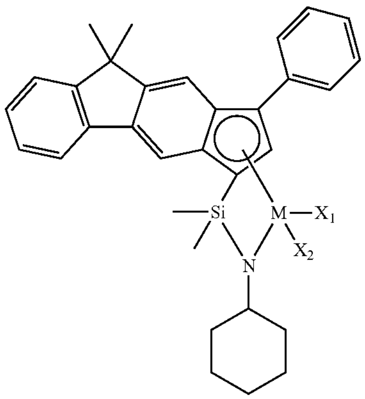
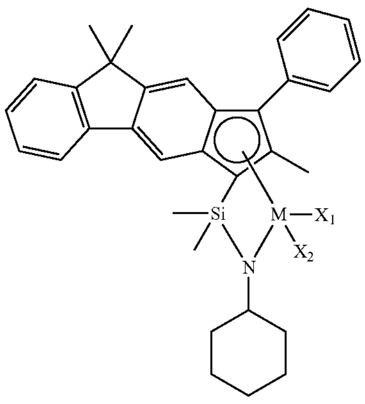
-continued
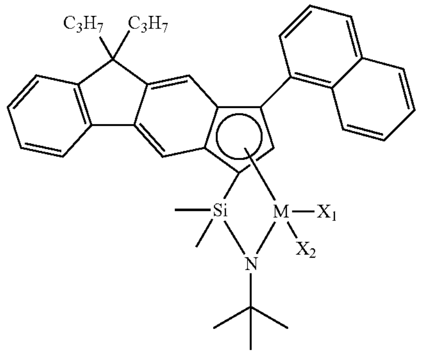
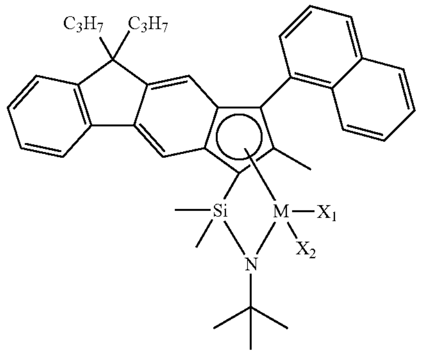
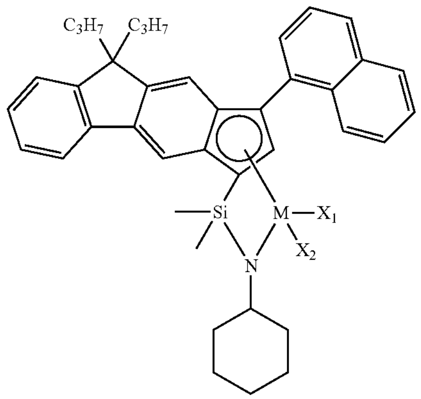
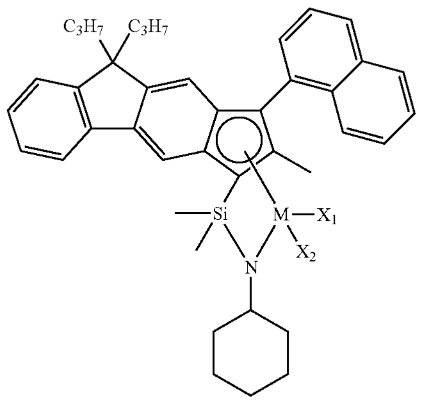

-continued
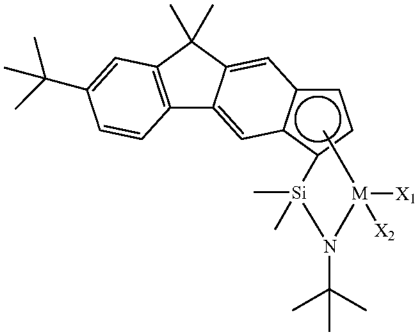
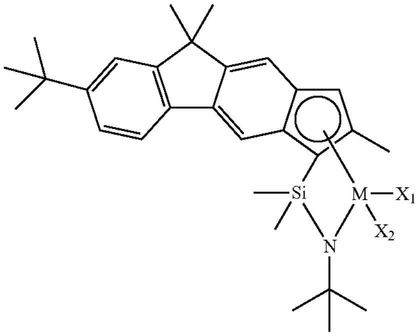
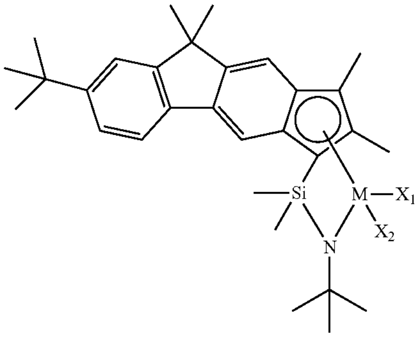
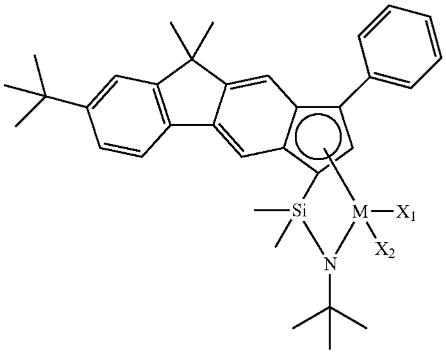
-continued
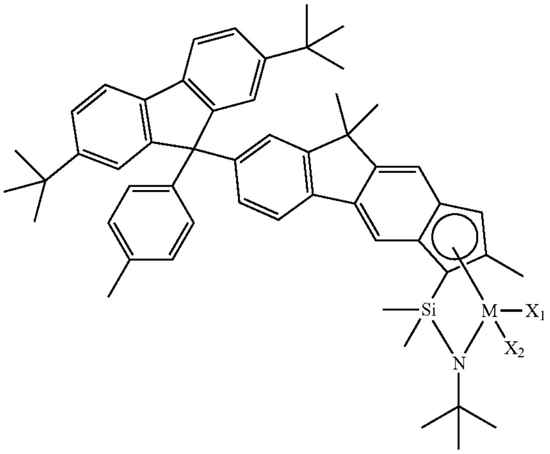
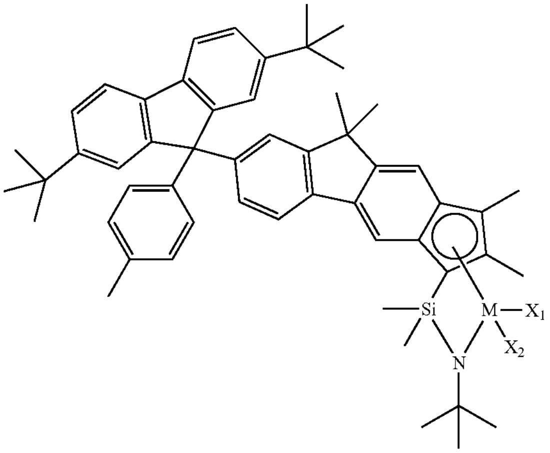
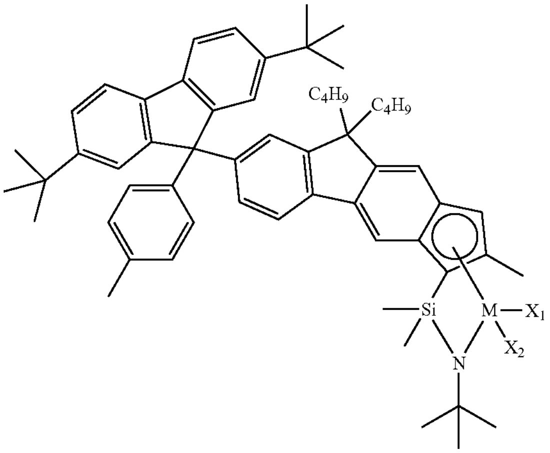

-continued
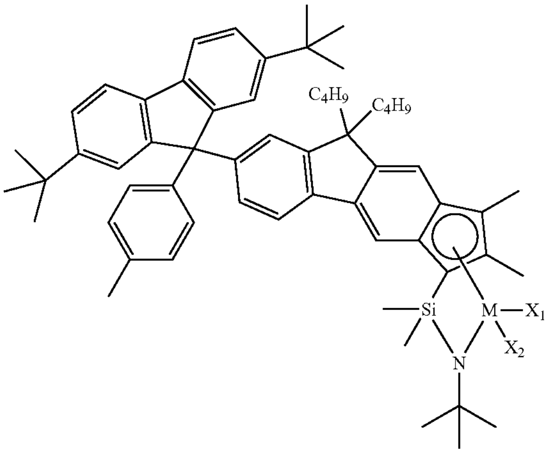
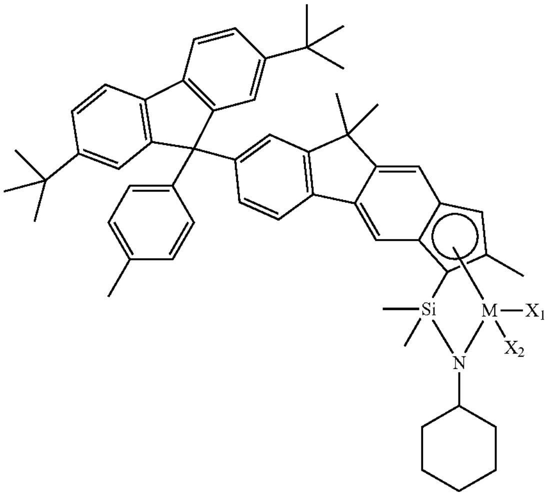
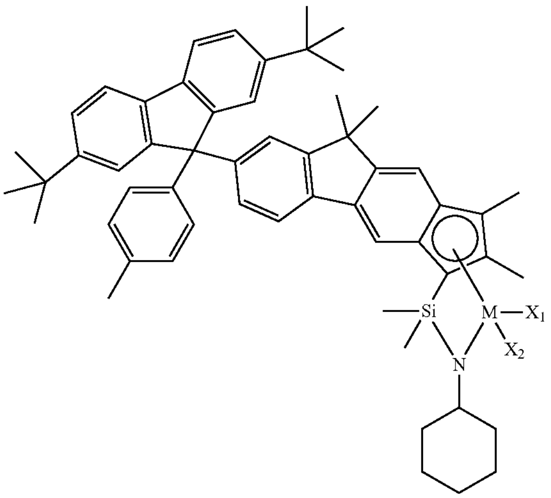
-continued
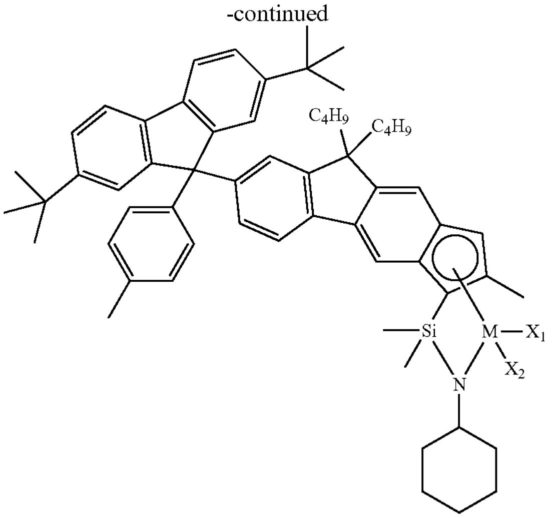
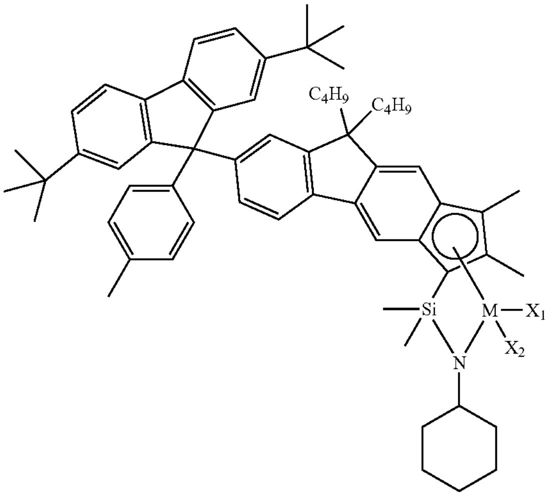
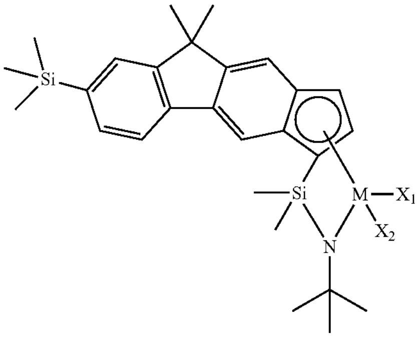
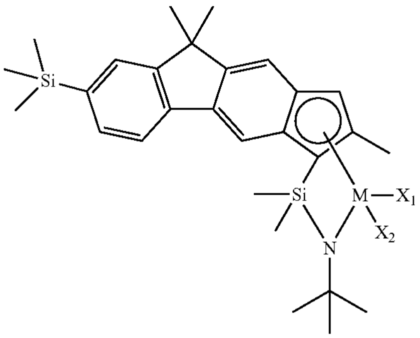

-continued
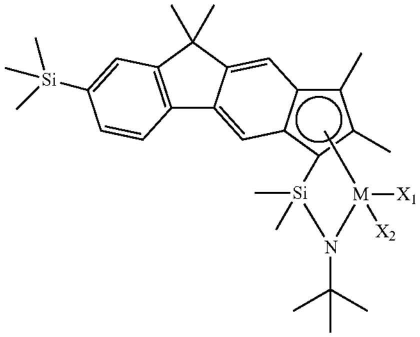
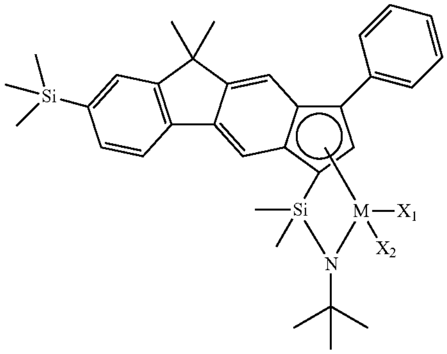
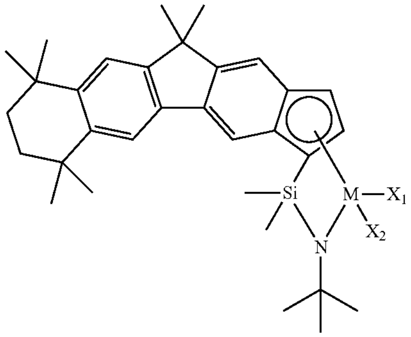
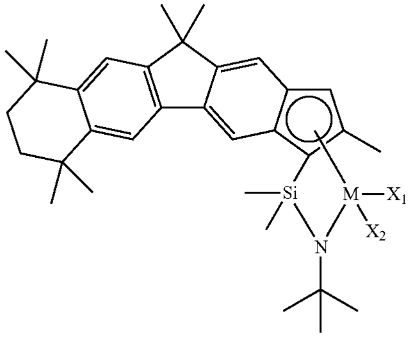
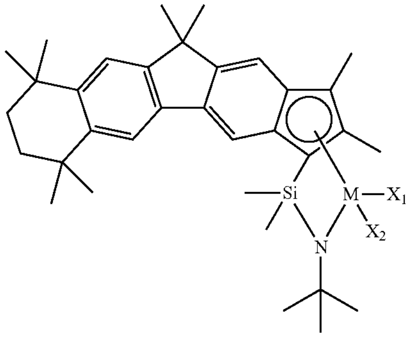
-continued
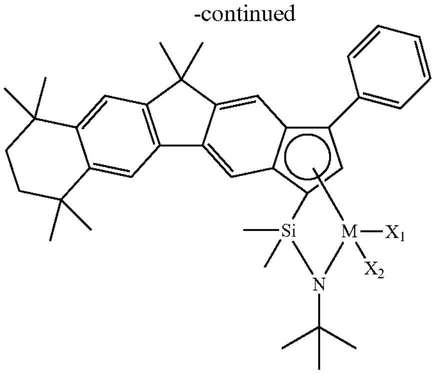
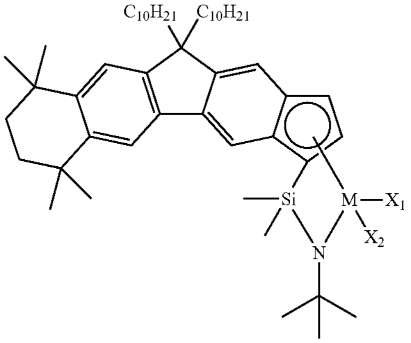
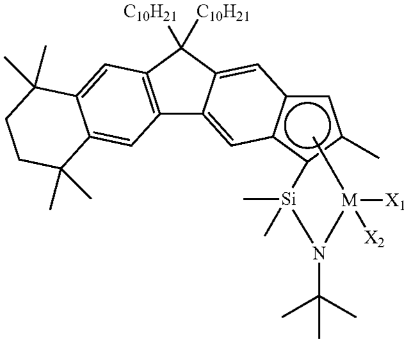
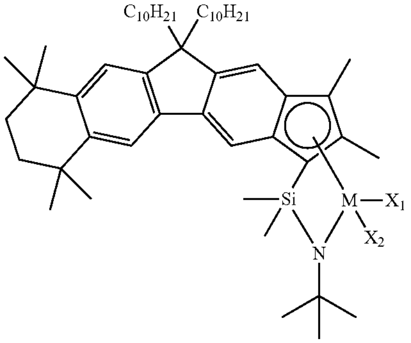
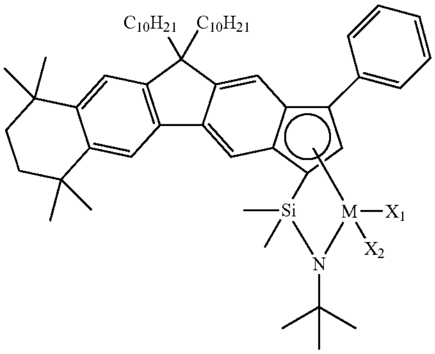

-continued
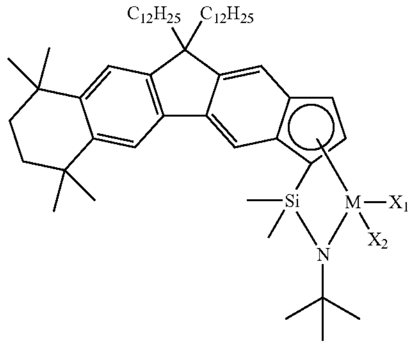
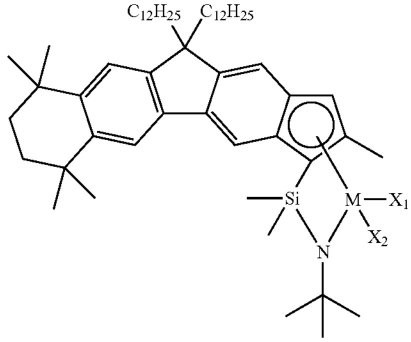
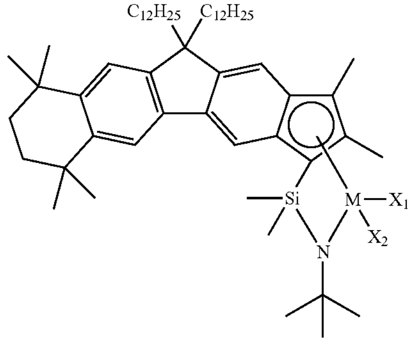
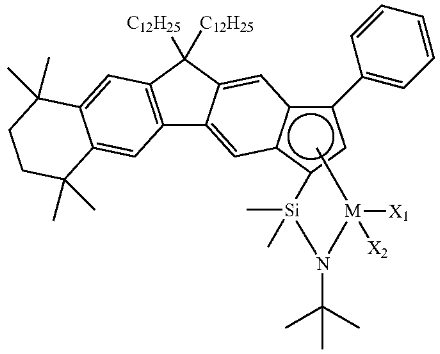
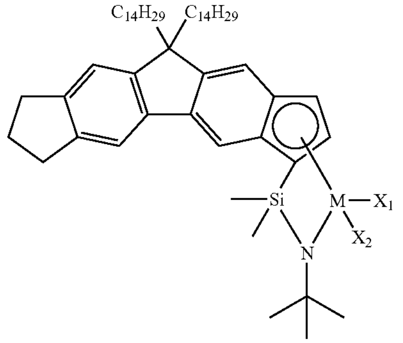
-continued
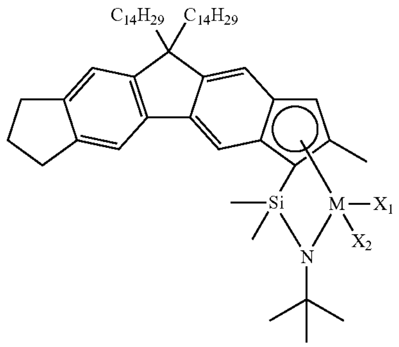
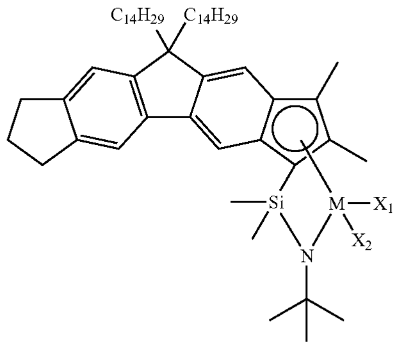
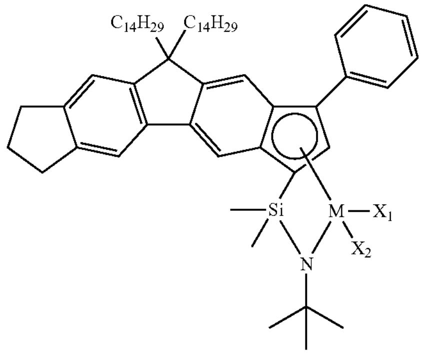
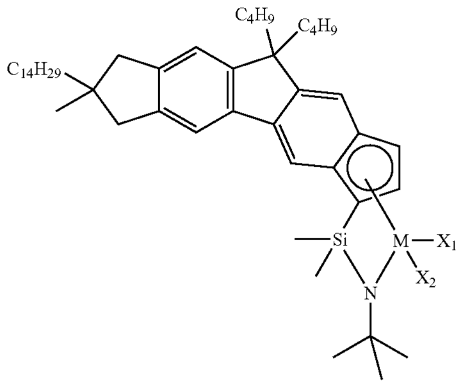

-continued
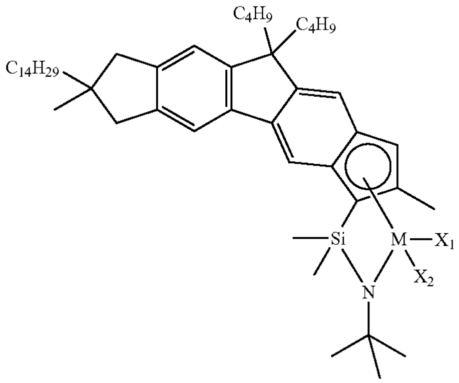
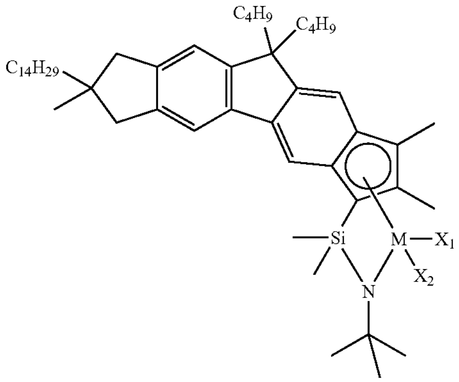
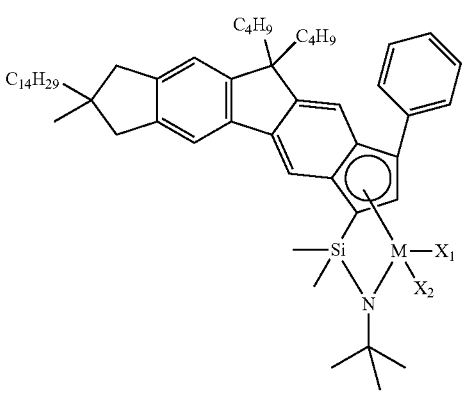
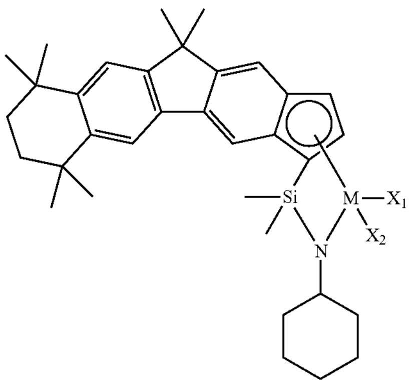
-continued
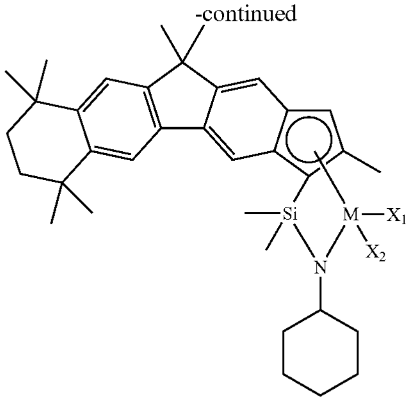
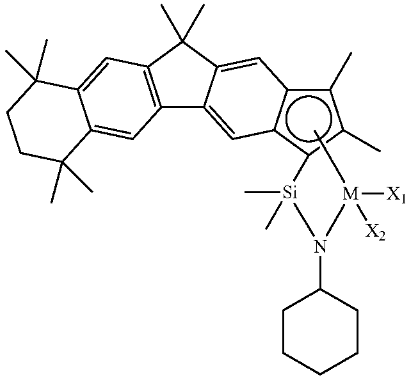
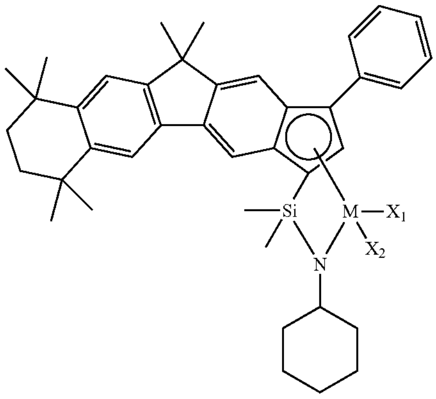
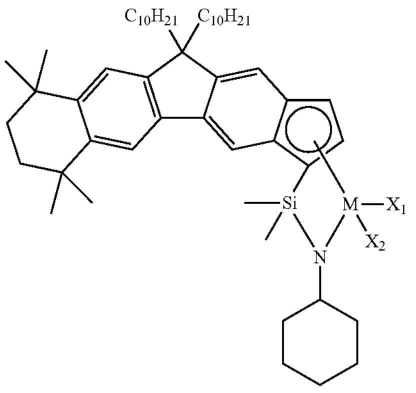

-continued
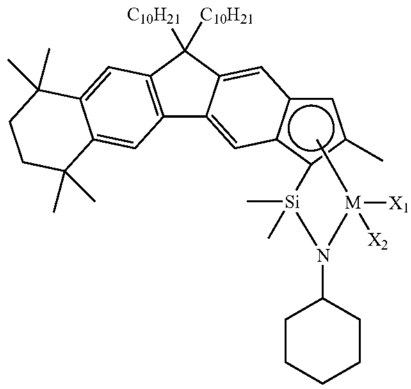
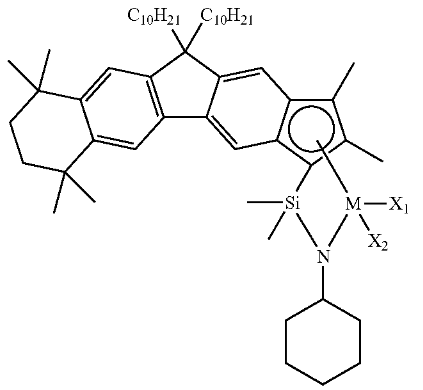
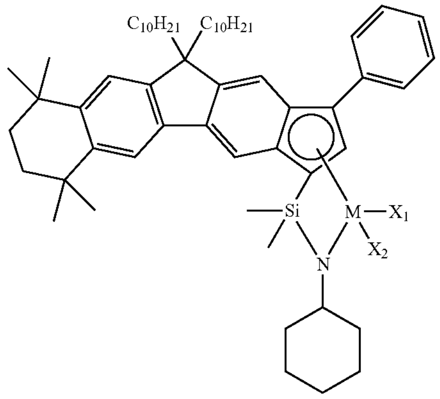
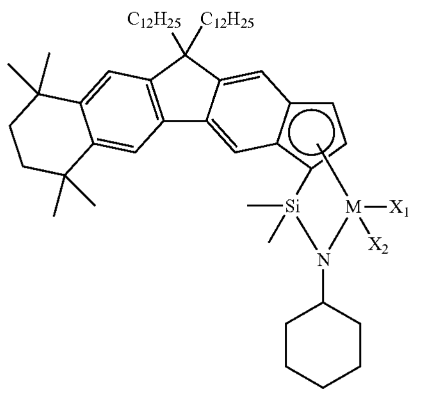
-continued
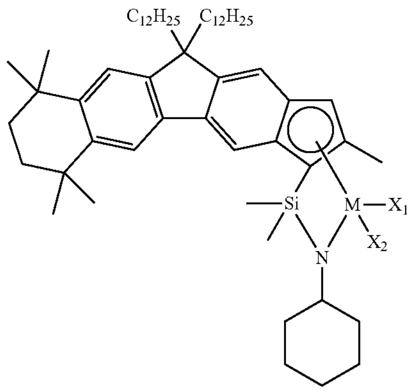
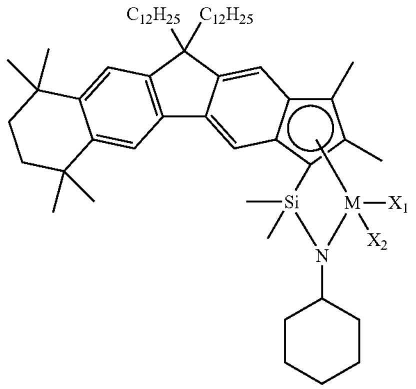
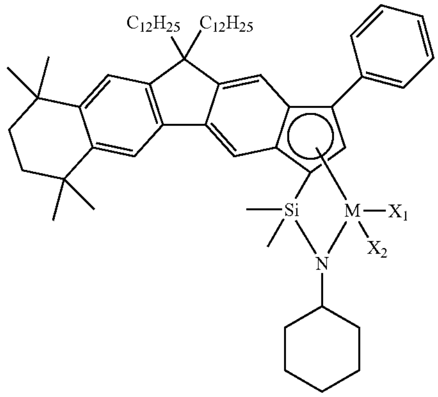
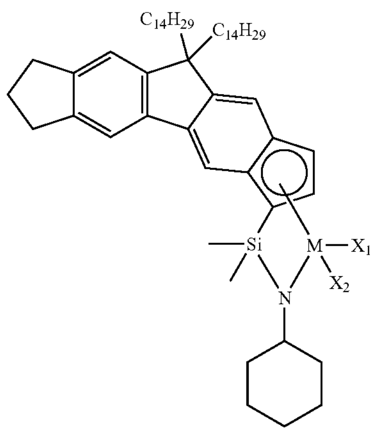

-continued
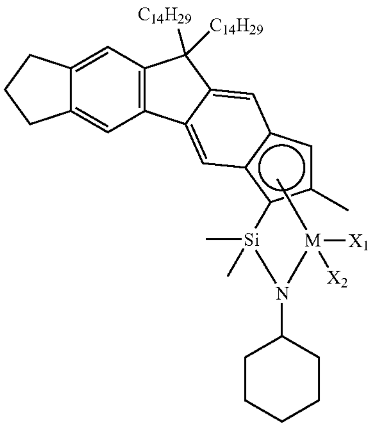
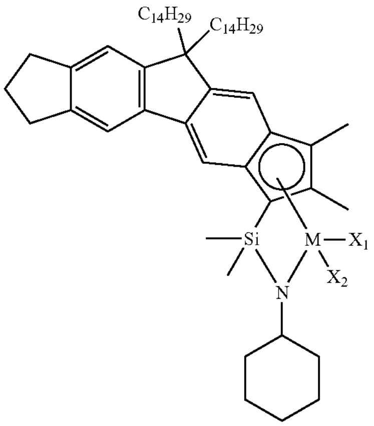
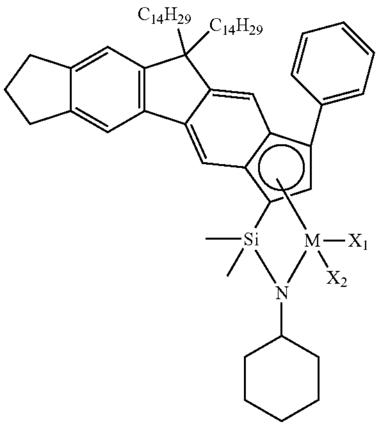
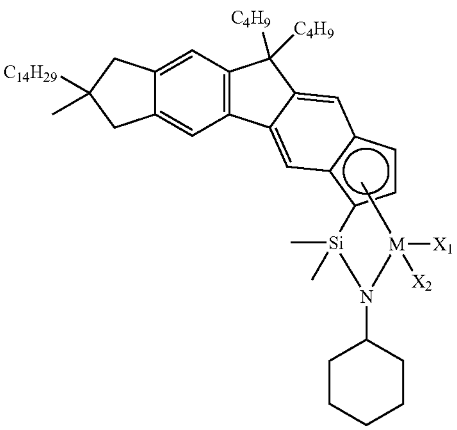
-continued
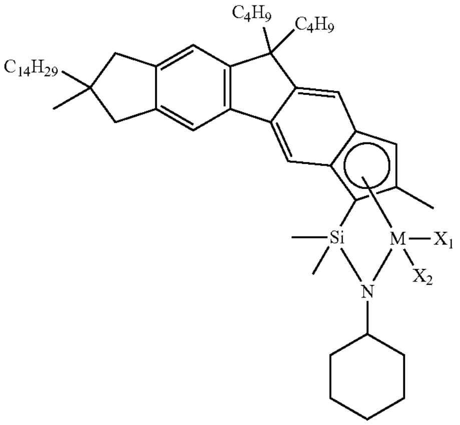
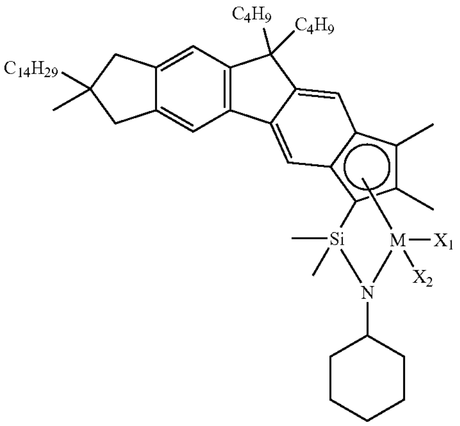
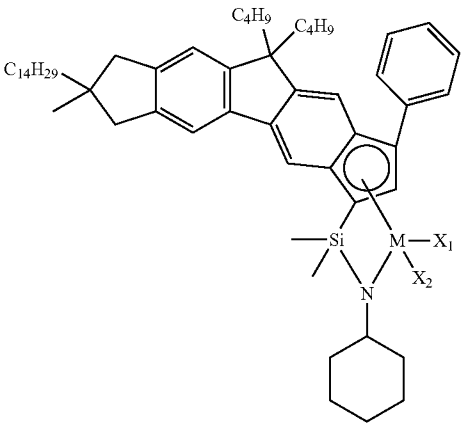

-continued
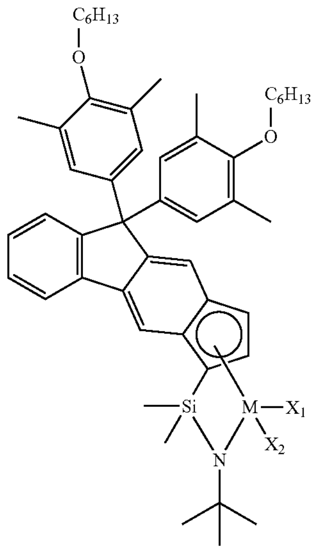
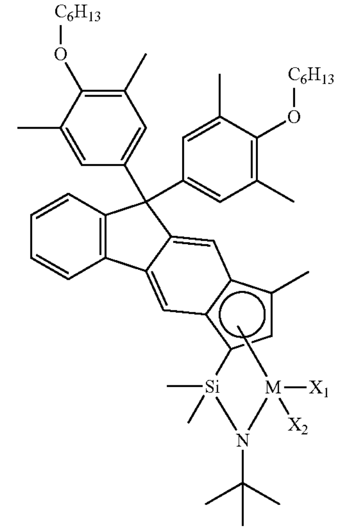
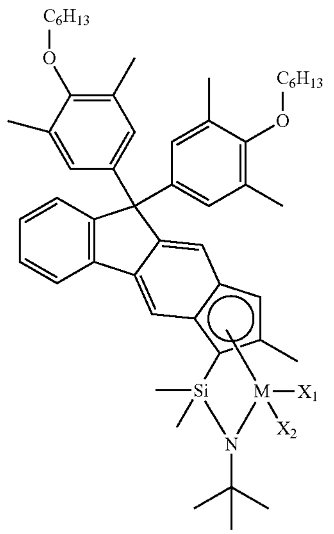
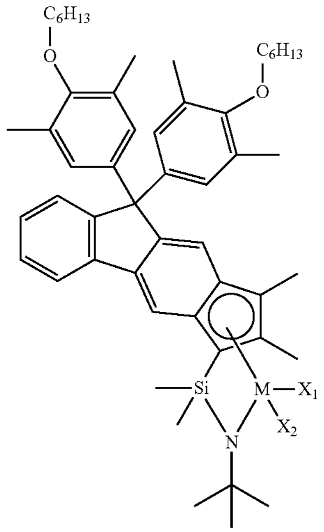
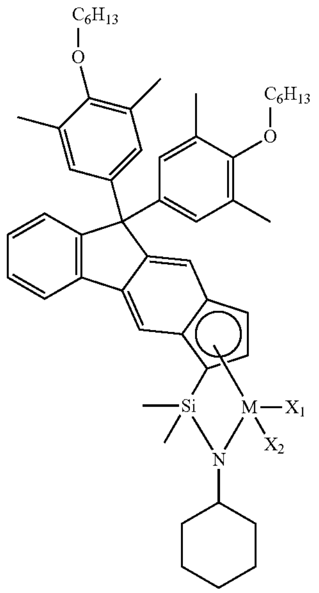
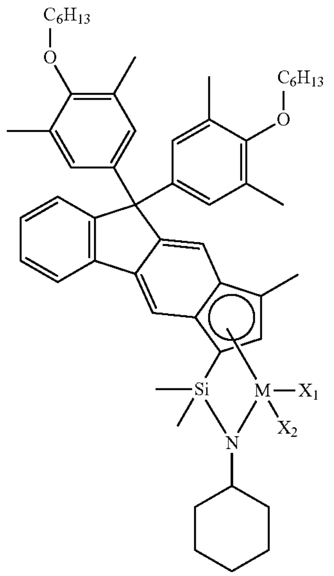

-continued
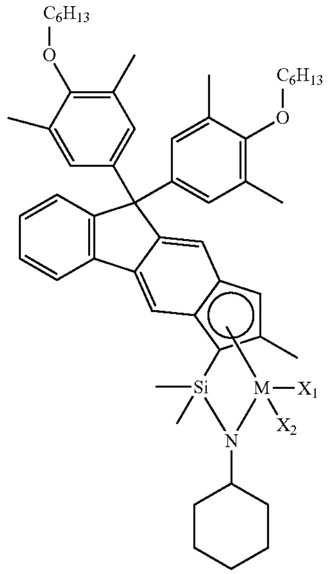
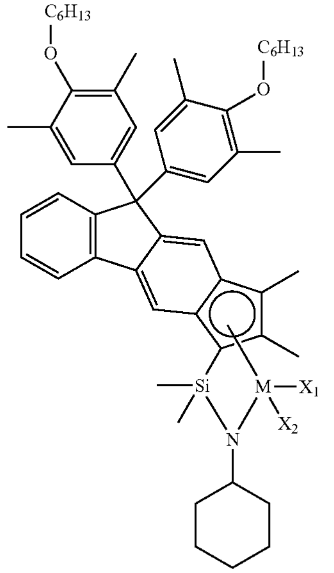
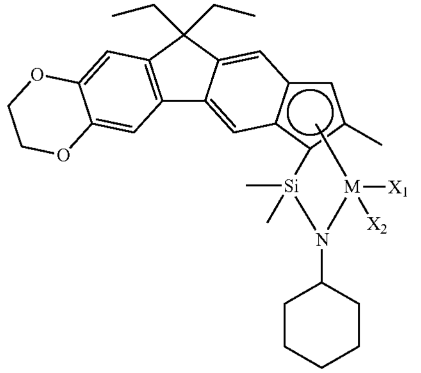
-continued
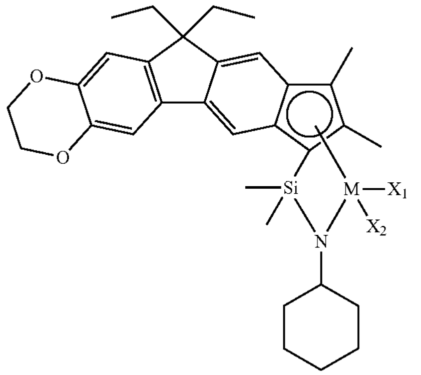
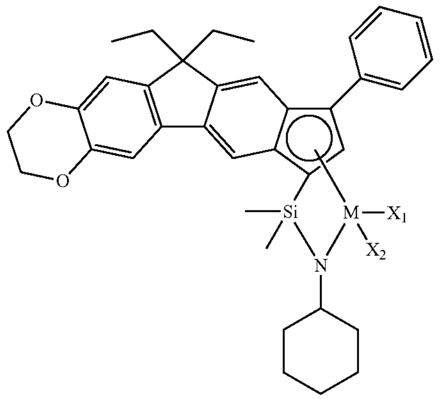
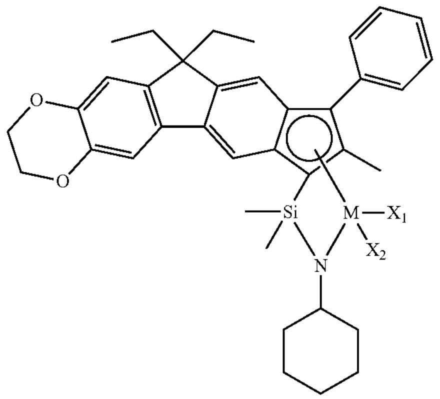
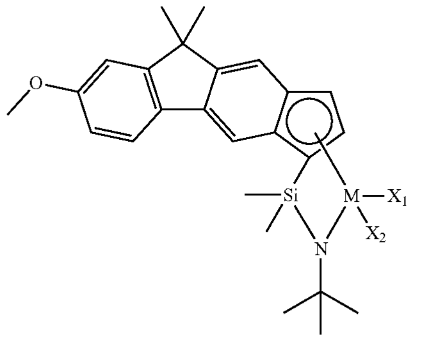

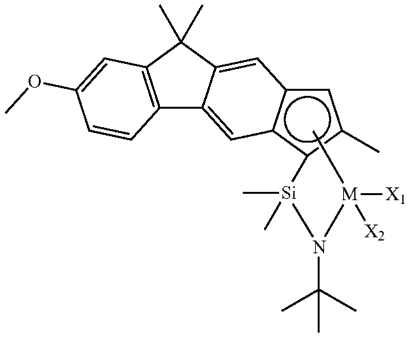
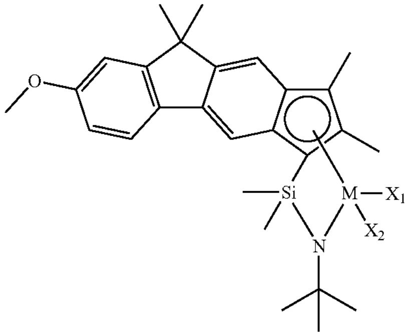
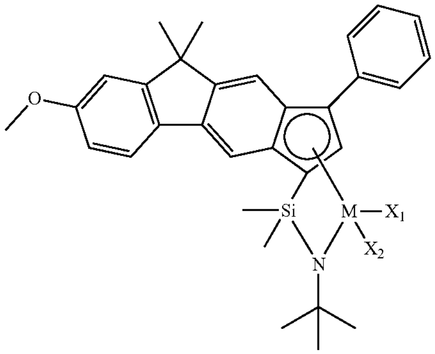
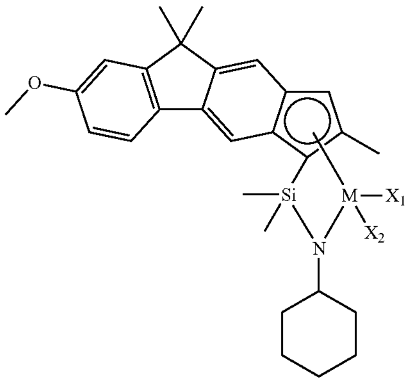
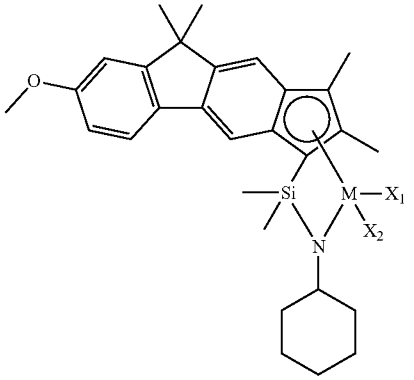
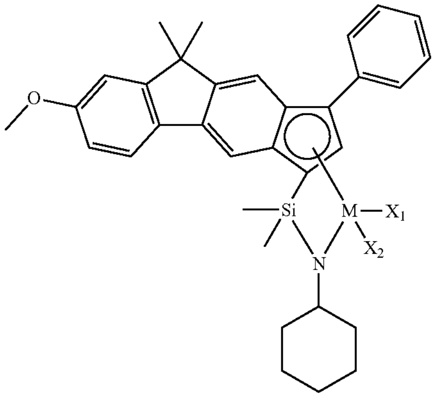
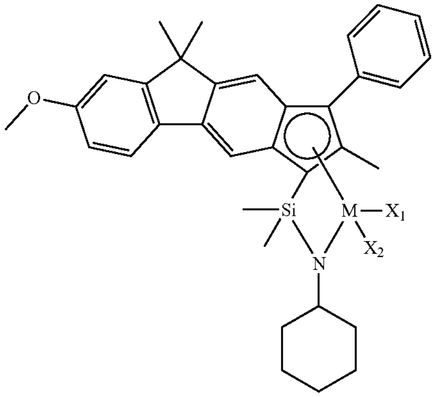
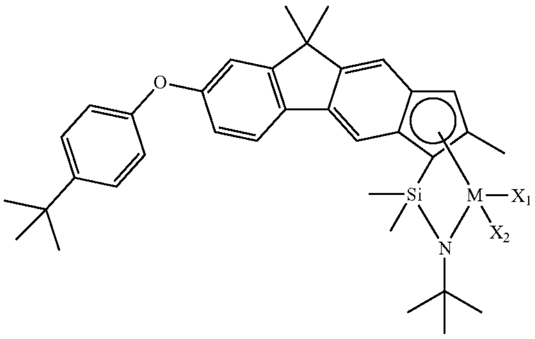

-continued
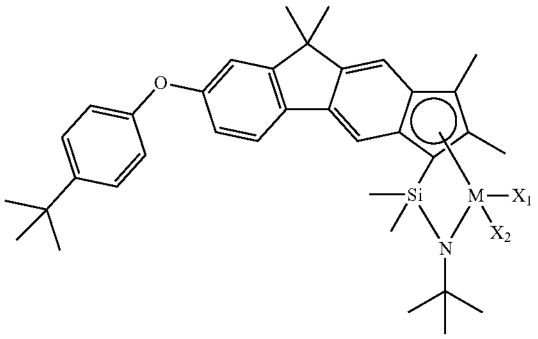
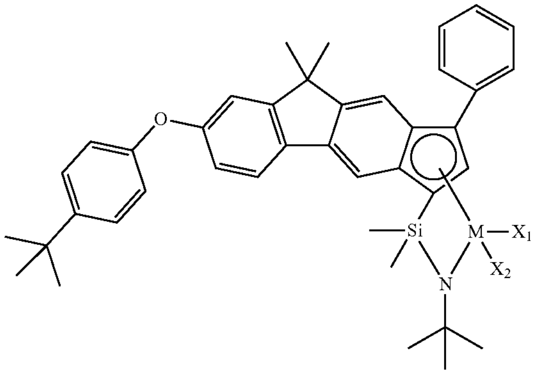
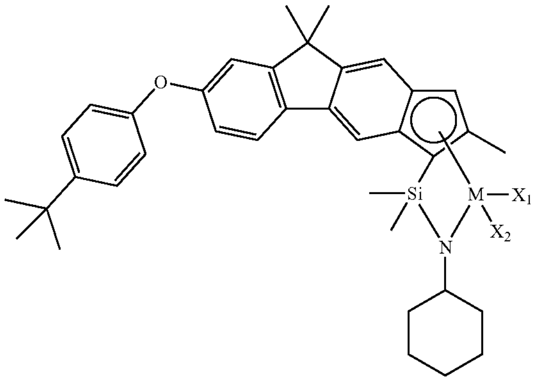
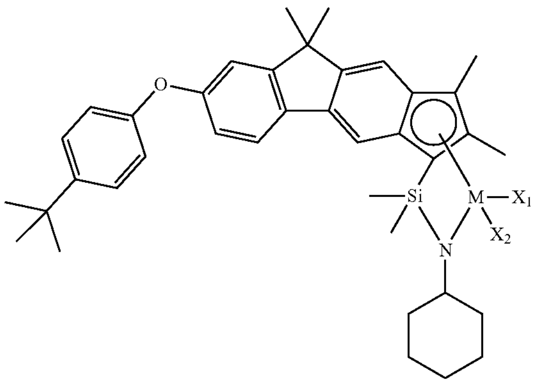
-continued
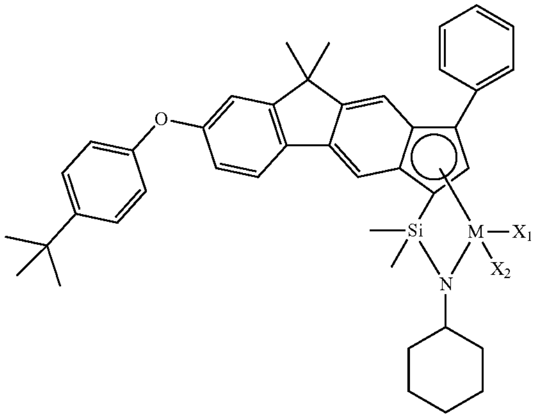
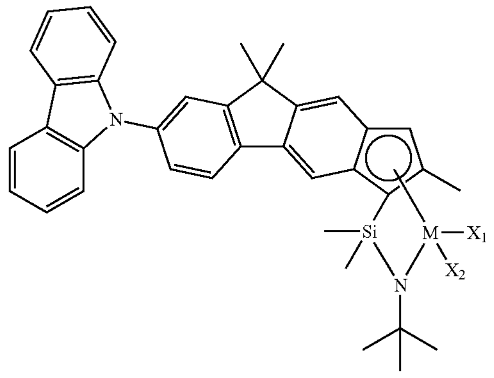
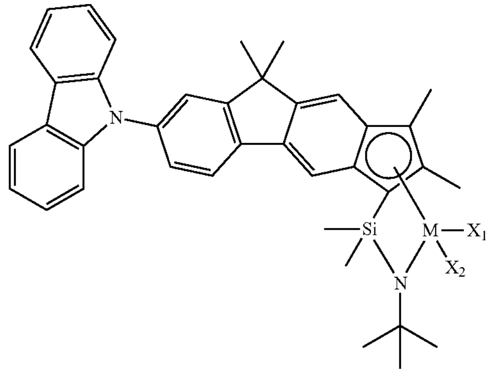
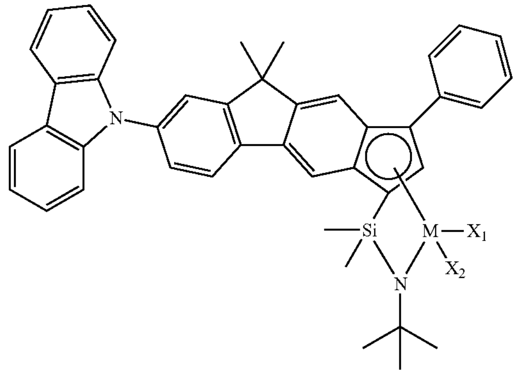

-continued
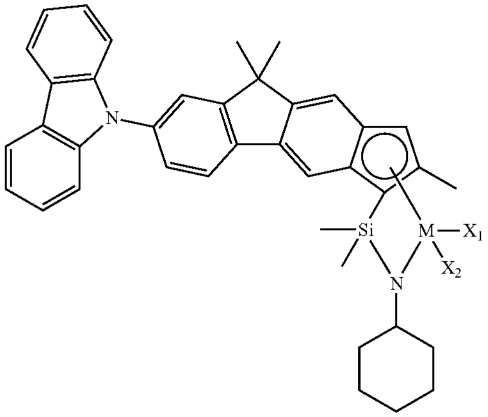
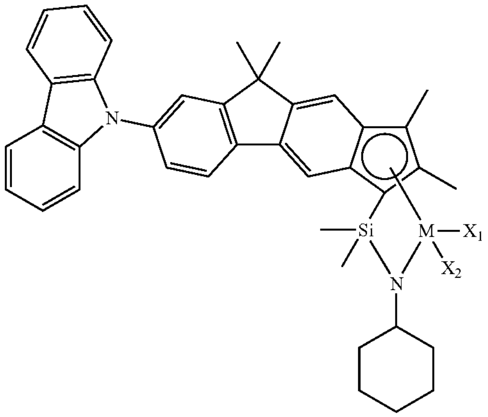
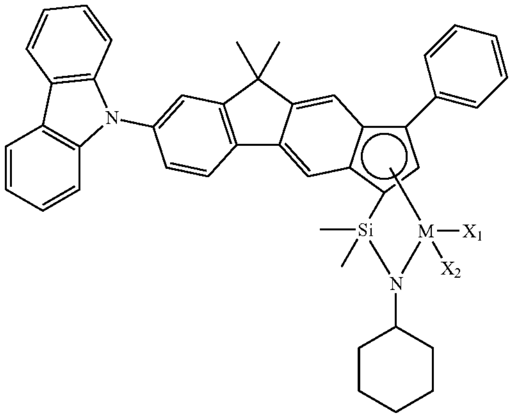
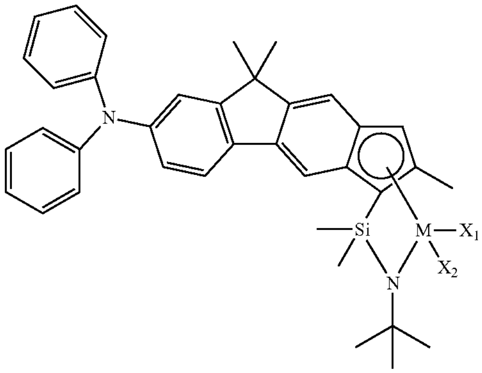
-continued
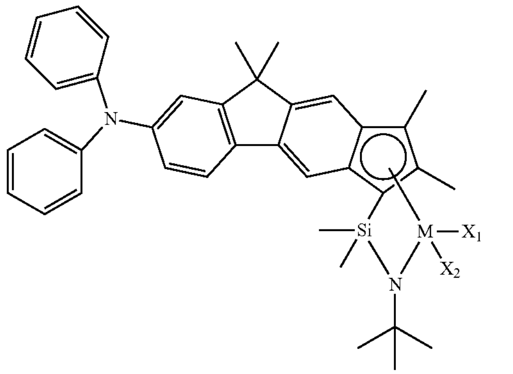
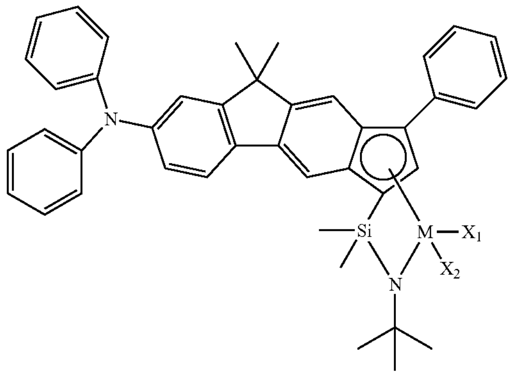
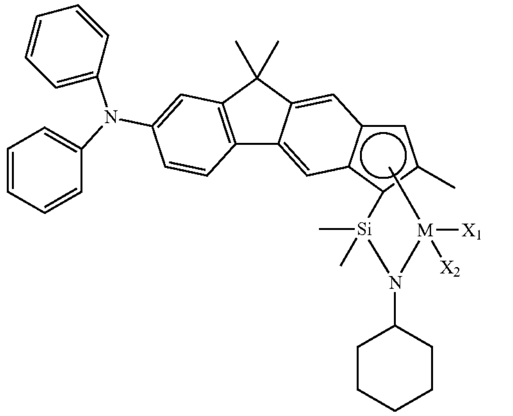
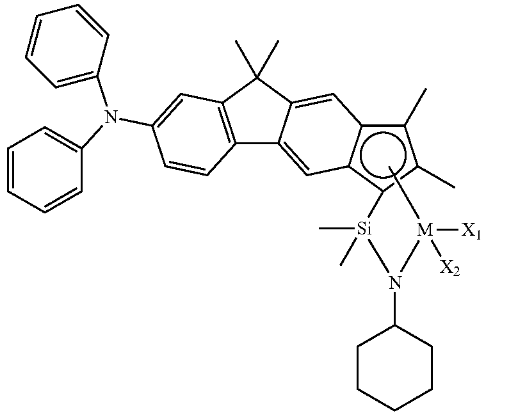

-continued
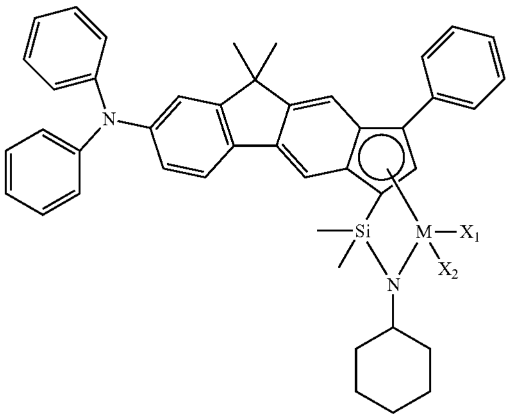
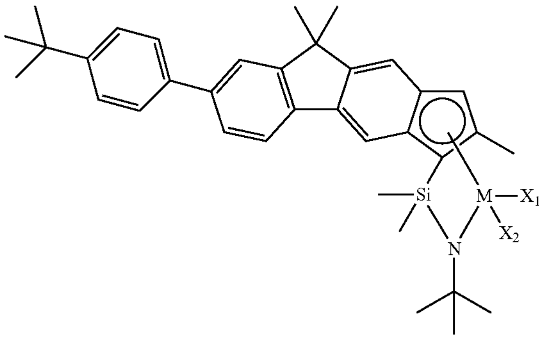
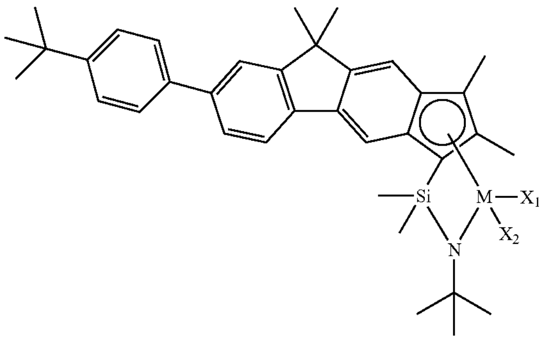
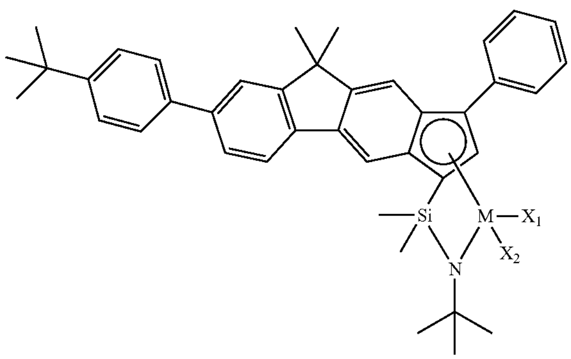
-continued
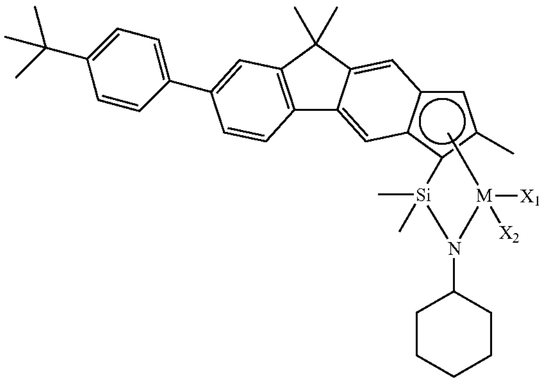
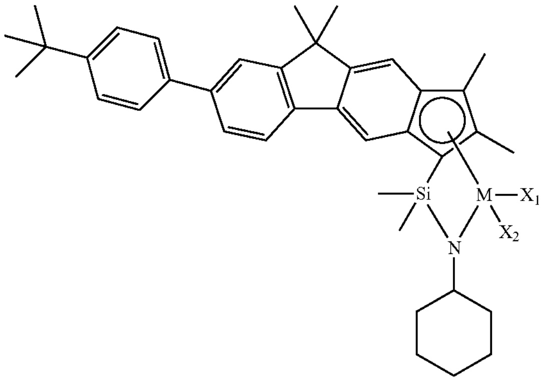
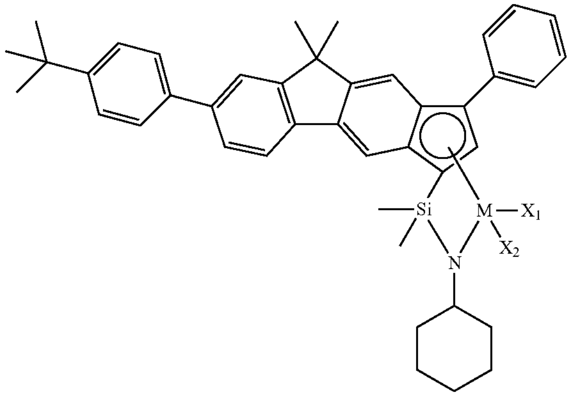
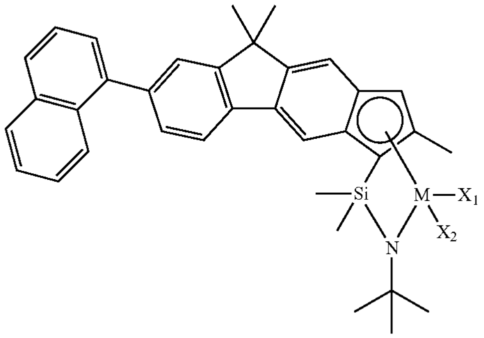

-continued
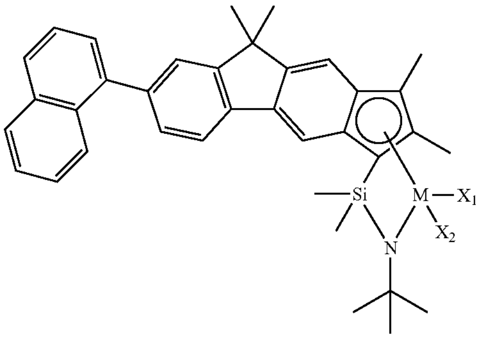
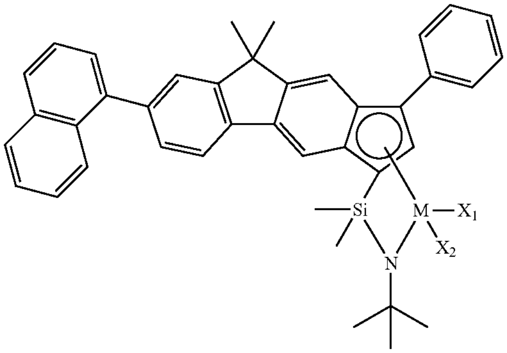
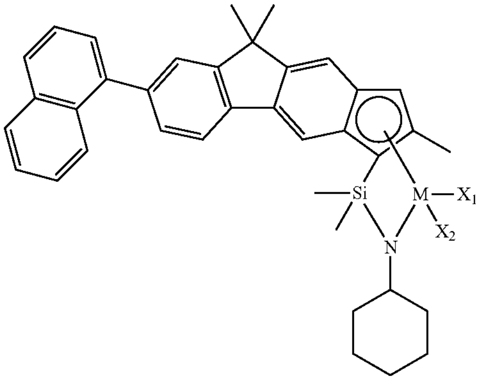
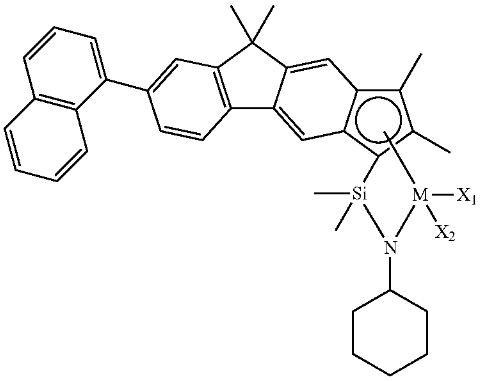
-continued
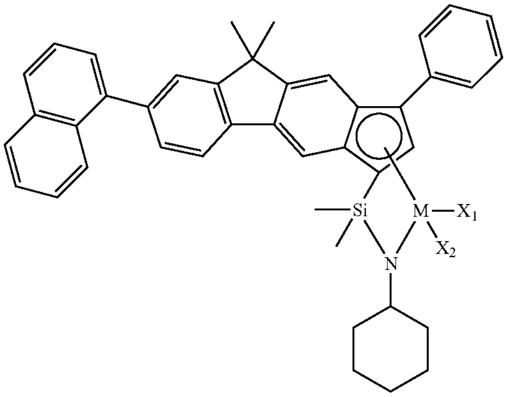
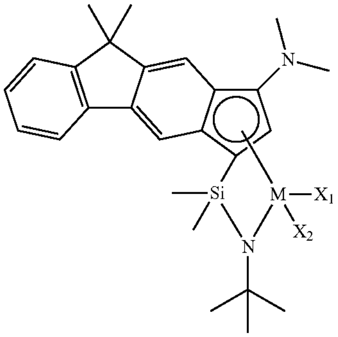
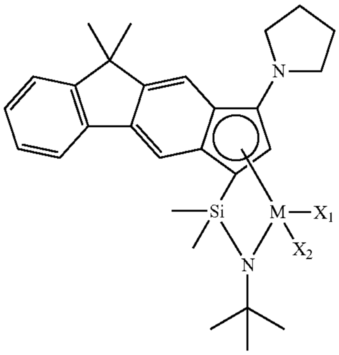
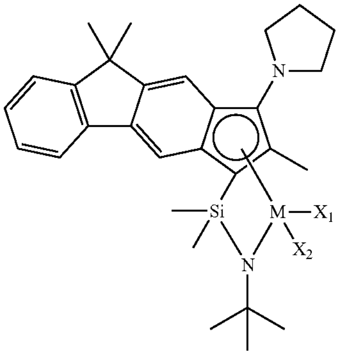

-continued
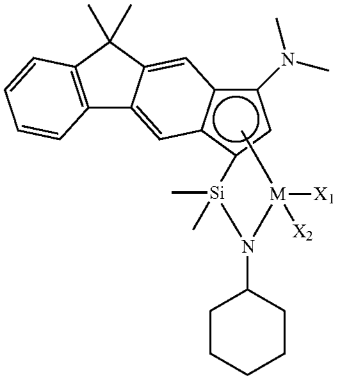
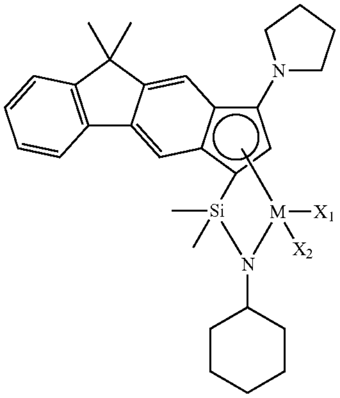
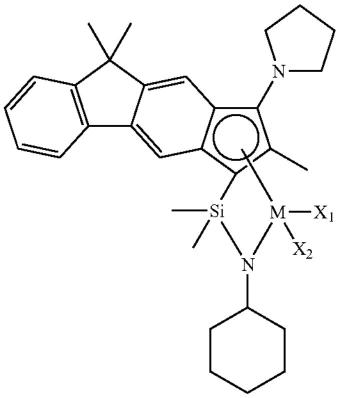
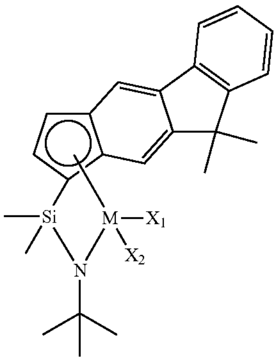
-continued
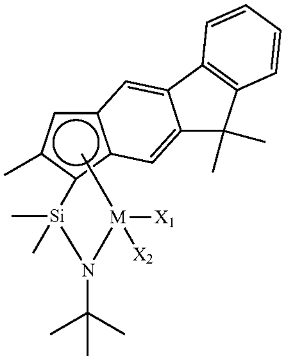
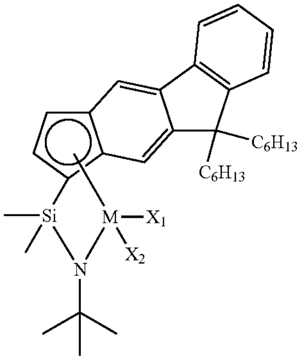
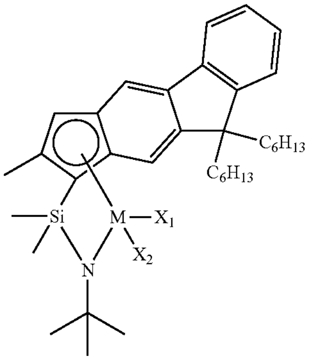
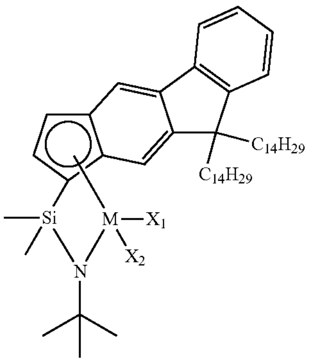

-continued
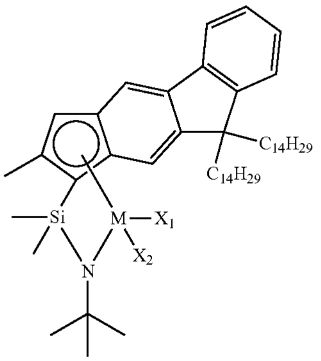
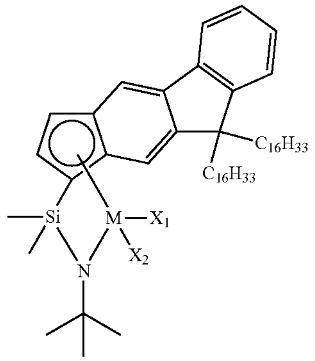
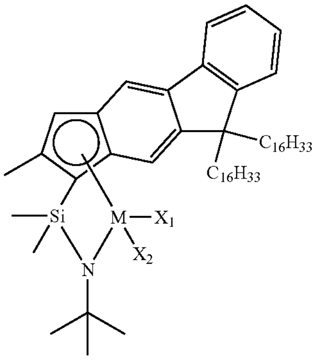
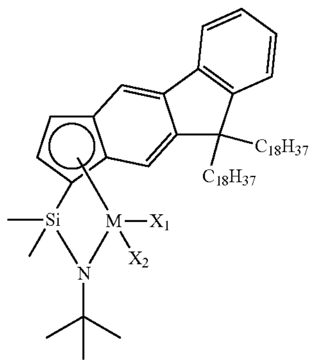
-continued
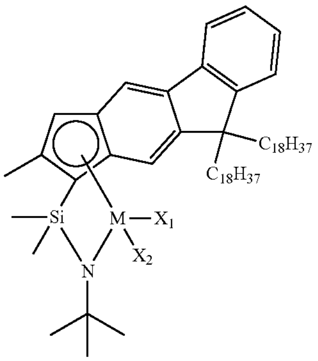
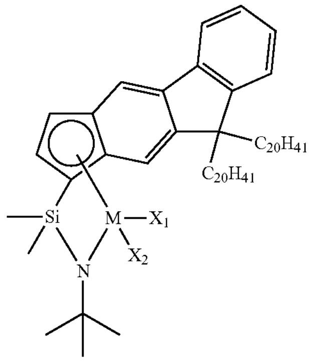
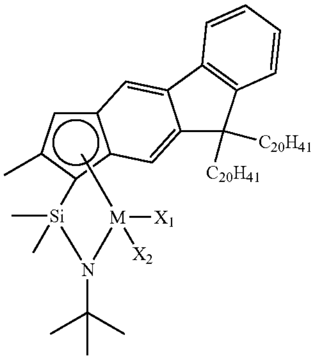
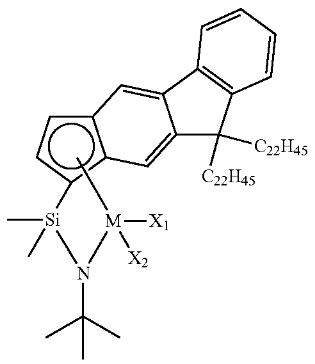

-continued
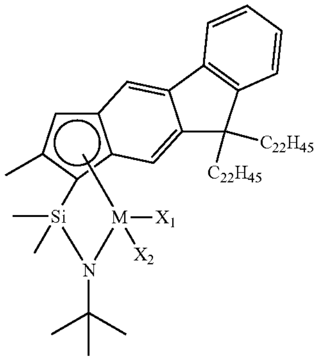
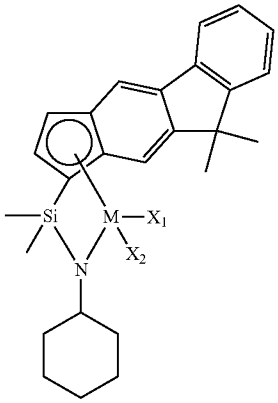
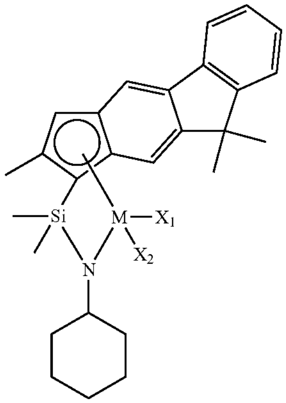
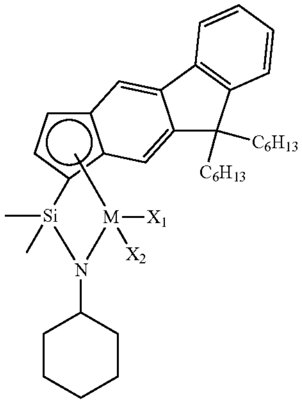
-continued
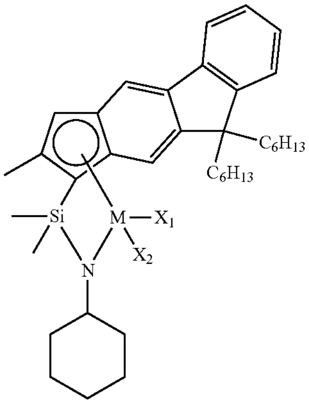
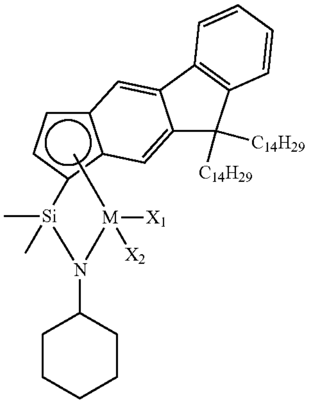
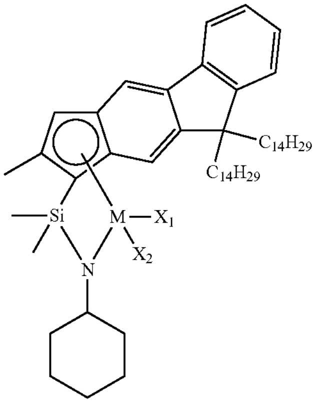
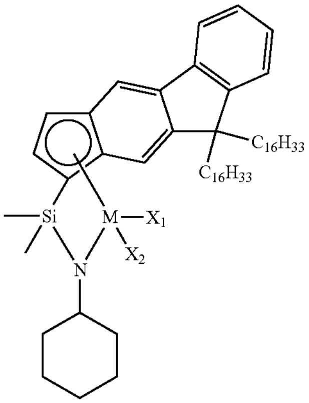

-continued
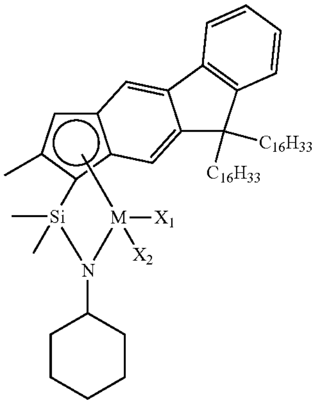
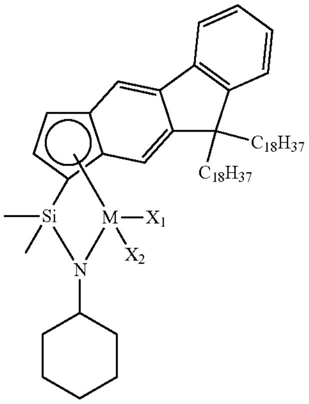
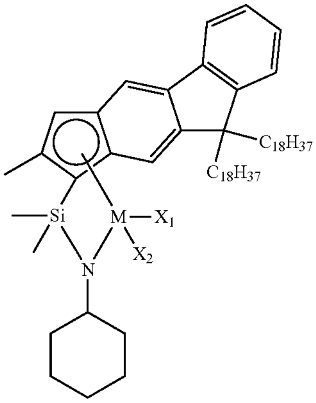
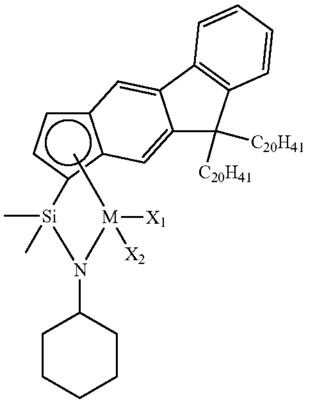
-continued
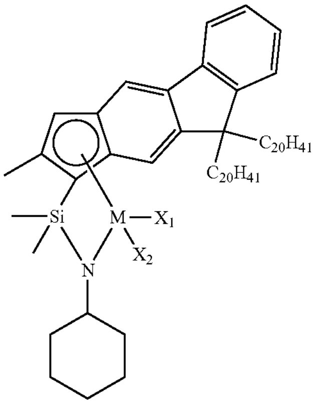
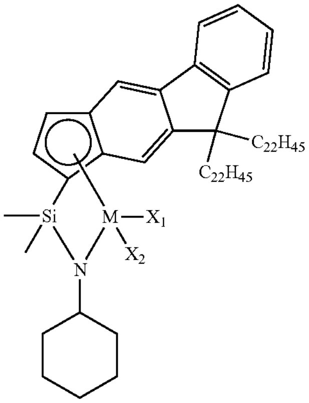
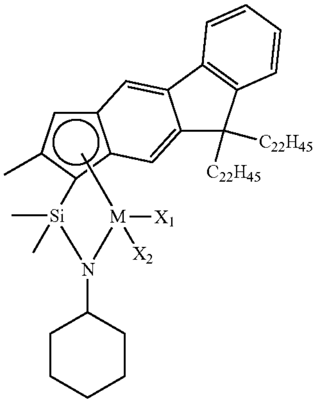
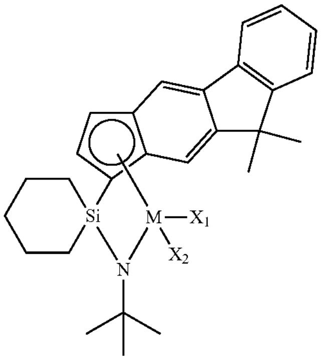

-continued
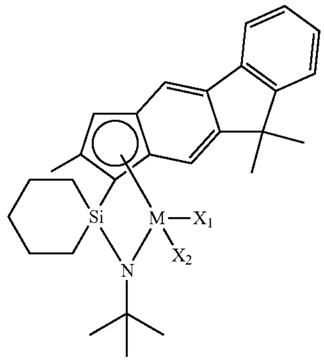
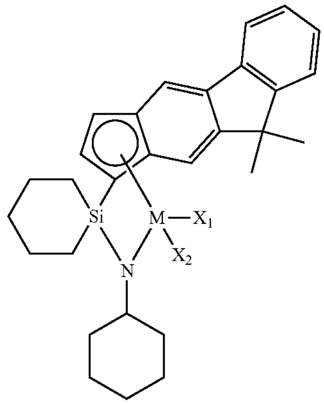
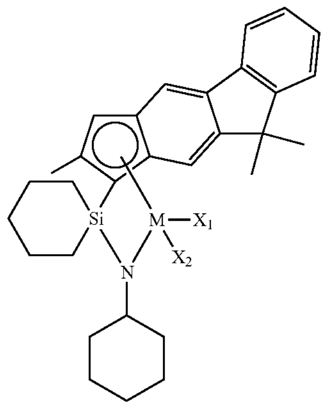
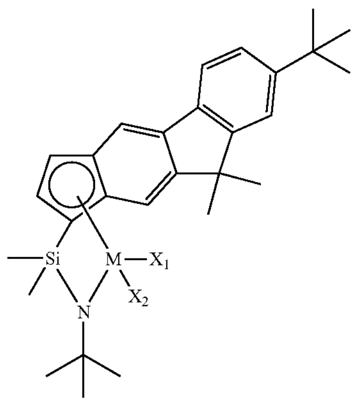
-continued
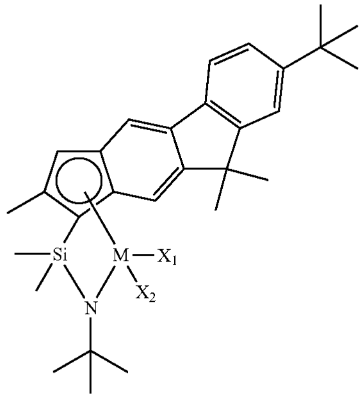
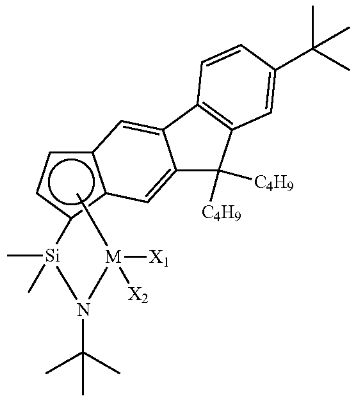
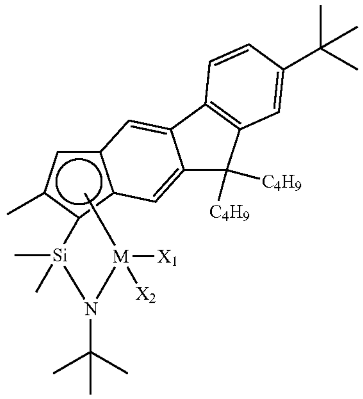
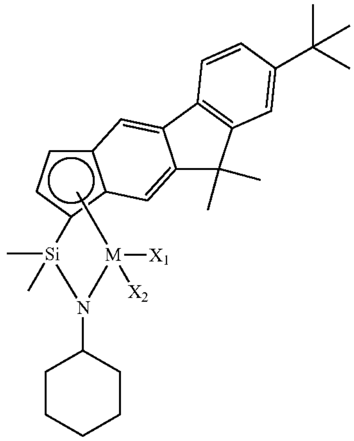

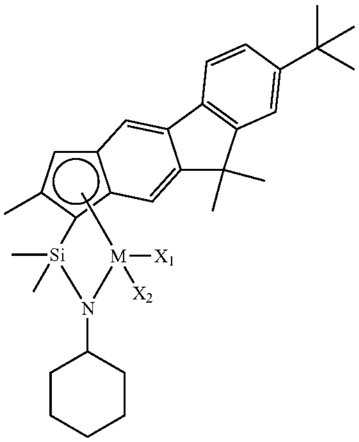
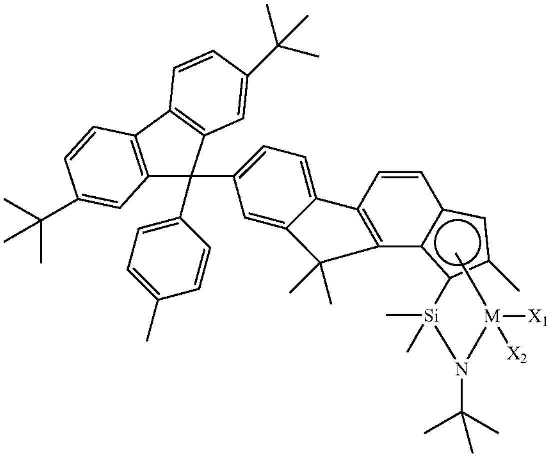
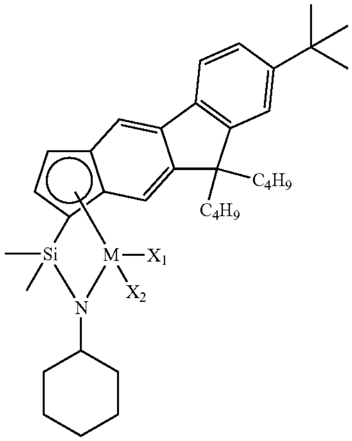
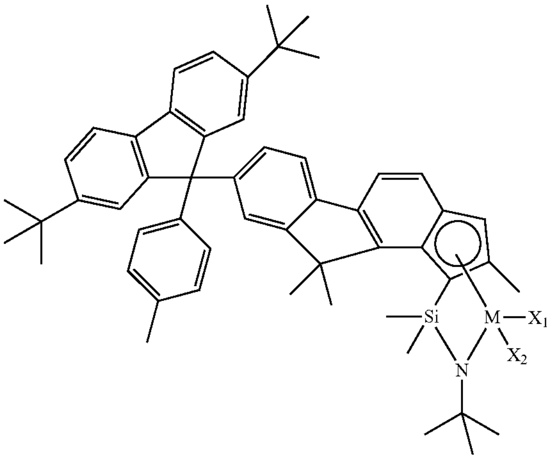
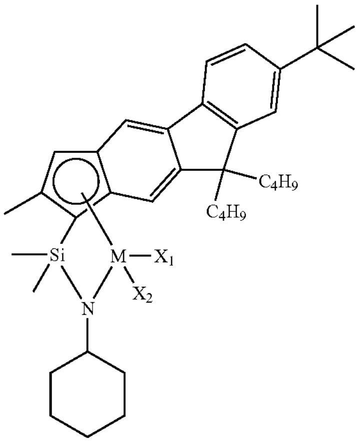
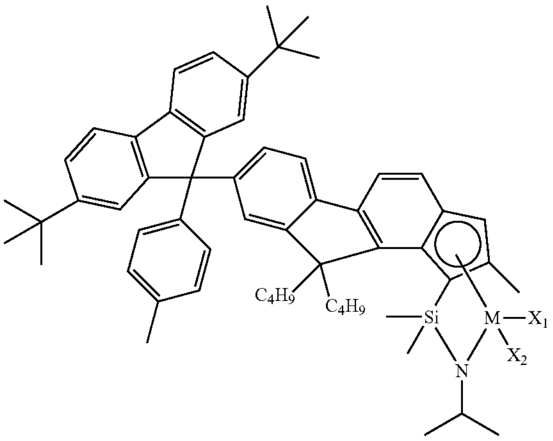

-continued
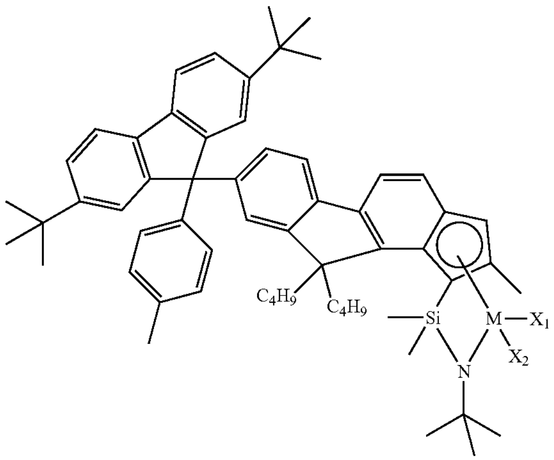
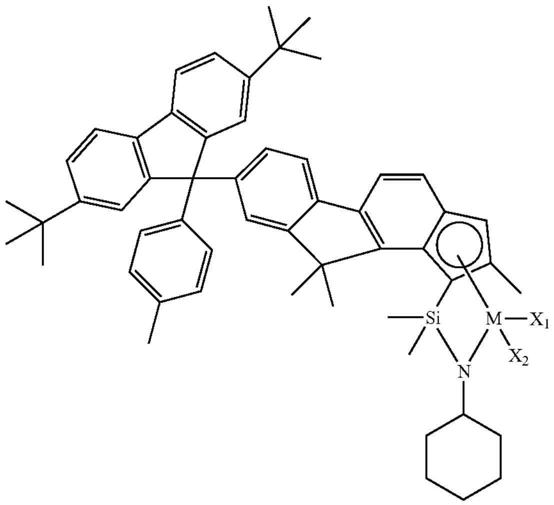
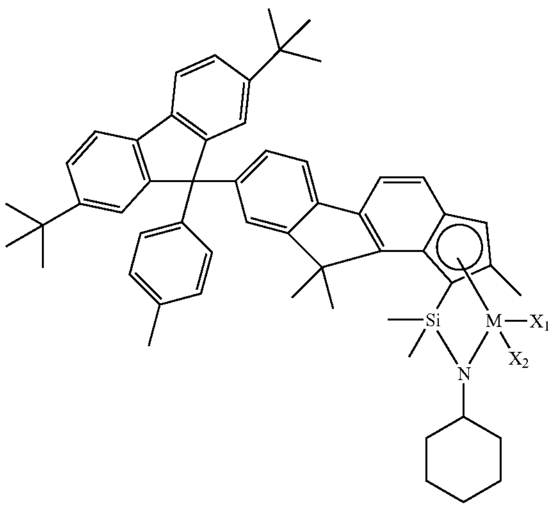
-continued
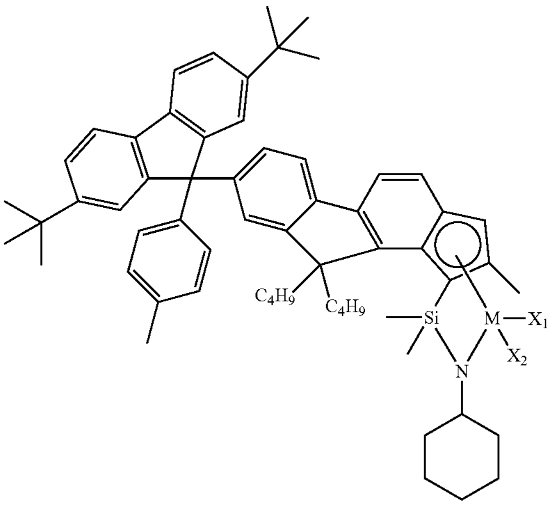
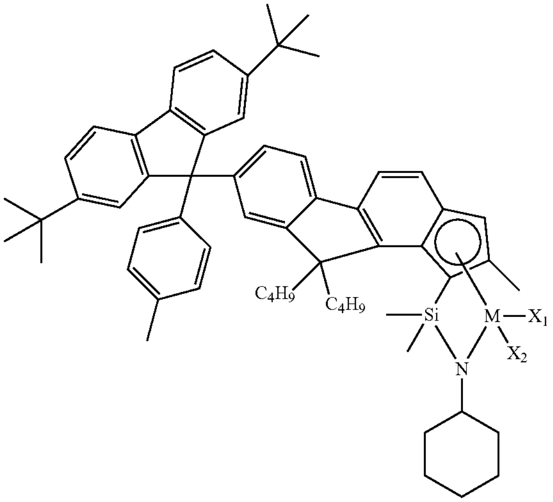
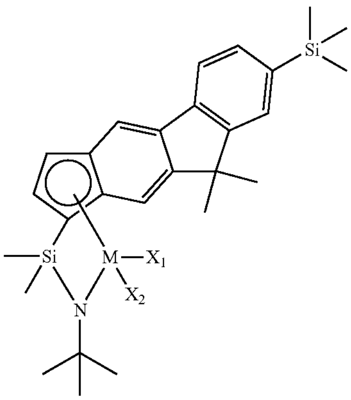

-continued
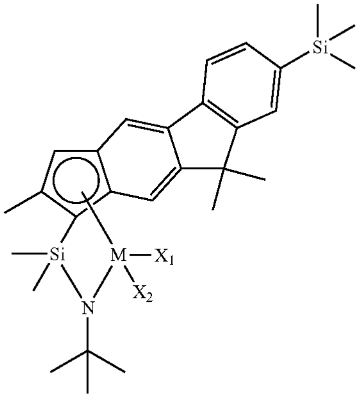
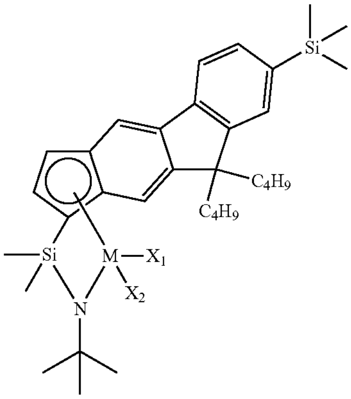
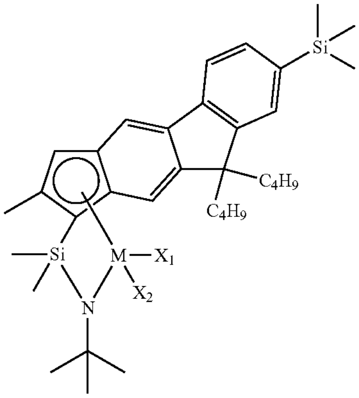
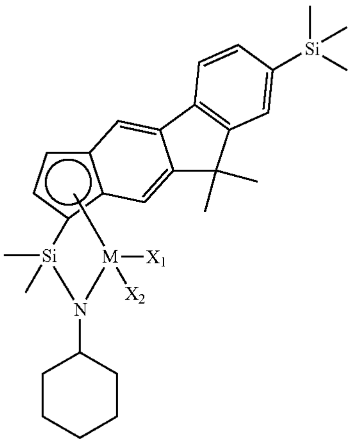
-continued
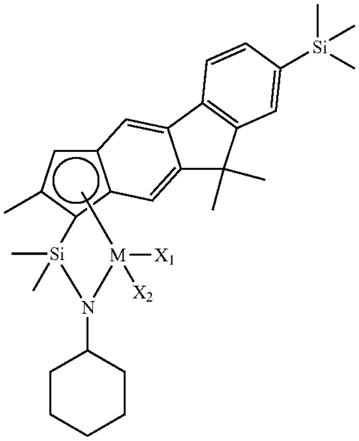
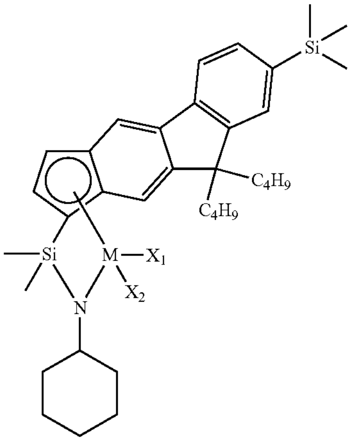
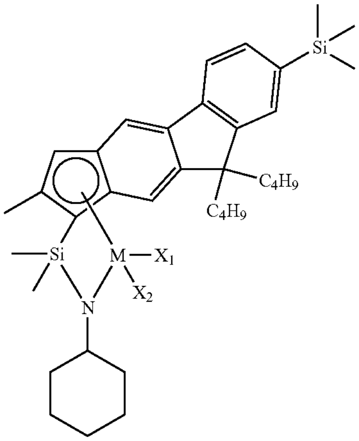

-continued
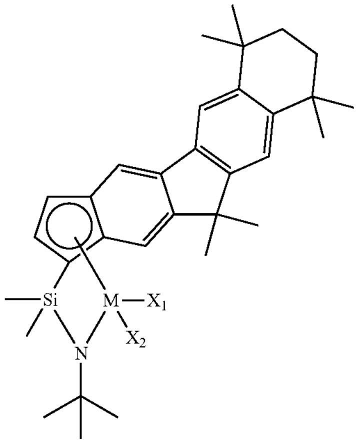
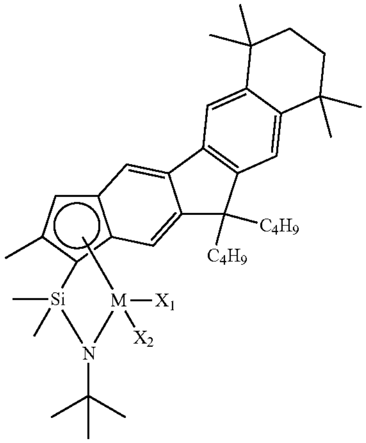
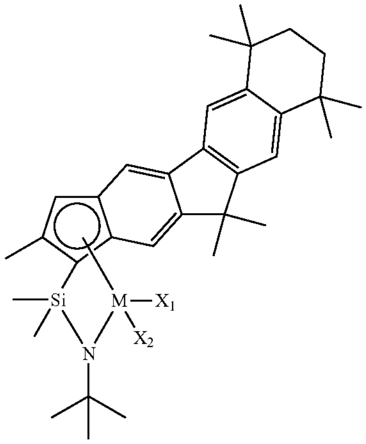
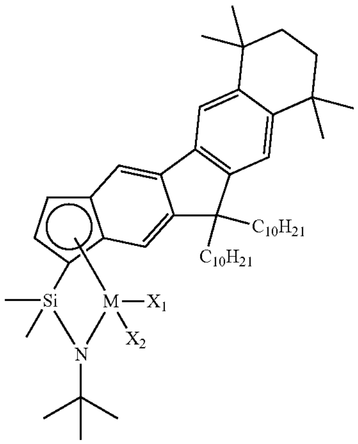
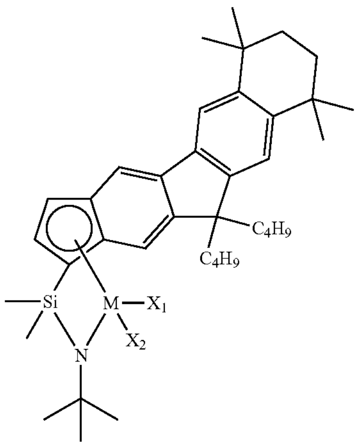
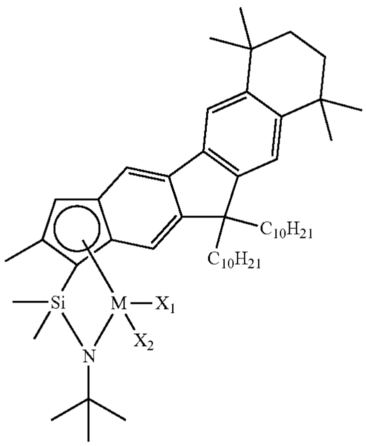

-continued
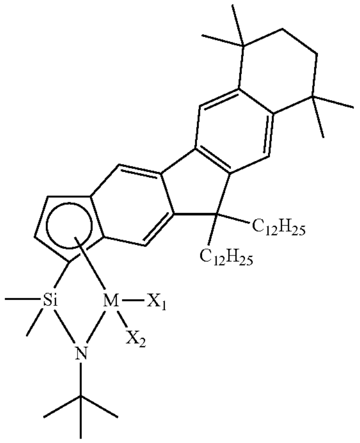
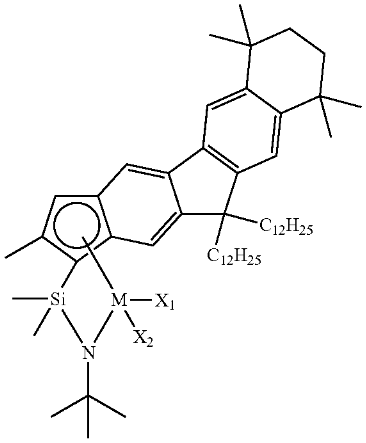
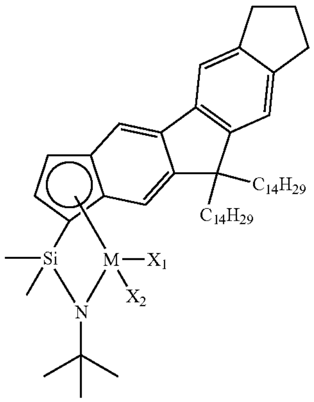
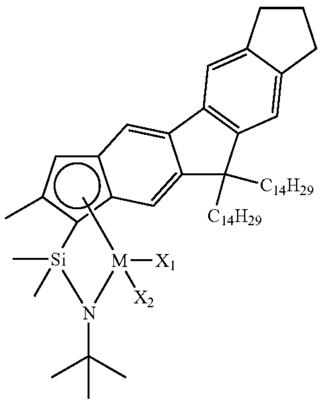
-continued
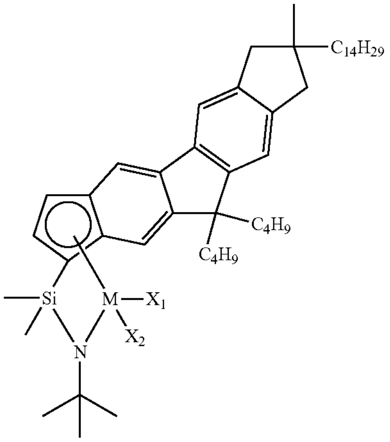
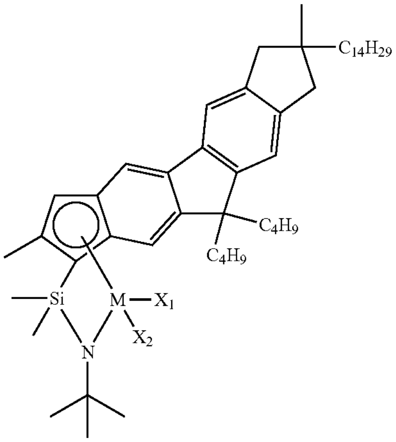
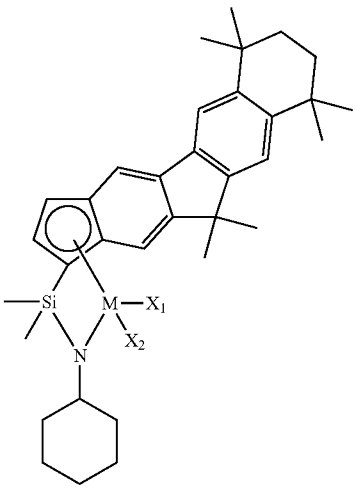

-continued
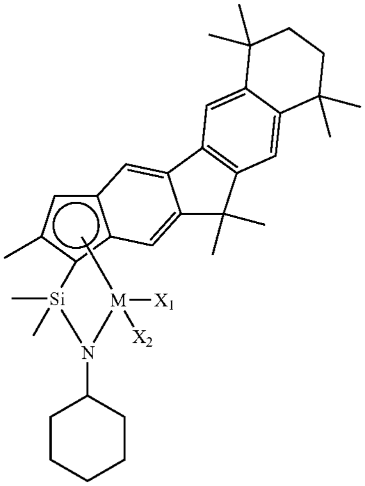
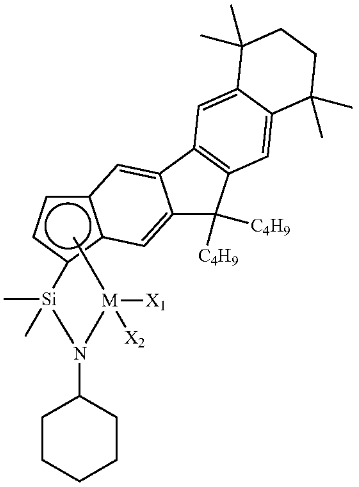
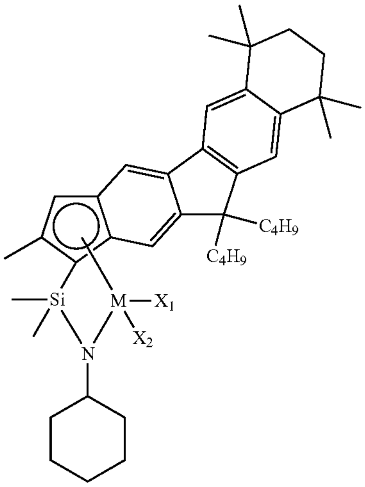
-continued
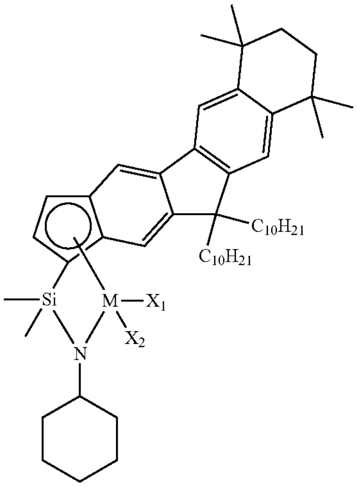
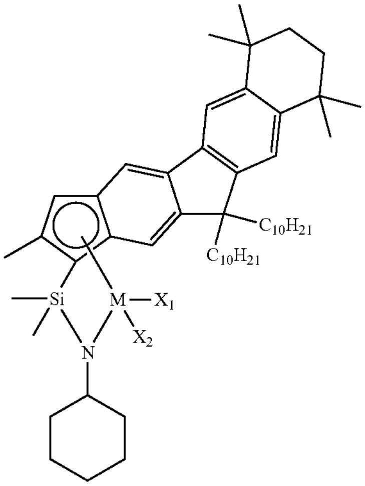
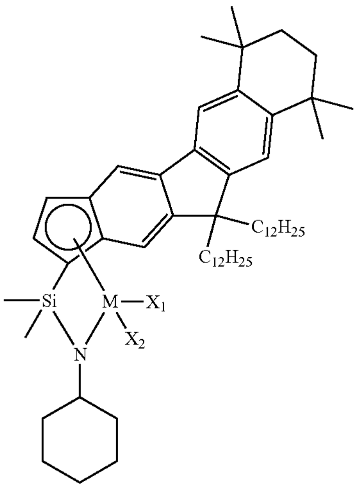

-continued
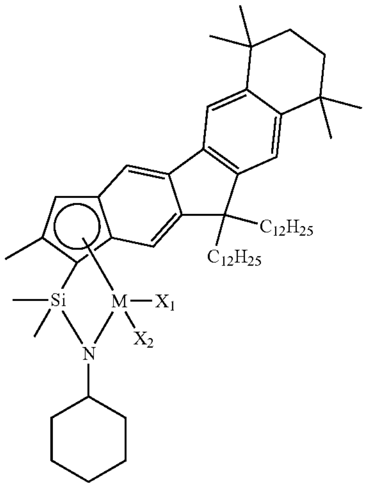
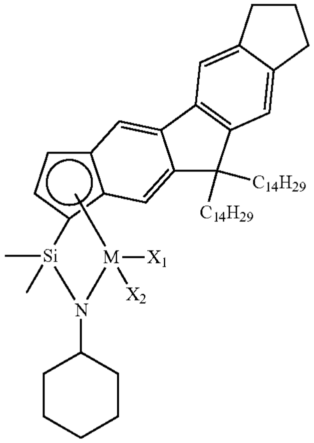
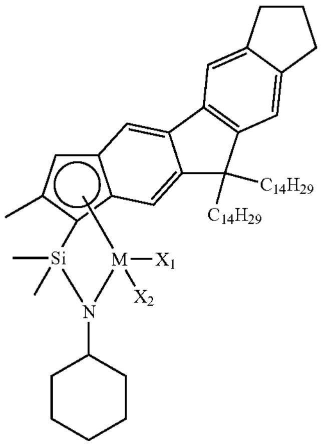
-continued
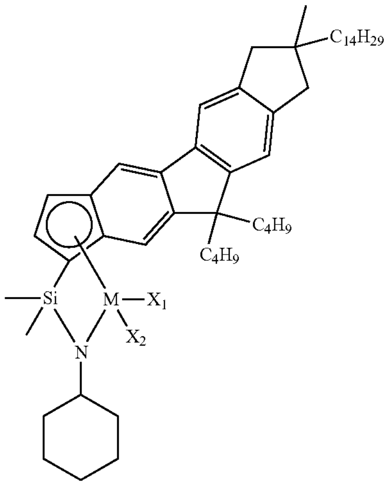
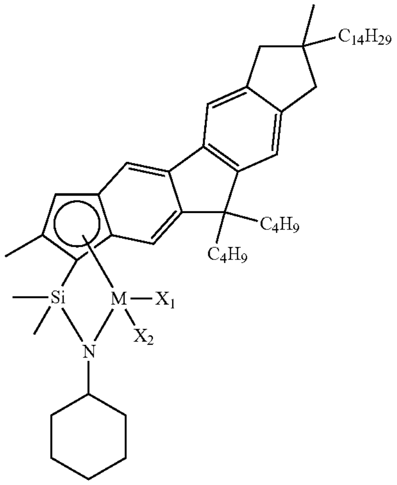
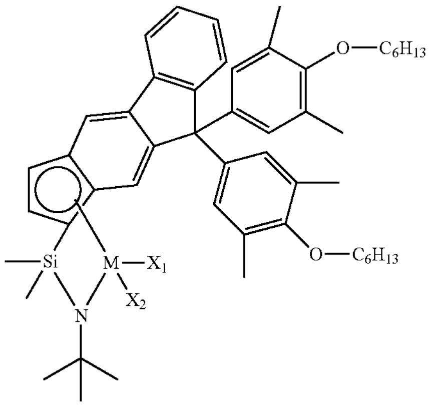

-continued
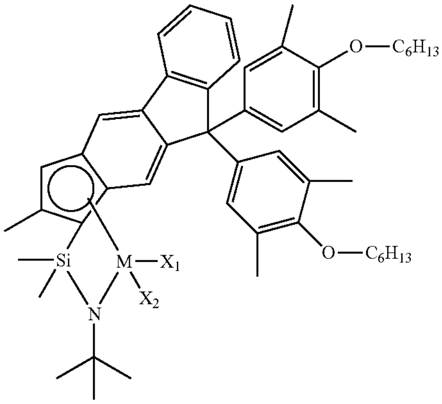
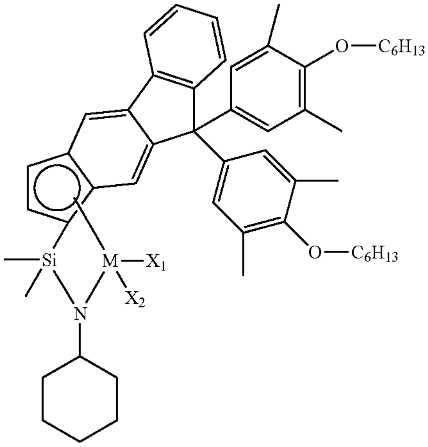
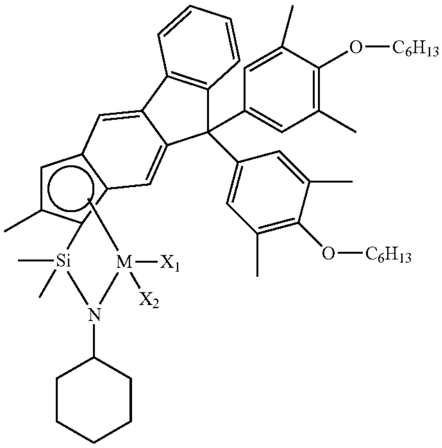
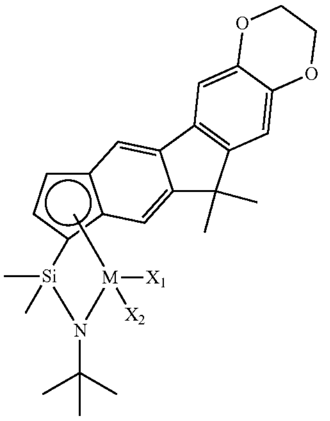
-continued
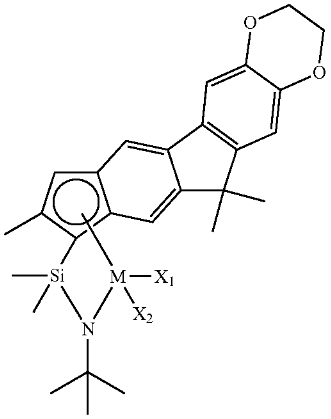
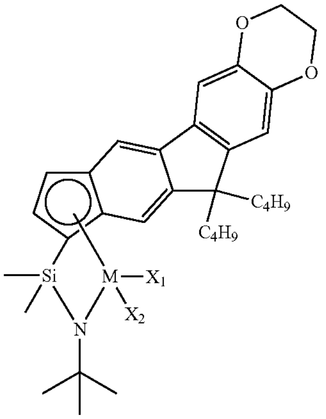
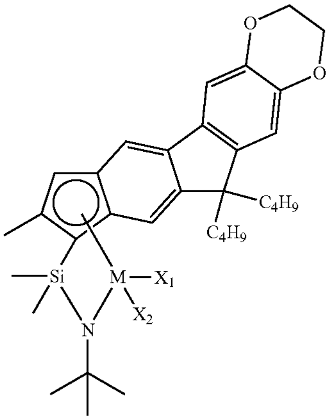
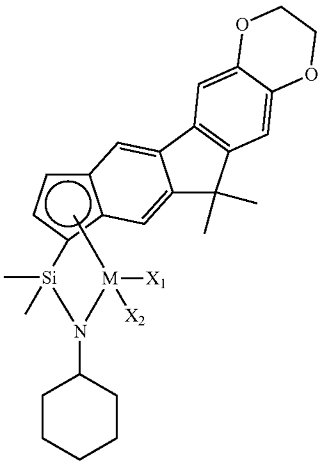

-continued
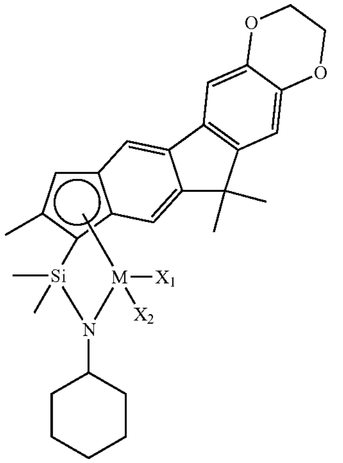
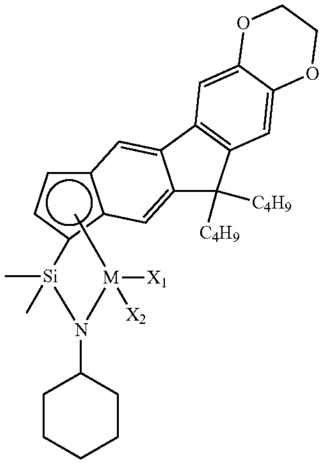
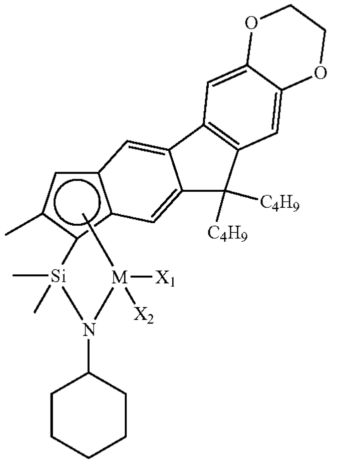
-continued
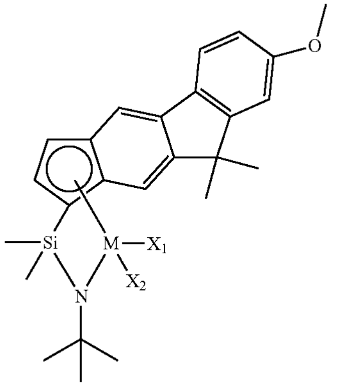
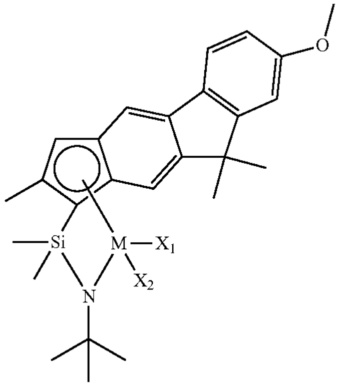
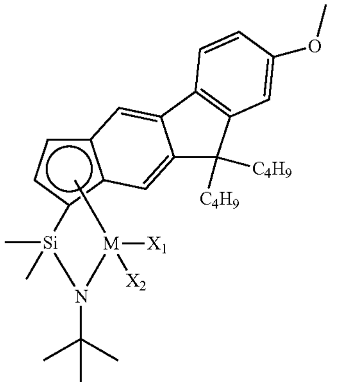
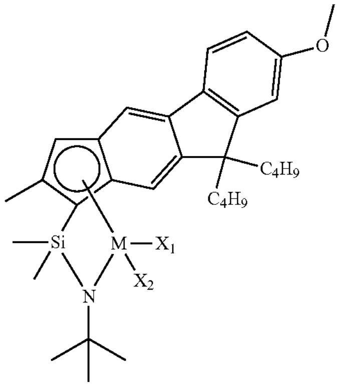

-continued
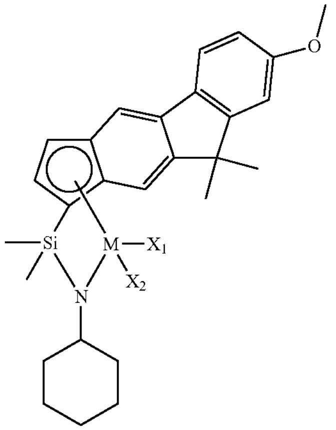
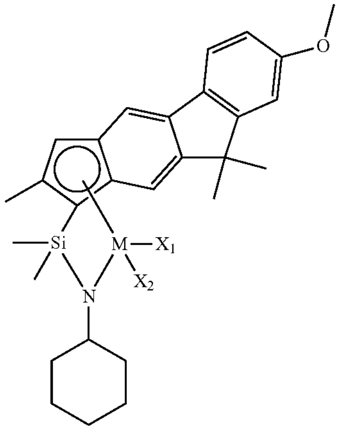
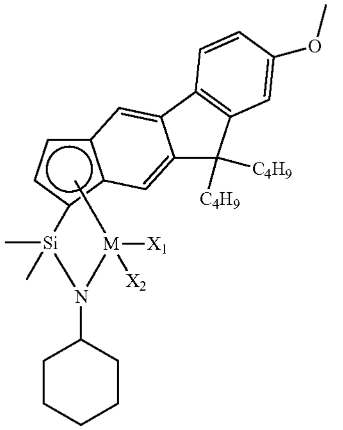
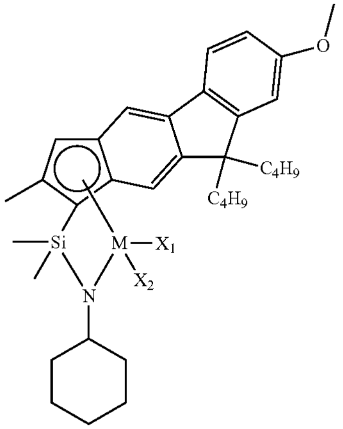
-continued
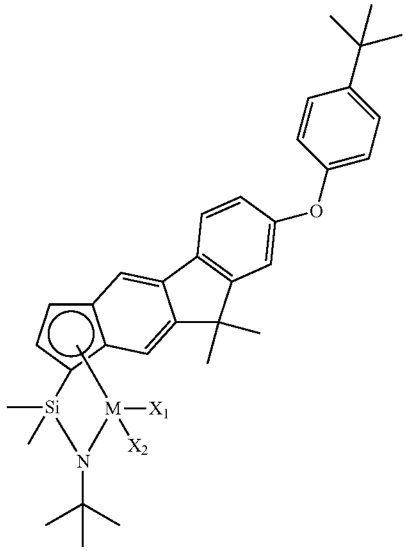
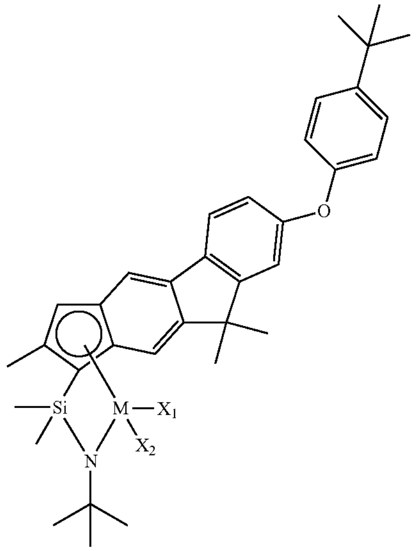
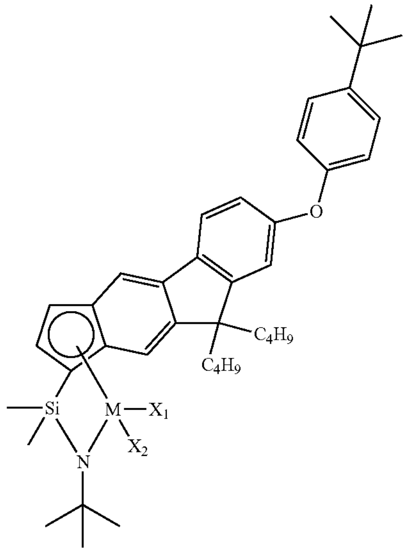

-continued
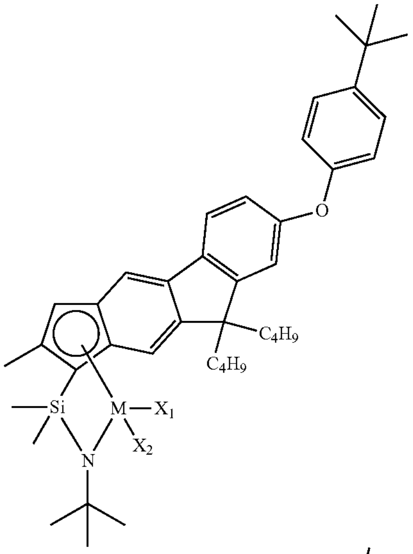
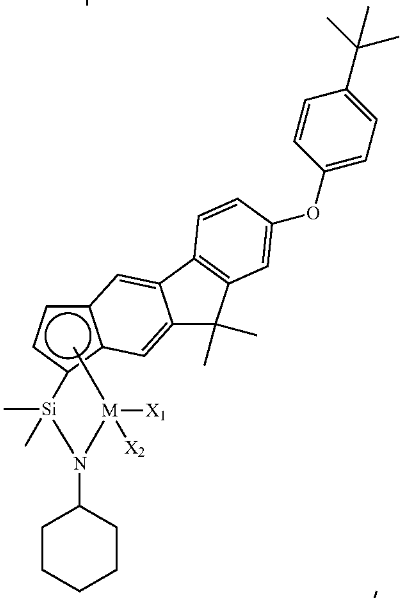
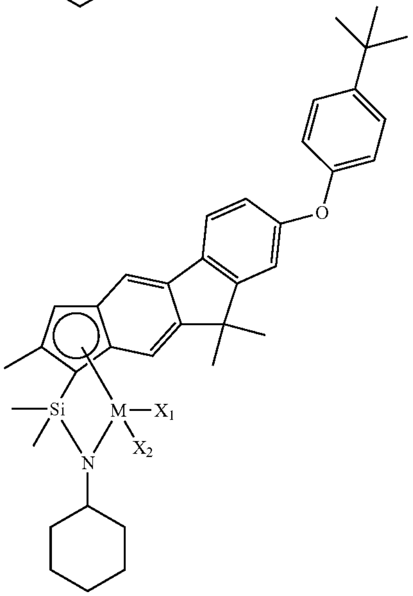
-continued
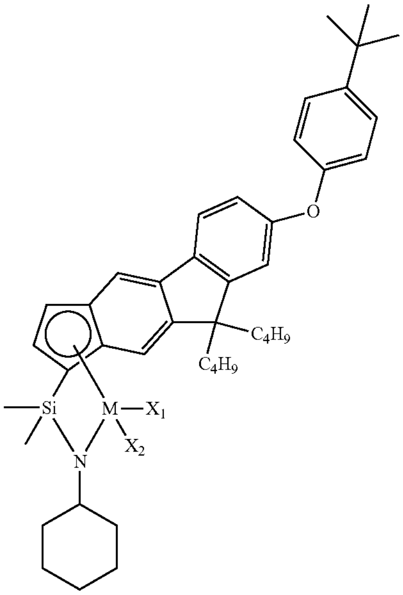
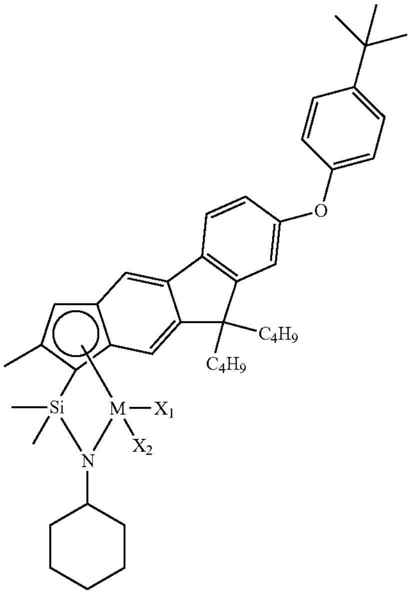
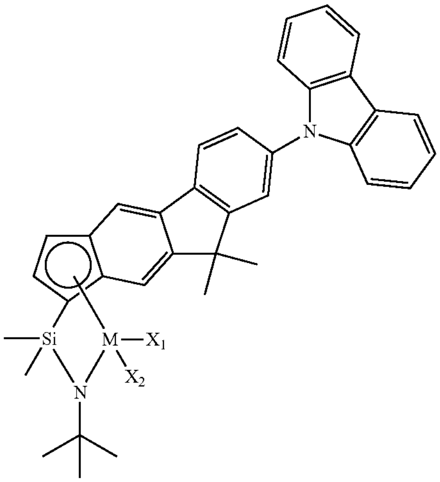

-continued
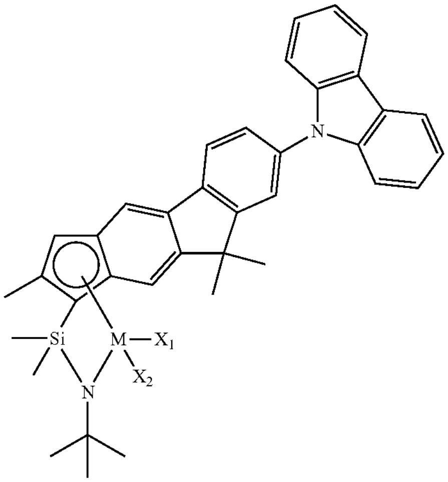
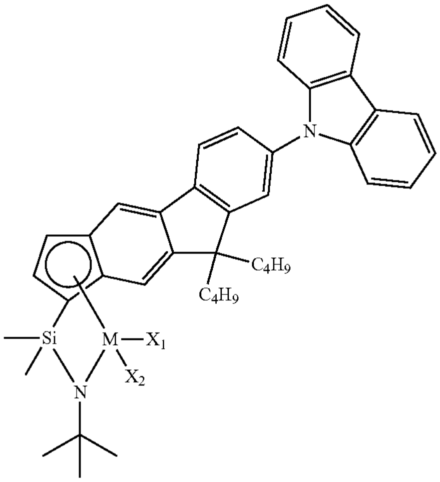
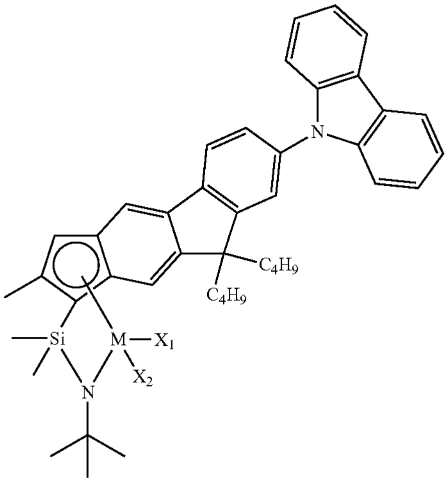
-continued
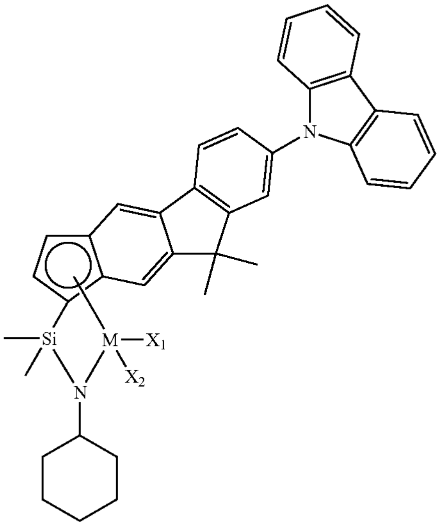
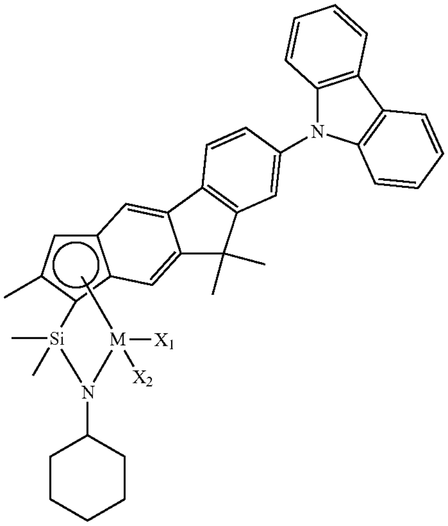
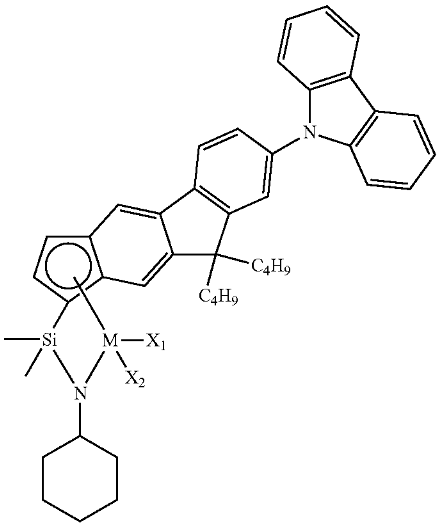

-continued
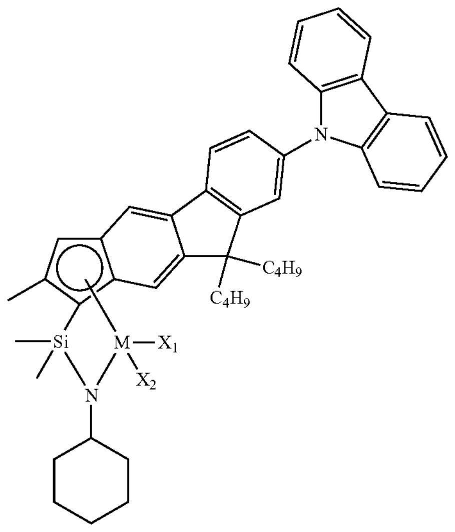
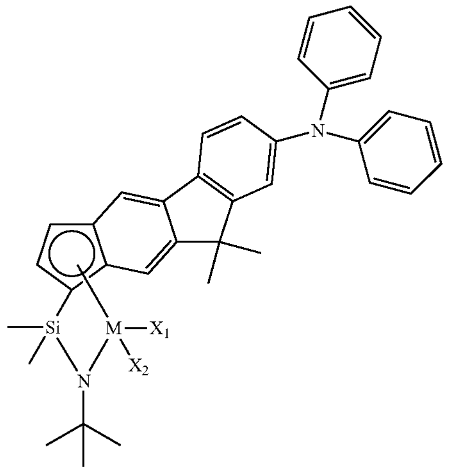
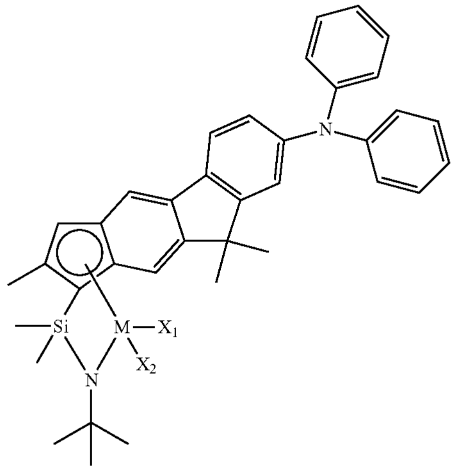
-continued
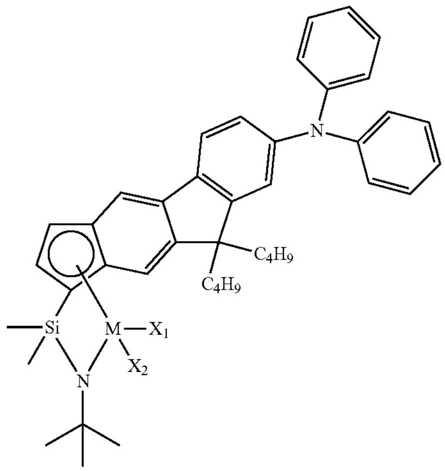
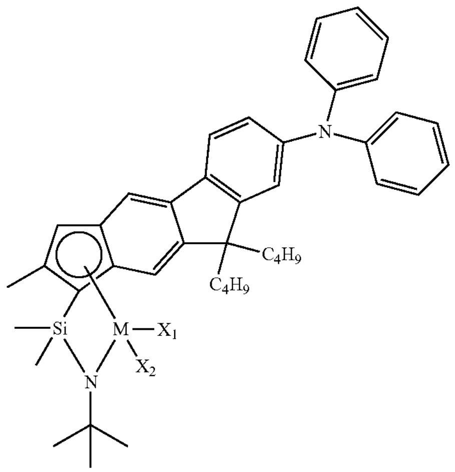
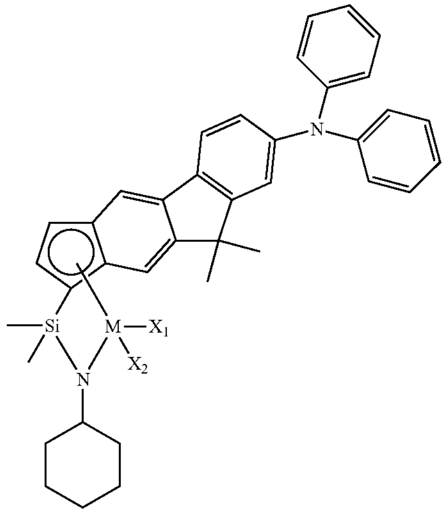

-continued
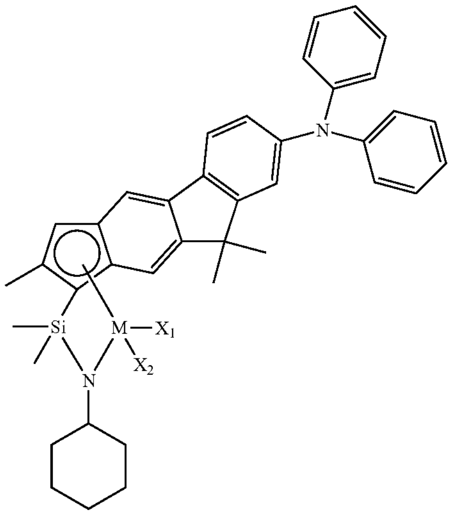
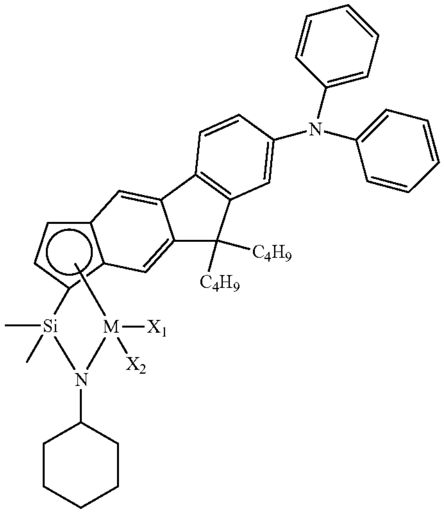
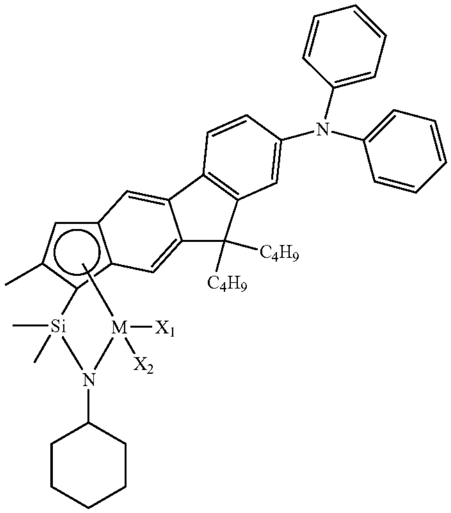
-continued
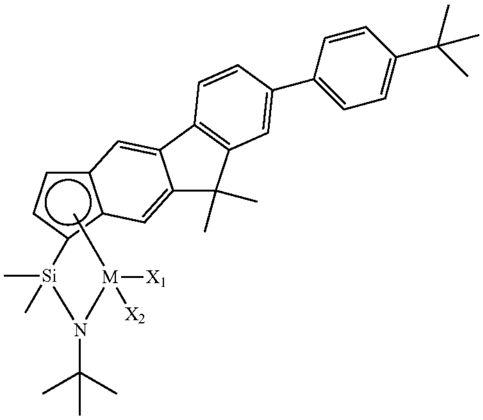
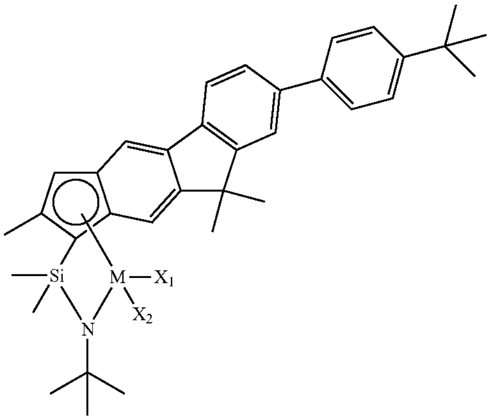
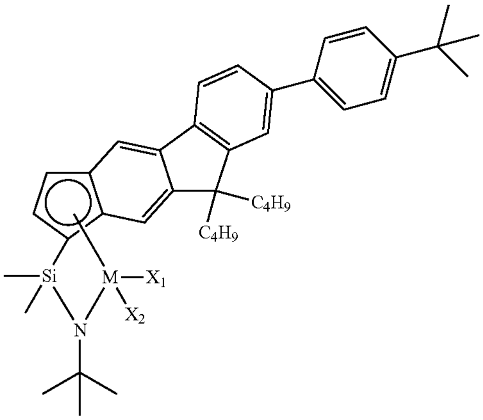
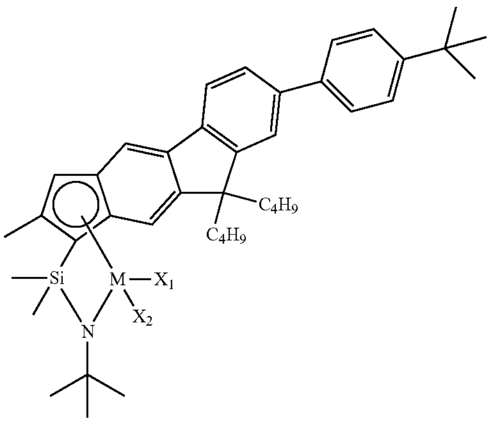

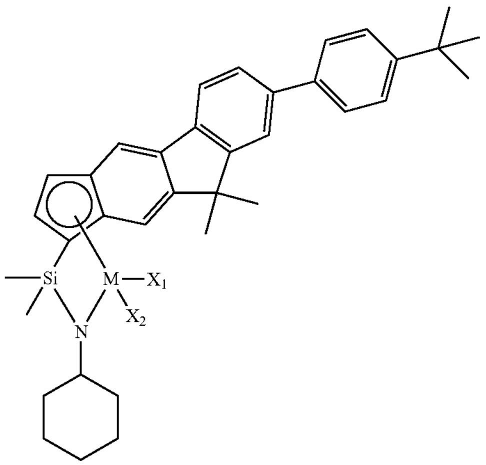
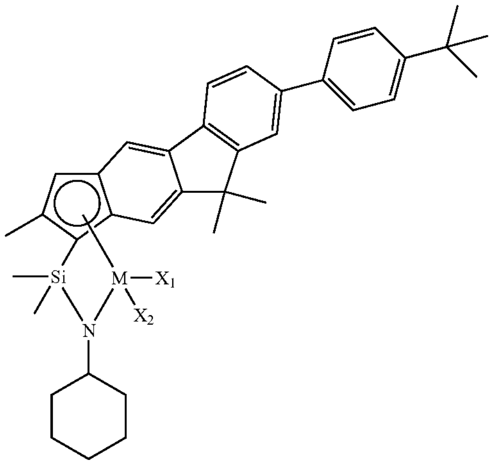
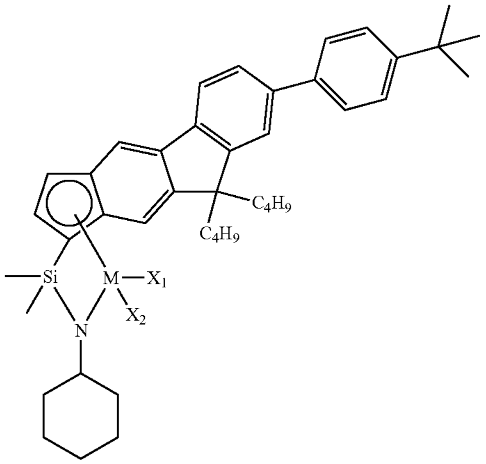
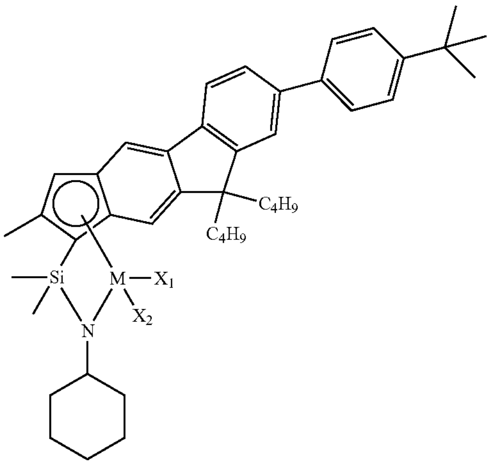
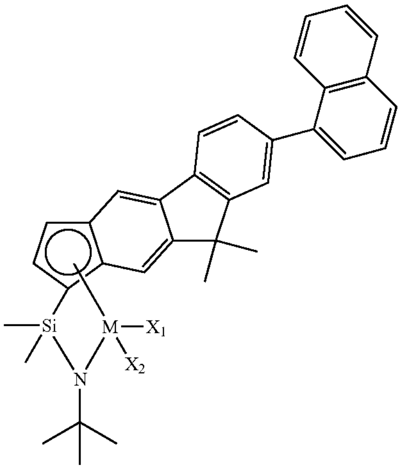
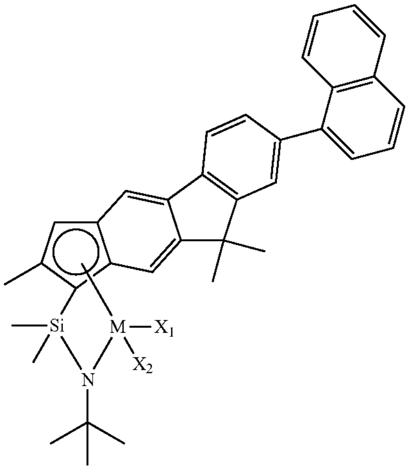

-continued

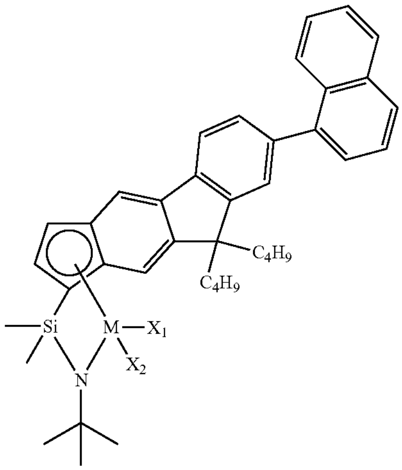

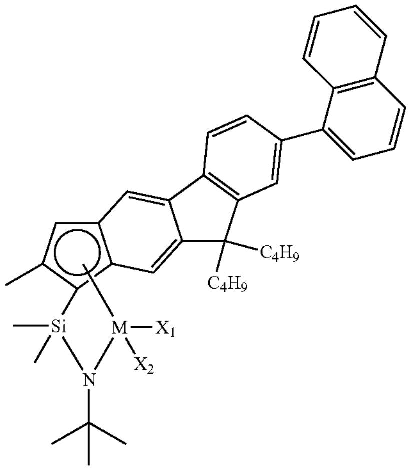

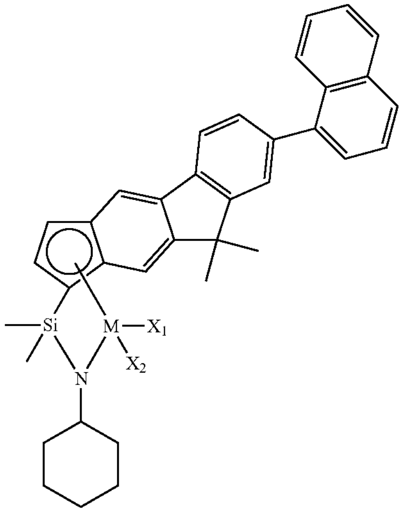

-continued

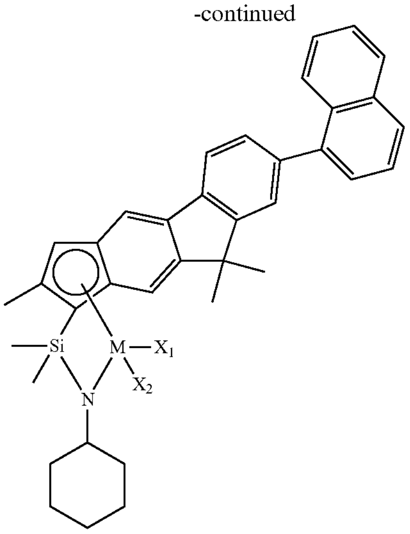

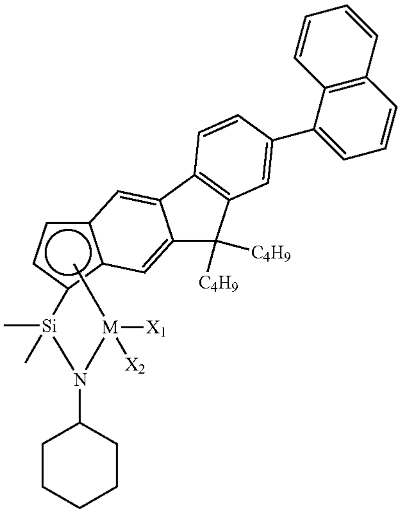

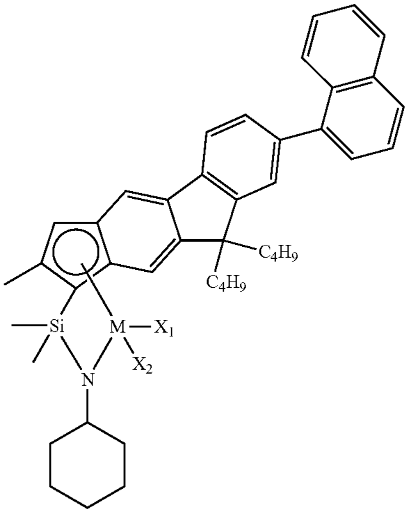

M is Ti, Zr, or Hf; and $X_1$ and $X_2$ each have the same definition as defined in Chemical Formula 1 above.

Meanwhile, in order to be an active catalyst component to be used for preparing an ethylene-α-olefin-diene copolymer, the transition metal compound of Chemical Formula 1 above may preferably act together with, as a cocatalyst, an aluminum compound, a boron compound, or a mixture thereof, which can extract an $X_1$ or $X_2$ ligand from the transition metal compound to cationize the core metal and act as a counterion having weak bond strength, that is, an anion.

That is, the transition metal catalyst composition may, preferably, further contain a cocatalyst selected from an aluminum compound, a boron compound, or a mixture thereof, as well as the transition metal compound of Chemical Formula 1.

The boron compound usable as the cocatalyst in the present invention has been known in U.S. Pat. No. 5,198,401, and may be selected from boron compounds represented by Chemical Formulas 4 to 6 below:

$B(R^{41})_3$ [Chemical Formula 4]

$[R^{42}]^+[B(R^{41})_4]^-$ [Chemical Formula 5]

$[(R^{43})_pZH]^+[B(R^{41})_4]^-$ [Chemical Formula 6]

In Chemical Formulas 4 to 6, B is a boron atom;

$R^{41}$ is phenyl, and the phenyl may be further substituted with 3 to 5 substituents selected from a fluorine atom, (C1-C50)alkyl substituted or unsubstituted with a fluorine atom, or (C1-C50)alkoxy substituted or unsubstituted with a fluorine atom;

$R^{42}$ is (C5-C7)aromatic radical or (C1-C50)alkyl(C6-C20) aryl radical, (C6-C30)aryl(C1-C50)alkyl radical, for example, triphenylmethyl radical;

Z is a nitrogen or phosphorus atom;

$R^{43}$ is (C1-C50)alkyl radical, or anilinium radical substituted with a nitrogen atom and two (C1-C50)alkyl groups; and p is an integer of 2 or 3.

Preferable examples of the boron based cocatalyst may include tris(pentafluorophenyl)borane, tris(2,3,5,6-tetrafluorophenyl)borane, tris(2,3,4,5-tetrafluorophenyl)borane, tris (3,4,5-trifluorophenyl)borane, tris(2,3,4-trifluorophenyl)borane, phenylbis(pentafluorophenyl)borane, tetrakis (pentafluorophenyl)borate, tetrakis(2,3,5,6-tetrafluorophenyl)borate, tetrakis(2,3,4,5-tetrafluorophenyl) borate, tetrakis(3,4,5-trifluorophenyl)borate, tetrakis(2,2,4-trifluorophenyl)borate, phenylbis(pentafluorophenyl)borate, and tetrakis(3,5-bistrifluoromethylphenyl)borate. In addition, certain compounded examples thereof may include ferrocenium tetrakis(pentafluorophenyl)borate, 1,1'-dimethylferrocenium tetrakis(pentafluorophenyl)borate, tetrakis (pentafluorophenyl)borate, triphenylmethyl tetrakis (pentafluorophenyl)borate, triphenylmethyl tetrakis(3,5-bistrifluoromethylphenyl)borate, triethylammonium tetrakis (pentafluorophenyl)borate, tripropylammonium tetrakis (pentafluorophenyl)borate, tri(n-butyl)ammonium tetrakis (pentafluorophenyl)borate, tri(n-butyl)ammonium tetrakis(3,5-bistrifluoromethylphenyl)borate, N,N-dimethylanilinium tetrakis(pentafluorophenyl)borate, N,N-diethylanilinium tetrakis(pentafluorophenyl)borate, N,N-2,4,6-pentamethylanilinium tetrakis(pentafluorophenyl)borate, N,N-dimethylanilinium tetrakis(3,5-bistrifluoromethylphenyl)borate, diisopropylammonium tetrakis(pentafluorophenyl)borate, dicyclohexylammonium tetrakis(pentafluorophenyl)borate, triphenylphosphonium tetrakis(pentafluorophenyl)borate, tri (methylphenyl)phosphonium tetrakis(pentafluorophenyl)borate, and tri(dimethylphenyl)phosphonium tetrakis(pentafluorophenyl)borate. Among them, preferable are N,N-dimethylanilinium tetrakis(pentafluorophenyl)borate, triphenylmethyl tetrakis(pentafluorophenyl)borate, and tris (pentafluorophenyl)borane.

In the present invention, the aluminum compounds usable as the cocatalyst may selected from aluminoxane compounds of Chemical Formula 7 or 8, organic aluminum compounds of Chemical Formula 9, or organic aluminum hydrocarbyloxide compounds of Chemical Formula 10 or 11:

$(—Al(R^{51})—O—)_m$ [Chemical Formula 7]

$(R^{51})_2Al—(—O(R^{51})—)_q—(R^{51})_2$ [Chemical Formula 8]

$(R^{52})_rAl(E)_{3-r}$ [Chemical Formula 9]

$(R^{53})_2AlOR^{54}$ [Chemical Formula 10]

$R^{53}Al(OR^{54})_2$ [Chemical Formula 11]

In Chemical Formulas 7 to 11, $R^{51}$ is (C1-C50)alkyl, preferably methyl or isobutyl; m and q each are independently an integer of 5 to 20; $R^{52}$ and $R^{53}$ each are independently (C1-C50)alkyl; E is a hydrogen or halogen atom; r is an integer of 1 to 3; and $R^{54}$ is (C1-C50)alkyl or (C6-C30)aryl.

Specific examples of the aluminum compound may include aluminoxane compounds, such as methylaluminoxane, modified methylaluminoxane, tetraisobutylaluminoxane; organic aluminum compounds, such as trialkylaluminum including trimethylaluminum, triethylaluminum, tripropylaluminum, triisobutylaluminum, and trihexylaluminum; dialkylaluminum chloride including dimethylaluminum chloride, diethylaluminum chloride, dipropylaluminum chloride, diisobutylaluminum chloride, and dihexylaluminum chloride; alkylaluminum dichloride including methylaluminum dichloride, ethylaluminum dichloride, propylaluminum dichloride, isobutylaluminum dichloride and hexylaluminum dichloride; and dialkylaluminum hydride including dimethylaluminum hydride, diethylaluminum hydride, dipropylaluminum hydride, diisobutylaluminum hydride and dihexylaluminum hydride. Among them, preferable is trialkylaluminum, and more preferable are triethylaluminum and triisobutylaluminum.

In the transition metal catalyst composition containing both of the primary catalyst and the cocatalyst, the transition metal compound as the primary catalyst and the cocatalyst have preferably a molar ratio of transition metal (M):boron atom (B):aluminum atom (Al) in the range of 1:0~100:1~2,000, and more preferably 1:0.5~5:10~500. The above ratio enables the preparation of the ethylene-α-olefin-diene copolymer, and the range of the ratio may be varied depending on purity of reaction.

The method of preparing an ethylene-α-olefin-diene copolymer by using the transition metal catalyst composition may be carried out by contacting the transition metal catalyst, cocatalyst, and ethylene, α-olefin comonomers, and diene monomer, in the presence of appropriate organic solvent. Here, the transition metal compound (primary catalyst) and the cocatalyst components may be separately fed to the reactor, or those components may be mixed in advance and then fed to the reactor. The mixing conditions, such as the order of feeding, temperature, or concentration, are not particularly restricted.

Preferable examples of organic solvents usable in the preparing method may include (C3-C20) hydrocarbon, and specific examples thereof may include butane, isobutane, pentane, hexane, heptane, octane, isooctane, nonane, decane, dodecane, cyclohexane, methylcyclohexane, benzene, toluene, xylene, and the like.

The ethylene-α-olefin-diene copolymer prepared according to the present invention is characterized by having Mooney viscosity (ASTM D1646-94, ML1+4@125° C.) of the entire copolymer in the range of 1 to 250, and containing 30 to 85 wt % of ethylene, 1 to 15 wt % of diene, and the rest of α-olefin.

Specifically, a pressure in a reactor for preparing the ethylene-α-olefin-diene copolymer is 1~1000 atm, and more preferably 6~150 atm. Also, effectively, the polymerization reaction temperature may be 25° C.~200° C., and preferably 50° C.~180° C.

As an α-olefin comonomer used in the present invention, straight or branched chain (C3-C18) α-olefin, (C5-C20) cycloolefin, styrene, or styrene derivatives may be used. Preferable examples of straight or branched chain (C3-C18) α-olefin may include propylene, 1-butene, 1-pentene, 4-methyl-1-pentene, 1-hexene, 1-octene, 1-decease, 1-undecene, 1-dodecene, 1-tetradecene, 1-hexadecene, 1-octadecene, and the like; preferable examples of (C5-C20) cycloolefin may include cyclopentene, cyclohexene, norbornene, phenylnorbornene, and the like; and preferable examples of styrene and derivatives thereof may include styrene, α-methylstyrene, p-methylstyrene, 3-chloromethylstyrene, and the like.

The diene monomer used in the present invention has two double bonds, and straight and branched chain C4~C20 diolefin or C5~C20 cyclodiolefin may be used therefor. Preferable examples of straight or branched chain C4~C20 diolefin may include 1,3-butadiene, 1,4-pentadiene, 2-methyl-1,3-butadiene, 1,4-hexadiene, 1,5-hexadiene, 1,5-heptadiene, 1,6-heptadiene, 1,6-octadiene, 1,7-octadiene, 1,7-nonadiene, 1,8-nonadiene, 1,8-decadiene, 1,9-decadiene, 1,12-tetradecadiene, 1,13-tetradecadiene, 3-methyl-1,4-hexadiene, 3-methyl-1,5-hexadiene, 3-ethyl-1,4-hexadiene, 3-ethyl-1,5-hexadiene, 3,3-dimethyl-1,4-hexadiene, 3,3-dimethyl-1,5-hexadiene, and the like; and preferable examples of C5~C20 cyclodiolefin may include cyclopentadiene, cyclohexadiene, 5-vinyl-2-norbornene, 2,5-norbornadiene, 7-methyl-2,5-norbornadiene, 7-ethyl-2,5-norbornadiene, 7-propyl-2,5-norbornadiene, 7-butyl-2,5-norbornadiene, 7-phenyl-2,5-norbornadiene, 7-hexyl-2,5-norbornadiene, 7,7-dimethyl-2,5-norbornadiene, 7-methyl-7-ethyl-2,5-norbornadiene, 7-chloro-2,5-norbornadiene, 7-bromo-2,5-norbornadiene, 7-fluoro-2,5-norbornadiene, 7,7-dichloro-2,5-norbornadiene, 1-methyl-2,5-norbornadiene, 1-ethyl-2,5-norbornadiene, 1-propyl-2,5-norbornadiene, 1-butyl-2,5-norbornadiene, 1-chloro-2,5-norbornadiene, 1-bromo-2,5-norbornadiene, 5-isopropyl-2-norbornene, 5-vinylidene-2-norbornene (VNB), 5-methylene-2-norbornene (MNB), 5-ethylidene-2-norbornene (ENB), and the like.

As described above, ethylene/propylene/diene (EPDM) elastomer can be excellently prepared by using the catalyst of the present invention. Especially, since high-price diene is easily injected, EPDM products having Mooney viscosity (ASTM D1646-94, ML1+4@ 125° C.) adjusted in the range of 1 to 250, and preferably 10 to 200 can be easily manufactured in an economical manner.

In addition, when the ethylene-α-olefin-diene copolymer according to the present invention is prepared, hydrogen may be used as a molecular weight regulator in order to regulate the molecular weight.

Generally, when solution polymerization is carried out at a high temperature as described above, the catalyst may be transformed or deteriorated due to the increase in temperature, which may cause activity of the catalyst to be lowered, and thus, polymers having desired physical properties can not be obtained. However, since the catalyst composition proposed by the present invention is present in a homogeneous state in the polymerization reactor, the catalyst composition may be preferably employed in a solution polymerization process carried out at a temperature higher than the melting point of the corresponding polymer. However, as disclosed by U.S. Pat. No. 4,752,597, the transition metal compound and cocatalyst may be supported on a porous metal oxide supporter, to thereby be used for slurry polymerization or a gas phase polymerization process, as a heterogeneous catalyst composition.

Advantageous Effects of Invention

As set forth above, in the method of preparing the ethylene-α-olefin-diene copolymer according to the present invention, the transition metal compound based on a cyclopenta[b]fluorenyl group is used as a polymerization catalyst, and thus, ethylene-α-olefin-diene copolymers having a high diene content, a high conversion ratio, and high Mooney viscosity can be prepared under the high-temperature (120° C. or higher) polymerization conditions at a high yield. Further, the catalyst composition containing the transition metal compound can be easily prepared at a high synthesis yield in an economical manner. Further, the transition metal compound or the catalyst composition according to the present invention can have excellent copolymerization reactivity with other olefins while maintaining high catalytic activity even at high temperature due to excellent thermal stability thereof and allow the preparation of high-molecular weight polymers at a high yield, resulting in higher commercial practicability as compared with the already known metallocene and non-metallocene based single activation point catalysts.

MODE FOR THE INVENTION

Hereinafter, the embodiments of the present invention will be described in detail with reference to accompanying Examples, which are not intended to restrict the scope of the invention.

Unless mentioned otherwise, all experiments for synthesizing ligands and catalysts were carried out under nitrogen atmosphere by using standard Schlenk or glove-box techniques. The organic solvents used in the reaction were subjected to reflux over sodium metal and benzophenone to thereby remove moisture, and then distilled immediately before use. $^1$H-NMR analyses of the synthesized ligands and catalysts were performed by using Bruker 500 MHz at room temperature.

Before use, n-heptane, as solvent for polymerization, was passed through a tube filled with molecular sieve 5 Å and activated alumina, and bubbled by high-purity nitrogen, to thereby sufficiently remove moisture, oxygen and other catalyst poison materials. The polymerized polymers were analyzed by the measurement methods described below.

1. Melt flow index (MI)

Measurement was conducted according to ASTM D 2839.

2. Density

Measurement was conducted by using density gradient tubes, according to ASTM D 1505.

3. Melting temperature (Tm)

Measurement was conducted in the conditions of 2$^{nd}$ heating at a rate of 10° C./min under nitrogen atmosphere, by using Dupont DSC 2910.

4. Molecular weight and molecular weight distribution

Measurement was conducted at 135° C. at a rate of 1.0 mL/min in the presence of 1,2,3-trichlorobenzene solvent, by using PL210 GPC equipped with PL Mixed-BX2+preCol, and molecular weight was calibrated by using PL polystyrene standards.

5. α-olefin content (wt %) in copolymer

Measurement was conducted by using 1,2,4-trichlorobenzene/$C_6D_6$ (7/3 by weight) mixture solvent at 120° C. in the $^{13}$C-NMR mode through Bruker DRX500 NMR spectrometer at 125 MHz. (Reference: Randal, J. C. *JMS-Rev. Macromol. Chem. Phys.* 1980, C29, 201)

The ratio of ethylene and α-olefin and the diene content in EPDM polymers were quantified by using an infrared spectrometer.
Preparation Example 1
Preparation of Mixture of Complex 1 and Complex 2
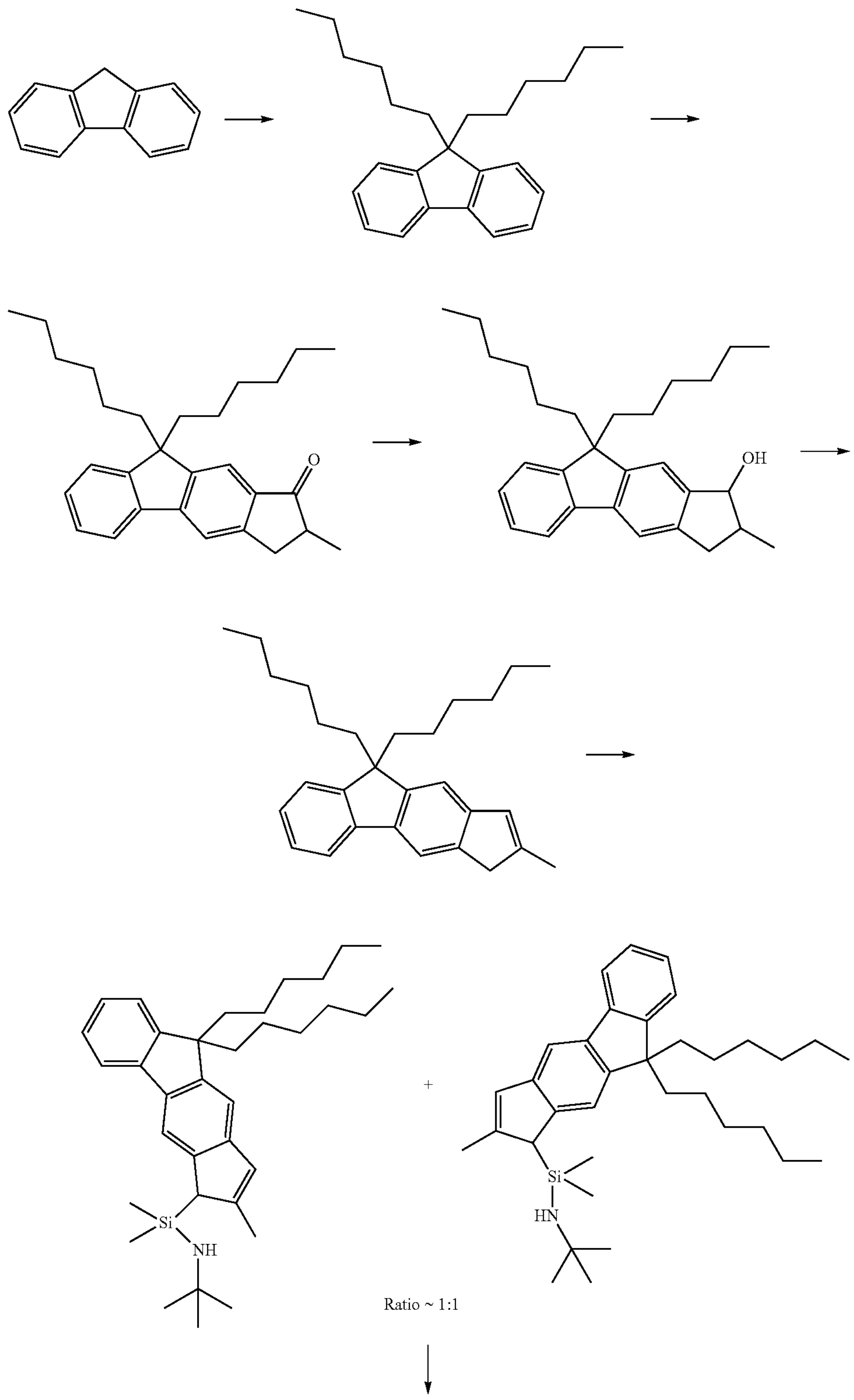

-continued

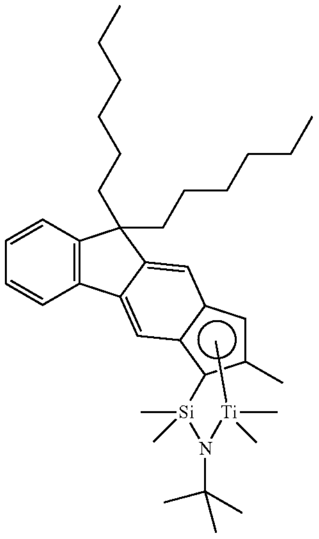

(1)

+

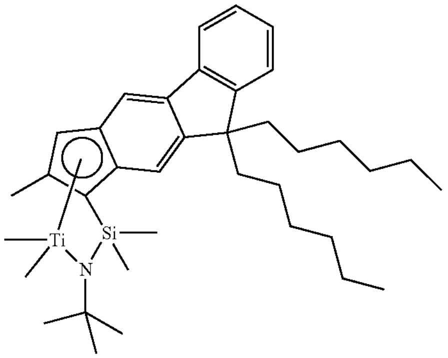

(2)

Synthesis of 9,9-dihexyl-9H-fluorene

A 2000 mL round flask was charged with 9H-fluorene (50 g, 300.1 mmol) and potassium t-butoxide (77.0 g, 721.9 mmol), and then 700 mL of DMSO was slowly injected thereto. 1-Bromohexane (119 g, 721.9 mmol) was slowly added thereto from a dropping funnel under nitrogen atmosphere. The mixture was stirred at room temperature for 24 hours, and the reaction was terminated by addition of 500 mL of distilled water. The organic layer collected by extraction with n-hexane was dried over magnesium sulfate, followed by removal of volatile materials, and then purified with n-hexane by using silica gel column chromatography, followed by drying and long-time storage at room temperature, to thereby obtain 90.0 g of 9,9-dihexyl-9H-fluorene (yield: 72.40%) as solid.

$^1$H-NMR (500 MHz, $CDCl_3$, ppm): δ 0.625-0.628 (m, 4H), 0.759-0.785 (m, 6H), 1.050-1.125 (m, 12H), 1.953-1.983 (t, 4H), 7.293-7.340 (m, 6H), 7.706-7.720 (d, 2H)

Synthesis of 9,9-dihexyl-2-methyl-2,3-dihydrocyclopenta[b]fluoren-1(9H)-one

A 2000 mL round flask was charged with 9,9-dihexyl-9H-fluorene (79 g, 236.2 mmol) and 2-bromo-2-methylpropanoyl bromide (54.3 g, 236.2 mmol), and then dissolved with 600 mL of carbon disulfide inputted thereto. Then, the reactor was cooled with ice water. Under nitrogen atmosphere, aluminum trichloride (78.7 g, 590.4 mmol) was slowly added thereto in ten lots over 2 hours. The mixture was stirred at room temperature for 8 hours, and then the reaction was terminated by addition of 500 mL of distilled water, followed by washing 3 times with 500 mL of distilled water. The organic layer was dried over magnesium sulfate, followed by removal of volatile materials and drying, to thereby obtain 89.0 g of 9,9-dihexyl-2-methyl-2,3-dihydrocyclopenta[b]fluoren-1(9H)-one (yield: 93.6%) as highly viscous oil.

$^1$H-NMR (500 MHz, $CDCl_3$, ppm): δ 0.601-0.627 (m, 4H), 0.741-0.774 (m, 6H), 1.000-1.126 (m, 12H), 1.366-1.380 (d, 3H), 1.961-2.202 (m, 4H), 2.789-2.801 (d, 2H), 3.445-3.498 (m, 1H), 7.375-7.383 (m, 3H), 7.731 (s, 2H), 7.764-7.779 (d, 1H)

Synthesis of 9,9-dihexyl-2-methyl-1,2,3,9-tetrahydrocyclopenta[b]fluoren-1-ol In a 1000 mL round flask, 9,9-dihexyl-2-methyl-2,3-dihydrocyclopenta[b]fluoren-1(9H)-one (85 g, 211.1 mmol) was dissolved in THF 400 mL and ethanol 400 mL, and then stirred. Sodium borohydride ($NaBH_4$) (10 g, 265.0 mmol) was added to the reaction product in five lots, and then stirred for 12 hours. The resultant mixture, after removal of solvent, was dissolved in ethylacetate, and then washed with water three times. The organic layer was dried over magnesium sulfate, followed by removal of volatile materials and drying, to thereby obtain 82.0 g of 9,9-dihexyl-2-methyl-1,2,3,9-tetrahydrocyclopenta[b]fluoren-1-ol (yield: 96.0%) (two isomers), as highly viscous oil.

$^1$H-NMR (500 MHz, $CDCl_3$, ppm): δ 0.628-0.631 (m, 8H), 0.762-0.788 (m, 12H), 1.109-1.136 (m, 24H), 1.198-1.212 (d, 3H), 1.314-1.327 (d, 3H), 1.522-1.535 (d, 1H), 1.830-1.846 (d, 1H), 1.956-1.963 (m, 8H), 2.323-2.352 (m, 1H), 2.525-2.572 (m, 1H), 2.628-2.655 (m, 1H), 2.733-2.779 (m, 1H), 3.011-3.057 (m, 1H), 3.164-3.210 (m, 1H), 4.783-4.812 (t, 1H), 5.052-5.077 (t, 1H), 7.289-7.380 (m, 8H), 7.525 (s, 1H), 7.558 (s, 1H), 7.672-7.685 (d, 2H)

Synthesis of 9,9-dihexyl-2-methyl-3,9-dihydrocyclopenta[b]fluorene

In a 500 mL round flask, 9,9-dihexyl-2-methyl-1,2,3,9-tetrahydrocyclopenta[b]fluoren-1-ol (80 g, 197.7 mmol) and p-toluene sulfonic acid (0.2 g) were dissolved in 320 mL of toluene, and then water was completely removed under reflux with Dean-Stark. The resultant material was cooled to room temperature, and then an aqueous ammonium chloride solution (150 mL) and 200 mL of diethyl ether were injected thereto, followed by separation of the organic layer. The organic layer collected by extracting the residue with diethyl ether was dried over magnesium sulfate, followed by removal of volatile materials, and then purified by using silica gel column chromatography tube, to thereby obtain 74.0 g of 9,9-dihexyl-2-methyl-3,9-dihydrocyclopenta[b]fluorene (yield: 96.8%).

$^1$H-NMR (500 MHz, $CDCl_3$, ppm): δ 0.611-0.671 (m, 4H), 0.755-0.784 (m, 6H), 1.041-1.140 (m, 12H), 1.943-1.976 (m, 4H), 2.200 (s, 3H), 3.373 (s, 2H), 6.556 (s, 1H), 7.208-7.381 (m, 4H), 7.653-7.668 (d, 1H), 7.700 (s, 1H)

Synthesis of N-tert-butyl-1-(9,9-dihexyl-2-methyl-3,9-dihydrocyclopenta[b]fluoren-3-yl)-1,1-dimethylsilanamine and N-tert-butyl-1-(9,9-dihexyl-2-methyl-1,9-dihydrocyclopenta[b]fluoren-1-yl)-1,1-dimethylsilanamine In a 500 mL round flask, 9,9-dihexyl-2-methyl-3,9-dihydrocyclopenta[b]fluorene (40.0 g, 103.5 mmol) was dissolved in 320 mL of diethyl ether, and then the temperature was lowered to −78° C. Then, n-butyllithium (2.5M hexane solution, 42 mL) was slowly injected thereto, followed by stirring at room temperature for 12 hours. After volatile materials were removed by vacuum, 350 mL of n-hexane was added to the mixture to lower the reactor temperature to −78° C., followed by addition of dichlorodimethylsilane (40 g). The temperature was again raised to room temperature, followed by stirring for 24 hours, and then salts were removed through filtering. Then, volatile materials were removed by vacuum. The product was again inputted to a 500 mL round flask, and dissolved in 320 mL of diethyl ether. The temperature was lowered to −78° C., and tert-butylamine (22.7 g, 310.4 mmol) was added thereto. The temperature was raised to room temperature, followed by stirring for 12 hours, and then volatile materials were completely removed by vacuum. Then, 200 mL of n-hexane was added to dissolve the resultant material, and salts were removed through filtering. The solvent was removed, to thereby obtain 48 g of a mixture of N-tert-butyl-1-(9,9-dihexyl-2-methyl-3,9-dihydrocyclopenta[b]fluoren-3-yl)-1,1-dimethylsilanamine and N-tert-butyl-1-(9,9-dihexyl-2-methyl-1,9-dihydrocyclopenta[b]fluoren-1-yl)-1,1-dimethylsilanamine (ratio=~1:1), (yield: 88.9%), as viscous material.

$^1$H-NMR (500 MHz, $C_6D_6$, ppm): δ 0.132 (s, 3H), 0.177-0.198 (d, 6H), 0.270 (s, 1H), 0.804-0.879 (m, 12H), 0.973-1.295 (m, 50H), 2.170-2.348 (m, 14H), 3.398-3.428 (d, 2H), 6.745 (s, 2H), 7.337-7.434 (m, 6H), 7.518-7.908 (m, 6H)

Synthesis of (t-butylamido)dimethyl(9,9-dihexyl-2-methyl-3,9-dihydrocyclopenta[b]fluoren-3-yl)silanetitanium(IV)dimethyl (Complex 1) and (t-butylamido)dimethyl(9,9-dihexyl-2-methyl-1,9-dihydrocyclopenta[b]fluoren-1-yl)silanetitanium(IV) (Complex 2)

In a 500 mL round flask, a mixture of N-tert-butyl-1-(9,9-dihexyl-2-methyl-3,9-dihydrocyclopenta[b]fluoren-3-yl)1,1-dimethylsilanamine and N-tert-butyl-1-(9,9-dihexyl-2-methyl-1,9-dihydrocyclopenta[b]fluoren-1-yl)-1-yl)-1,1-dimethylsilanamine (ratio=~1:1) (8.64 g, 16.75 mmol) was dissolved in 130 mL of diethyl ether, and then the temperature was lowered to −78° C. Then, methyllithium (1.5M diethyl ether solution, 49.4 mL) was slowly injected thereto. The temperature was raised to room temperature, followed by stirring for 12 hours, to prepare lithium salt. In addition, in a dry box, $TiCl_4$ (16.75 mmol) and 150 mL of anhydrous n-hexane were inputted to a 500 mL round flask, and then the temperature was lowered to −78° C. Then, the prepared lithium salt was slowly added thereto. The temperature was again raised to room temperature, followed by stirring for 4 hours, and the solvent was removed by vacuum. The resultant material was dissolved in n-hexane, and then the filtrate was extracted through filtering. Again, the solvent was removed by vacuum, to thereby obtain 8.1 g of a mixture of Complex 1 and Complex 2 (ratio of approximately 1:1), as solid.

$^1$H-NMR (500 MHz, $C_6D_6$, ppm): δ 0.079-0.091 (d, 6H), 0.623-0.645 (d, 6H), 0.813-1.336 (m, 56H), 1.601-1.619 (d, 18H), 2.071-2.514 (m, 14H), 7.025-7.035 (d, 2H), 7.330-8.099 (m, 12H)

Preparation Example 2

Preparation of Mixture of Complex 3 and Complex 4

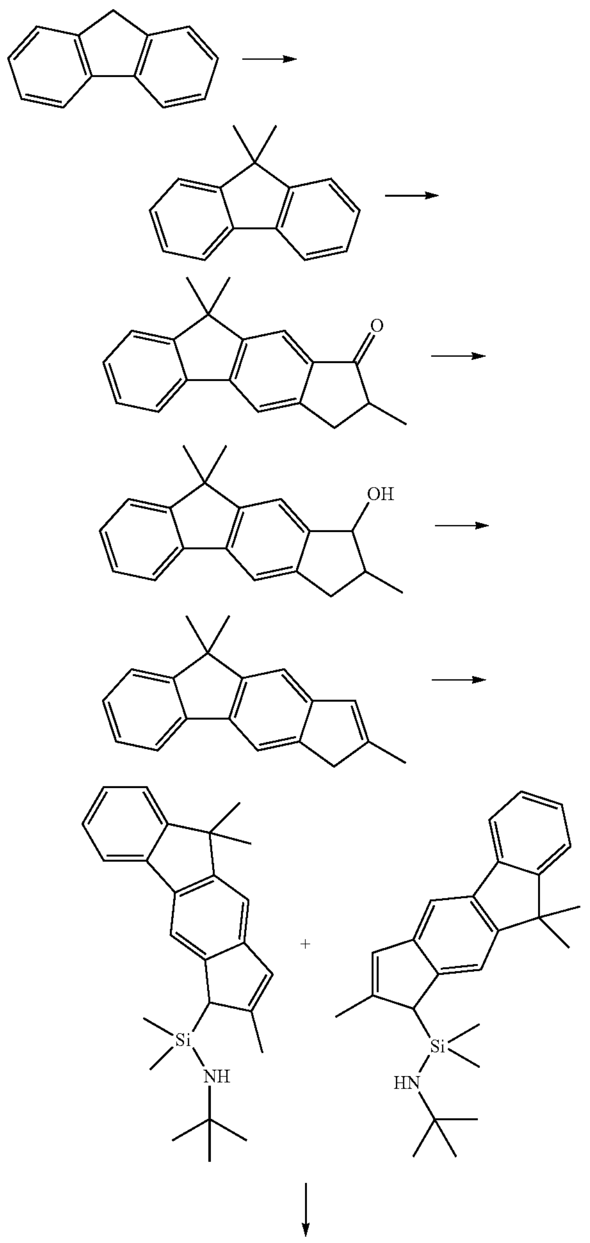

-continued

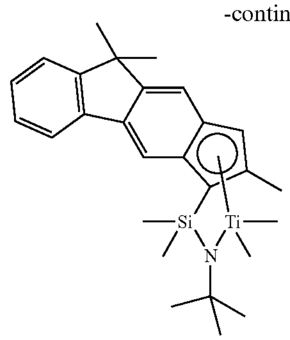

(3)

+

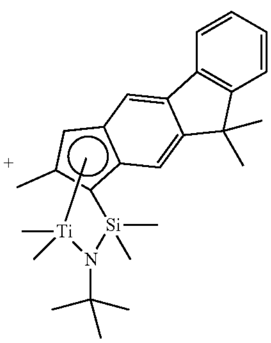

(4)

Synthesis of 9,9-dimethyl-9H-fluorene

A 2000 mL round flask was charged with 9H-fluorene (50 g, 300.1 mmol) and potassium t-butoxide (77.0 g, 721.9 mmol), and then 700 mL of DMSO was slowly injected thereto. Under nitrogen atmosphere, iodomethane (113.5 g, 800 mmol) was slowly dropped through a dropping funnel while the reactor temperature was maintained at 10° C. or lower. The mixture was stirred at room temperature for 24 hours, and the reaction was terminated by addition of 500 mL of distilled water. The organic layer collected by extraction with n-hexane was dried over magnesium sulfate, followed by removal of volatile materials, and then purified with n-hexane by using silica gel column chromatography tube, followed by drying, to thereby obtain 47.5 g of 9,9-dimethyl-9H-fluorene (yield: 81.50%) as white solid.

$^1$H-NMR (500 MHz, $CDCl_3$, ppm): δ 1.547 (s, 6H), 7.368-7.393 (t, 4H), 7.488-7.499 (d, 2H), 7.777-7.791 (d, 2H)

Synthesis of 2,9,9-trimethyl-2,3-dihydrocyclopenta[b]fluoren-1(9H)-one

A 2000 mL round flask was charged with 9,9-dimethyl-9H-fluorene (50 g, 257.4 mmol) and 2-bromo-2-methylpropanoyl bromide (61.0 g, 265.1 mmol), and then dissolved with 700 mL of carbon disulfide inputted thereto. Then, the reactor was cooled with ice water. Under nitrogen atmosphere, aluminum trichloride (85.8 g, 643.4 mmol) was slowly added thereto in ten lots over 2 hours. The mixture was stirred at room temperature for 8 hours, and then the reaction was terminated by addition of 500 mL of distilled water. The resultant mixture was diluted by adding 500 mL of methyl chloride and washed with 500 mL of distilled water three times. The organic layer was dried over magnesium sulfate, followed by removal of volatile materials and drying, and then recrystallized by using methyl chloride and methanol, to thereby obtain 64.0 g of 2,9,9-trimethyl-2,3-dihydrocyclopenta[b]fluoren-1(9H)-one (yield: 94.8%) as white solid.

$^1$H-NMR (500 MHz, $CDCl_3$, ppm): δ 1.354-1.369 (d, 3H), 1.517 (s, 6H), 2.784-2.811 (d, 2H), 3.444-3.496 (m, 1H), 7.376-7.429 (m, 2H), 7.471-7.485 (d, 2H), 7.763 (s, 1H), 7.795-7.808 (d, 2H), 7.832 (s, 1H)

Synthesis of 2,9,9-trimethyl-3,9-dihydrocyclopenta[b]fluorene

In a 1000 mL round flask, 2,9,9-trimethyl-2,3-dihydrocyclopenta[b]fluoren-1(9H)-one (50 g, 190.6 mmol) was dissolved THF 400 mL and ethanol 400 mL, and then stirred. Sodium borohydride ($NaBH_4$) (9.4 g, 247.8 mmol) was added to the reaction product in five lots, and then stirred for 12 hours. The resultant mixture, after removal of solvent, was dissolved in ethylacetate, and then washed with water three times. The organic layer was dried over magnesium sulfate, followed by removal of volatile materials. The dried reaction product was dissolved in 320 mL, of toluene, and then inputted to a 500 mL round flask. After that, p-toluene sulfonic acid (0.2 g) was inputted thereto, and then water was completely removed under reflux with Dean-Stark. The resultant material was cooled to room temperature, and then an aqueous ammonium chloride solution (150 mL) and 200 mL of diethyl ether were injected thereto, followed by separation of the organic layer. The organic layer collected by extracting the residue with diethyl ether was dried over magnesium sulfate, followed by removal of volatile materials, and then purified by using silica gel column chromatography, to thereby obtain 42.0 g of 2,9,9-trimethyl-3,9-dihydrocyclopenta[b]fluorene (yield: 89.42%).

$^1$H-NMR (500 MHz, $CDCl_3$, ppm): δ 1.515 (s, 6H), 2.203 (s, 3H), 3.375 (s, 2H), 6.559 (s, 1H), 7.279-7.332 (m, 3H), 7.425-7.440 (d, 1H), 7.697-7.711 (d, 1H), 7.740 (s, 1H)

Synthesis of N-tert-butyl-1-(2,9,9-trimethyl-3,9-dihydrocyclopenta[b]fluoren-3-yl)-1,1-dimethylsilanamine and N-tert-butyl-1-(2,9,9-trimethyl-1,9-dihydrocyclopenta[b]fluoren-1-yl)-1,1-dimethylsilanamine In a 500 mL round flask, 2,9,9-trimethyl-3,9-dihydrocyclopenta[b]fluorene (15.0 g, 60.9 mmol) was dissolved in 300 mL of diethyl ether, and then the temperature was lowered to −78° C. Then, n-butyllithium (2.5M hexane solution, 24.8 mL) was slowly injected thereto, followed by stirring at room temperature for 12 hours. After volatile materials were removed by vacuum, 350 mL of n-hexane was added to the mixture to lower the reactor temperature to −78° C., followed by addition of dichlorodimethylsilane (23 g). The temperature was again raised to room temperature, followed by stirring for 24 hours, and then salts were removed through filtering. Then, volatile materials were removed by vacuum. The product was again inputted to a 500 mL round flask, and dissolved in 320 mL of diethyl ether. The temperature was lowered to −78° C., and tert-butylamine (16.1 g, 152.2 mmol) was added thereto. The temperature was raised to room temperature, followed by stirring for 12 hours, and then volatile materials were completely removed by vacuum. Then, 200 mL of toluene was added to dissolve the resultant material, and salts were removed through filtering. The solvent was removed, to thereby obtain 21.0 g of a mixture of N-tert-butyl-1-(2,9,9-trimethyl-3,9-dihydrocyclopenta[b]fluoren-3-yl)-1,1- dimethylsilanamine and N-tert-butyl-1-(2,9,9-trimethyl-1,9-dihydrocyclopenta[b]fluoren-1-yl)-1,1-dimethylsilanamine (yield: 91.8%), as a viscous material.

$^1$H-NMR (500 MHz, $C_6D_6$, ppm): δ 0.085-0.098 (d, 6H), 0.229-0.253 (d, 6H), 0.555 (s, 2H), 1.161-1.179 (d, 18H), 1.534-1.559 (d, 12H), 2.304 (s, 6H), 3.385-3.422 (d, 2H), 6.747 (s, 2H), 7.303-8.049 (m, 12H)

Synthesis of (t-butylamido)dimethyl(2,9,9-trimethyl-3,9-dihydrocyclopenta[b]fluoren-3-yl)silanetitanium(IV)dimethyl (Complex 3) and (t-butylamido)dimethyl(2,9,9-trimethyl-1,9-dihydrocyclochloropenta[b]fluoren-1-yl)silanetitanium(IV)dimethyl (Complex 4)

In a 250 mL round flask, a mixture of N-tert-butyl-1-(2,9,9-trimethyl-3,9-dihydrocyclopenta[b]-fluoren-3-yl)-1,1-dimethylsilanamine and N-tert-butyl-1-(2,9,9-trimethyl-1,9-dihydrocyclopenta[b]fluoren-1-yl)-1,1-dimethylsilanamine (10.4 g, 27.69 mmol) was dissolved in 200 mL of diethyl ether, and then the temperature was lowered to −78° C. Then, methyllithium (1.5M diethyl ether solution, 75.6 mL) was slowly injected thereto. The temperature was raised to room temperature, followed by stirring for 12 hours, to prepare lithium salt. In addition, in a dry box, $TiCl_4$ (5.25 g, 27.69 mmol) and 150 mL of anhydrous n-hexane were inputted to a 500 mL round flask, and then the temperature was lowered to −78° C. Then, the prepared lithium salt was slowly added thereto. Again, the temperature was raised to room temperature, followed by stirring for 4 hours, and then the solvent was removed by vacuum. The resultant material was again dissolved in toluene, and then the undissolved part was removed through filtering. Again, toluene was removed by vacuum, to thereby obtain 10.8 g of a mixture of Complex 3 and Complex 4, as solid.

$^1$H-NMR (500 MHz, $C_6D_6$, ppm): δ −0.019-−0.010 (d, 6H), 0.641-0.647 (d, 6H), 0.794-2.212 (m, 48H), 7.004-7.025 (d, 2H), 7.106-8.092 (m, 12H)

Preparation Example 3

Preparation of Mixture of Complex 5 and Complex 6

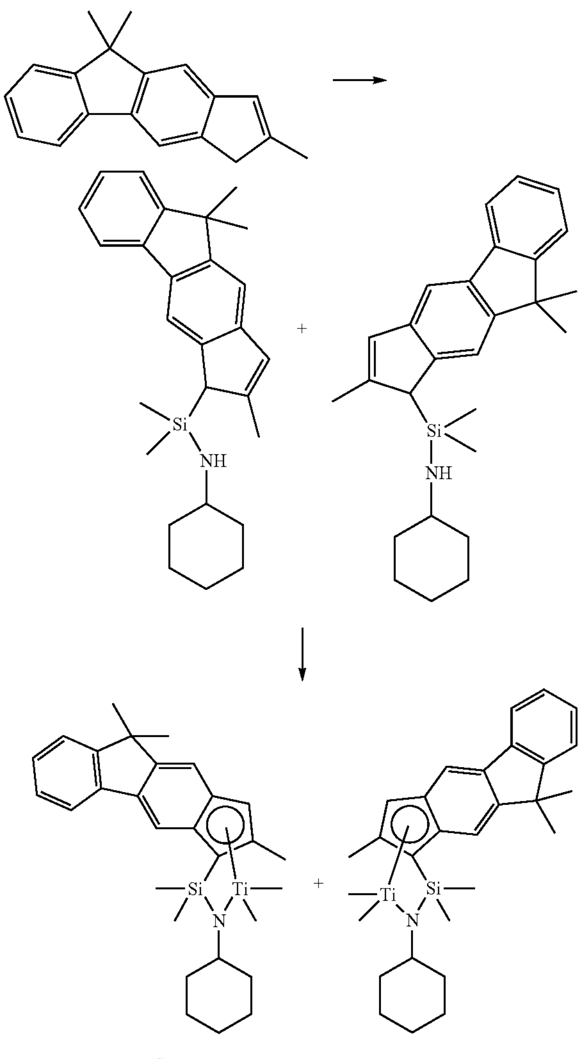

(5) (6)

Synthesis of N-cyclohexyl-1-(2,9,9-trimethyl-3,9-dihydrocyclopenta[b]fluoren-3-yl)-1,1-dimethylsilanamine and N-cyclohexyl-1-(2,9,9-trimethyl-1,9-dihydrocyclopenta[b]fluoren-1-yl)-1,1-dimethylsilanamine In a round flask, 2,9,9-trimethyl-3,9-dihydrocyclopenta[b]fluorene (7.5 g, 30.5 mmol) was dissolved in 300 mL of diethyl ether, and then the temperature was lowered to −78° C. Then, n-butyllithium (2.5M hexane solution, 12.4 mL) was slowly injected thereto, followed by stirring at room temperature for 12 hours. After the volatile materials were removed by vacuum, 200 mL of n-hexane was added to the mixture to lower the reactor temperature to −78° C., followed by addition of dichlorodimethylsilane (11.8 g, 91.4 mmol). The temperature was again raised to room temperature, followed by stirring for 24 hours, and then salts were removed through filtering. Then, volatile materials were removed by vacuum. The product was again inputted to a 200 mL round flask, and dissolved in 150 mL of diethyl ether. The temperature was lowered to −78° C., and cyclohexaneamine (9.05 g, 91.4 mmol) was added thereto. The temperature was raised to room temperature, followed by stirring for 12 hours, and then volatile materials were completely removed by vacuum. Then, 100 mL of toluene was added to dissolve the resultant material, and salts were removed through filtering. The solvent was removed, to thereby obtain 10.6 g of a mixture of N-cyclohexyl-1-(2,9,9-trimethyl-3,9-dihydrocyclopenta[b]fluoren-3-yl)-1,1-dimethylsilanamine and N-cyclohexyl-1-(2,9,9-trimethyl-1,9-dihydrocyclopenta[b]fluoren-1-yl)-1,1-dimethylsilanamine, as viscous material.

Synthesis of (cyclohexylamido)dimethyl(2,9,9-trimethyl-3,9-dihydrocyclopenta[b]fluoren-3-yl)silanetitanium(IV)dimethyl (Complex 5) and (cyclohexylamido)dimethyl(2,9,9-trimethyl-1,9-dihydrocyclochloropenta[b]fluoren-1-yl) silanetitanium(IV)dimethyl (Complex 6)

In a 250 mL of three-neck round flask, the well-dried mixture of N-cyclohexyl-1-(2,9,9-trimethyl-3,9-dihydrocyclopenta[b]fluoren-3-yl)-1,1-dimethylsilanamine and N-cyclohexyl-1-(2,9,9-trimethyl-1,9-dihydrocyclopenta[b]fluoren-1-yl)-1,1-dimethylsilanamine (10.6 g, 26.39 mmol) was dissolved in 200 mL of diethyl ether, and then the temperature was lowered to −78° C. Then, methyllithium (1.5M diethyl ether solution, 72.1 mL) was slowly injected thereto. The temperature was raised to room temperature, followed by stirring for 12 hours, to prepare lithium salt. In addition, in a dry box, $TiCl_4$ (5.00 g, 26.39 mmol) and 150 mL of anhydrous n-hexane were inputted to a 500 mL round flask, and then the temperature was lowered to −78° C. Then, the prepared lithium salt was slowly added thereto. Again, the temperature was raised to room temperature, followed by stirring for 4 hours, and then the solvent was removed by vacuum. The resultant material was again dissolved in toluene, and then the undissolved part was removed through filtering. Again, toluene was removed by vacuum, to thereby obtain 11.5 g of a mixture of Complex 5 and Complex 6, as solid.

$^1$H-NMR (500 MHz, $C_6D_6$, ppm): δ −0.070-−0.049 (d, 6H), 0.628-0.634 (d, 6H), 0.764-2.195 (m, 50H), 4.779 (m, 2H), 6.985-7.002 (d, 2H), 7.100-8.095 (m, 12H)

Preparation Example 4

Preparation of Mixture of Complex 7 and Complex 8

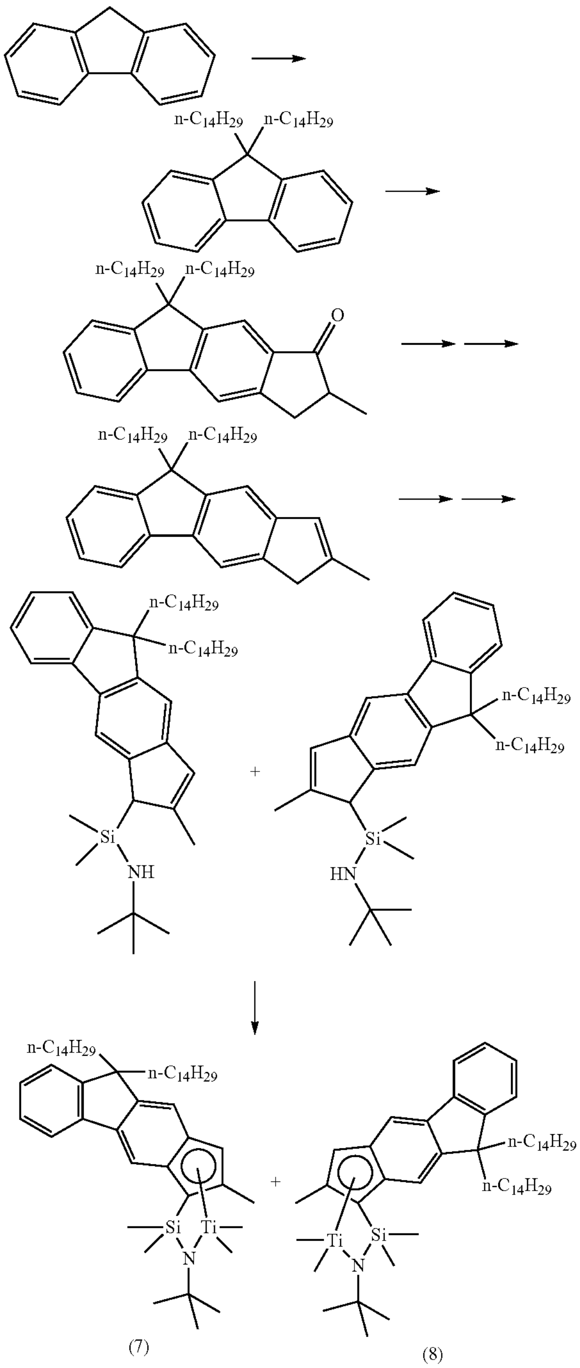

(7) (8)

Synthesis of 9,9-ditetradecyl-9H-fluorene

A 2000 mL round flask was charged with 9H-fluorene (15 g, 90.24 mmol) and potassium tert-butoxide (21.2 g, 198.5 mmol), and then 300 mL of DMSO was slowly injected thereto. Under nitrogen atmosphere, 1-bromotetradecane (54 g, 198.5 mmol) was slowly dropped through a dropping funnel while the reactor temperature was maintained at 10° C. or lower. The mixture was stirred at room temperature for 24 hours, and the reaction was terminated by addition of 500 mL of distilled water. The organic layer collected by extraction with n-hexane was dried over magnesium sulfate, followed by removal of volatile materials, and then purified with n-hexane by using silica gel column chromatography tube, followed by drying, to thereby obtain 42.0 g of 9,9-ditetradecyl-9H-fluorene (yield: 83.26%) as white solid.

$^1$H-NMR (500 MHz, $CDCl_3$, ppm): δ 0.616-0.634 (m, 4H), 0.881-0.909 (m, 6H), 1.051-1.323 (m, 44H), 1.951-1.984 (t, 4H), 7.292-7.355 (m, 6H), 7.708-7.722 (d, 2H)

Synthesis of 2-methyl-9,9-ditetradecyl-2,3-dihydro-cyclopenta[b]fluoren-1(9H)-one A 5000 mL round flask was charged with 9,9-ditetradecyl-9H-fluorene (30 g, 53.7 mmol) and 2-bromo-2-methylpropanoyl bromide (12.7 g, 55.3 mmol), and then dissolved with 300 mL of carbon disulfide inputted thereto. Then, the reactor was cooled with ice water. Under nitrogen atmosphere, aluminum trichloride (15.7 g, 118.1 mmol) was slowly added thereto in ten lots over 2 hours. The mixture was stirred at room temperature for 8 hours, and then the reaction was terminated by addition of 100 mL of distilled water, followed by washing with 500 mL of distilled water three times. The organic layer was dried over magnesium sulfate, followed by removal of volatile materials and drying, to thereby obtain 30.0 g of 2-methyl-9,9-ditetradecyl-2,3-dihydrocyclopenta[b]fluoren-1(9H)-one (yield: 89.1%) as highly viscous oil.

$^1$H-NMR (500 MHz, $CDCl_3$, ppm): δ 0.590 (m, 4H), 0.867-0.895 (m, 6H), 1.024-1.295 (m, 44H), 1.367-1.382 (d, 3H), 1.963-2.204 (t, 4H), 2.792-2.826 (d, 2H), 3.448-3.500 (m, 1H), 7.372-7.400 (m, 3H), 7.726-7.780 (m, 3H)

Synthesis of 2-methyl-9,9-ditetradecyl-3,9-dihydro-cyclopenta[b]fluorene

In a 500 mL round flask, 2 methyl-9,9-ditetradecyl-2,3-dihydrocyclopenta[b]fluoren-1(9H)-one (20 g, 31.9 mmol) was dissolved in 150 mL of THF and 150 mL of ethanol, and then stirred. Sodium borohydride ($NaBH_4$) (1.8 g, 47.8 mmol) was added to the reactant in five lots, and then stirred for 12 hours. The resultant mixture, after removal of solvent, was dissolved in ethylacetate, and then washed with water three times. The organic layer was dried over magnesium sulfate, followed by removal of volatile materials. The dried reactant was dissolved in 150 mL of toluene, and then inputted to a round flask. After that, p-toluene sulfonic acid (0.08 g) was inputted thereto, and then water was completely removed under reflux with Dean-Stark. The resultant material was cooled to room temperature, and then an aqueous ammonium chloride solution (100 mL) and 200 mL of diethyl ether were injected thereto, followed by separation of the organic layer. The organic layer collected by extracting the residue with diethyl ether was dried over magnesium sulfate, followed by removal of volatile materials, and then purified by using silica gel column chromatography, to thereby obtain 15.3 g of 2 methyl-9,9-ditetradecyl-3,9-dihydrocyclopenta[b]fluorene (yield: 78.5%).

$^1$H-NMR (500 MHz, $CDCl_3$, ppm): δ 0.649-0.665 (m, 4H), 0.891-0.918 (m, 6H), 1.059-1.319 (m, 44H), 1.953-1.986 (t, 4H), 2.206 (s, 3H), 3.378 (s, 2H), 6.562 (s, 1H), 7.237-7.332 (m, 4H), 7.663-7.678 (d, 1H), 7.710 (s, 1H)

Synthesis of N-tert-butyl-1-(9,9-ditetradecyl-2-methyl-3,9-dihydrocyclopenta[b]fluoren-3-yl)-1,1-dimethylsilanamine and N-tert-butyl-1-(9,9-ditetradecyl-2-methyl-1,9-dihydrocyclopenta[b]fluoren-1-yl)-1,1-dimethylsilanamine In a 250 mL round flask, 2-methyl-9,9-ditetradecyl-3,9-dihydrocyclopenta[b]fluorene (4.9 g, 8.0 mmol) was dissolved in 100 mL of anhydrous diethyl ether, and then the temperature was lowered to −78° C. Then, n-butyllithium (1.6M hexane solution, 5.5 mL) was slowly injected thereto, followed by stirring at room temperature for 12 hours. After volatile materials were removed by vacuum, 100 mL of n-hexane was added to the mixture to lower the reactor temperature to −78° C., followed by addition of dichlorodimethylsilane (2.9 g). The temperature was again raised to room temperature, followed by stirring for 24 hours, and then salts were removed through filtering. Then, volatile materials were removed by vacuum. The product was again inputted to a 250 mL round flask, and dissolved in 100 mL of diethyl ether. The temperature was lowered to −78° C., and tert-butylamine (1.8 g, 24.1 mmol) was added thereto. The temperature was raised to room temperature, followed by stirring for 12 hours, and then volatile materials were completely removed by vacuum. Then, 200 mL of n-hexane was added to dissolve the resultant material, and salts were removed through filtering. The solvent was removed, to thereby obtain 5.5 g of a mixture of N-tert-butyl-1-(9,9-ditetradecyl-2-methyl-3,9-dihydrocyclopenta[b]fluoren-3-yl)-1,1-dimethylsilanamine and N-tert-butyl-1-(9,9-ditetradecyl-2-methyl-1,9-dihydrocyclopenta[b]fluoren-1-yl)-1,1-dimethylsilanamine (ratio=~1:1), (yield: 92.7%), as high viscous material.

$^1$H-NMR (500 MHz, $C_6D_6$, ppm): δ 0.145 (s, 3H), 0.183-0.204 (d, 6H), 0.290 (s, 3H), 0.552 (s, 1H), 0.603 (s, 1H), 0.998-1.370 (m, 126H), 2.228-2.301 (m, 14H), 3.408-3.435 (d, 2H), 6.749-6.760 (d, 2H), 7.353-7.461 (m, 6H), 7.546-8.073 (m, 6H)

Synthesis of (t-butylamido)dimethyl(9,9-ditetradecyl-2-methyl-3,9-dihydrocyclopenta[b]fluoren-3-yl) silanetitanium(IV)dimethyl (Complex 7) and (t-butylamido)dimethyl(9,9-ditetradecyl-2-methyl-1,9-dihydrocyclopenta[b]fluoren-1-yl)silanetitanium(IV) dimethyl (Complex 8)

In a 250 mL round flask, a mixture of N-tert-butyl-1-(9,9-ditetradecyl-2-methyl-3,9-dihydrocyclopenta[b]fluoren-3-yl)-1,1-dimethylsilanamine and N-tert-butyl-1-(9,9-ditetradecyl-2-methyl-1,9-dihydrocyclopenta[b]fluoren-1-yl)-1,1-dimethylsilanamine (ratio=~1:1) (5.0 g, 6.8 mmol) was dissolved in 100 mL of diethyl ether, and then the temperature was lowered to −78° C. Then, methyllithium (1.5M diethyl ether solution, 18.5 mL) was slowly injected thereto. The temperature was raised to room temperature, followed by stirring for 12 hours, to prepare lithium salt. In addition, in a dry box, $TiCl_4$ (16.75 mmol) and 50 mL of anhydrous n-hexane were inputted to a 250 mL round flask, and then the temperature was lowered to −78° C. Then, the prepared lithium salt was slowly added thereto. The temperature was again raised to room temperature, followed by stirring for 4 hours, and the solvent was removed by vacuum. The resultant material was dissolved in n-hexane, and then the filtrate was extracted through filtering. Again, n-hexane was removed by vacuum, to thereby obtain 5.2 g of a mixture of Complex 7 and Complex 8 (ratio of approximately 1:1), as solid.

$^1$H-NMR (500 MHz, $C_6D_6$, ppm): δ 0.093-0.104 (d, 6H), 0.630-0.647 (d, 6H), 0.856-1.392 (m, 120H), 1.609-1.643 (d, 18H), 2.095-2.214 (m, 14H), 7.023-7.041 (d, 2H), 7.305-8.097 (m, 12H)

Comparative Preparation Example 1

Preparation of (t-butylamido)dimethyl(2-methylindenyl)silanetitanium(IV)dimethyl

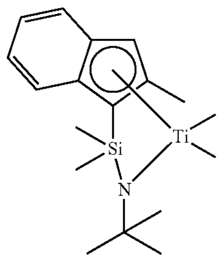

It was prepared starting from 2-methylindene by a synthesizing method disclosed in the reference "Journal of Organometallic Chemistry 666 (2002) 5-26".

Preparation of EPDM

Example 1-Example 8

Preparation of EPDM by Continuous Solution Polymerization Process

Ethylene, propylene, and 5-ethylidene-2-norbornene (ENB) were polymerized through the catalyst prepared in the present invention by using a continuous type polymerization apparatus, to thereby prepare EPDM. The catalysts synthesized in Preparation Examples 1 to 4 and Comparative Preparation Example 1 were used as single activation point catalysts, and cyclohexane was used as the solvent. The amounts of catalysts used are described in Table 1 below. Ti, Al, and B indicate a single activation point catalyst, triisobutyl aluminum as a cocatalyst, and triphenylmethyl tetrakis(pentafluorophenyl)borate, respectively. The respective catalysts were injected while they each were dissolved in toluene in a concentration of 0.2 g/l, and the synthesis was carried out by using propylene as an α-olefin comonomer and 5-ethylidene-2-norbornene (ENB) as a diene monomer. The conversion ratio of the reactor may be estimated through reaction conditions and temperature gradient in the reactor when one kind of polymer was prepared by polymerization in the respective reaction conditions. The molecular weight, in the case of a single activation point catalyst, was controlled as a function of the reactor temperature, conversion ratio, and hydrogen content, and detailed polymerization conditions and polymerization results are shown in Table 1 below.

TABLE 1

| | | Example 1 | Example 2 | Example 3 | Example 4 | Example 5 | Example 6 |
|---|---|---|---|---|---|---|---|
| Polymerization conditions | Catalyst | Preparation Example 1 | Preparation Example 1 | Preparation Example 1 | Preparation Example 2 | Preparation Example 2 | Preparation Example 2 |
| | Total solution flux (kg/h) | 5 | 5 | 5 | 5 | 5 | 5 |
| | Feeding amount of ethylene (wt %) | 5 | 5 | 5 | 5 | 5 | 5 |
| | Feeding weight ratio of monomer (C2/C3/ENB) | 1/1.5/0.3 | 1/1/0.3 | 1/0.7/0.3 | 1/1.5/0.3 | 1/1/0.3 | 1/0.7/0.3 |
| | Feeding amount of Ti (μmol/kg) | 7 | 7 | 7 | 10 | 10 | 10 |
| | Al/Ti ratio | 70 | 70 | 70 | 50 | 50 | 50 |
| | B/Ti ratio | 2.5 | 2.5 | 2.5 | 2.5 | 2.5 | 2.5 |
| | Reaction Temperature (° C.) | 120 | 120 | 120 | 100 | 100 | 100 |
| Polymerization results | C2 weight % | 57.74 | 64.89 | 71.53 | 51.66 | 59.39 | 66.02 |
| | ENB weight % | 7.1 | 8.1 | 8.9 | 9.5 | 10.1 | 10.5 |
| | C2 conversion ratio (%) | 66.7 | 66.3 | 69.2 | 90.0 | 84.3 | 81.7 |
| | Mooney Viscosity (@125° C.) | 30.6 | 52.4 | 76.2 | 70.7 | 109.6 | 141.6 |

| | | Example 7 | Example 8 | Comparative Example 1 | Comparative Example 2 | Comparative Example 3 |
|---|---|---|---|---|---|---|
| Polymerization conditions | Catalyst | Preparation Example 3 | Preparation Example 4 | Comparative Preparation Example 1 | Comparative Preparation Example 1 | Comparative Preparation Example 1 |
| | Total solution flux (kg/h) | 5 | 5 | 5 | 5 | 5 |
| | Feeding amount of ethylene (wt %) | 5 | 5 | 5 | 5 | 5 |
| | Feeding weight ratio of monomer (C2/C3/ENB) | 1/1/0.3 | 1/0.7/0.3 | 1/1.5/0.3 | 1/1/0.3 | 1/0.7/0.3 |
| | Feeding amount of Ti (μmol/kg) | 10 | 7 | 15 | 15 | 15 |
| | Al/Ti ratio | 50 | 50 | 35 | 35 | 35 |
| | B/Ti ratio | 2.5 | 2.5 | 2.5 | 2.5 | 2.5 |
| | Reaction Temperature (° C.) | 90 | 120 | 120 | 120 | 120 |
| Polymerization results | C2 weight % | 57.6 | 69.6 | 56.53 | 65.08 | 64.78 |
| | ENB weight % | 7.85 | 9.82 | 5.0 | 5.2 | 5.2 |
| | C2 conversion ratio (%) | 44.0 | 80.5 | 46.4 | 50.1 | 52.6 |
| | Mooney Viscosity (@125° C.) | 34.1 | 28.0 | 17.6 | 16.2 | 16.7 |

Ti: Ti in the single activation point catalyst

Al: Triisobutylaluminum as cocatalyst

B: Triphenylmethyl tetrakis(pentafluorophenyl)borate as cocatalyst.

It can be seen from Table 1 above that, in Examples 1 to 8 prepared by using the catalyst developed in the present invention, EPDM products allowing easy injection of comonomers (C3 and ENB) and having a high conversion ratio and high Mooney viscosity can be prepared even under the high-temperature polymerization conditions. Therefore, it can be confirmed that an EPDM polymerization system using the single activation point catalyst developed in the present invention is a more economical catalyst system than the EPDM polymerization system using the existing single activation catalyst due to easy control of physical properties (molecular weight and composition of comonomer) of products and high activity.

The present invention has been described in detail with reference to examples as set forth above, but those skilled in the art to which the invention pertains can make various modifications without departing from the spirit and scope of the invention defined in appended claims. Therefore, alterations and modifications of the examples of the present invention would not depart from the technique of the present invention.

INDUSTRIAL APPLICABILITY

As set forth above, in the method of preparing the ethylene-α-olefin-diene copolymer according to the present invention, the transition metal compound based on a cyclopenta[b]fluorenyl group is used as a polymerization catalyst, and thus, ethylene-α-olefin-diene copolymers having a high diene content, a high conversion ratio, and high Mooney viscosity can be prepared under the high-temperature (120° C. or higher) polymerization conditions at a high yield. Further, the catalyst composition containing the transition metal compound can be easily prepared at a high synthesis yield in an economical manner. Further, the transition metal compound or the catalyst composition according to the present invention can have excellent copolymerization reactivity with other olefins while maintaining high catalytic activity even at high temperature due to excellent thermal stability thereof and allow the preparation of high-molecular weight polymers at a high yield, resulting in higher commercial practicability as compared with the already known metallocene and non-metallocene based single activation point catalysts.

The invention claimed is:

1. A method of preparing an ethylene-α-olefin-diene copolymer by using a transition metal catalyst composition including a transition metal compound represented by Chemical Formula 1 below:

[Chemical Formula 1]

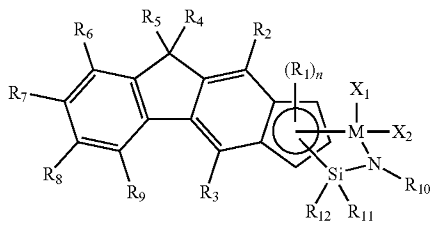

In Chemical Formula 1, M is a Group 4 transition metal in the Periodic Table of Elements;

n is an integer of 1 or 2, each $R_1$ may be the same or different when n is 2;

$R_1$ is hydrogen, (C1-C50)alkyl, halo(C1-C50)alkyl, (C3-C50)cycloalkyl, (C6-C30)aryl, (C6-C30)aryl(C1-C50)alkyl, ((C1-C50)alkyl(C6-C30)aryl)(C1-C50)alkyl, —$NR^aR^b$, —$SiR^cR^dR^e$, or 5- through 7-membered N-heterocycloalkyl containing at least one nitrogen atom;

$R_2$ and $R_3$ each are independently hydrogen, (C1-C50)alkyl, (C1-C50)alkoxy, halo(C1-C50)alkyl, (C3-C50)cycloalkyl, (C6-C30)aryl, (C6-C30)aryloxy, (C1-C50)alkyl(C6-C30)aryloxy, (C6-C30)aryl(C1-C50)alkyl, ((C1-C50)alkyl(C6-C30)aryl)(C1-C50)alkyl, —$NR^aR^b$ or —$Si^cR^dR^e$;

$R_4$, $R_5$, $R_{10}$, $R_{11}$ and $R_{12}$ each are independently (C1-C50)alkyl, halo(C1-C50)alkyl, (C3-C50)cycloalkyl, (C6-C30)aryl, (C6-C30)aryl(C1-C50)alkyl, ((C1-C50)alkyl(C6-C30)aryl)(C1-C50)alkyl, —$NR^aR^b$, or —$SiR^cR^dR^e$, and $R_{11}$ and $R_{12}$ are optionally linked via (C4-C7)alkylene to form a ring;

$R_6$, $R_7$, $R_8$ and $R_9$ each are independently hydrogen, (C1-C50)alkyl, halo(C1-C50)alkyl, (C3-C50)cycloalkyl, (C1-C50)alkoxy, (C6-C30)aryl, (C6-C30)aryl(C1-C50)alkyl, ((C1-C50)alkyl(C6-C30)aryl)(C1-C50)alkyl, (C6-C30)aryloxy, (C1-C50)alkyl(C6-C30)aryloxy, N-carbazolyl, —$NR^aR^b$, or —$SiR^cR^dR^e$, or are optionally linked to an adjacent substituent via (C1-C5)alkylene to form a ring, and at least one —$CH_2$— of the alkylene is optionally substituted by a hetero atom selected from —O—, —S—, and —NR'—, and the alkylene is optionally further substituted with (C1-C50)alkyl;

aryl of $R_1$ to $R_{12}$ is optionally further substituted with at least one substituent selected from the group consisting of (C1-C50)alkyl, halo(C1-C50)alkyl, (C1-C50)alkoxy, (C6-C30)aryloxy, (C6-C30)aryl, (C1-C50)alkyl(C6-C30)aryl, and (C6-C30)aryl(C1-C50)alkyl;

R' and $R^a$ to $R^e$ each are independently (C1-C50)alkyl or (C6-C30)aryl; and $X_1$ and $X_2$ each are independently halogen, (C1-C50)alkyl, (C2-C50)alkenyl, (C3-C50)cycloalkyl, (C6-C30)aryl, (C6-C30)aryl(C1-C50)alkyl, ((C1-C50)alkyl(C6-C30)aryl)(C1-C50)alkyl, (C1-C50)alkoxy, (C6-C30)aryloxy, (C1-C50)alkyl(C6-C30)aryloxy, (C1-C50)alkoxy(C6-C30)aryloxy, (C1-C50)alkylidene, or an anion or dianion ligand consisting of 60 or less atoms containing N, P, O, S, Si, and halogen, except hydrogen, provided that one of $X_1$ and $X_2$ is a dianion ligand, the other is ignored.

2. The method of claim 1, wherein the transition metal compound is represented by Chemical Formula 2 or 3 below:

[Chemical Formula 2]

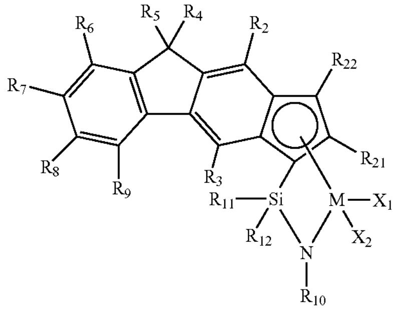

[Chemical Formula 3]

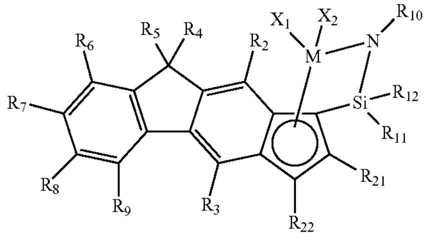

In Chemical Formulas 2 and 3, M, $R_2$ to $R_{12}$, $X_1$ and $X_2$ have the same definition in Chemical Formula 1 of claim 1; $R_{21}$ and $R_{22}$ each are independently hydrogen, (C1-C50)alkyl, halo(C1-C50)alkyl, (C3-C50)cycloalkyl, (C6-C30)aryl, (C6-C30)aryl(C1-C50)alkyl, ((C1-C50)alkyl(C6-C30)aryl)(C1-C50)alkyl, —$NR^aR^b$, —$SiR^cR^dR^e$, or 5- through 7-membered N-heterocycloalkyl containing at least one nitrogen atom; aryls of $R_{21}$ and $R_{22}$ are optionally further substituted with at least one substituent selected from the group consisting of halogen, (C1-C50)alkyl, halo(C1-C50)alkyl, (C1-C50)alkoxy, (C6-C30)aryloxy, (C6-C30)aryl, (C1-C50)alkyl(C6-C30)aryl, and (C6-C30)aryl(C1-C50)alkyl; and $R^a$ to $R^e$ each are independently (C1-C50)alkyl or (C6-C30)aryl.

3. The method of claim 2, wherein the transition metal compound is selected from the compounds below:

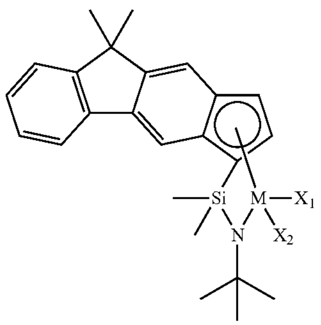

-continued
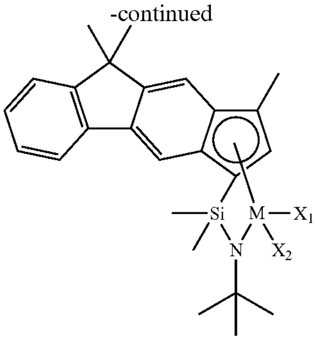
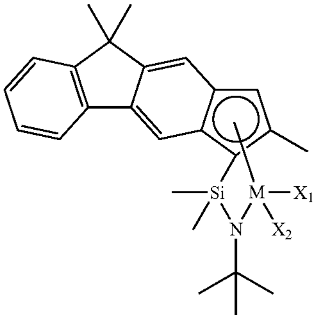
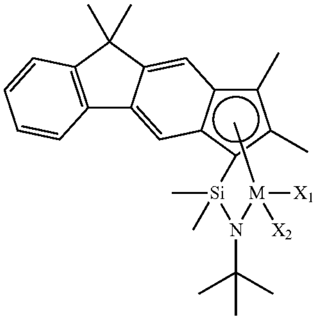
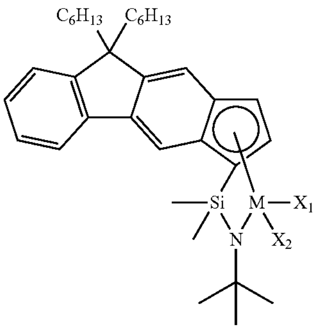
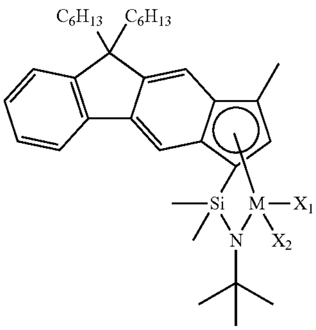
-continued
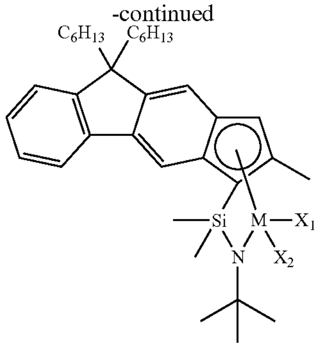
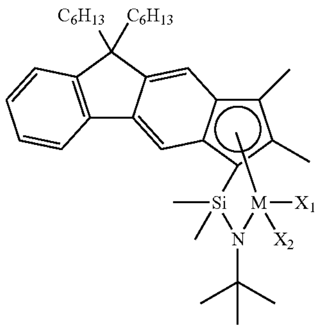
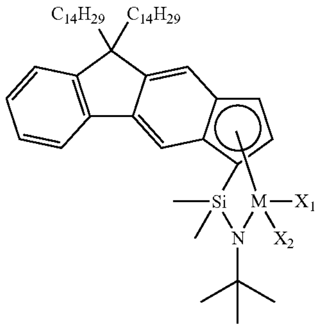
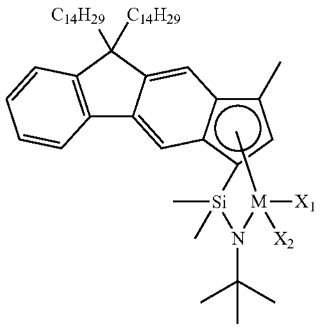
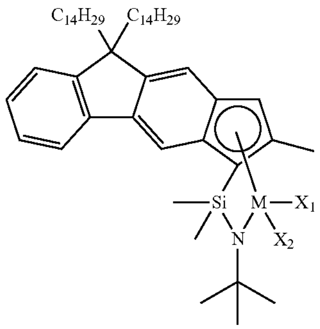

-continued
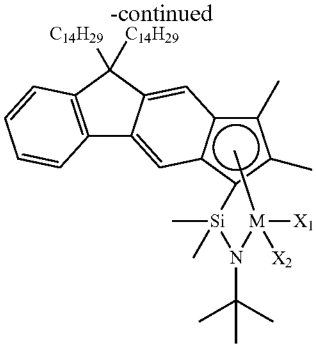
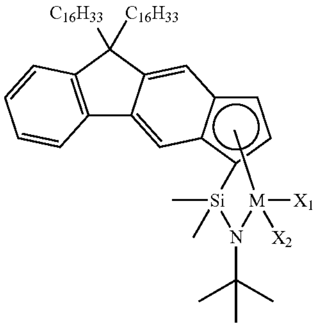
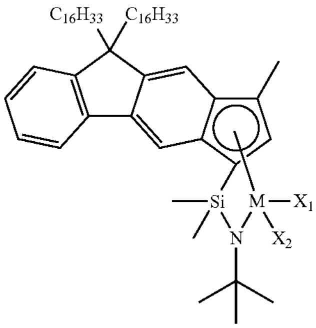
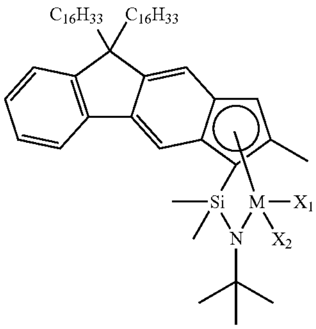
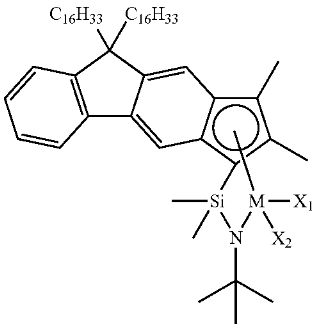
-continued
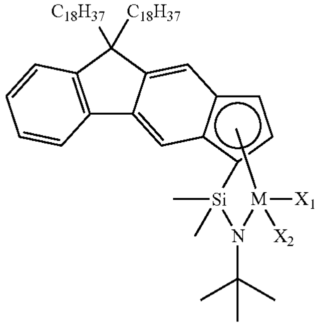
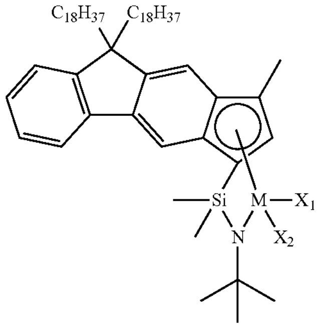
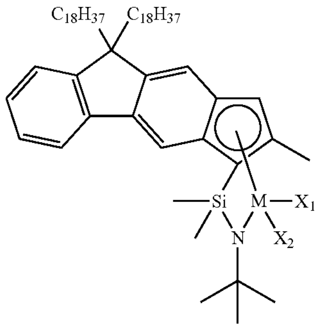
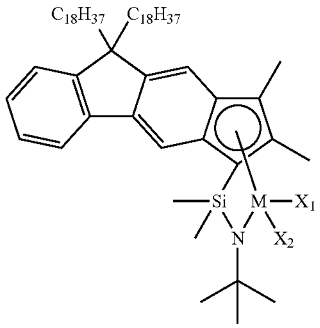
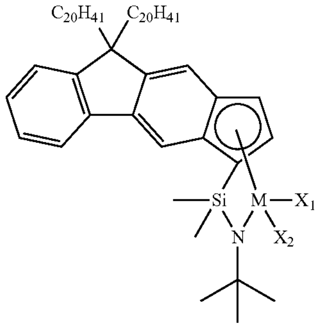

-continued
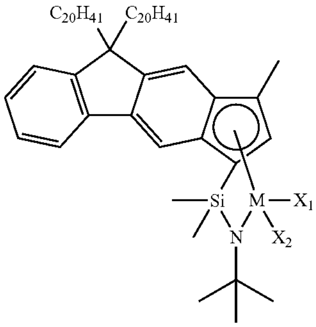
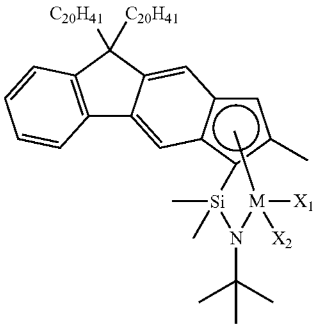
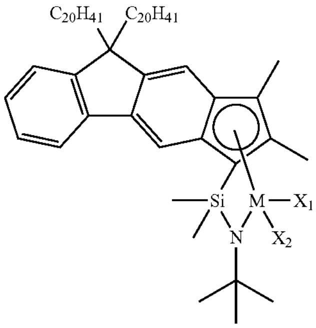
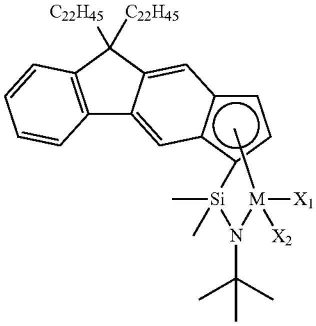
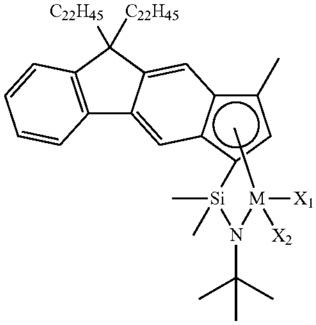
-continued
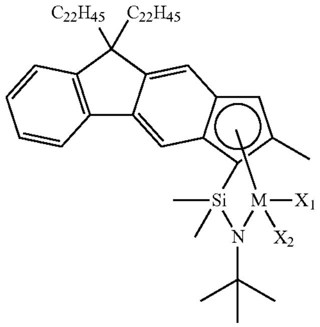
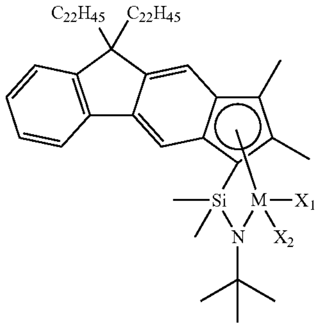
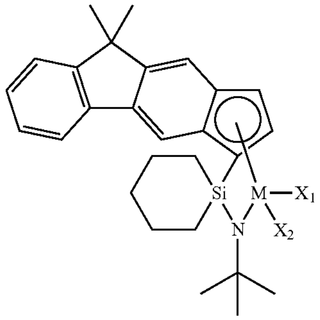
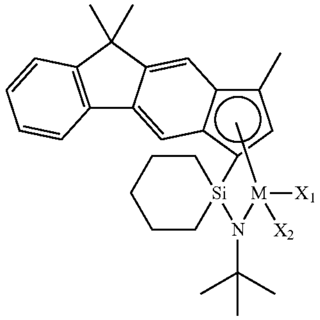
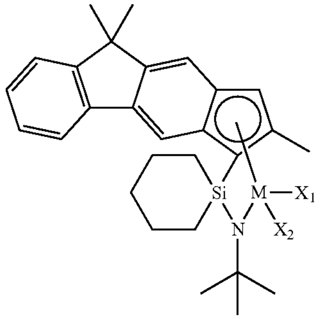

-continued
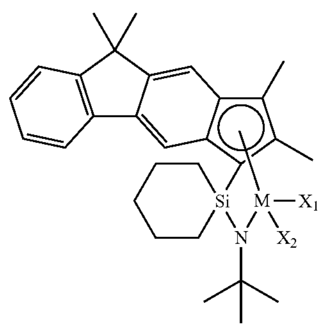
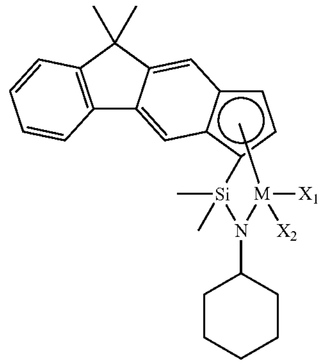
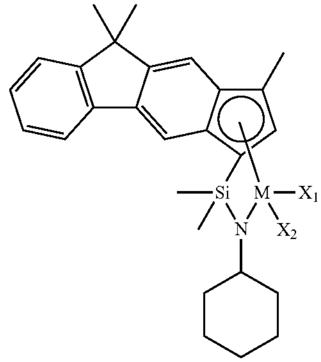
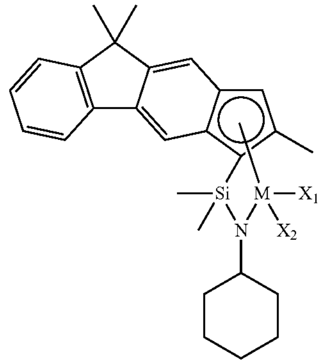
-continued
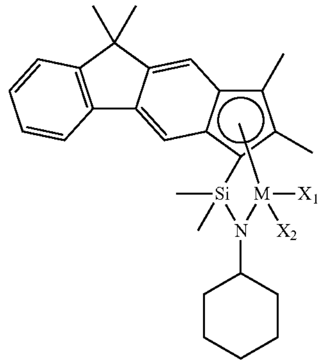
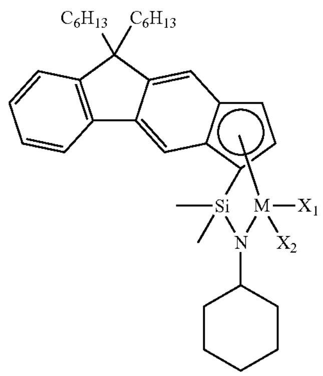
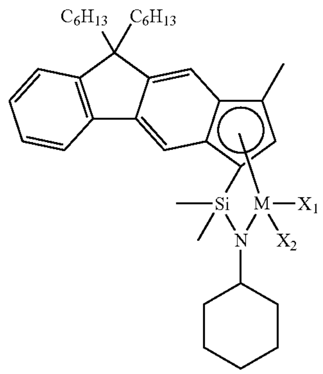
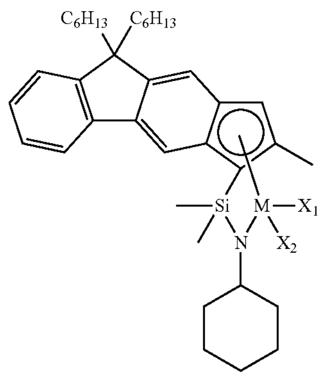

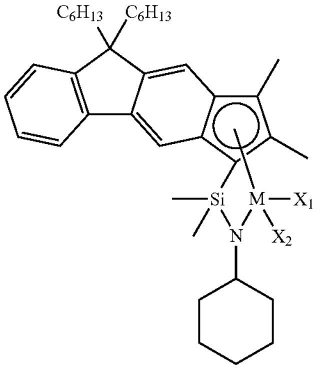
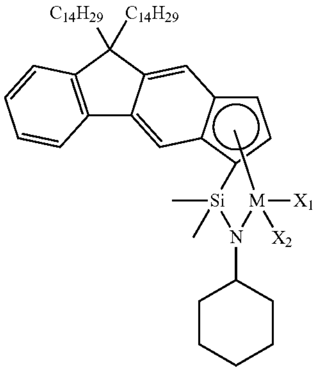
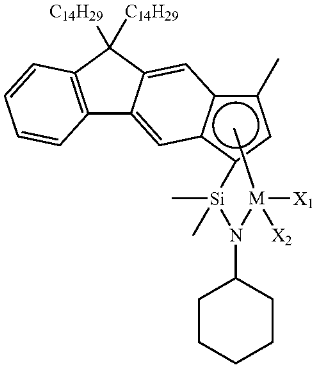
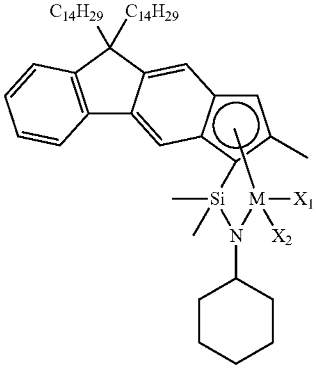
-continued
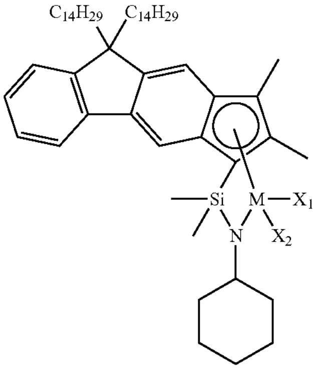
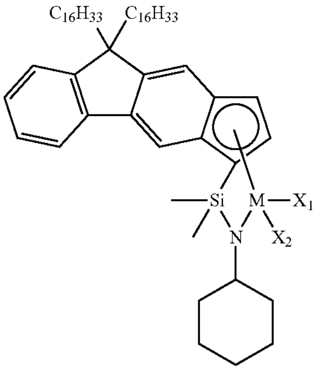
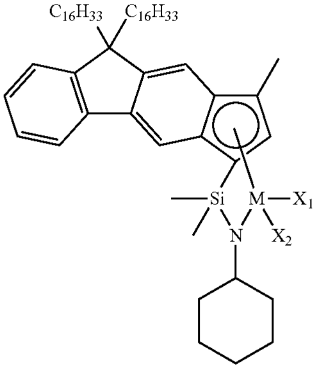
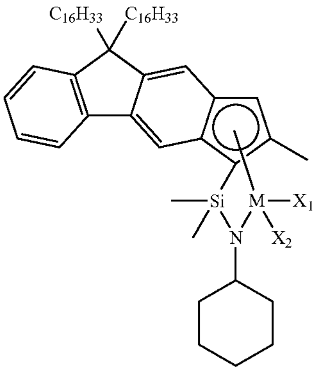

-continued
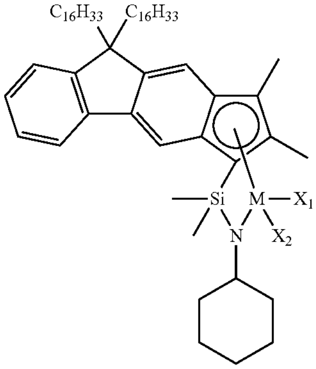
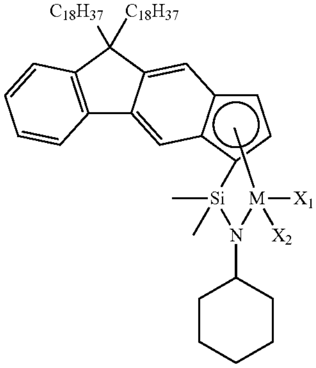
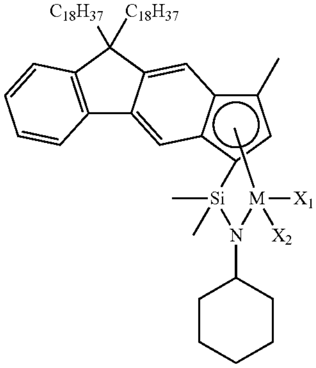
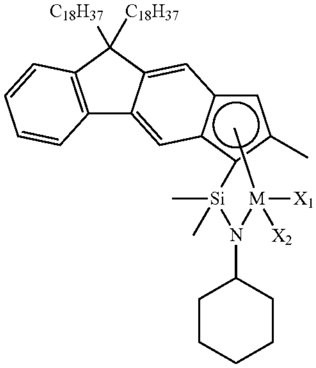
-continued
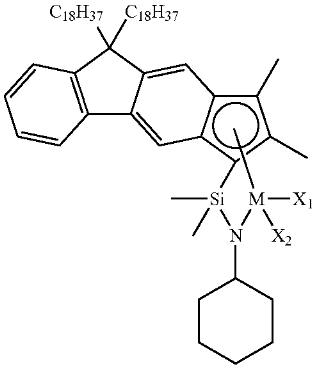
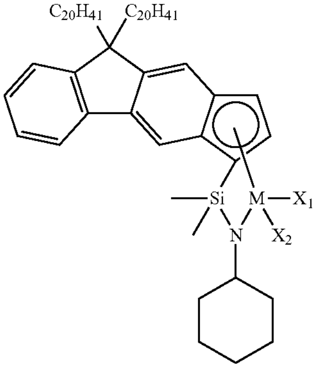
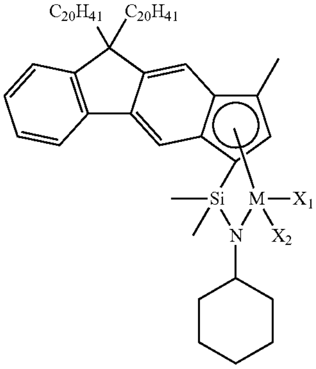
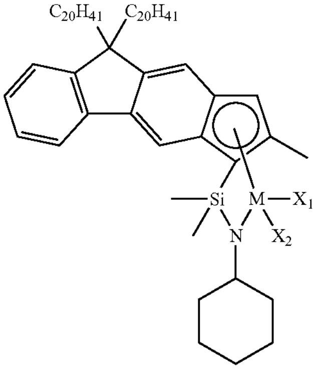

-continued
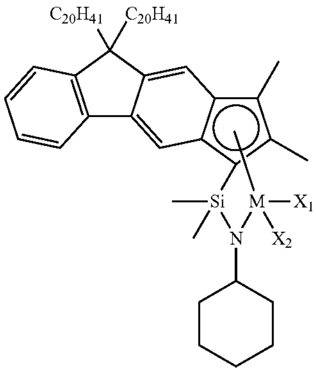
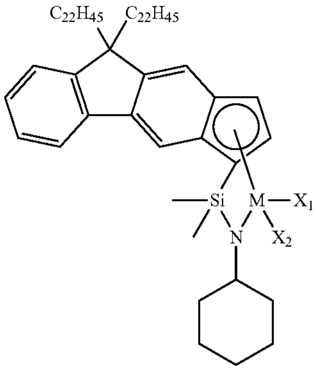
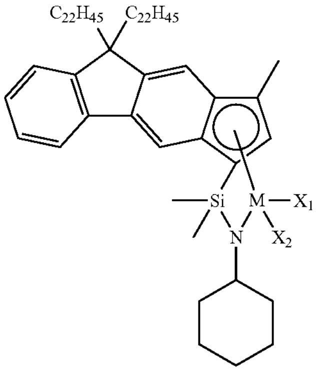
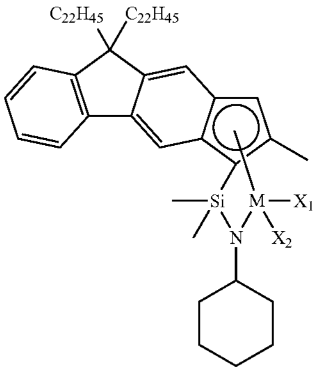
-continued
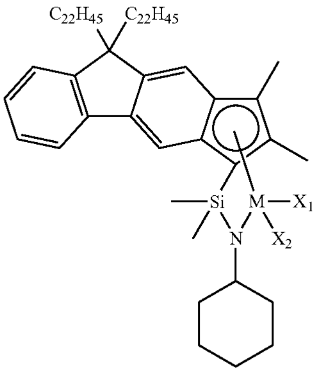
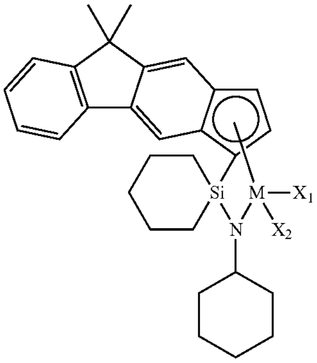
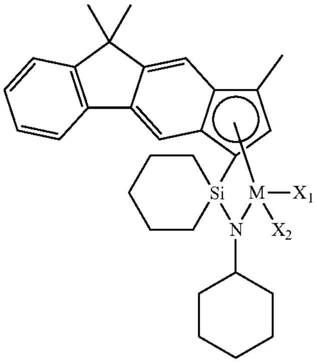
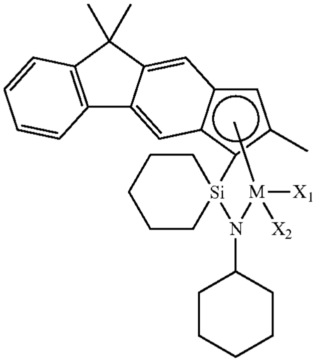

-continued
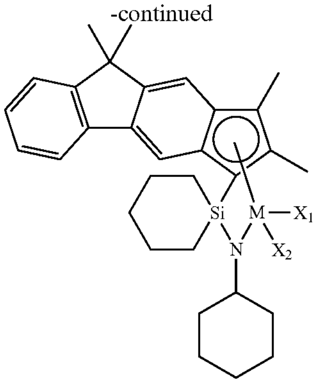
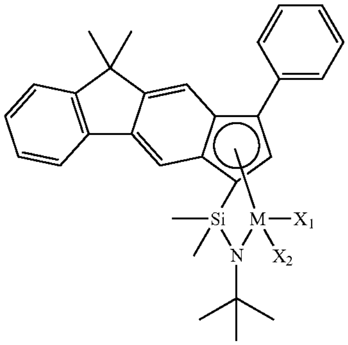
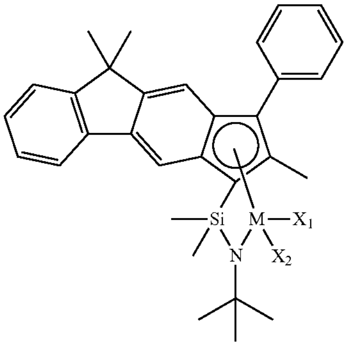
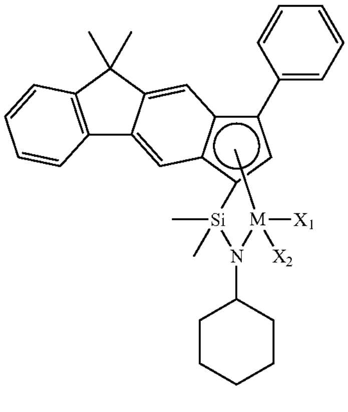
-continued
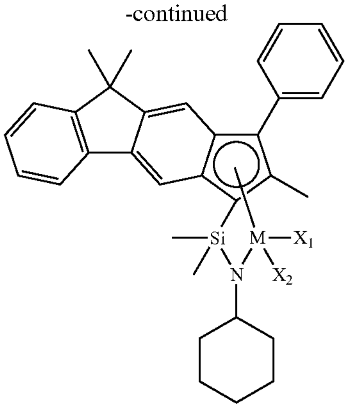
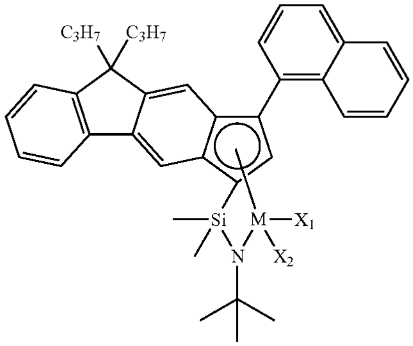
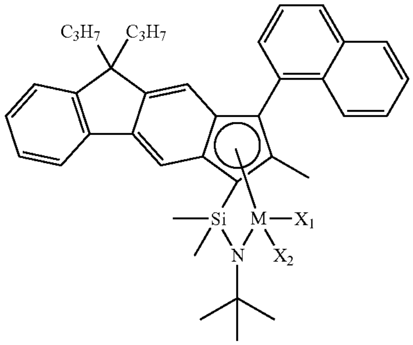
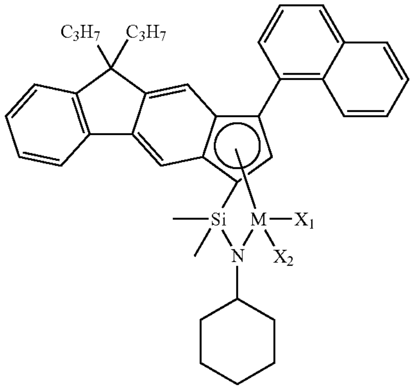

-continued
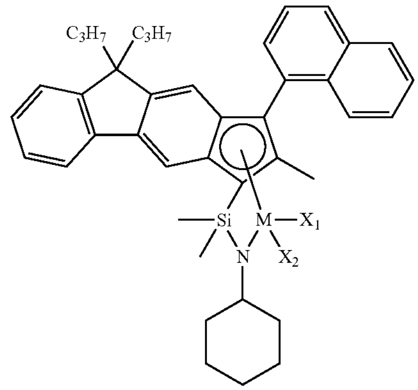
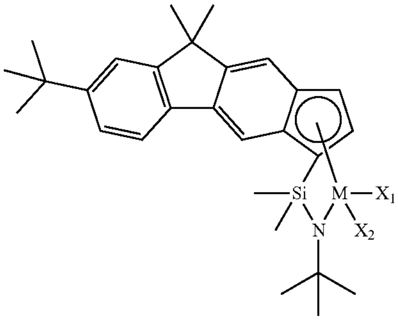
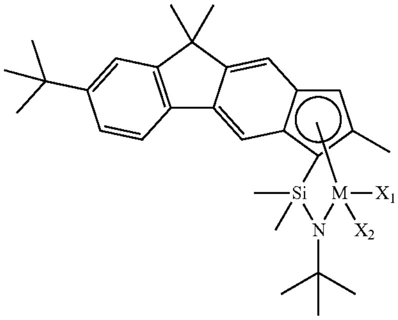
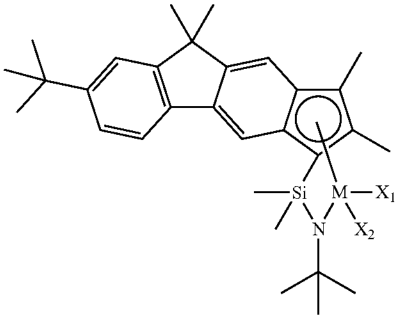
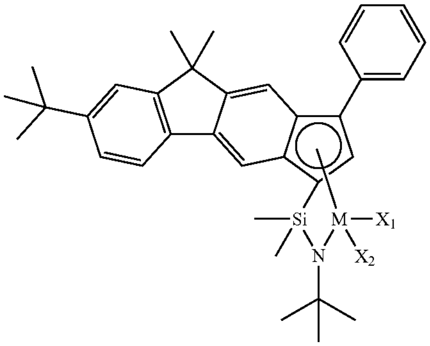
-continued
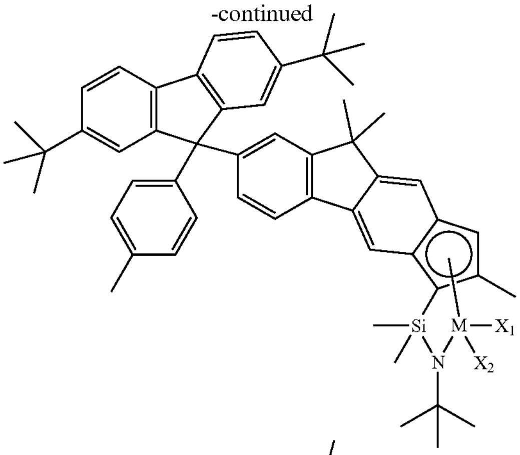
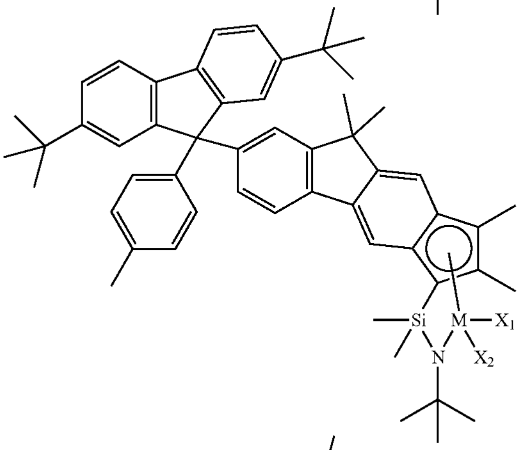
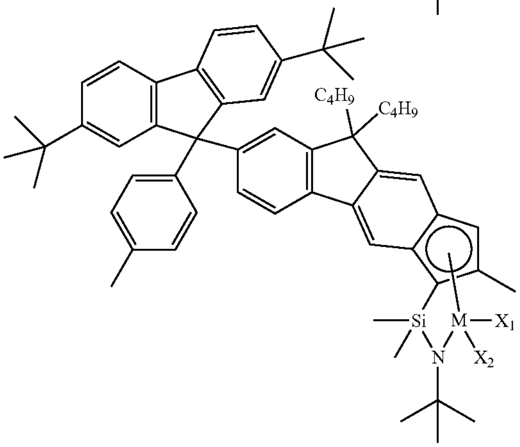
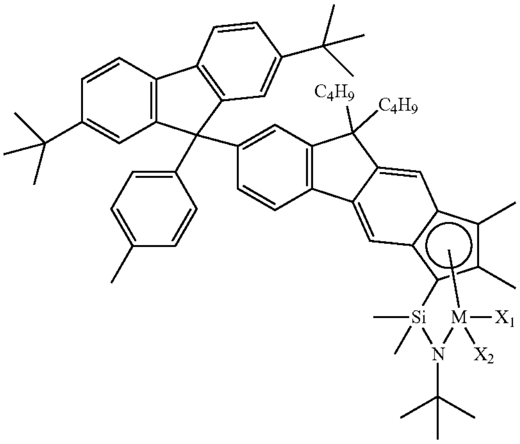

-continued
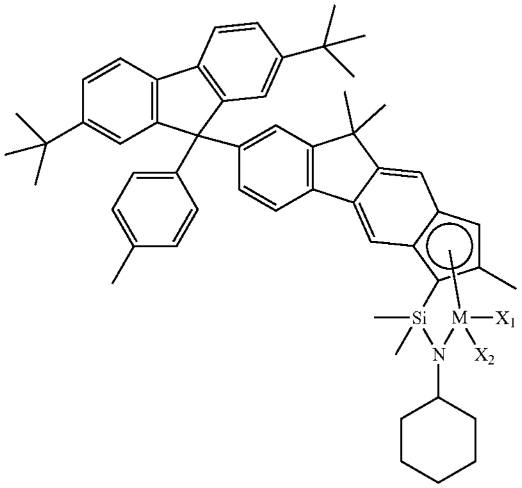
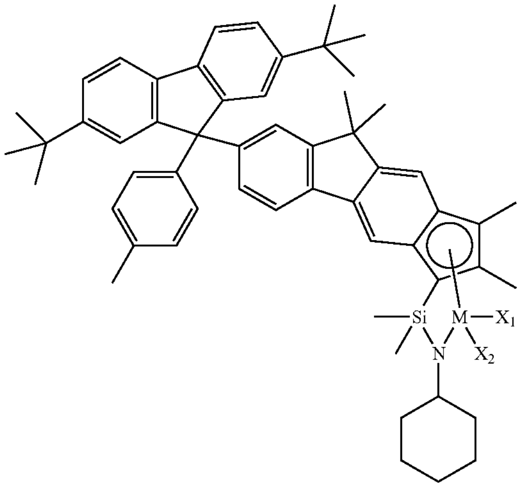
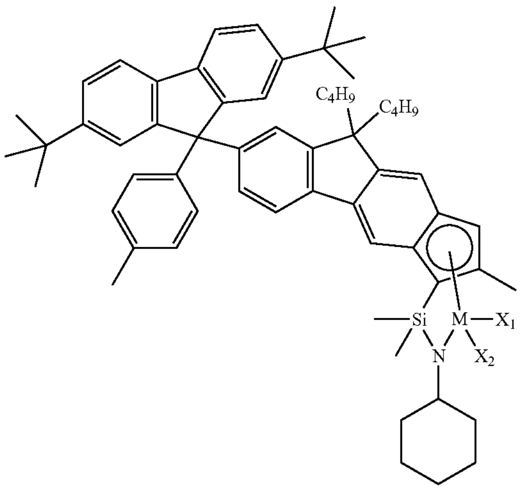
-continued
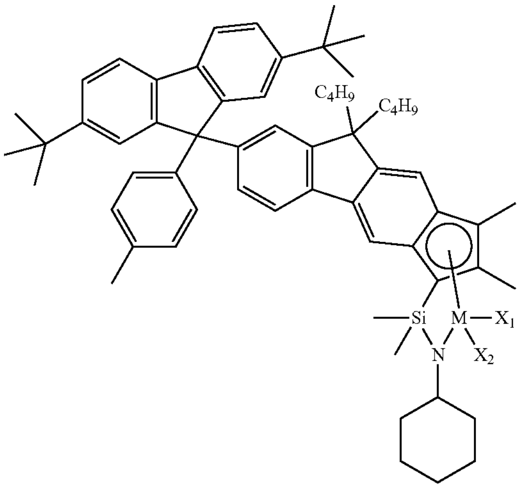
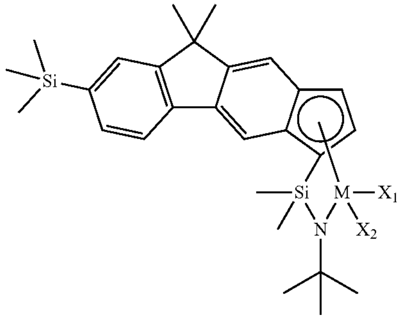
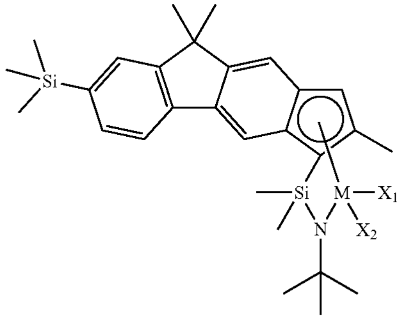
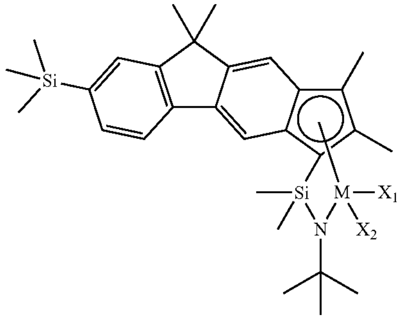

-continued
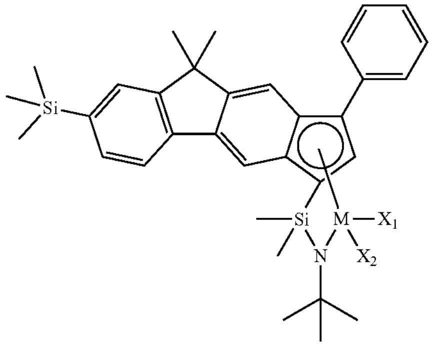
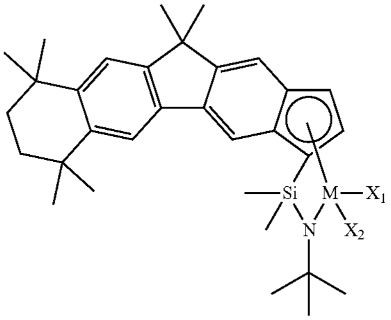
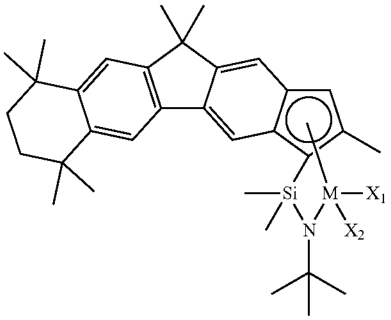
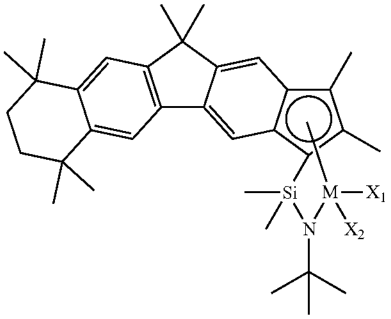
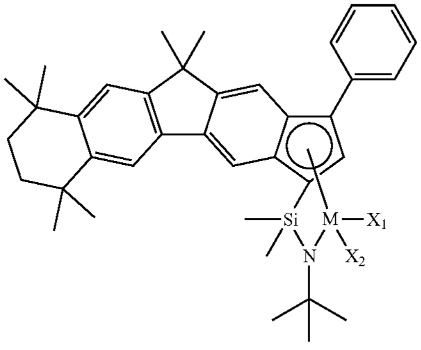
-continued
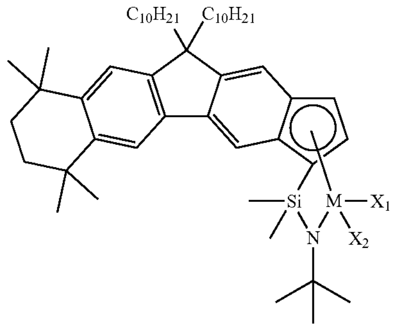
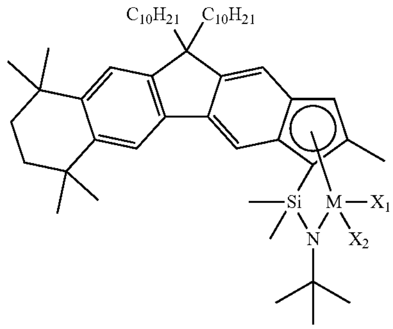
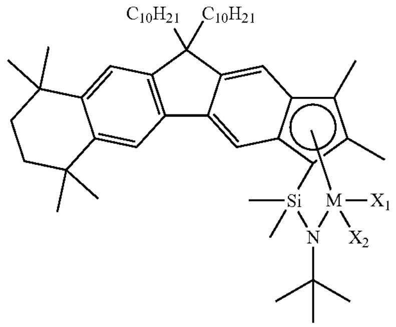
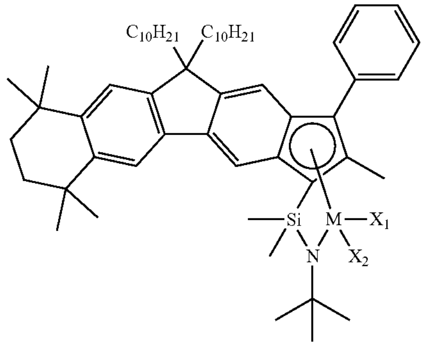
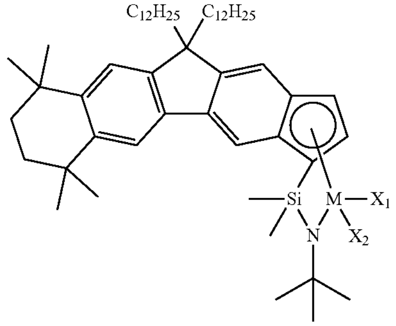

-continued
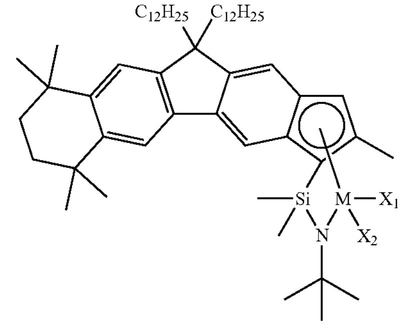
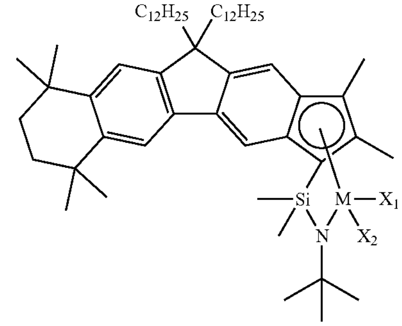
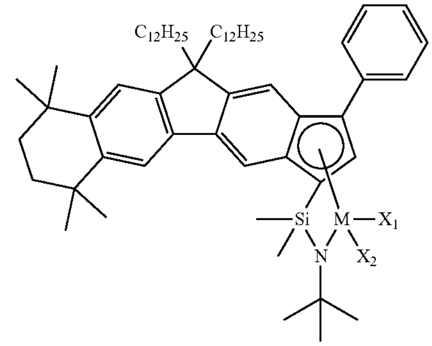
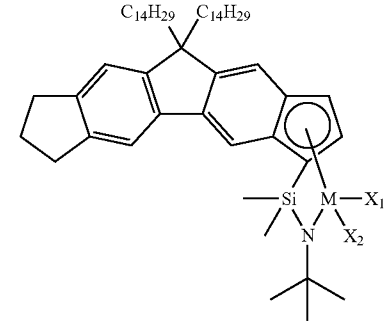
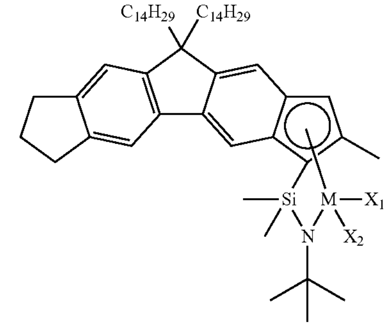
-continued
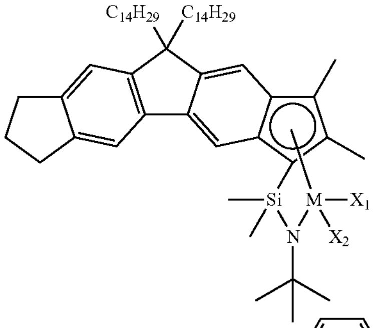
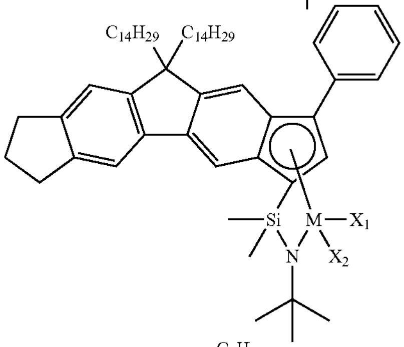
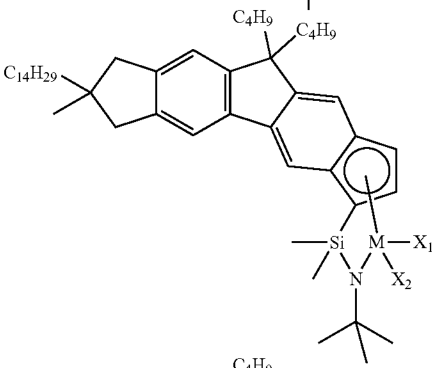
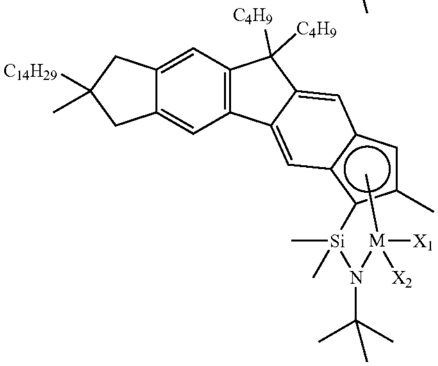
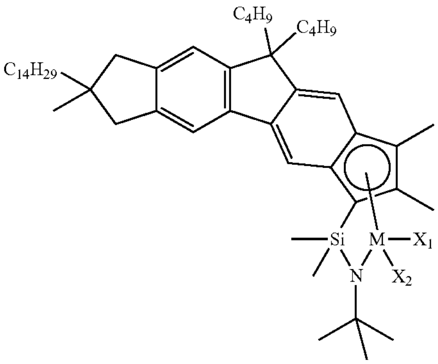

-continued
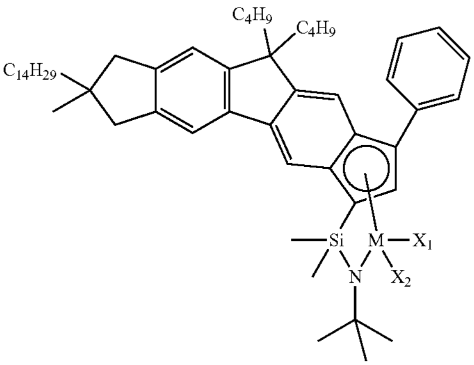
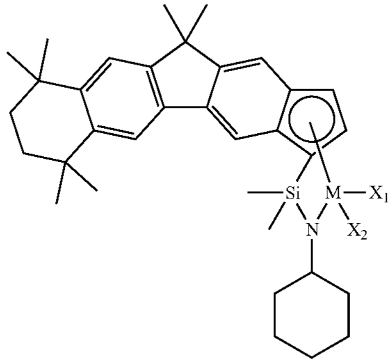
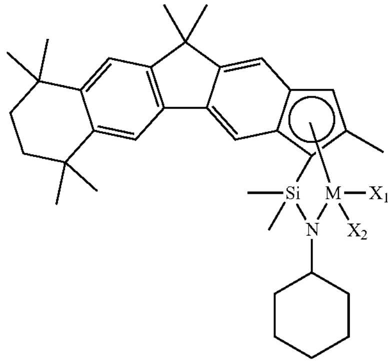
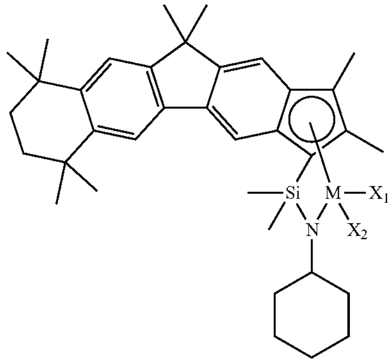
-continued
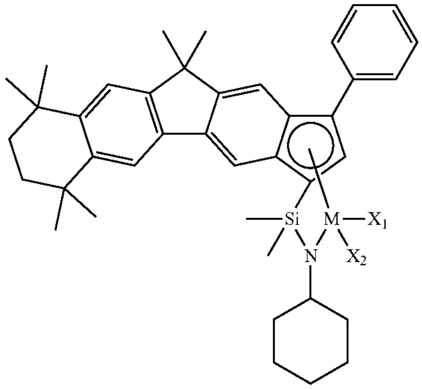
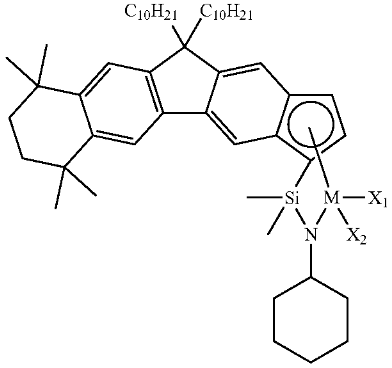
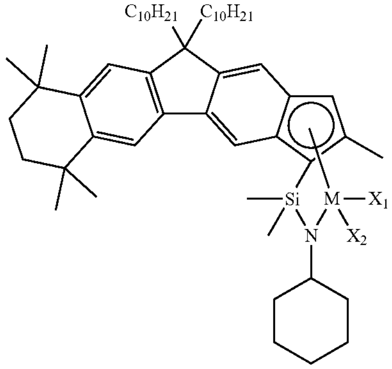
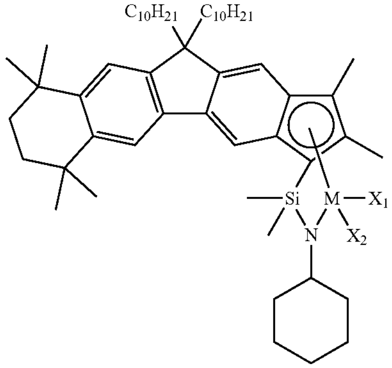

-continued
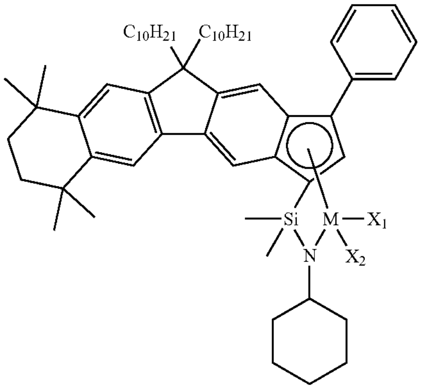
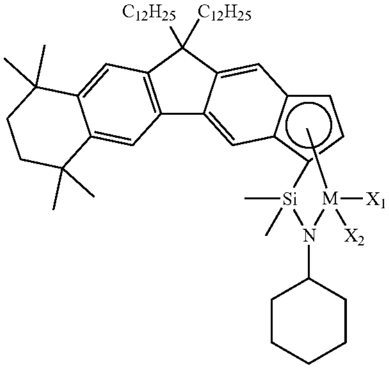
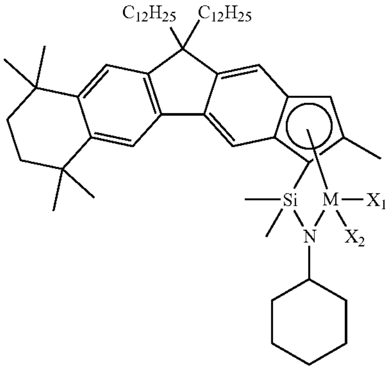
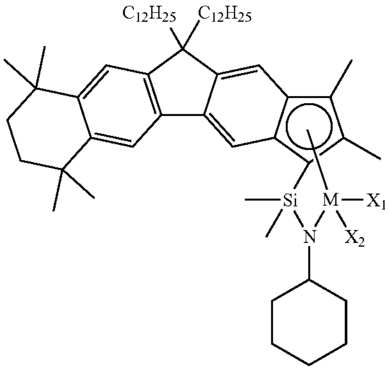
-continued
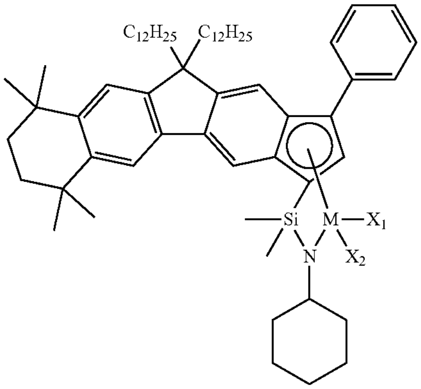
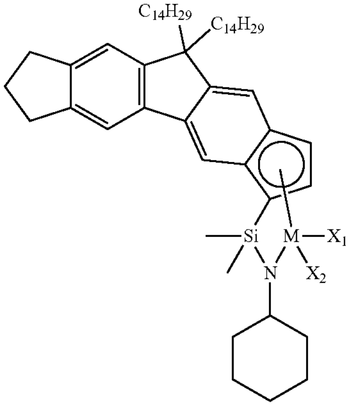
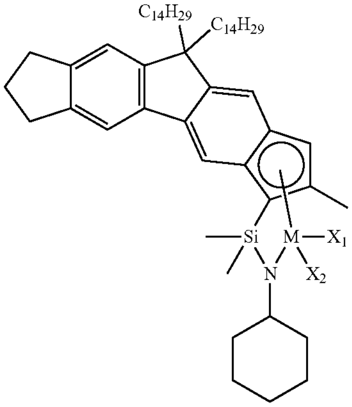
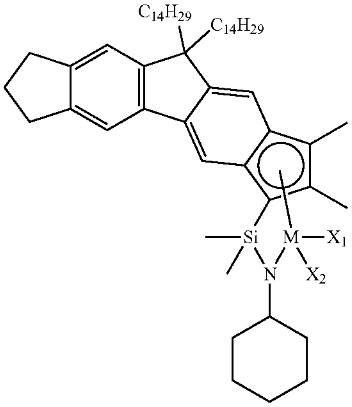

-continued
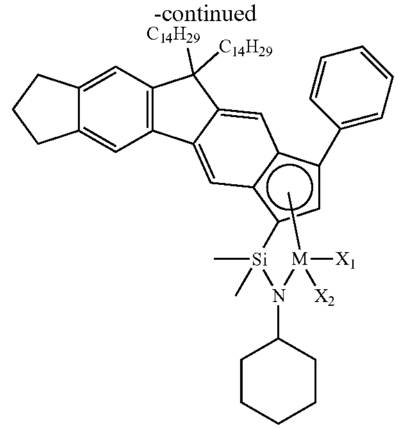
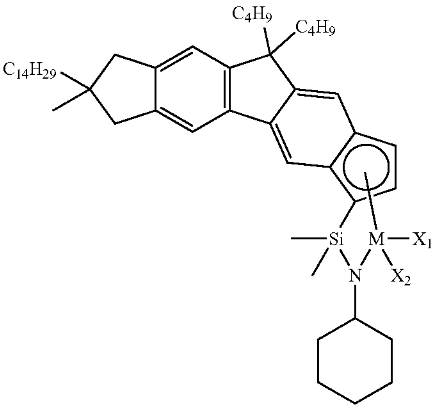
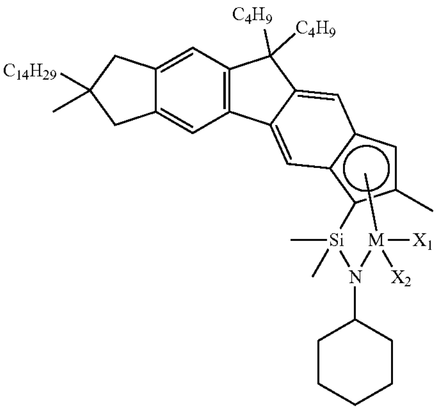
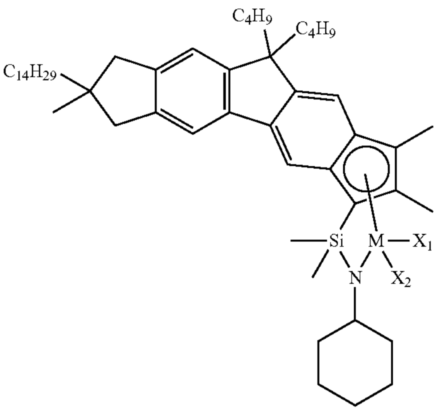
-continued
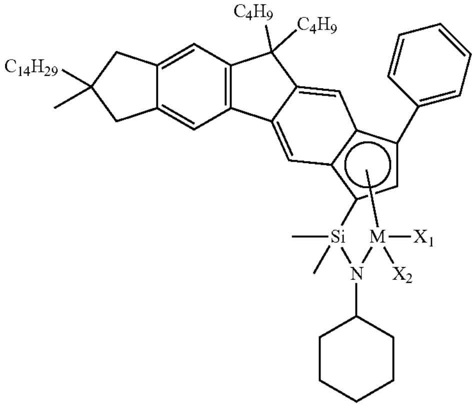
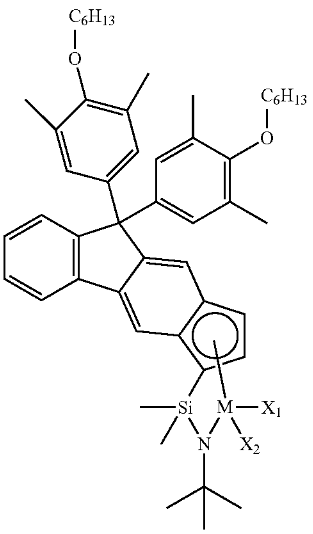
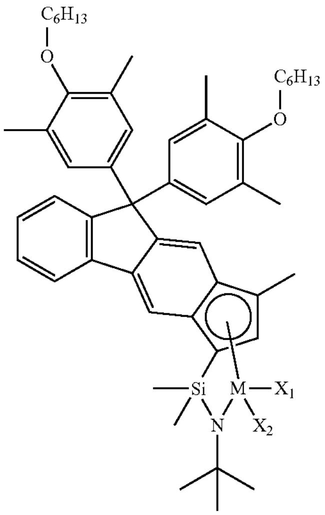

-continued
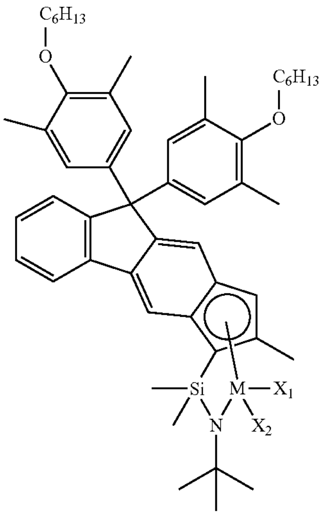
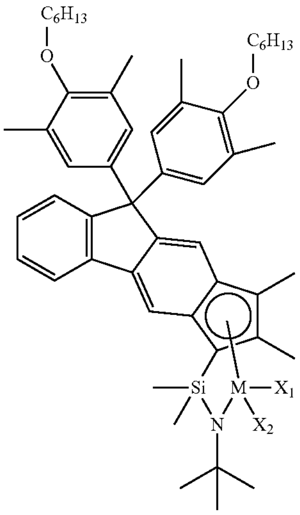
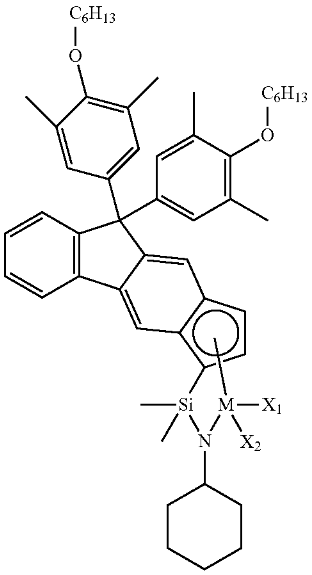
-continued
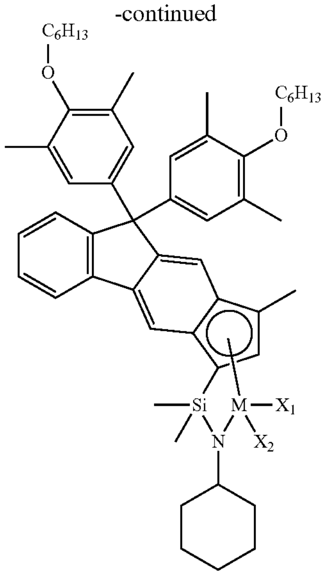
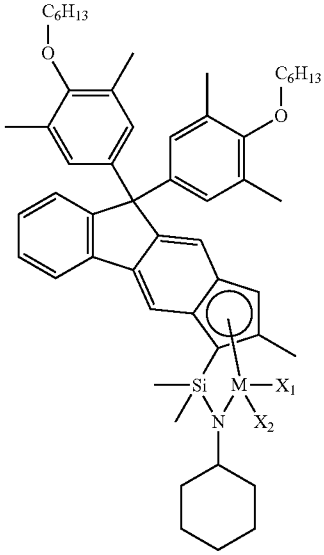
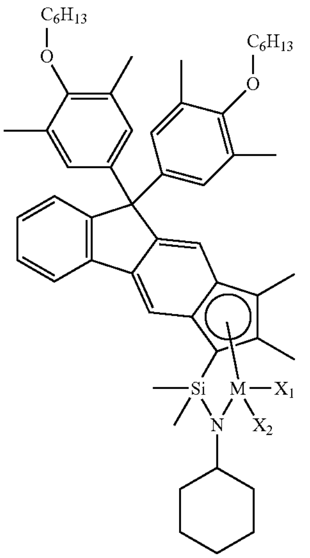

-continued
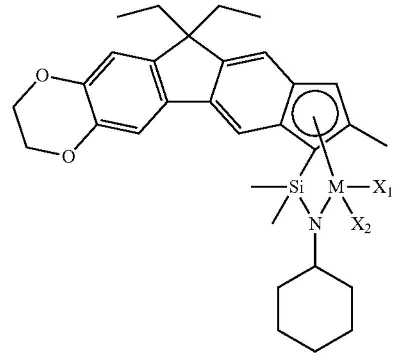
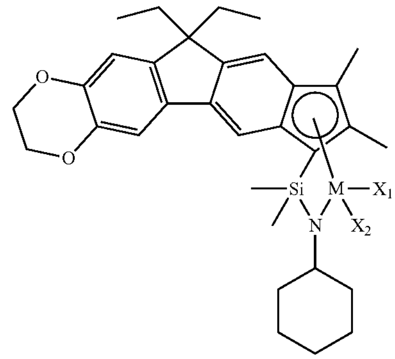
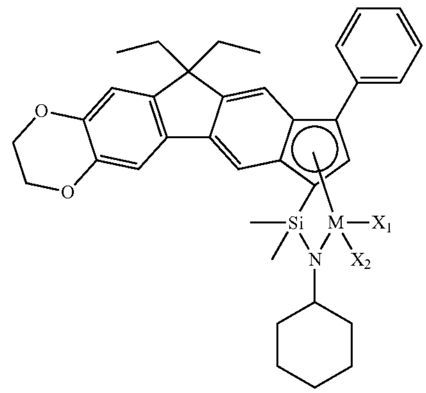
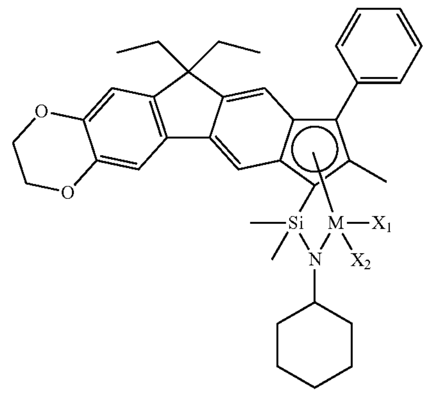
-continued
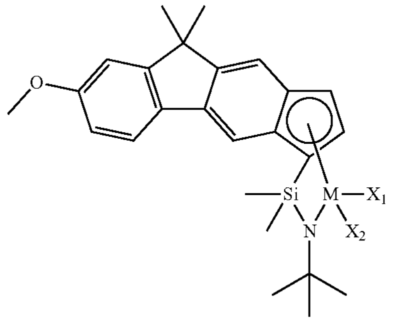
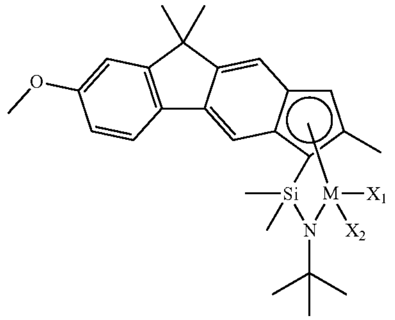
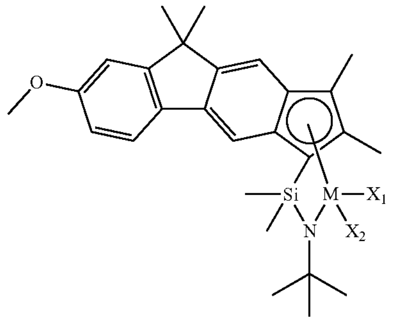
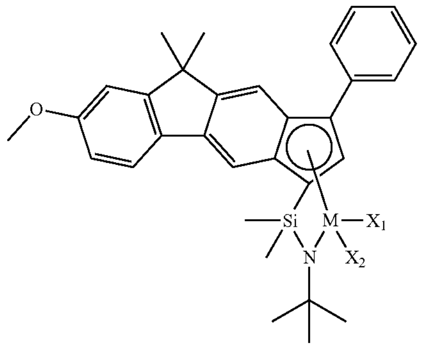
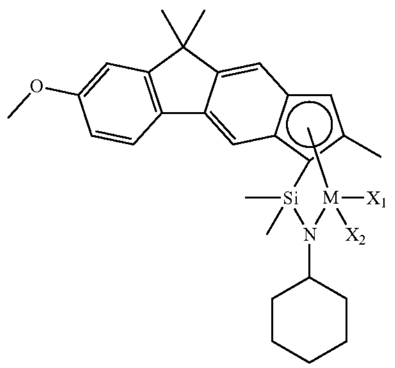

-continued
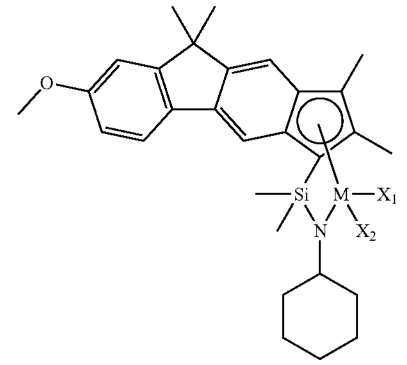
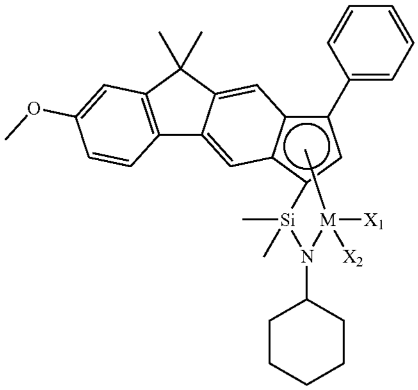
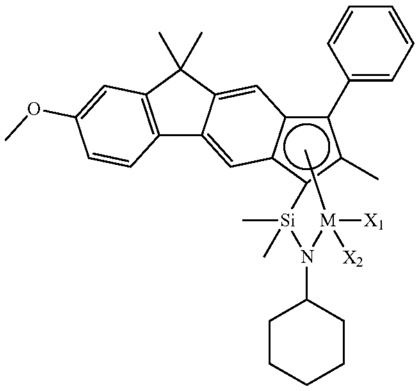
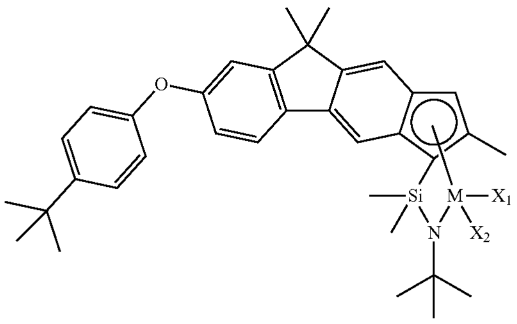
-continued
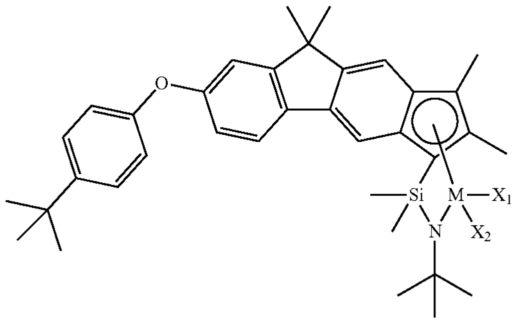
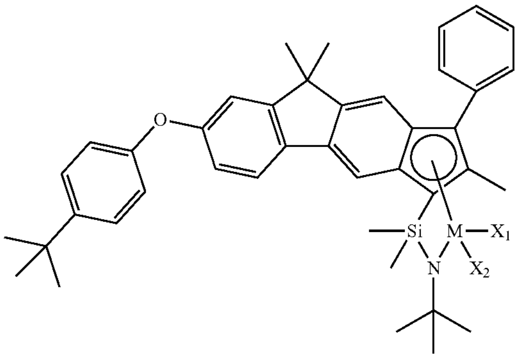
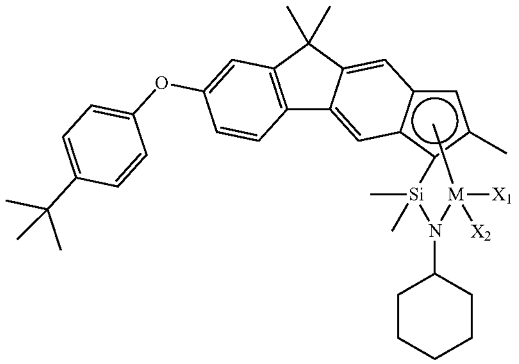
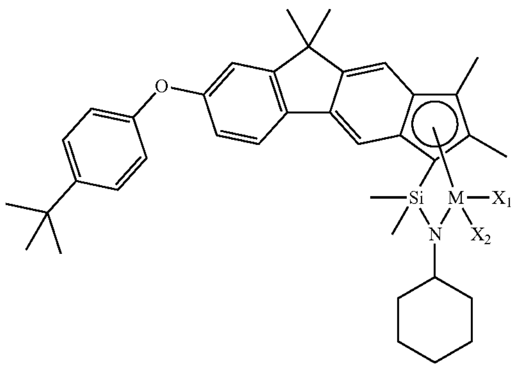

-continued
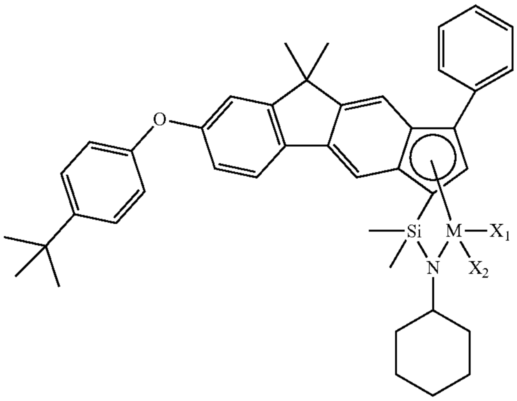
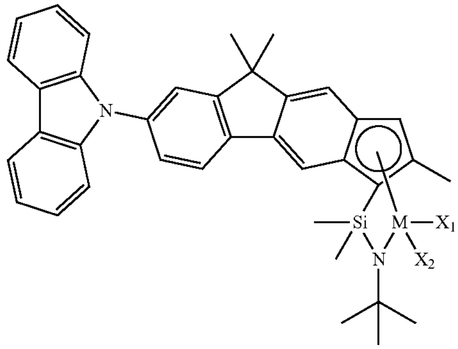
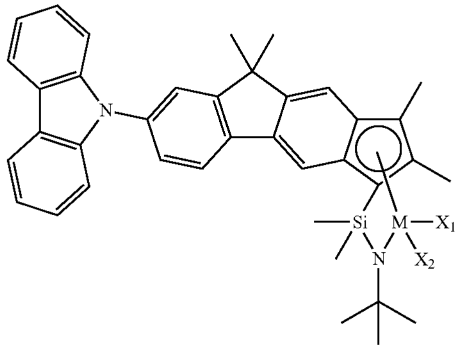
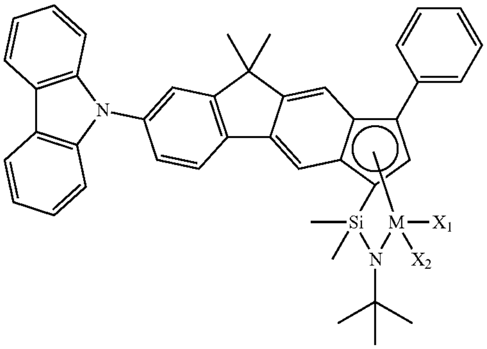
-continued
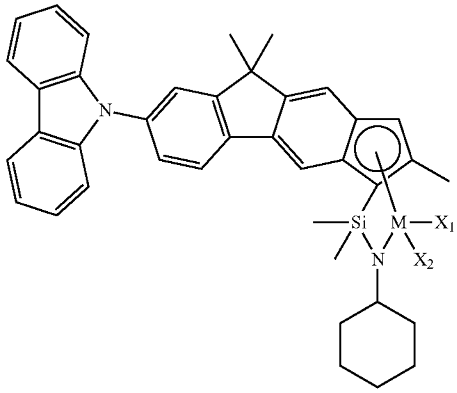
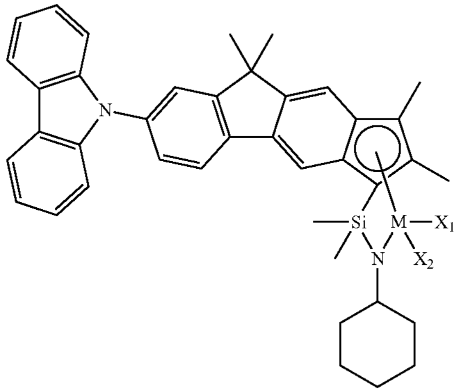
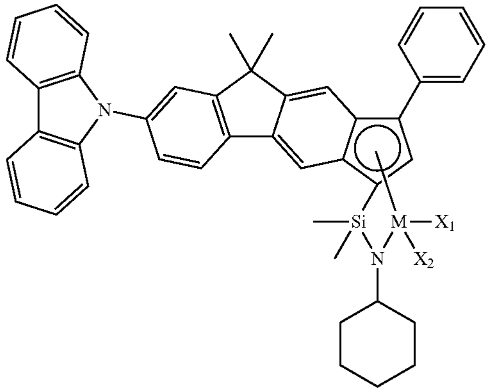
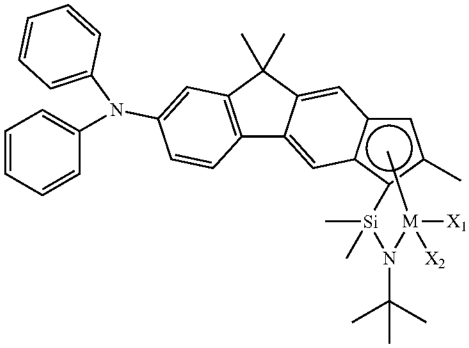

-continued
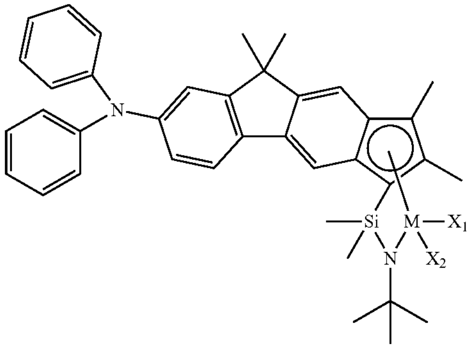
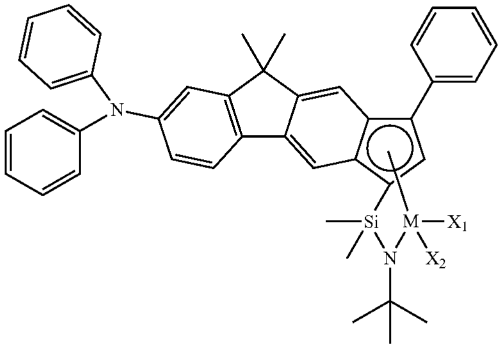
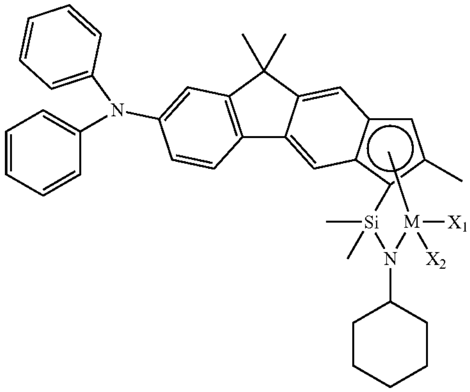
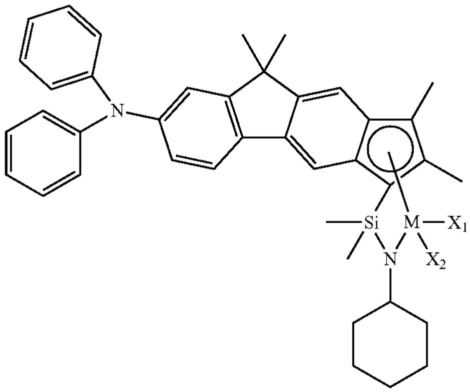
-continued
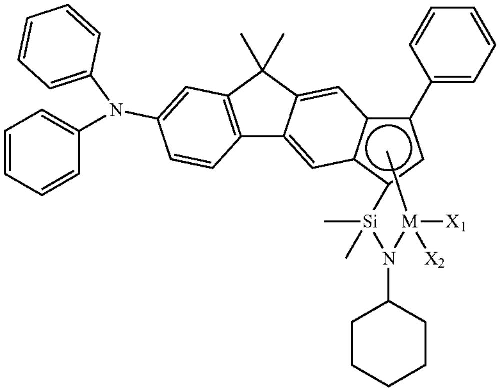
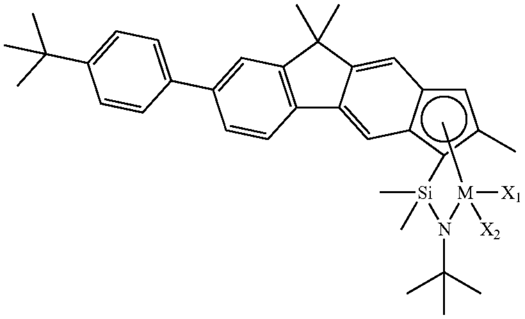
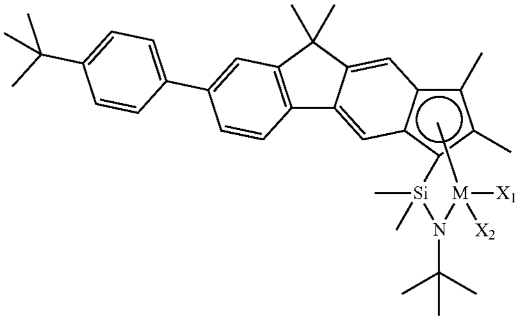
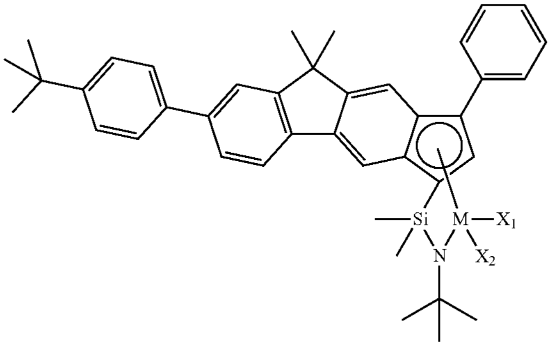

-continued
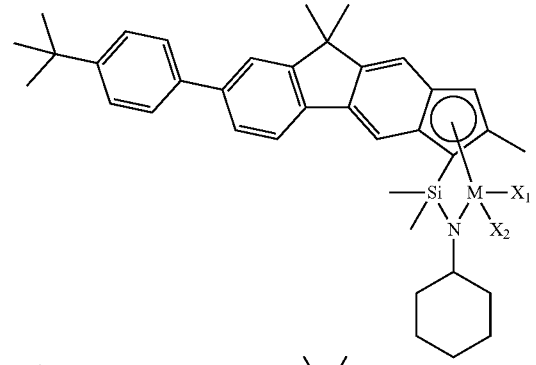
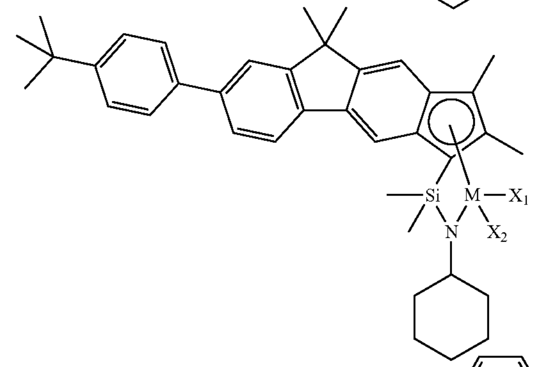
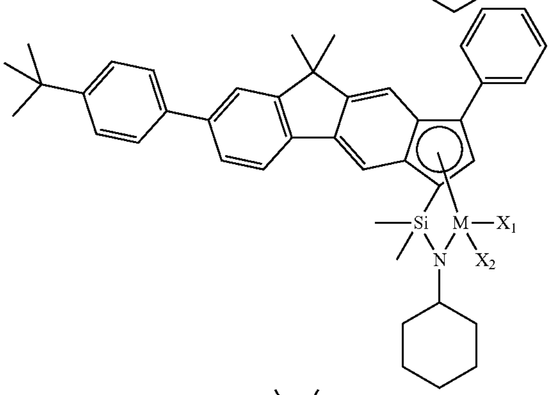
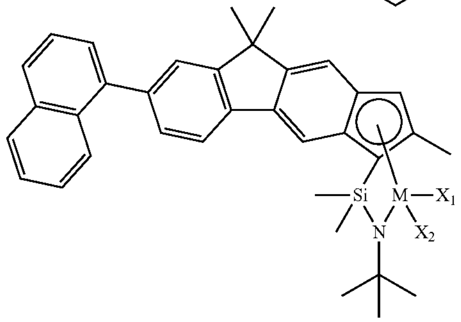
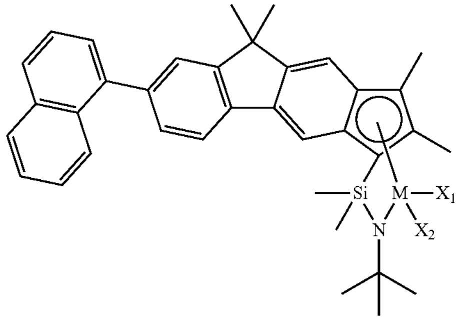
-continued
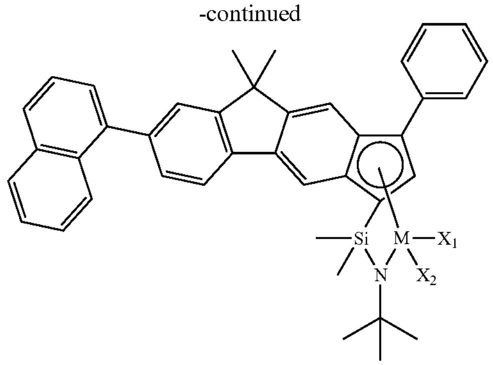
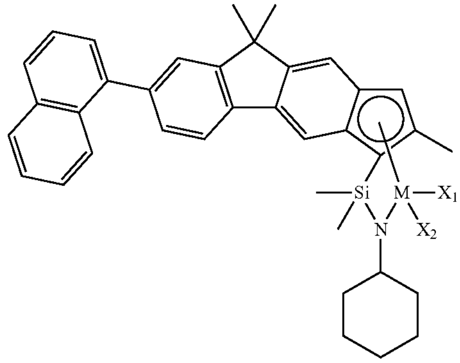
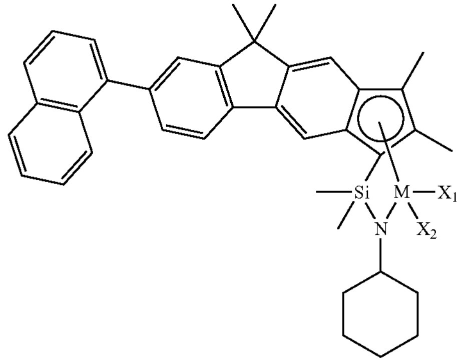
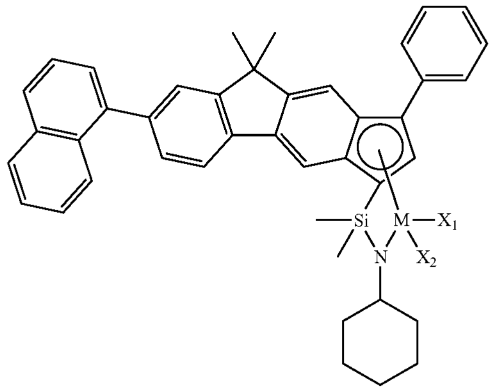

-continued
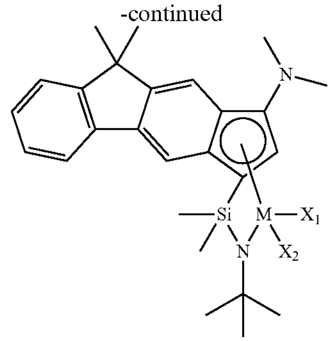
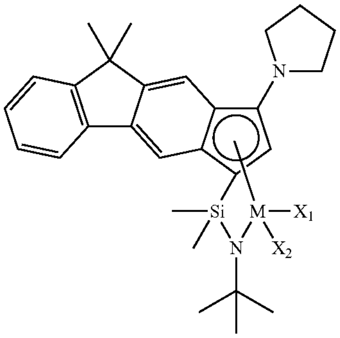
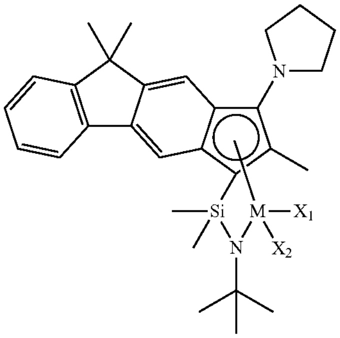
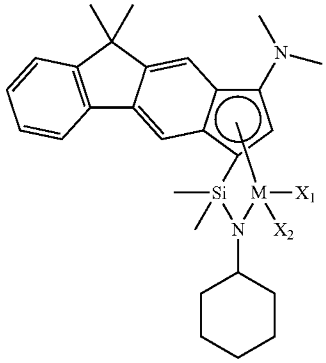
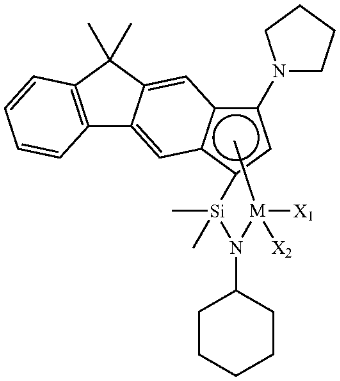
-continued
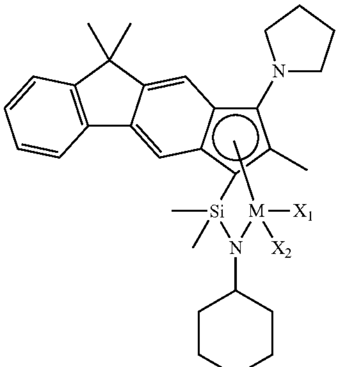
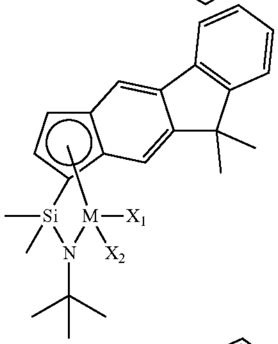
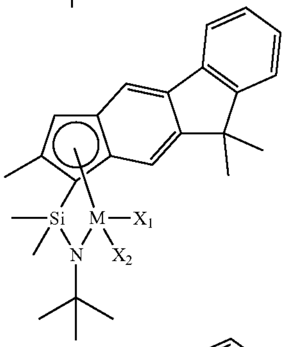
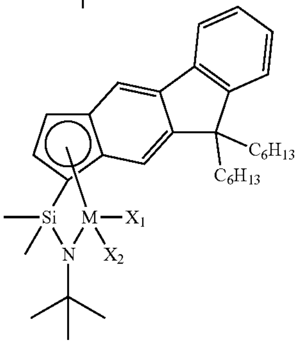
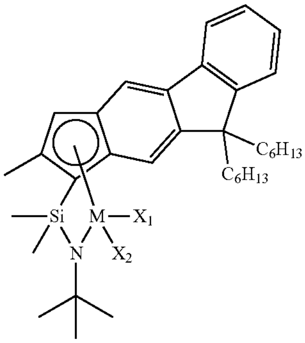

-continued
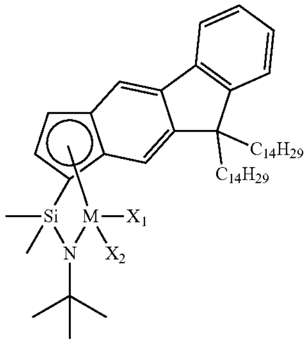
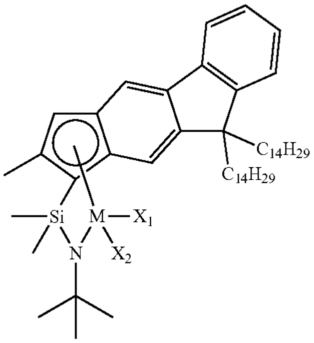
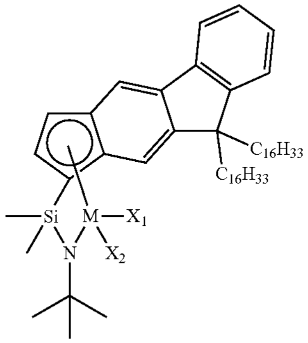
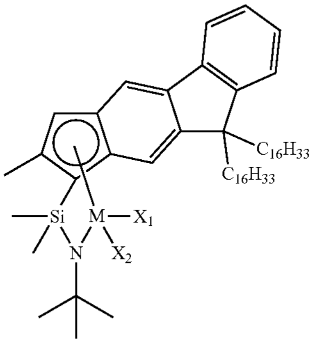
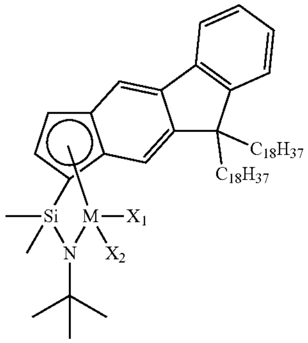
-continued
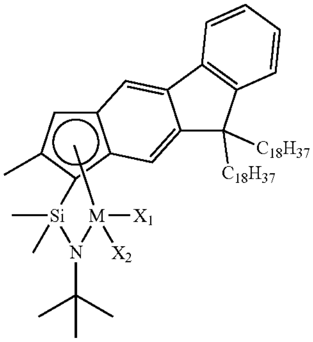
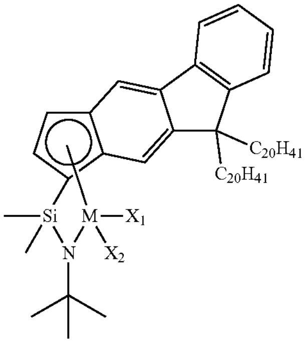
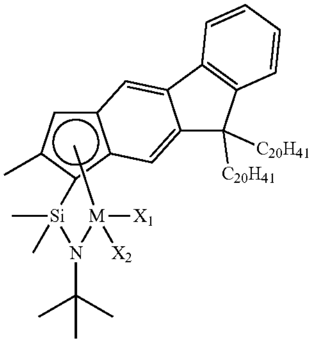
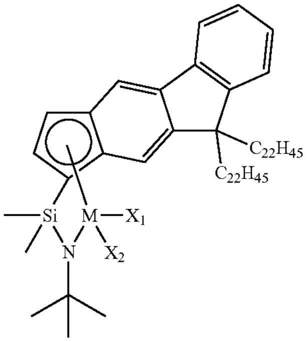
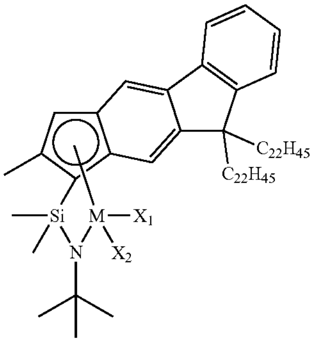

-continued
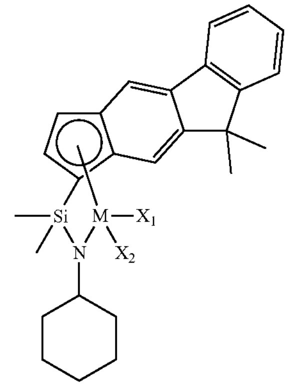
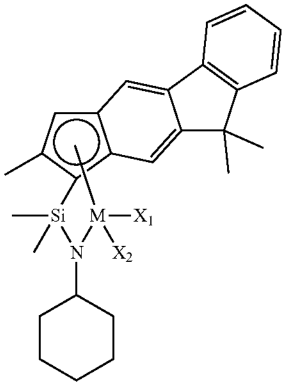
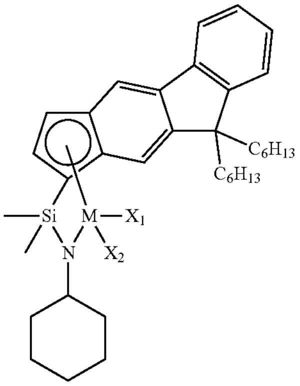
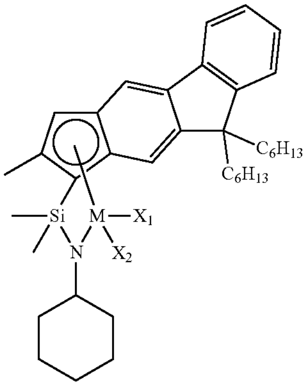
-continued
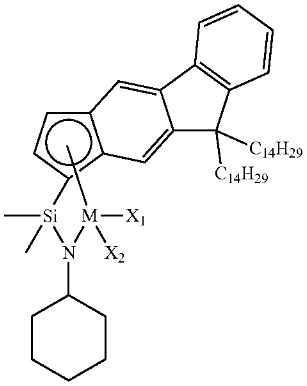
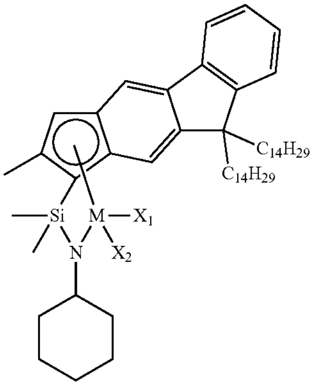
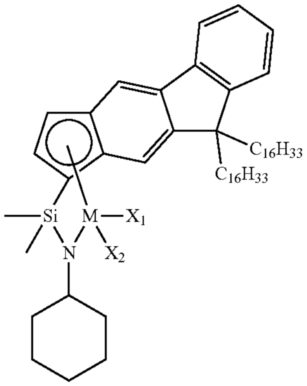
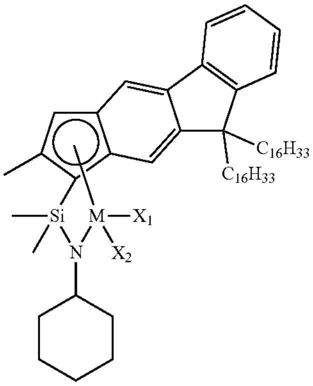

-continued
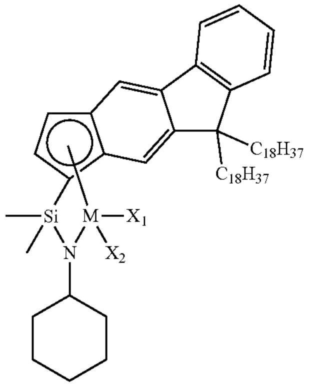
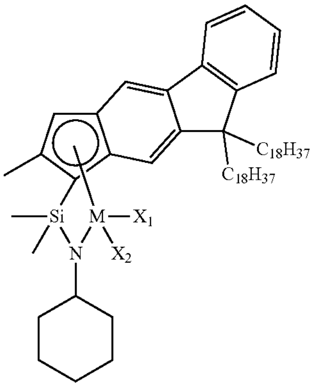
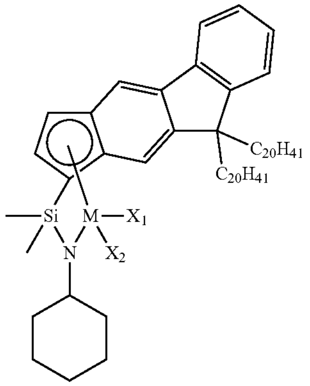
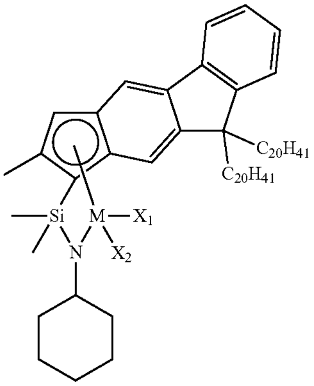
-continued
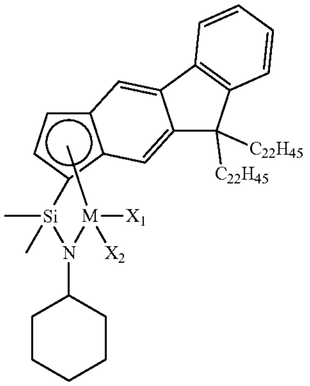
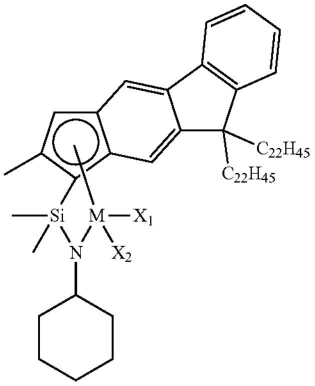
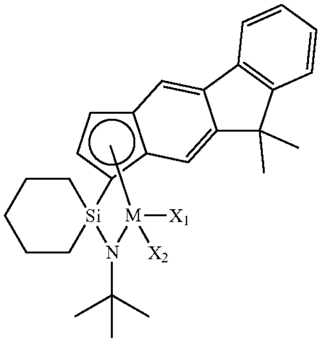
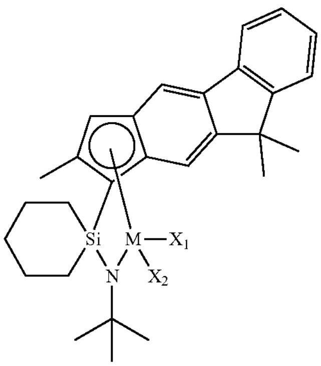

-continued
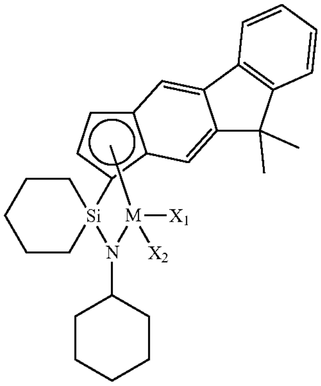
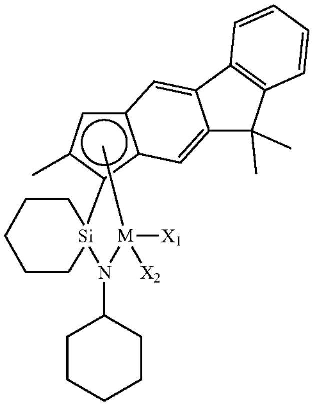
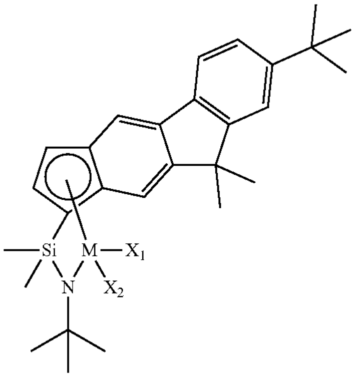
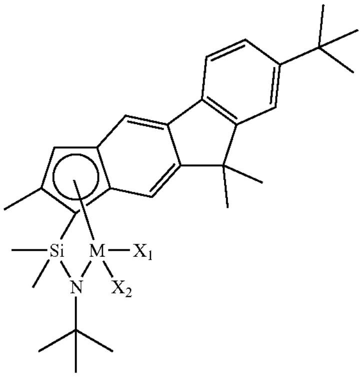
-continued
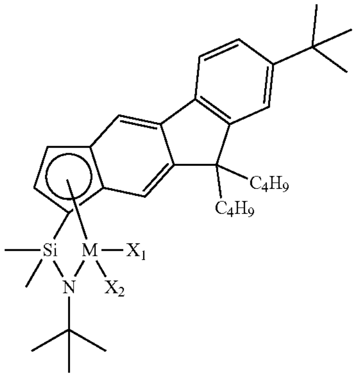
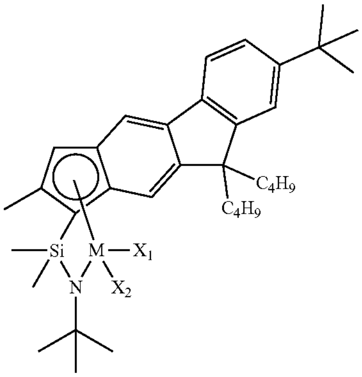
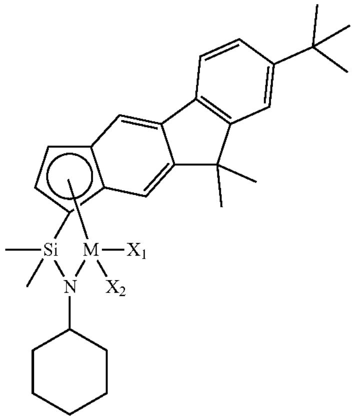
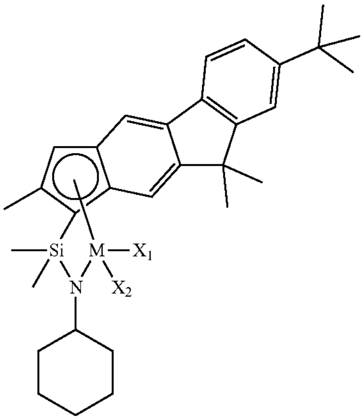

-continued
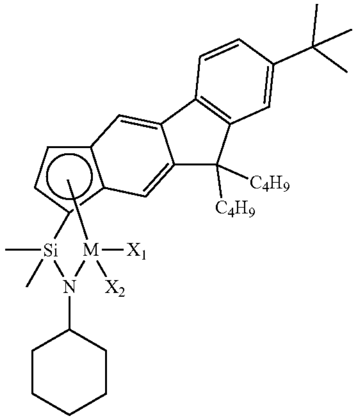
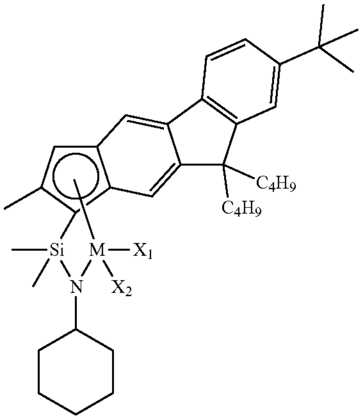
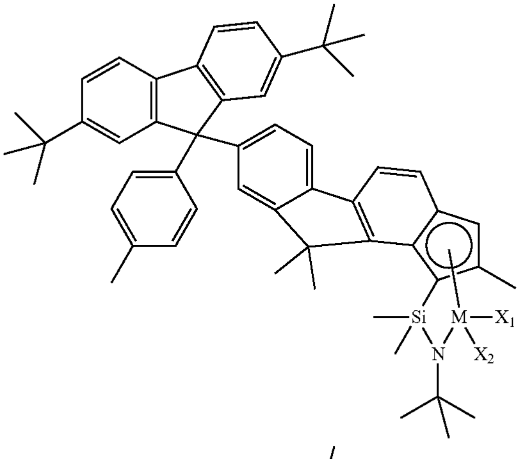
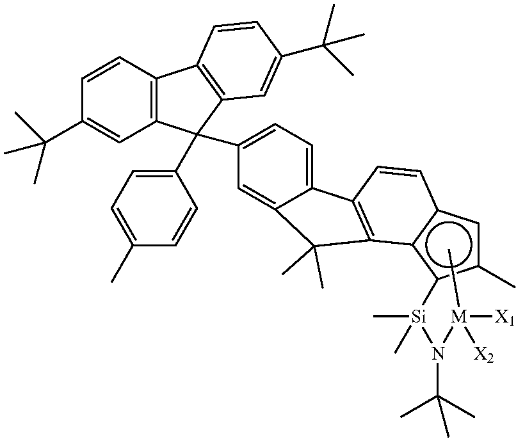
-continued
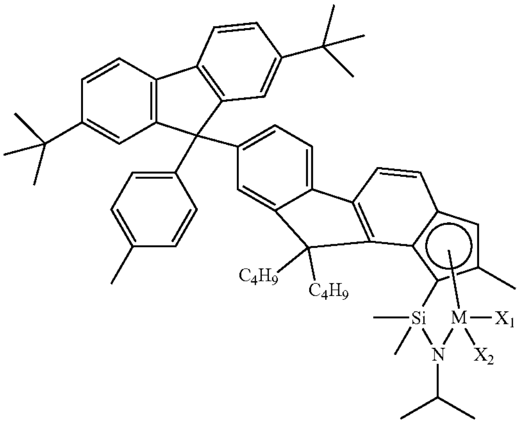
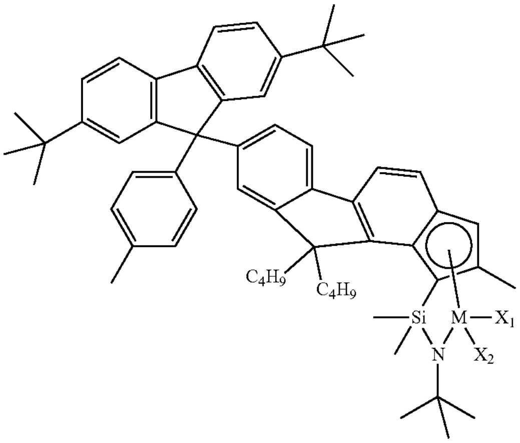
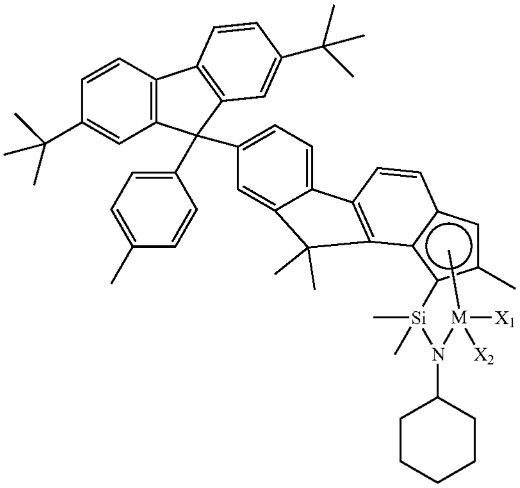

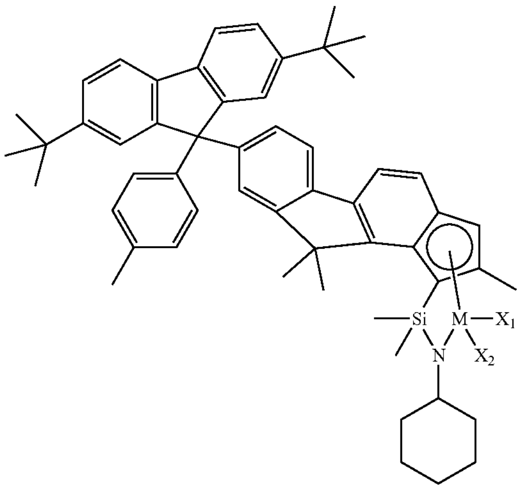
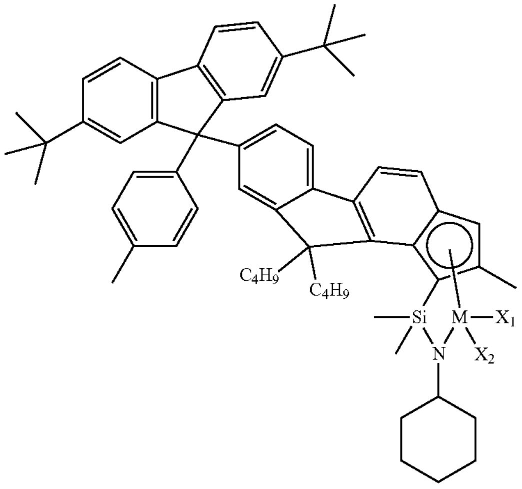
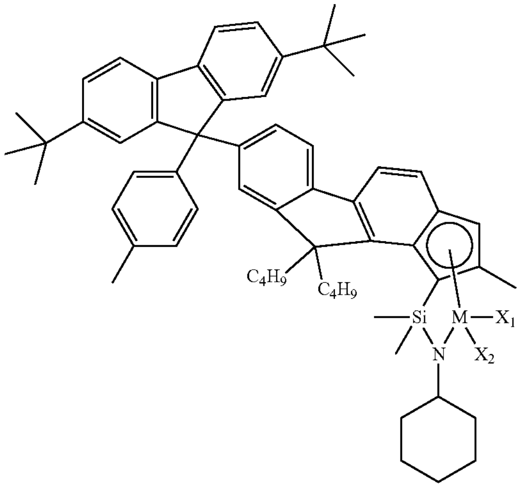
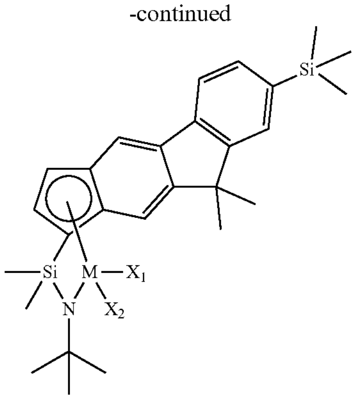
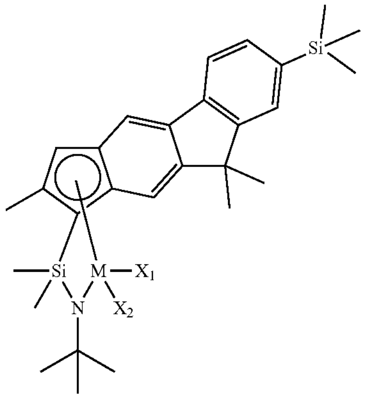
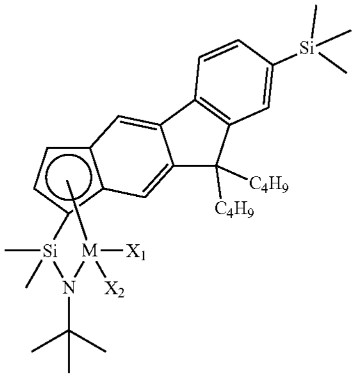
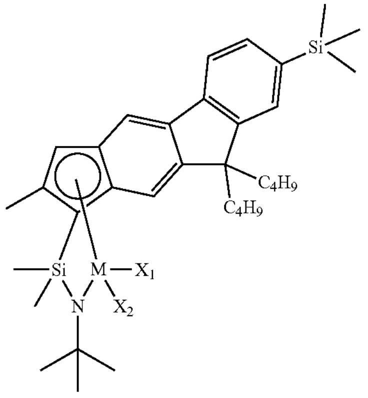

-continued
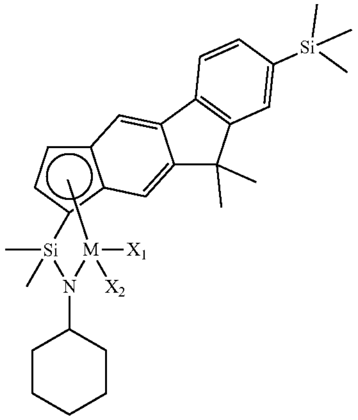
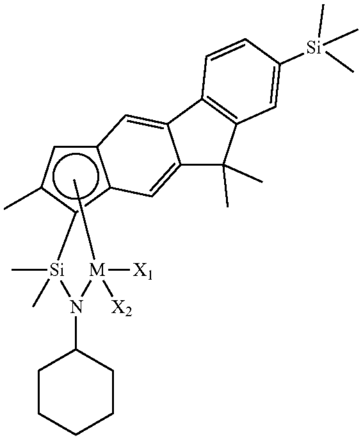
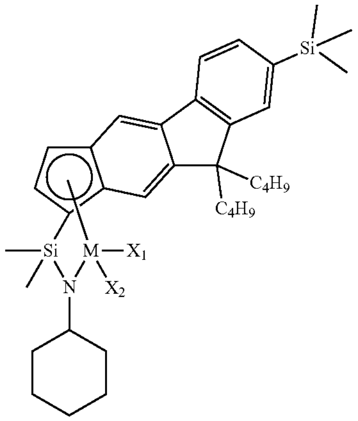
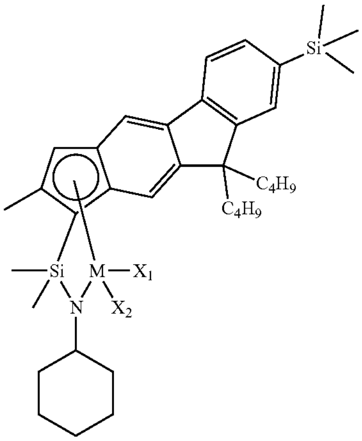
-continued
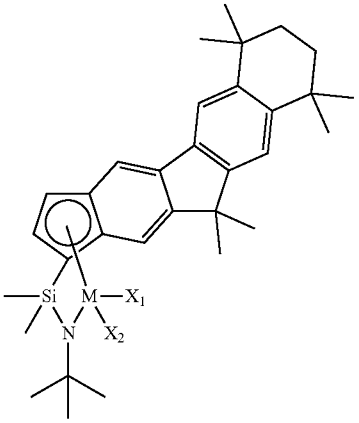
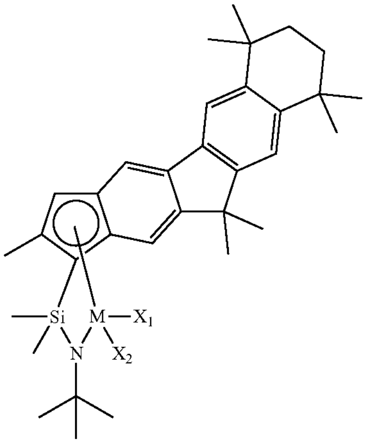
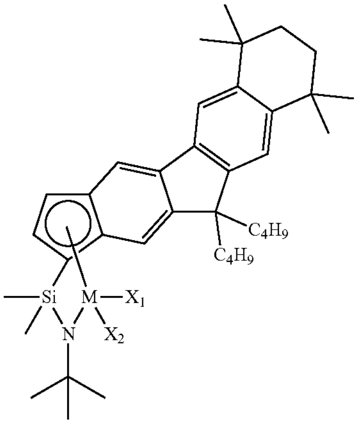
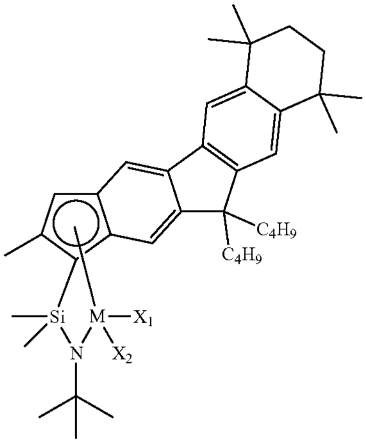

-continued
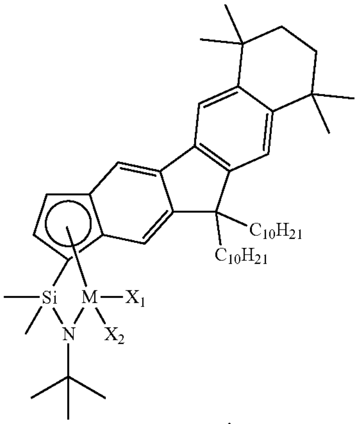
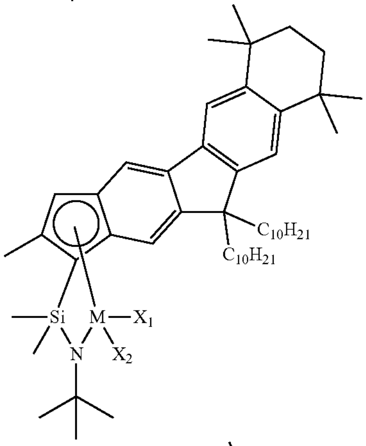
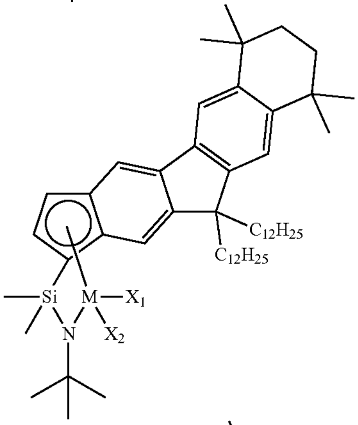
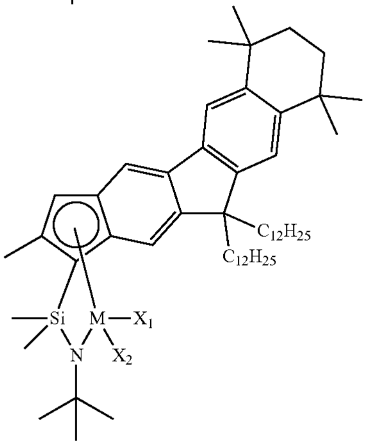
-continued
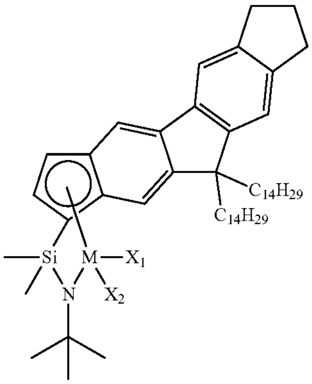
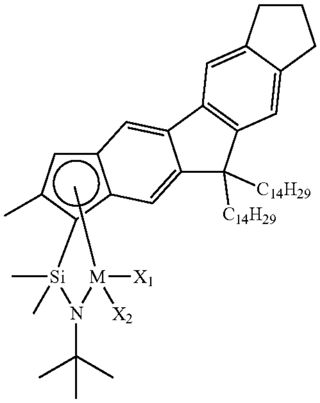
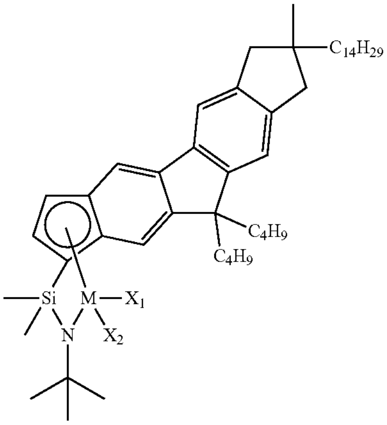
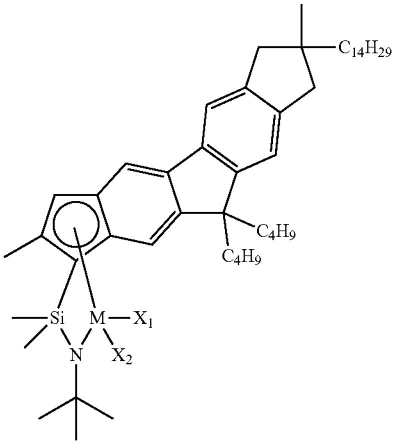

-continued
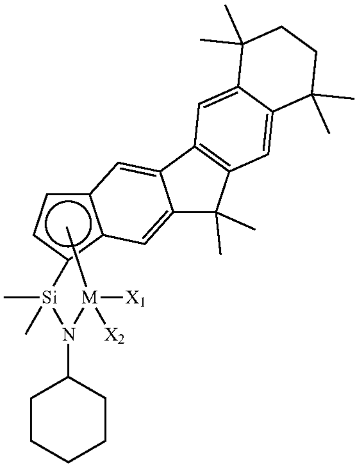
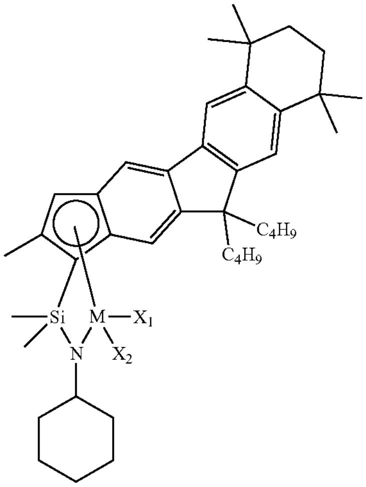
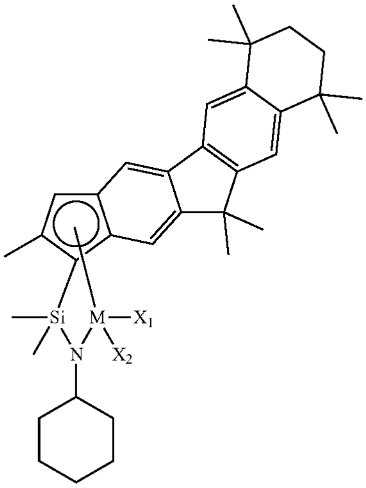
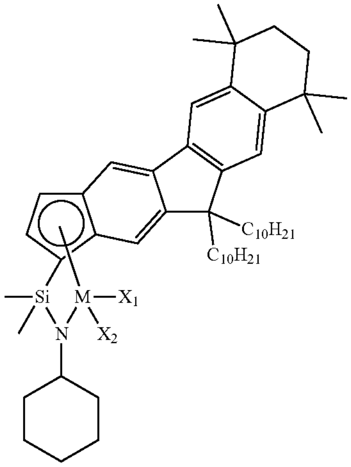
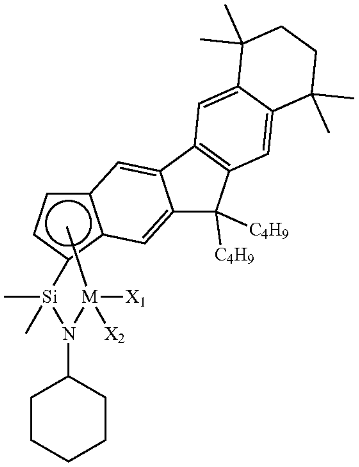
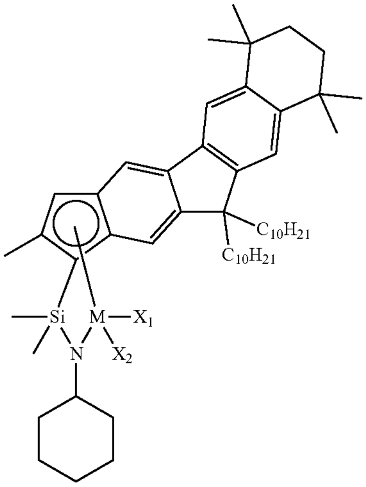
-continued -continued
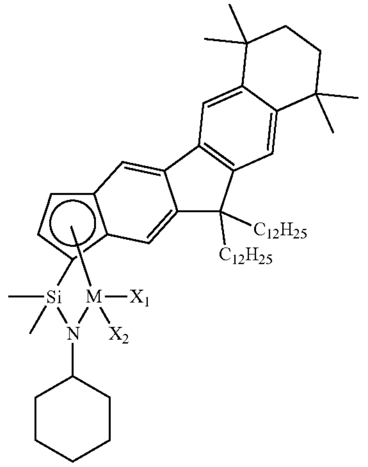
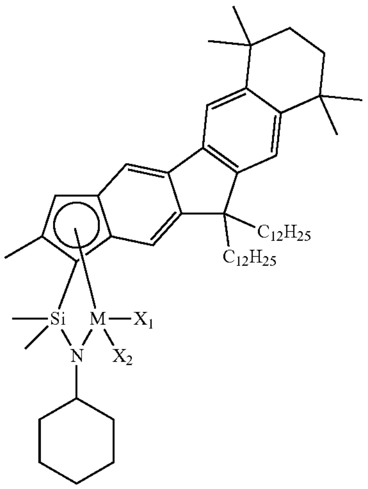
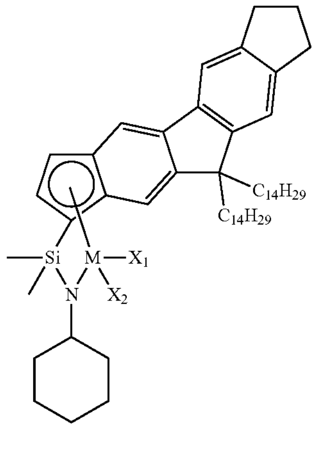
-continued
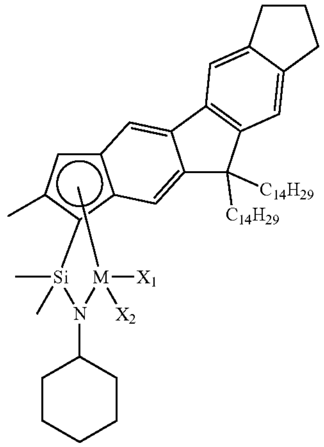
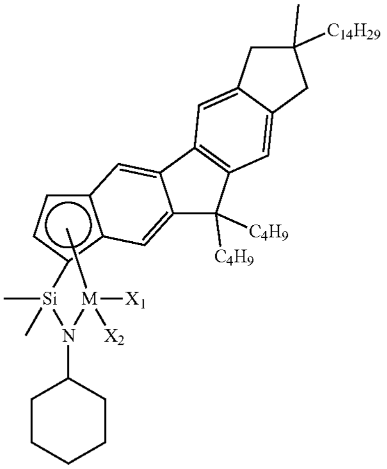
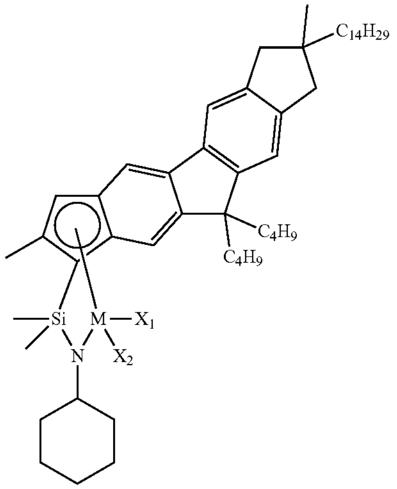

-continued
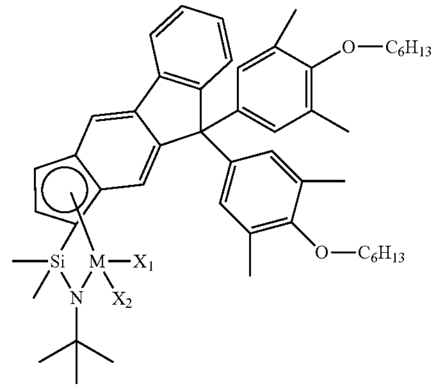
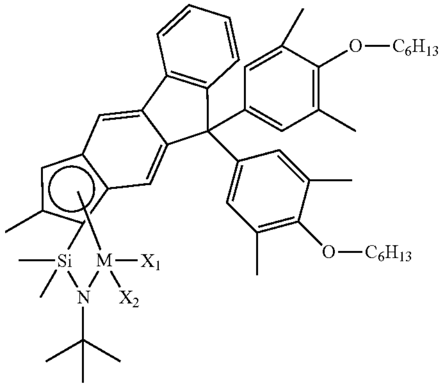
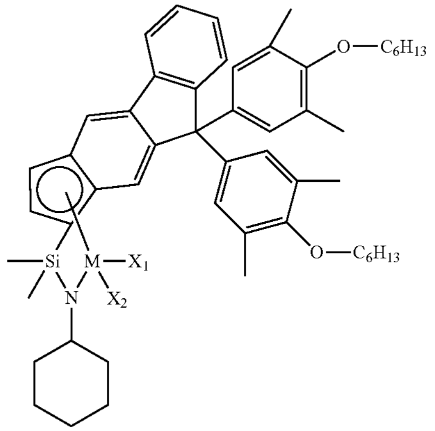
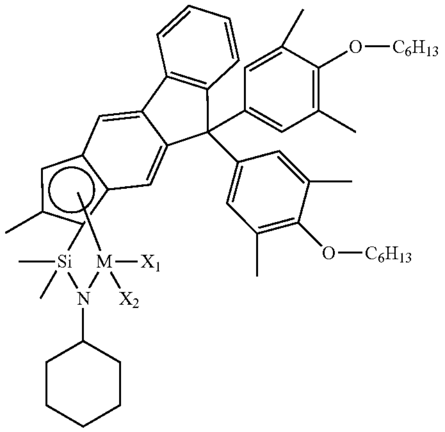
-continued
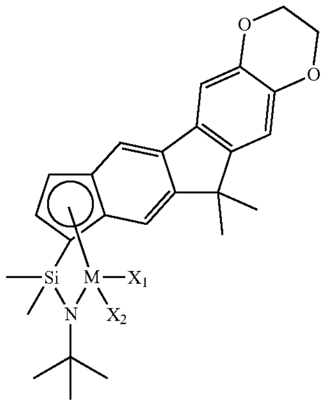
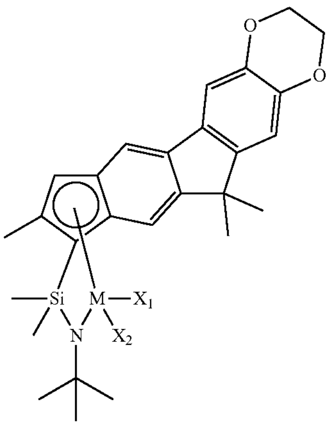
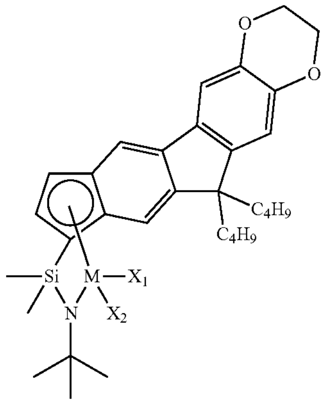
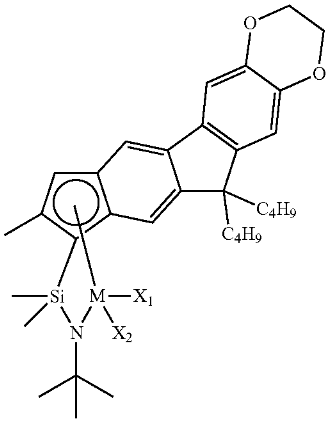

-continued
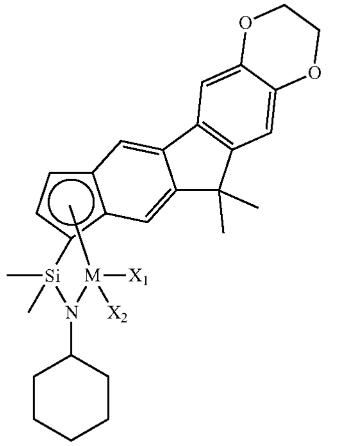
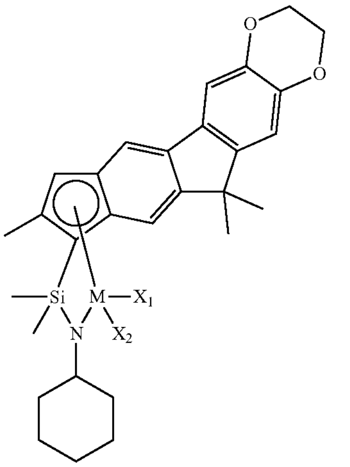
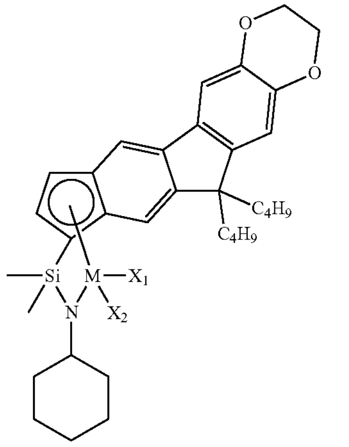
-continued
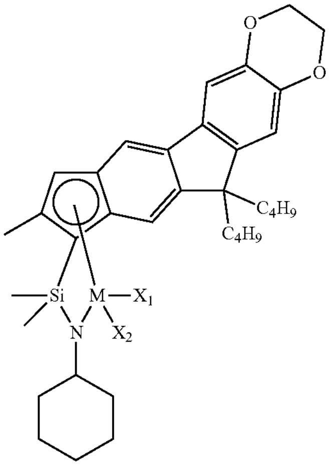
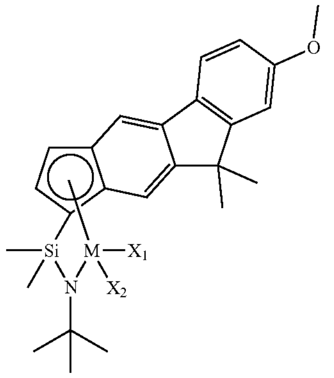
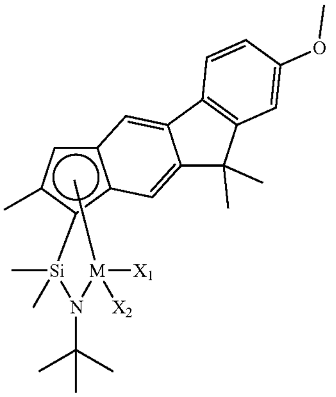
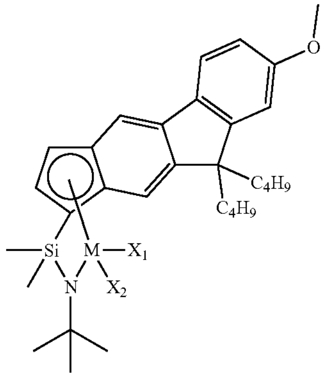

-continued
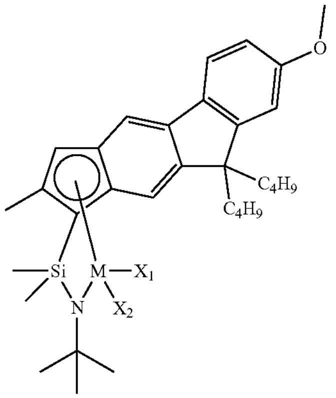
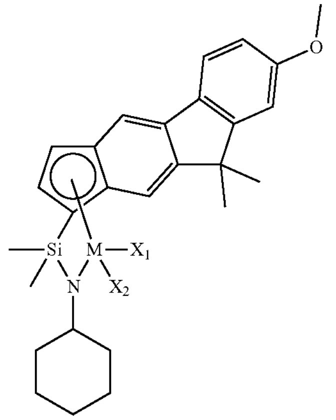
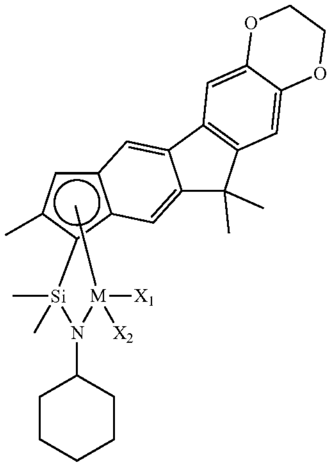
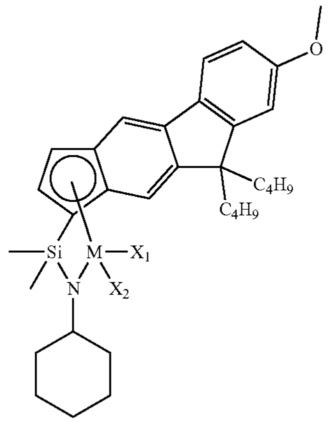
-continued
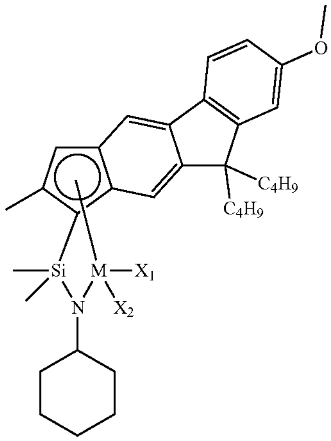
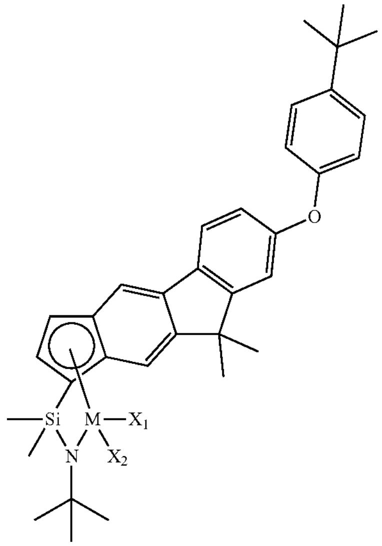
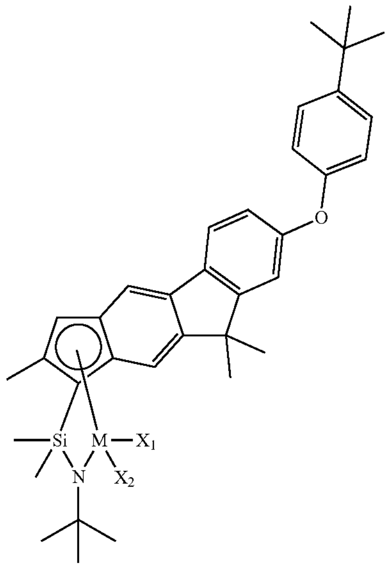

-continued
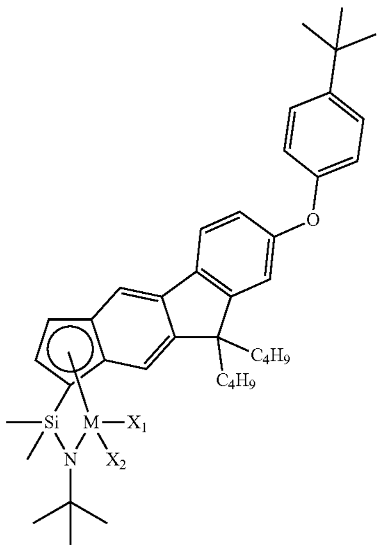
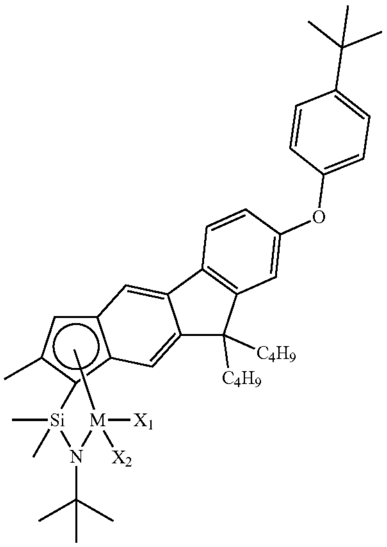
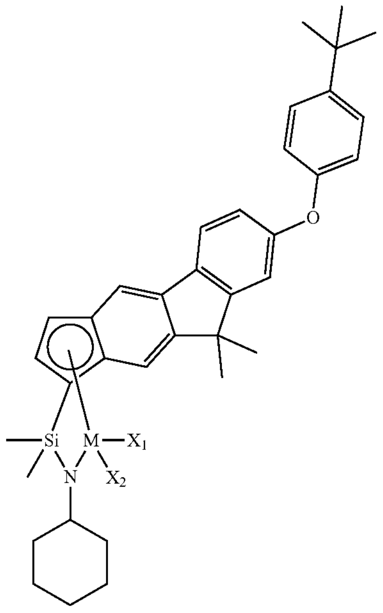
-continued
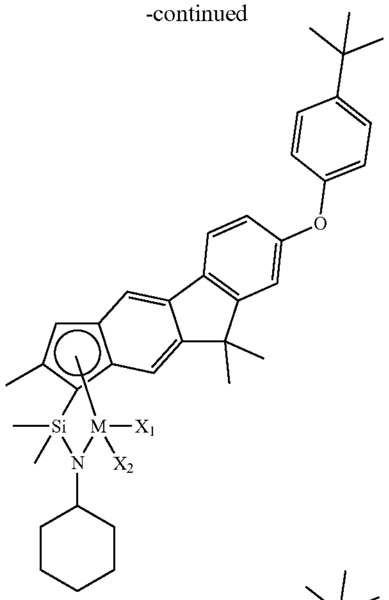
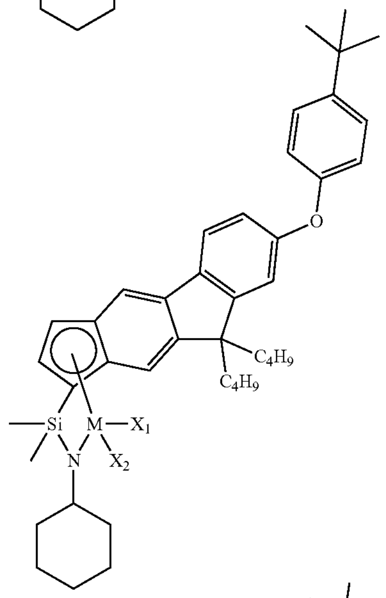
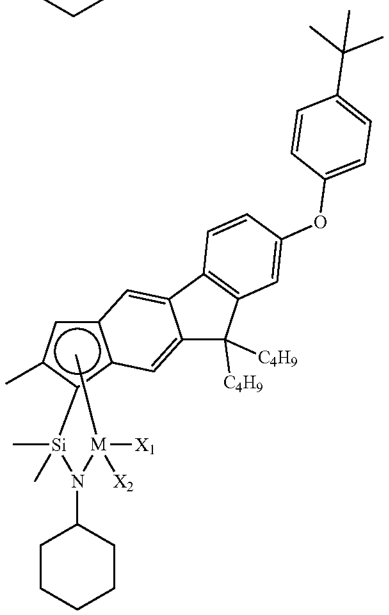

-continued
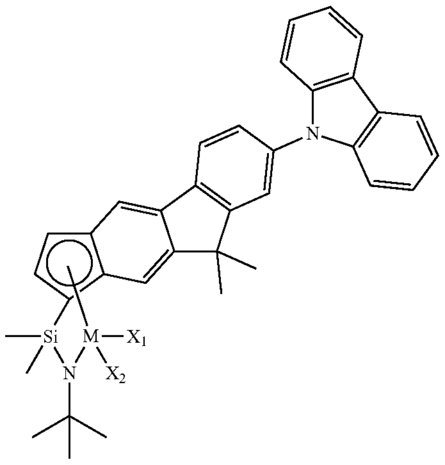
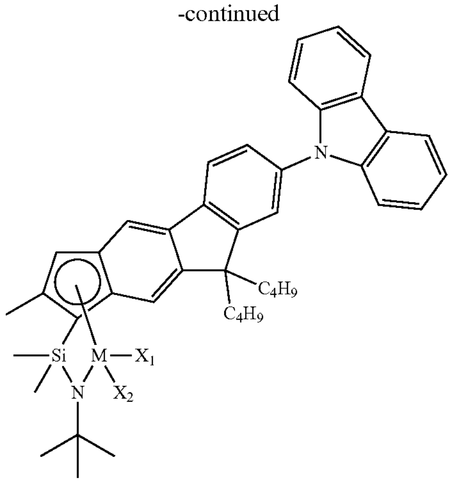
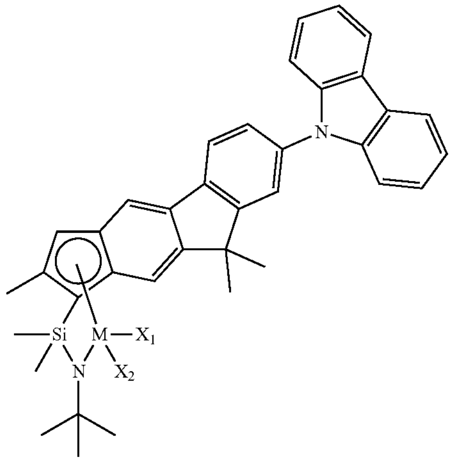
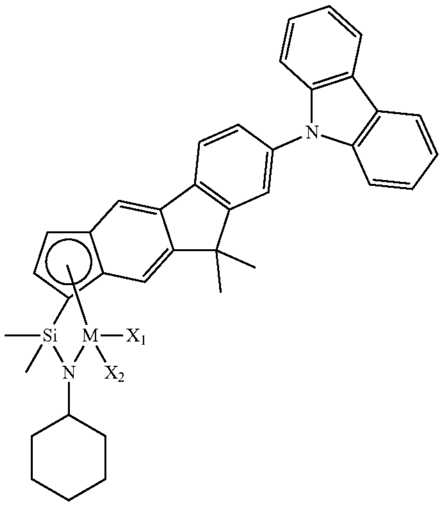
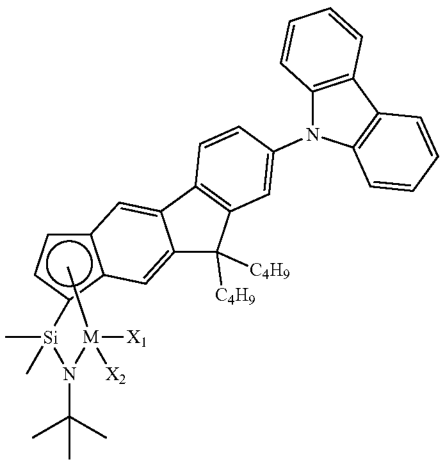
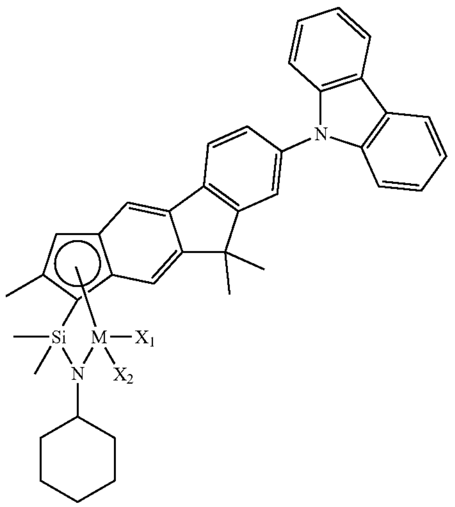
-continued -continued
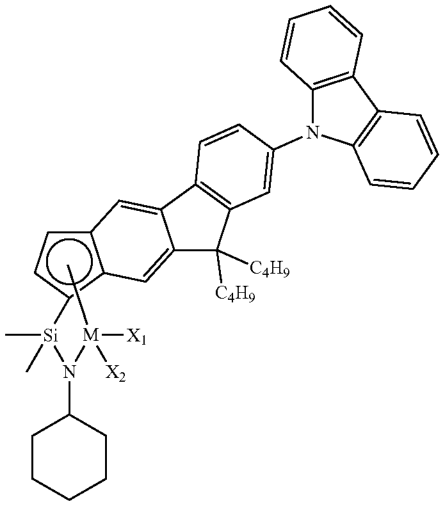
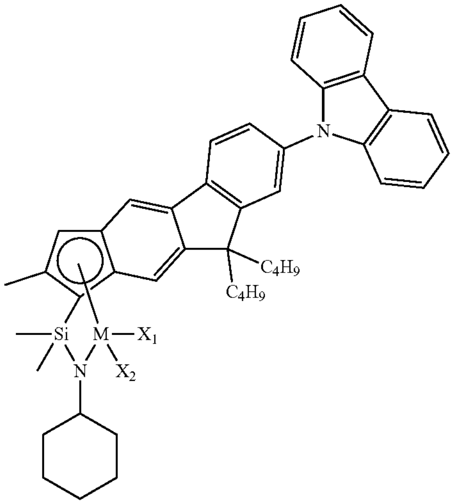
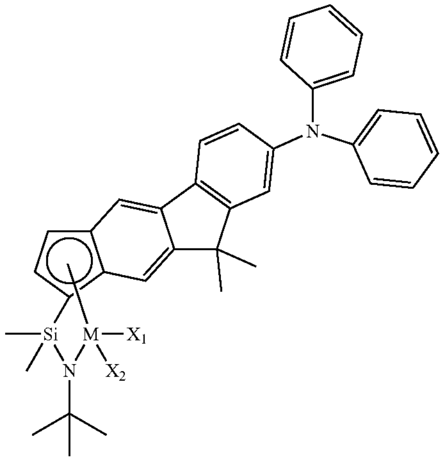
-continued
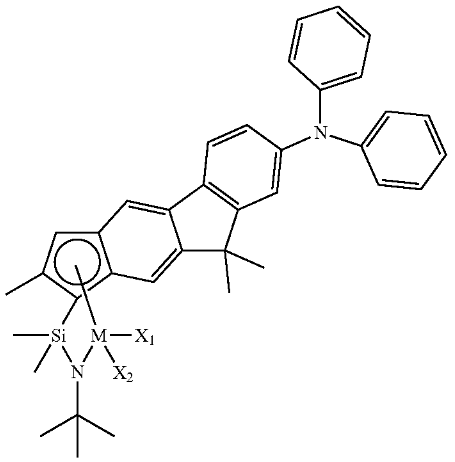
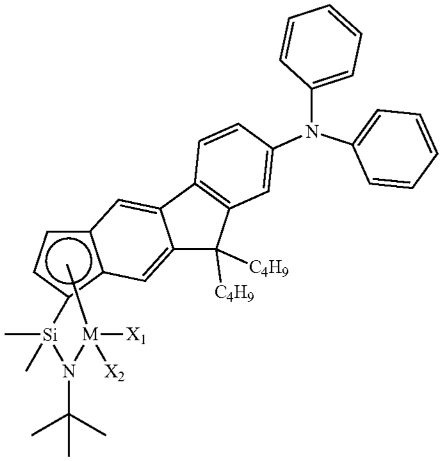
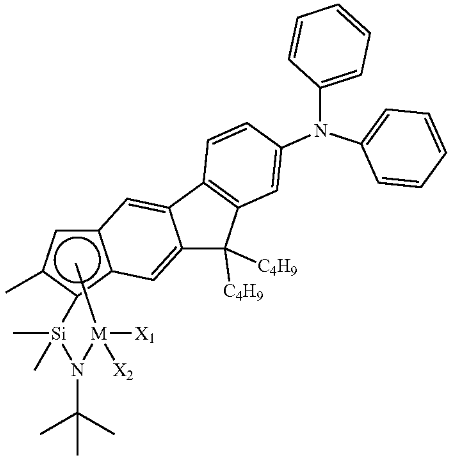

-continued
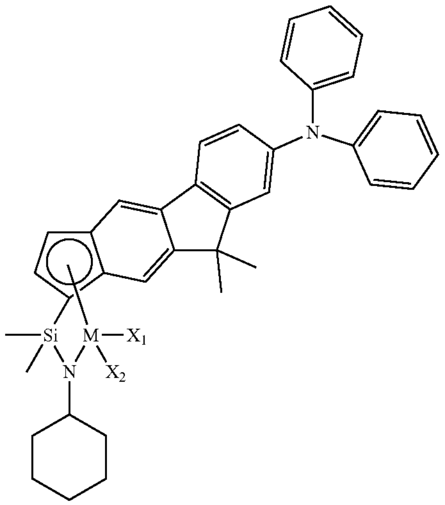
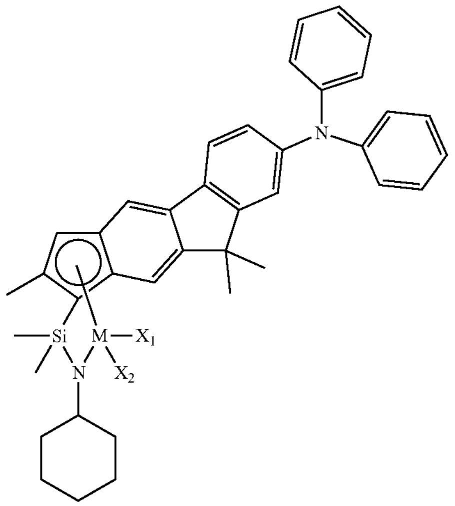
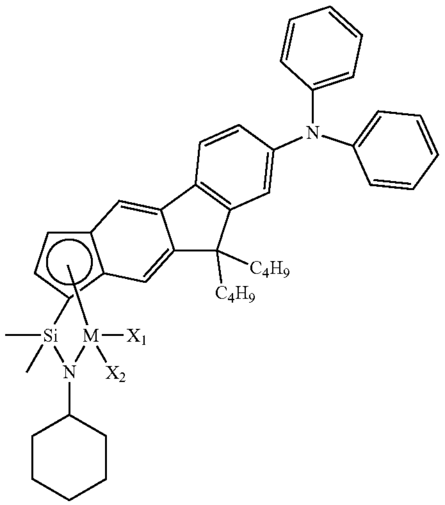
-continued
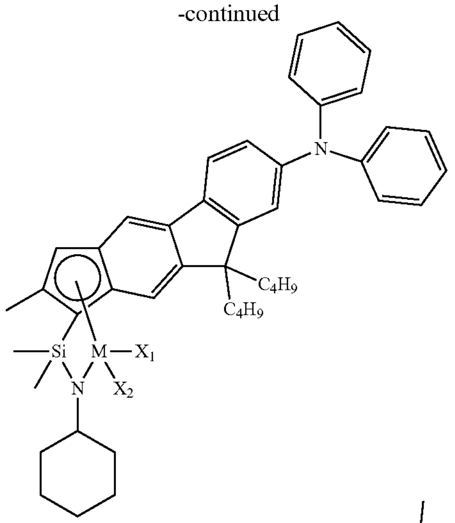
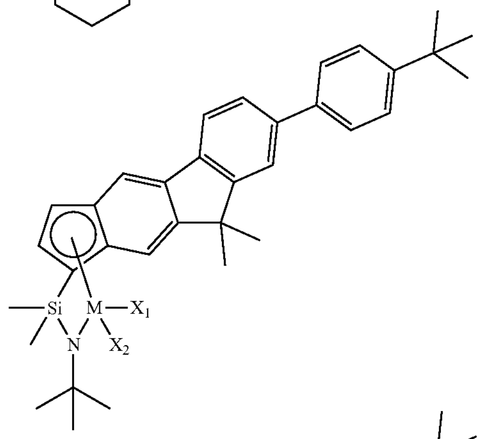
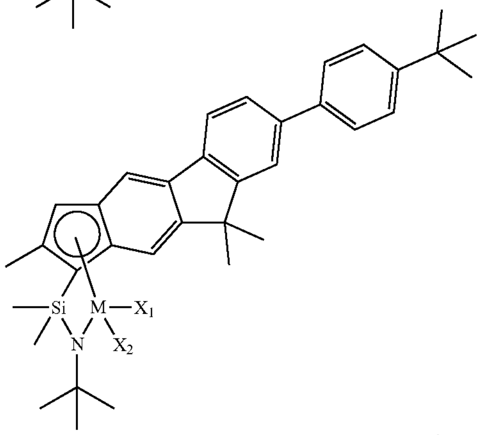
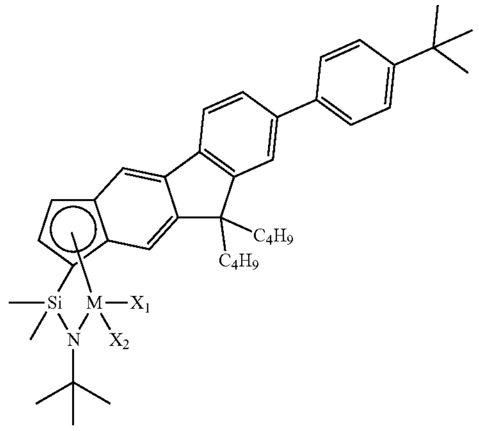

-continued
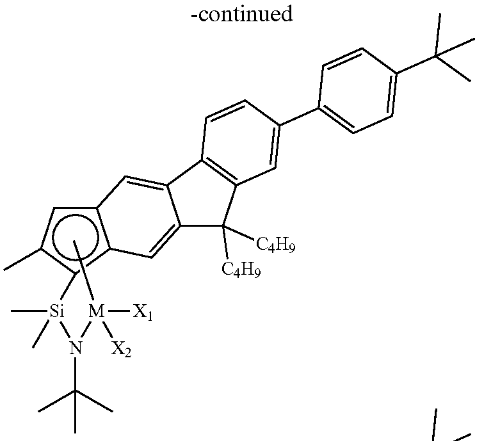
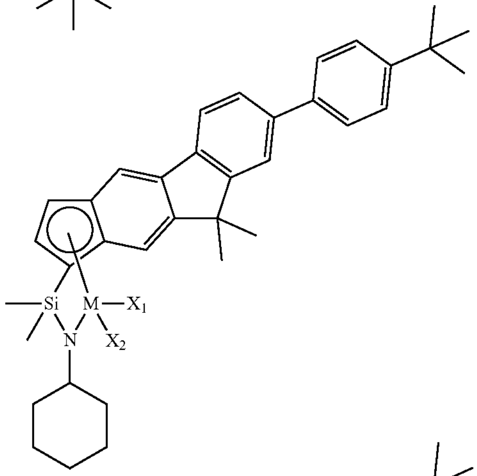
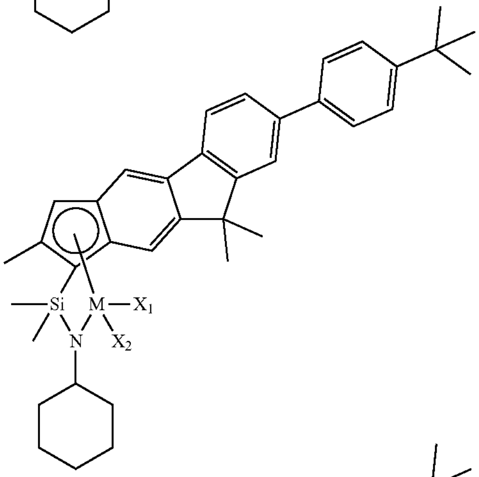
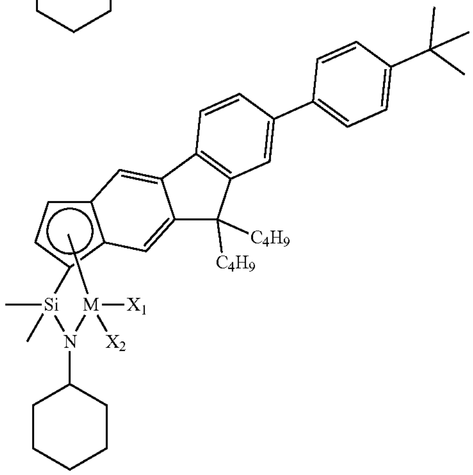
-continued
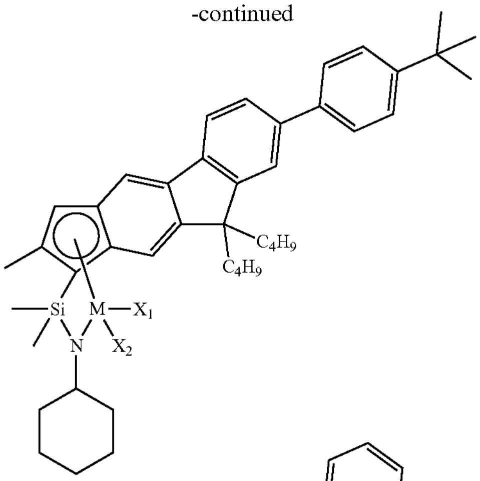
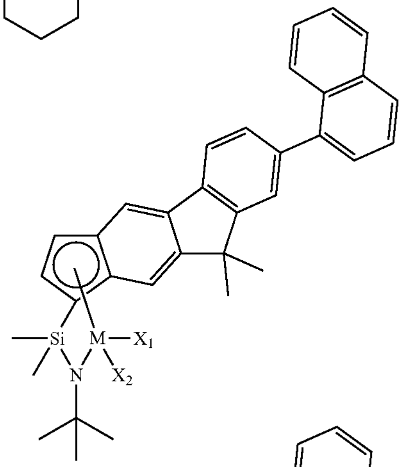
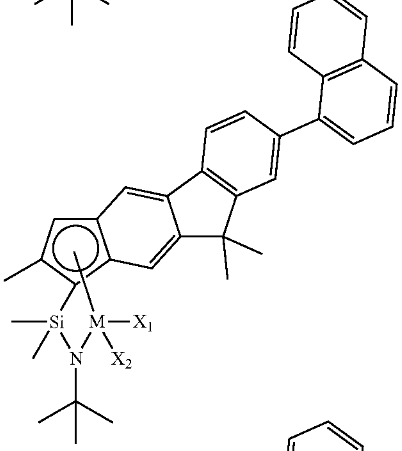
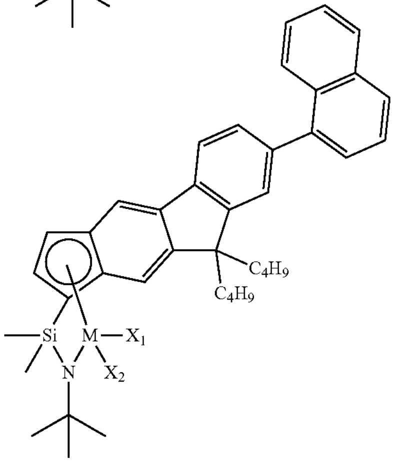

-continued

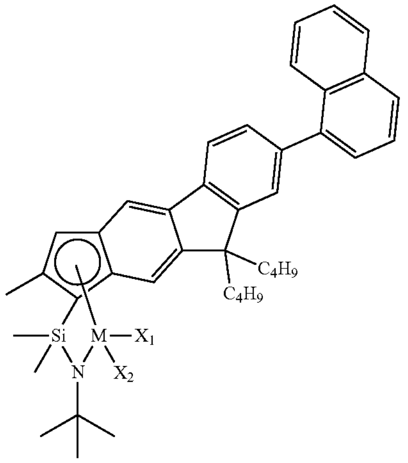

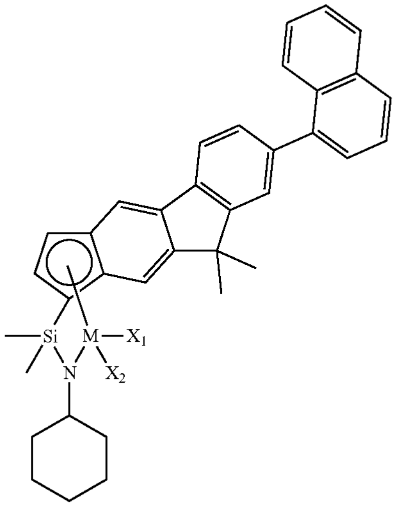

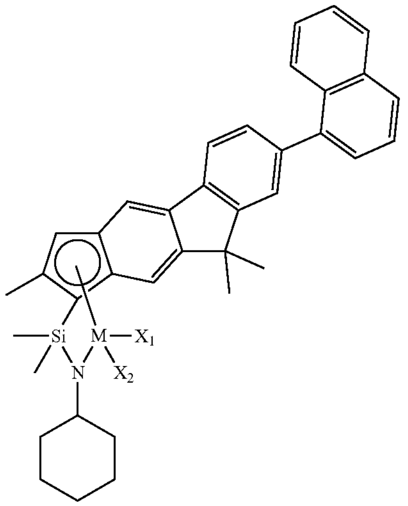

-continued

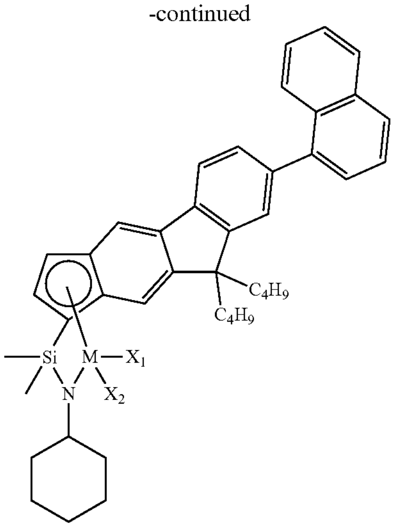

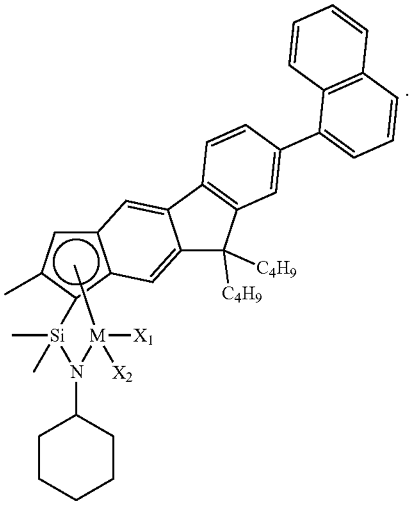

4. The method of claim 1, wherein the transition metal catalyst composition further includes a cocatalyst selected from an aluminum compound, a boron compound, or a mixture thereof.

5. The method of claim 4, wherein the transition metal compound and the cocatalyst have a molar ratio of transition metal (M):boron atom (B):aluminum atom (Al) in the range of 1:0~100:1~2,000.

6. The method of claim 5, wherein the transition metal compound and the cocatalyst have a molar ratio of transition metal (M):boron atom (B):aluminum atom (Al) in the range of 1:0.5~5:10~500.

7. The method of claim 1, wherein the α-olefin monomer is at least one selected from the group consisting of propylene, 1-butene, 1-pentene, 4-methyl-1-pentene, 1-hexene, 1-heptene, 1-octene, 1-decene, 1-undecene, 1-dodecene, 1-tetradecene, 1-hexadecene, 1-octadecene, cyclopentene, cyclohexene, norbornene, phenylnorbornene, styrene, α-methylstyrene, p-methylstyrene, and 3-chloromethylstyrene; and the diene monomer is at least one selected from 1,3-butadiene, 1,4-pentadiene, 2-methyl-1,3-butadiene, 1,4-hexadiene, 1,5-hexadiene, 1,5-heptadiene, 1,6-heptadiene, 1,6-octadiene, 1,7-octadiene, 1,7-nonadiene, 1,8-nonadiene, 1,8-decadiene, 1,9-decadiene, 1,12-tetradecadiene, 1,13-tetradecadiene, 3-methyl-1,4- hexadiene, 3-methyl-1,5-hexadiene, 3-ethyl-1,4-hexadiene, 3-ethyl-1,5-hexadiene, 3,3-dimethyl-1,4-hexadiene, 3,3-dimethyl-1,5-hexadiene, cyclopentadiene, cyclohexadiene, 5-vinyl-2-norbornene, 2,5-norbornadiene, 7-methyl-2,5-norbornadiene, 7-ethyl-2,5-norbornadiene, 7-propyl-2,5-norbornadiene, 7-butyl-2,5-norbornadiene, 7-phenyl-2,5-norbornadiene, 7-hexyl-2,5-norbornadiene, 7,7-dimethyl-2,5-norbornadiene, 7-methyl-7-ethyl-2,5-norbornadiene, 7-chloro-2,5-norbornadiene, 7-bromo-2,5-norbornadiene, 7-fluoro-2,5-norbornadiene, 7,7-dichloro-2,5-norbornadiene, 1-methyl-2,5-norbornadiene, 1-ethyl-2,5-norbornadiene, 1-propyl-2,5-norbornadiene, 1-butyl-2,5-norbornadiene, 1-chloro-2,5-norbornadiene, 1-bromo-2,5-norbornadiene, 5-isopropyl-2-norbornene, 5-vinylidene-2-norbornene (VNB), 5-methylene-2-norbornene (MNB), and 5-ethylidene-2-norbornene (ENB).

8. The method of claim 1, wherein the ethylene-α-olefin-diene copolymer contains 30 to 85 wt % of ethylene, 1 to 15 wt % of diene, and the rest of α-olefin.

9. The method of claim 7, wherein a pressure in a reactor for copolymerization of ethylene monomers, α-olefin monomers, and diene monomers is 1~1000 atm, and a polymerization reaction temperature is 25~200° C.

10. The method of claim 9, wherein at the time of preparing the ethylene-α-olefin-diene copolymer, the pressure in the reactor is 6~150 atm, and the polymerization reaction temperature is 50~180° C.

11. The method of claim 1, wherein the ethylene-α-olefin-diene copolymer has Mooney viscosity (ASTM D1646-94, ML1+4@125° C.) of 1 to 250.

12. The method of claim 11, wherein the ethylene-α-olefin-diene copolymer has Mooney viscosity (ASTM D1646-94, ML1+4@125° C.) of 10 to 200.

* * * * *